US009688680B2

(12) United States Patent
Hodous

(10) Patent No.: US 9,688,680 B2
(45) Date of Patent: Jun. 27, 2017

(54) COMPOSITIONS USEFUL FOR TREATING DISORDERS RELATED TO KIT

(71) Applicant: BLUEPRINT MEDICINES CORPORATION, Cambridge, MA (US)

(72) Inventor: Brian L. Hodous, Cambridge, MA (US)

(73) Assignee: BLUEPRINT MEDICINES CORPORATION, Cambridge, MA (US)

( * ) Notice: Subject to any disclaimer, the term of this patent is extended or adjusted under 35 U.S.C. 154(b) by 0 days.

(21) Appl. No.: 14/817,931

(22) Filed: Aug. 4, 2015

(65) Prior Publication Data
US 2016/0031892 A1 Feb. 4, 2016

Related U.S. Application Data

(60) Provisional application No. 62/032,731, filed on Aug. 4, 2014.

(51) Int. Cl.
| C07D 487/04 | (2006.01) |
| C07D 403/04 | (2006.01) |
| C07D 403/14 | (2006.01) |
| C07D 401/04 | (2006.01) |
| C07D 401/14 | (2006.01) |
| A61K 31/53 | (2006.01) |
| A61K 31/5025 | (2006.01) |
| A61P 35/02 | (2006.01) |

(52) U.S. Cl.
CPC ........ *C07D 487/04* (2013.01); *A61K 31/5025* (2013.01); *A61K 31/53* (2013.01); *C07D 401/04* (2013.01); *C07D 401/14* (2013.01); *C07D 403/04* (2013.01); *C07D 403/14* (2013.01)

(58) Field of Classification Search
CPC .. C07D 487/04; C07D 401/04; C07D 401/14; C07D 403/04; C07D 403/14; A61K 31/53; A61K 31/5025; A61K 31/4523
USPC .......................... 514/243, 248; 544/183, 235
See application file for complete search history.

(56) References Cited

U.S. PATENT DOCUMENTS

| 6,982,265 B1 | 1/2006 | Hunt et al. |
| 8,609,672 B2 | 12/2013 | Russu et al. |
| 9,200,002 B2 | 12/2015 | Hodous et al. |
| 9,334,263 B2 | 5/2016 | Hodous et al. |

FOREIGN PATENT DOCUMENTS

| WO | 0071129 A1 | 11/2000 |
| WO | 01/25220 A1 | 4/2001 |
| WO | 2005117909 A2 | 12/2005 |
| WO | 2007085188 A1 | 8/2007 |
| WO | 2008005956 A2 | 1/2008 |
| WO | 2009015254 A1 | 1/2009 |
| WO | 2009117157 A1 | 9/2009 |
| WO | 2010022055 A2 | 2/2010 |
| WO | 2010144345 A1 | 12/2010 |
| WO | 2011005119 A1 | 1/2011 |
| WO | 2011103196 A1 | 8/2011 |
| WO | 2012027495 A1 | 3/2012 |
| WO | 2014160521 A1 | 10/2014 |
| WO | 2015057873 A1 | 4/2015 |
| WO | 2015058129 A1 | 4/2015 |

OTHER PUBLICATIONS

Antonescu, "What lessons can be learned from the GIST paradigm that can be applied to other kinase-driven cancers" J. Pathol. (2011) vol. 223, No. 2, pp. 251-261.
Cairoli et al. "Prognostic impact of c-KIT mutations in core binding factor leukemias: an Italian retrospective study" Blood (2006) vol. 107, pp. 3463-3468.
Cecil Textbook of Medicine, Edited by Bennet and Plum (1996) 20th edition, vol. 1, pp. 1004-1010.
Cohen et al., "The development and therapeutic potential of protein kinase inhibitors" Current Opinion in Chemical Biology (1999) vol. 3, pp. 459-465.
Dermer "Another Anniversary for the War on Cancer" Bio/Technology (1994) vol. 12, pp. 320.
Fresheny et al., "Culture of Animal Cells, A Manual of Basic Technique" Alan R. Liss, Inc. (1983) pp. 1-6.
International Search Report and Written Opinion for International Application No. PCT/US2014/027008 dated Jul. 17, 2014.
International Search Report and Written Opinion for International Application No. PCT/US2014/060746 dated Dec. 17, 2014.
International Search Report and Written Opinion for International Application No. PCT/US2014/061211 dated Oct. 12, 2014.
International Search Report for International Application No. PCT/US2015/043624 dated Oct. 6, 2015.
Lee et al. "Correlation of Imatinib Resistance with the Mutational Status of KIT and ODGFRA Genes in Gastrointestinal Stromal Tumors: a Meta-analysis" J. Gastrointestin Liver Dis. (2013) vol. 22, No. 4, pp. 413-418.
Paschka et al. "Adverse Prognostic Significance of KIT Mutations in Adult Acute Myeloid Leukemia with inv(16) and t (8;21):A Cancer and Leukemia Group Study" Journal of Clinical Oncology (2006) vol. 24, No. 24, pp. 3904-3911.
Quintela et al, "A Ready One-pot Preparation for Pyrrolo[2,1-f]-[1,2,4]triazine and Pyrazolo[5,1-c]pyrimido[4,5-e]-[1,2,4]triazine Derivatives" Tetrahedron (1996) vol. 52, No. 8, pp. 3037-3048.
Schnittger et al. "KIT-D816 mutations in AML1-ETO-positive AML are associated with impaired event-free and Dveral survival" Blood (2006) vol. 107, pp. 1791-1799.
U.S. Appl. No. 14/210,526, filed Mar. 14, 2014.
U.S. Appl. No. 14/887,614, filed Oct. 20, 2015.
U.S. Appl. No. 15/093,354, filed Apr. 7, 2016.

*Primary Examiner* — Venkataraman Balasubramanian
(74) *Attorney, Agent, or Firm* — Lando & Anastasi, LLP

(57) ABSTRACT

Compounds and compositions useful for treating disorders related to Kit are described herein.

21 Claims, No Drawings

COMPOSITIONS USEFUL FOR TREATING DISORDERS RELATED TO KIT

CLAIM OF PRIORITY

This application claims priority to U.S. Ser. No. 62/032,731, filed Aug. 4, 2014, the content of which is incorporated by reference in its entirety.

BACKGROUND

The invention relates to compounds and compositions useful for treating disorders related to Kit.

The enzyme Kit (also called CD117) is a receptor tyrosine kinase (RTK) expressed on a wide variety of cell types. The Kit molecule contains a long extracellular domain, a trans-membrane segment, and an intracellular portion. The ligand for Kit is stem cell factor (SCF), whose binding to the extracellular domain of Kit induces receptor dimerization and activation of downstream signaling pathways. Kit mutations generally occur in the DNA encoding the juxtumembrane domain (exon 11). They also occur, with less frequency, in exons 7, 8, 9, 13, 14, 17, and 18. Mutations make Kit function independent of activation by SCF, leading to a high cell division rate and possibly genomic instability. Mutant Kit has been implicated in the pathogenesis of several disorders and conditions including including systemic mastocytosis, GIST (gastrointestinal stromal tumors), AML (acute myeloid leukemia), melanoma, and seminoma. As such, there is a need for therapeutic agents that inhibit Kit, and especially agents that inhibit mutant Kit.

SUMMARY OF THE INVENTION

The present invention provides compounds and compositions for treating or preventing conditions such as mastocytosis by modulating the activity of Kit, such compounds having the structural Formula (I):

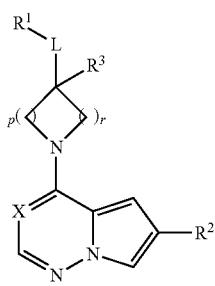

(I)

or a pharmaceutically acceptable salt thereof, wherein:

X is selected from CH or N;

L is a bond, —$(CR^cR^c)_n$—, —$(CR^cR^c)_nNR^b$—, —$NR^b(CR^cR^c)_n$—, —$S(O)_2$—, —$S(O)$—, —$C(O)$—, —$OC(O)$—, —$C(O)O$—, —$(CR^cR^c)_n$—$OC(O)$—, —$OC(O)$—$(CR^cR^c)_n$—, —$(CR^cR^c)_n$—$C(O)$—, —$C(O)$—$(CR^cR^c)_n$—, —$NR^bC(O)(CR^cR^c)$, —$C(O)NR^b$—$(CR^cR^c)$, where the two $R^c$'s, together with the carbon to which they are attached, can form a carbocycle, —$C(O)NR^b$—$(CR^cR^c)$, —$(CR^cR^c)_nNR^b$—$(CR^cR^c)$, —$NR^bC(S)$—, —$C(S)NR^b$—, —$NR^bC(O)$—, —$C(O)NR^b$—, —$NR^bS(O)_2$, -or —$S(O)_2NR^b$—;

$R^1$ is alkyl, carbocyclyl, carbocyclylalkyl, aryl, aralkyl, heteroaryl, heteroaralkyl, heterocyclyl, or heterocyclylalkyl each of which is substituted with 0-5 occurrences of $R^d$;

$R^2$ is H, halo, aryl, alkenyl, heteroaryl, carbocyclyl, or heterocyclyl, wherein each of aryl, alkenyl, heteroaryl, carbocyclyl, and heterocyclyl is substituted with 0-5 occurrences of $R^d$;

$R^3$ is H, alkyl, heteroalkyl, haloalkyl, haloalkoxyl, —$OR^c$, —$C(O)OR^c$, —$C(O)NR^aR^b$, —$(CR^cR^c)_nNR^b$—$(CR^cR^c)$—H, —$NR^aR^b$, or cyano, wherein each of alkyl, heteroalkyl, haloalkyl, and haloalkoxyl is substituted with 0-5 occurrences of $R^d$;

$R^a$ and $R^b$ are each independently H, alkyl, heteroalkyl, aryl, aralkyl, heteroaryl, heterocyclyl, or heterocyclylalkyl, wherein each of alkyl, heteroalkyl, aryl, aralkyl, heterocyclyl, and heterocyclylalkyl is substituted with 0-5 occurrences of $R^d$; or $R^a$ and $R^b$ together with the nitrogen atom to which they are attached form a heterocyclyl substituted with 0-5 occurrences of $R^d$;

$R^c$ is H or alkyl;

each $R^d$ is independently halo, heteroalkyl, haloalkyl, haloalkoxyl, alkyl, alkynyl, hydroxyalkyl, carbocyclyl, carbocyclylalkyl, aryl, aralkyl, heteroaryl, heterocyclyl, heterocyclylalkyl, nitro, cyano, hydroxyl, —$C(O)R^{a1}$, —$OC(O)R^{a1}$, —$C(O)OR^{a1}$, —$SR^{a1}$, —$S(O)_2R^{a1}$, —$NR^{a1}R^{b1}$, —$C(O) NR^{a1}R^{b1}$, —$NR^{a1}S(O)_2R^{a1}$, or —$OR^{a1}$; wherein each of heteroalkyl, haloalkyl, haloalkoxyl, alkyl, alkynyl, hydroxyalkyl, carbocyclyl, carbocyclylalkyl, aryl, aralkyl, heteroaryl, heterocyclyl, and heterocyclylalkyl is substituted with 0-5 occurrences of $R^{c1}$; or two $R^d$ together with the atoms to which they are attached form a carbocyclyl or heterocyclyl, each optionally substituted with halo or alkyl;

$R^{a1}$ and $R^{b1}$ are each independently H, alkyl, aralkyl, carbocyclyl, heteroaryl, or heterocyclyl; or $R^{a1}$ and $R^{b1}$ together with the nitrogen atom to which they are attached form a heterocyclyl optionally substituted with halo or alkyl;

each $R^{c1}$ is independently halo, —$OR^{c2}$, —$NR^{a1}R^{b1}$, alkyl, cyano, heteroalkyl, haloalkyl, haloalkoxyl, carbocyclyl, carbocyclylalkyl, heterocyclyl, heterocyclylalkyl, heteroaryl, heteroaralkyl, aryl, or aralkyl;

$R^{c2}$ is H or alkyl;

p and r are each independently 1 or 2; and n is 1, 2, 3 or 4.

Compounds disclosed herein may be at least 5 times, but less than 10 times, more active against the D816V mutation of Kit than against wild-type Kit when measured in a biochemical assay; at least 10 times, but less than 25 times, more active against the D816V mutation of Kit than against wild-type Kit when measured in a biochemical assay; at least 25 times, but less than 50 times, more active against the D816V mutation of Kit than against wild-type Kit when measured in a biochemical assay; at least 50 times, but less than 100 times, more active against the D816V mutation of Kit than against wild-type Kit when measured in a biochemical assay; at least 100 times, but less than 500 times, more active against the D816V mutation of Kit than against wild-type Kit when measured in a biochemical assay; at least 500 times, but less than 1000 times, more active against the D816V mutation of Kit than against wild-type Kit when measured in a biochemical assay; or greater than 1000 times more active against the D816V mutation of Kit than against wild-type Kit when measured in a biochemical assay.

Any of the compounds disclosed herein may be used to treat any of the diseases disclosed herein.

DETAILED DESCRIPTION OF THE INVENTION

"Aliphatic group" means a straight-chain, branched-chain, or cyclic hydrocarbon group and includes saturated and unsaturated groups, such as an alkyl group, an alkenyl group, and an alkynyl group.

"Alkenyl" means an aliphatic group containing at least one double bond.

"Alkoxyl" or "alkoxy" means an alkyl group having an oxygen radical attached thereto. Representative alkoxyl groups include methoxy, ethoxy, propyloxy, tert-butoxy and the like.

"Alkyl" refers to a monovalent radical of a saturated straight or branched hydrocarbon, such as a straight or branched group of 1-12, 1-10, or 1-6 carbon atoms, referred to herein as $C_1$-$C_{12}$ alkyl, $C_1$-$C_{10}$ alkyl, and $C_1$-$C_6$ alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, etc.

"Alkylene" refers to a divalent radical of an alkyl group, e.g., —$CH_2$—, —$CH_2CH_2$—, and $CH_2CH_2CH_2$—.

"Alkynyl" refers to a straight or branched hydrocarbon chain containing 2-12 carbon atoms and characterized in having one or more triple bonds. Examples of alkynyl groups include, but are not limited to, ethynyl, propargyl, and 3-hexynyl. One of the triple bond carbons may optionally be the point of attachment of the alkynyl substituent.

"Hydroxyalkyl" refers to an alkyl radical in which an alkyl hydrogen atom is replaced by a hydroxyl group. Hydroxyalkyl includes groups in which more than one hydrogen atom has been replaced by a hydroxyl group.

"Aromatic ring system" is art-recognized and refers to a monocyclic, bicyclic or polycyclic hydrocarbon ring system, wherein at least one ring is aromatic.

"Aryl" refers to a monovalent radical of an aromatic ring system. Representative aryl groups include fully aromatic ring systems, such as phenyl, naphthyl, and anthracenyl, and ring systems where an aromatic carbon ring is fused to one or more non-aromatic carbon rings, such as indanyl, phthalimidyl, naphthimidyl, or tetrahydronaphthyl, and the like.

"Arylalkyl" or "aralkyl" refers to an alkyl moiety in which an alkyl hydrogen atom is replaced by an aryl group. Aralkyl includes groups in which more than one hydrogen atom has been replaced by an aryl group. Examples of "arylalkyl" or "aralkyl" include benzyl, 2-phenylethyl, 3-phenylpropyl, 9-fluorenyl, benzhydryl, and trityl groups.

"Halo" refers to a radical of any halogen, e.g., —F, —Cl, —Br, or —I.

"Haloalkyl" and "haloalkoxyl" refers to alkyl and alkoxyl radicals that are substituted with one or more halo groups or with combinations thereof. For example, the terms "fluoroalkyl" and "fluoroalkoxyl" include haloalkyl and haloalkoxyl groups, respectively, in which the halo is fluorine.

"Heteroalkyl" refers to an alkyl radical, which has one or more skeletal chain atoms selected from an atom other than carbon, e.g., oxygen, nitrogen, sulfur, phosphorus or combinations thereof. A numerical range may be given, e.g. $C_1$-$C_6$ heteroalkyl which refers to the number of carbons in the chain, which in this example includes 1 to 6 carbon atoms. For example, a —$CH_2OCH_2CH_3$ radical is referred to as a "$C_3$" heteroalkyl. In some embodiments, a heteroalkyl refers to an alkyl, which has one or more skeletal chain carbon atoms replaced with nitrogen, e.g., a —$CH_2NHCH_2CH_3$ radical. Connection to the rest of the molecule may be through either a heteroatom or a carbon in the heteroalkyl chain.

"Carbocyclic ring system" refers to a monocyclic, bicyclic or polycyclic hydrocarbon ring system, wherein each ring is either completely saturated or contains one or more units of unsaturation, but where no ring is aromatic.

"Carbocyclyl" refers to a monovalent radical of a carbocyclic ring system. Representative carbocyclyl radicals include cycloalkyl groups (e.g., cyclopentyl, cyclobutyl, cyclopentyl, cyclohexyl and the like), and cycloalkenyl groups (e.g., cyclopentenyl, cyclohexenyl, cyclopentadienyl, and the like).

"Carbocyclylalkyl" refers to an alkyl radical substituted with a carbocyclyl.

"Cycloalkyl" refers to a cyclic, bicyclic, tricyclic, or polycyclic non-aromatic hydrocarbon groups having 3 to 12 carbons. Any substitutable ring atom can be substituted (e.g., by one or more substituents). The cycloalkyl groups can contain fused or spiro rings. Fused rings are rings that share a common carbon atom. Examples of cycloalkyl moieties include, but are not limited to, cyclopropyl, cyclohexyl, methylcyclohexyl, adamantyl, and norbornyl.

"Heteroaromatic ring system" refers to monocyclic, bicyclic or polycyclic ring system wherein at least one ring is both aromatic and comprises at least one heteroatom (e.g., N, O or S); and wherein no other rings are heterocyclyl (as defined below). In certain instances, a ring which is aromatic and comprises a heteroatom contains 1, 2, 3, or 4 ring heteroatoms in such ring.

"Heteroaryl" refers to a monovalent radical of a heteroaromatic ring system. Representative heteroaryl groups include ring systems where (i) each ring comprises a heteroatom and is aromatic, e.g., imidazolyl, oxazolyl, thiazolyl, triazolyl, pyrrolyl, furanyl, thiophenyl pyrazolyl, pyridinyl, pyrazinyl, pyridazinyl, pyrimidinyl, indolizinyl, purinyl, naphthyridinyl, and pteridinyl; (ii) each ring is aromatic or carbocyclyl, at least one aromatic ring comprises a heteroatom and at least one other ring is a hydrocarbon ring or e.g., indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, carbazolyl, acridinyl, phenazinyl, phenothiazinyl, phenoxazinyl, pyrido[2,3-b]-1,4-oxazin-3-(4H)-one, 5,6,7,8-tetrahydroquinolinyl and 5,6,7,8-tetrahydroisoquinolinyl; and (iii) each ring is aromatic or carbocyclyl, and at least one aromatic ring shares a bridgehead heteroatom with another aromatic ring, e.g., 4H-quinolizinyl.

"Heteroarylalkyl" and "heteroaralkyl" refers to an alkyl radical substituted with a heteroaryl group.

"Heterocyclic ring system" refers to monocyclic, bicyclic and polycyclic ring systems where at least one ring is saturated or partially unsaturated (but not aromatic) and comprises at least one heteroatom. A heterocyclic ring system can be attached to its pendant group at any heteroatom or carbon atom that results in a stable structure and any of the ring atoms can be optionally substituted.

"Heterocyclyl" refers to a monovalent radical of a heterocyclic ring system. Representative heterocyclyls include ring systems in which (i) every ring is non-aromatic and at least one ring comprises a heteroatom, e.g., tetrahydrofuranyl, tetrahydrothienyl, pyrrolidinyl, pyrrolidonyl, piperidinyl, pyrrolinyl, decahydroquinolinyl, oxazolidinyl, piperazinyl, dioxanyl, dioxolanyl, diazepinyl, oxazepinyl, thiazepinyl, morpholinyl, and quinuclidinyl; (ii) at least one ring is non-aromatic and comprises a heteroatom and at least one other ring is an aromatic carbon ring, e.g., 1,2,3,4-tetrahydroquinolinyl, 1,2,3,4-tetrahydroisoquinolinyl; and (iii) at least one ring is non-aromatic and comprises a heteroatom and at least one other ring is aromatic and comprises a heteroatom, e.g., 3,4-dihydro-1H-pyrano[4,3-c]pyridine, and 1,2,3,4-tetrahydro-2,6-naphthyridine.

"Heterocyclylalkyl" refers to an alkyl group substituted with a heterocyclyl group.

"Cyano" refers to a —CN radical.

"Nitro" refers to —NO$_2$.

"Oxo" refers to an oxygen atom, which forms a carbonyl when attached to carbon, an N-oxide when attached to nitrogen, and a sulfoxide or sulfone when attached to sulfur.

"Hydroxy" or "hydroxyl" refers to —OH.

"Substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at each position. Combinations of substituents envisioned under this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

As used herein, the definition of each expression, e.g., alkyl, m, n, etc., when it occurs more than once in any structure, is intended to be independent of its definition elsewhere in the same structure.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Unless otherwise indicated, when a disclosed compound is named or depicted by a structure without specifying the stereochemistry and has one or more chiral centers, it is understood to represent all possible stereoisomers of the compound, as well as enantiomeric mixtures thereof.

The "enantiomeric excess" or "% enantiomeric excess" of a composition can be calculated using the equation shown below. In the example shown below a composition contains 90% of one enantiomer, e.g., the S enantiomer, and 10% of the other enantiomer, i.e., the R enantiomer.

$ee$=(90−10)/100=80%.

Thus, a composition containing 90% of one enantiomer and 10% of the other enantiomer is said to have an enantiomeric excess of 80%.

The compounds or compositions described herein may contain an enantiomeric excess of at least 50%, 75%, 90%, 95%, or 99% of one form of the compound, e.g., the S-enantiomer. In other words such compounds or compositions contain an enantiomeric excess of the S enantiomer over the R enantiomer.

The compounds described herein may also contain unnatural proportions of atomic isotopes at one or more of the atoms that constitute such compounds. For example, the compounds may be radiolabeled with radioactive isotopes, such as for example deuterium ($^2$H), tritium ($^3$H), carbon-13 ($^{13}$C), or carbon-14 ($^{14}$C). All isotopic variations of the compounds disclosed herein, whether radioactive or not, are intended to be encompassed within the scope of the present invention. In addition, all tautomeric forms of the compounds described herein are intended to be within the scope of the invention.

The compound can be useful as the free base or as a salt. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1-19.)

Certain compounds disclosed herein can exist in unsolvated forms as well as solvated forms, including hydrated forms. In general, the solvated forms are equivalent to unsolvated forms and are encompassed within the scope of the present invention. Certain compounds disclosed herein may exist in multiple crystalline or amorphous forms. In general, all physical forms are equivalent for the uses contemplated by the present invention and are intended to be within the scope of the present invention.

As used herein, the term "patient" refers to organisms to be treated by the methods of the present invention. Such organisms preferably include, but are not limited to, mammals (e.g., murines, simians, equines, bovines, porcines, canines, felines, and the like), and most preferably includes humans.

As used herein, the term "effective amount" refers to the amount of a compound (e.g., a compound of the present invention) sufficient to effect beneficial or desired results. An effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof.

Compounds

In one aspect, the invention provides a compound having structural Formula (I):

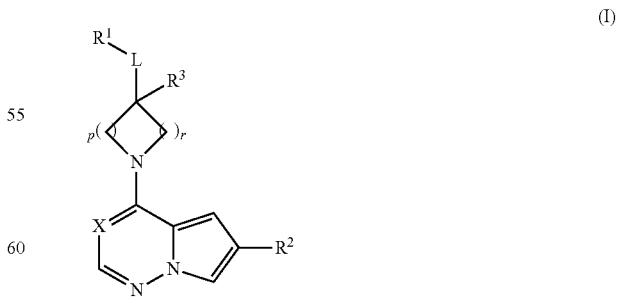

or a pharmaceutically acceptable salt thereof, wherein:

X is selected from CH or N;

L is a bond, —(CR$^c$R$^c$)$_n$—, —(CR$^c$R$^c$)$_n$NR$^b$—, —NR$^b$(CR$^c$R$^c$)$_n$—, —S(O)$_2$—, —S(O)—, —C(O)—, —OC(O)—, —C(O)O—, —(CR$^c$R$^c$)$_n$—OC(O)—, —OC(O)—(CR$^c$R$^c$)$_n$—, —(CR$^c$R$^c$)$_n$—C(O)—, —C(O)—(CR$^c$R$^c$)$_n$—, —NR$^b$C(O)(CR$^c$R$^c$), —C(O)NR$^b$—(CR$^c$R$^c$), where the two R$^c$'s, together with the carbon to which they are attached, can form a carbocycle, —C(O)NR$^b$—(CR$^c$R$^b$), —(CR$^c$R$^c$)$_n$NR$^b$—(CR$^c$R$^c$), —NR$^b$C(S)—, —C(S)NR$^b$—, —NR$^b$C(O)—, —C(O)NR$^b$—, —NR$^b$S(O)$_2$, -or —S(O)$_2$NR$^b$—;

R$^1$ is alkyl, carbocyclyl, carbocyclylalkyl, aryl, aralkyl, heteroaryl, heteroaralkyl, heterocyclyl, or heterocyclylalkyl each of which is substituted with 0-5 occurrences of R$^d$;

R$^2$ is H, halo, aryl, alkenyl, heteroaryl, carbocyclyl, or heterocyclyl, wherein each of aryl, alkenyl, heteroaryl, carbocyclyl, and heterocyclyl is substituted with 0-5 occurrences of R$^d$;

R$^3$ is H, alkyl, heteroalkyl, haloalkyl, haloalkoxyl, —OR', —C(O)OR$^c$, —C(O)NR$^a$R$^b$, —(CR$^c$R$^c$)$_n$NR$^b$—(CR$^c$R$^c$)—H, —NR$^a$R$^b$, or cyano, wherein each of alkyl, heteroalkyl, haloalkyl, and haloalkoxyl is substituted with 0-5 occurrences of R$^d$;

R$^a$ and R$^b$ are each independently H, alkyl, heteroalkyl, aryl, aralkyl, heteroaryl, heterocyclyl, or heterocyclylalkyl, wherein each of alkyl, heteroalkyl, aryl, aralkyl, heterocyclyl, and heterocyclylalkyl is substituted with 0-5 occurrences of R$^d$; or R$^a$ and R$^b$ together with the nitrogen atom to which they are attached form a heterocyclyl substituted with 0-5 occurrences of R$^d$;

R$^c$ is H or alkyl;

each R$^d$ is independently halo, heteroalkyl, haloalkyl, haloalkoxyl, alkyl, alkynyl, hydroxyalkyl, carbocyclyl, carbocyclylalkyl, aryl, aralkyl, heteroaryl, heterocyclyl, heterocyclylalkyl, nitro, cyano, hydroxyl, —C(O)R$^{a1}$, —OC(O)R$^{a1}$, —C(O)OR$^{a1}$, —SR$^{a1}$, —S(O)$_2$R$^{a1}$, —NR$^{a1}$R$^{b1}$, —C(O) NR$^{a1}$R$^{b1}$, —NR$^{a1}$S(O)$_2$R$^{a1}$, or —OR$^{a1}$; wherein each of heteroalkyl, haloalkyl, haloalkoxyl, alkyl, alkynyl, hydroxyalkyl, carbocyclyl, carbocyclylalkyl, aryl, aralkyl, heteroaryl, heterocyclyl, and heterocyclylalkyl is substituted with 0-5 occurrences of R$^{c1}$; or two R$^d$ together with the atoms to which they are attached form a carbocyclyl or heterocyclyl, each optionally substituted with halo or alkyl;

R$^{a1}$ and R$^{b1}$ are each independently H, alkyl, aralkyl, carbocyclyl, heteroaryl, or heterocyclyl; or R$^{a1}$ and R$^{b1}$ together with the nitrogen atom to which they are attached form a heterocyclyl optionally substituted with halo or alkyl;

each R$^{c1}$ is independently halo, —OR$^{c2}$, —NR$^{a1}$R$^{b1}$, alkyl, cyano, heteroalkyl, haloalkyl, haloalkoxyl, carbocyclyl, carbocyclylalkyl, heterocyclyl, heterocyclylalkyl, heteroaryl, heteroaralkyl, aryl, or aralkyl;

R$^{c2}$ is H or alkyl;

p and r are each independently 1 or 2; and n is 1, 2, 3 or 4.

In some embodiments, the compound is a compound of Formula (II):

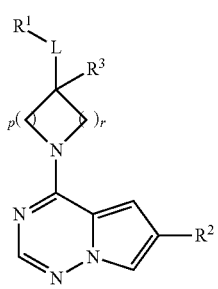

(II)

or a pharmaceutically acceptable salt thereof.

In some embodiments, the compound is a compound of Formula (III):

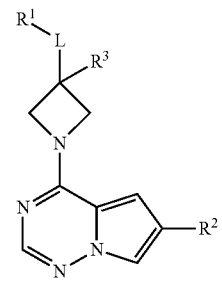

(III)

or a pharmaceutically acceptable salt thereof.

In some embodiments, the compound is a compound of Formula (IV):

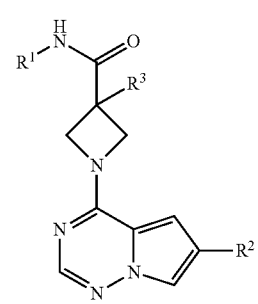

(IV)

or a pharmaceutically acceptable salt thereof.

The below Schemes are meant to provide general guidance in connection with preparing the compounds of the invention. One skilled in the art would understand that the preparations shown in the Schemes can be modified or optimized using general knowledge of organic chemistry to prepare various compounds of the invention. The following examples are intended to be illustrative, and are not meant in any way to be limiting.

Synthetic Protocol 1

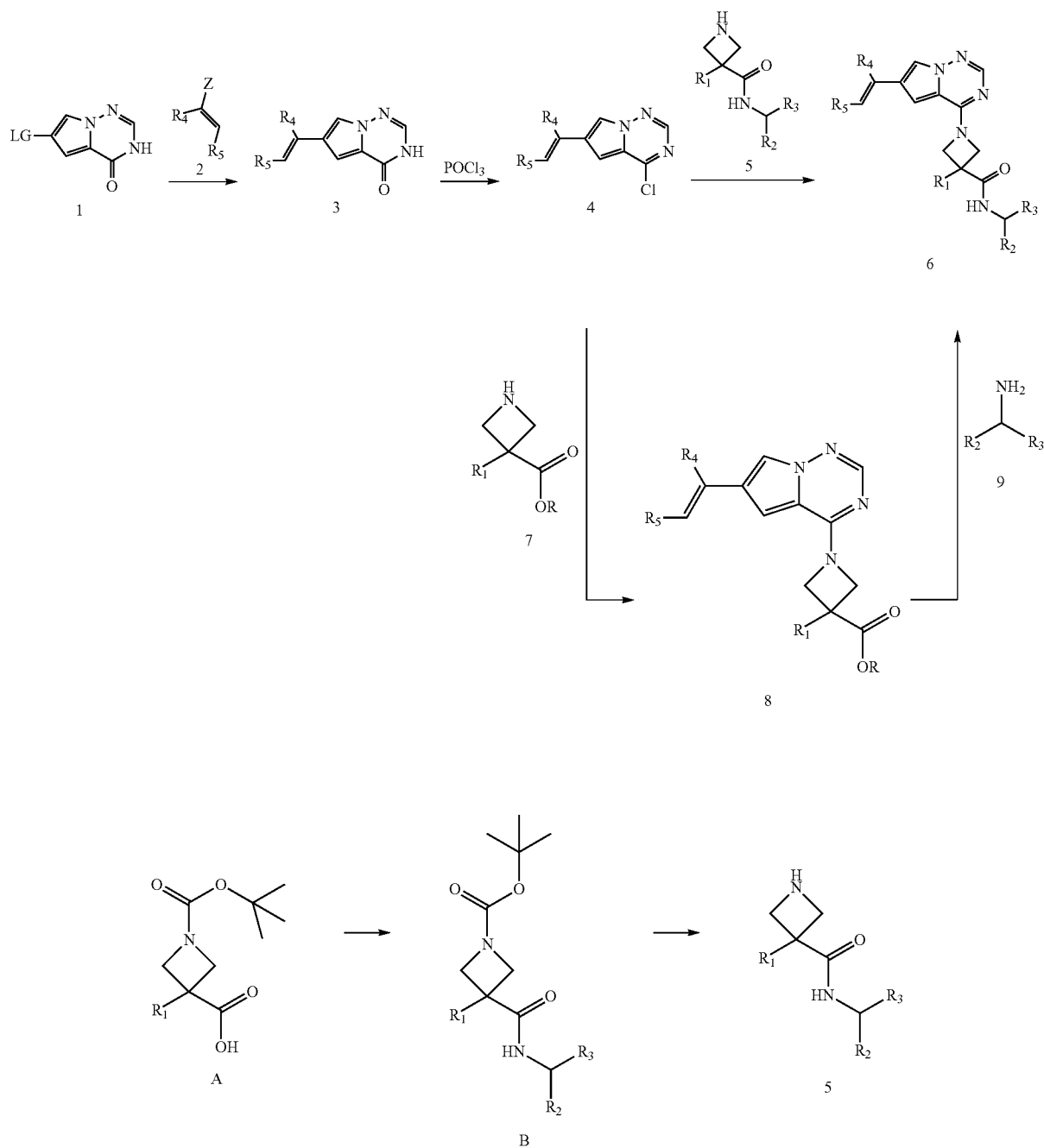

LG = halogen (e.g. chloro)
Z = B or Sn or Zn (substituted)

Synthetic Protocol 1 is shown above. Pyrrolotriazinone (1) can be coupled (LG typically Cl, Br, I) to a boron, tin or zinc aryl, heteroaryl, alkenyl, alkyl reagent (2) via a palladium-mediated coupling reaction, e.g., Suzuki, Stille, Negishi coupling, to provide compound (3). Pyrrolotriazinone (3) can be transformed into pyrrolotriazine (4) via treatment with POCl₃ or other similar reagents. Pyrrolotriazine (4) can be substituted with azetidines (5 or 7) under nucleophilic aromatic substitution reaction conditions using an amine base such as diisopropylethylamine (DIPEA) or triethylamine (TEA) in a polar solvent such as dioxane to provide the piperazine-substituted pyrrolotriazine (6 or 8). Azetidine (5) can be synthesized by reaction of A via an amide bond coupling to generate intermediate B followed by deprotection. Pyrrolotriazine (6) can also be achieved via an amide bond coupling reaction as the final synthetic step.

As shown below, Compounds 6 and 10 were prepared using Synthetic Protocol 1.

Synthesis of 1-(6-(1-methyl-1H-pyrazol-4-yl)pyrrolo[1,2-f][1,2,4]triazin-4-yl)-N-(4-methylbenzyl)azetidine-3-carboxamide (Compound 6)

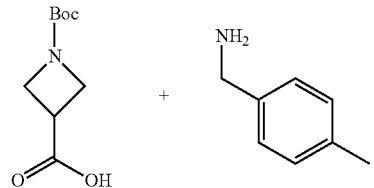

HBTU, DIPEA
DMF

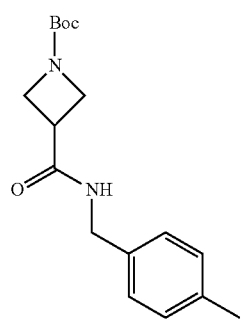

HCl/Diox

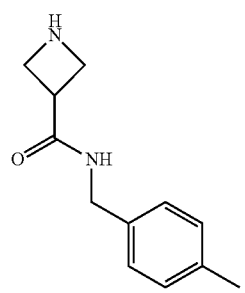

+

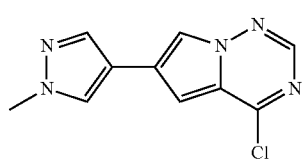

DIPEA/dioxane

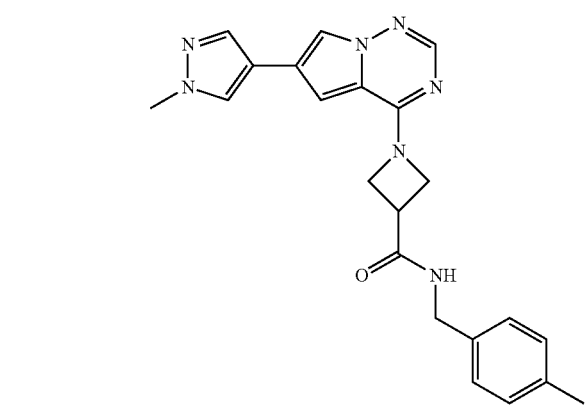

Synthesis of 4-chloro-6-(1-methyl-1H-pyrazol-4-yl)pyrrolo[1,2-f][1,2,4]triazine

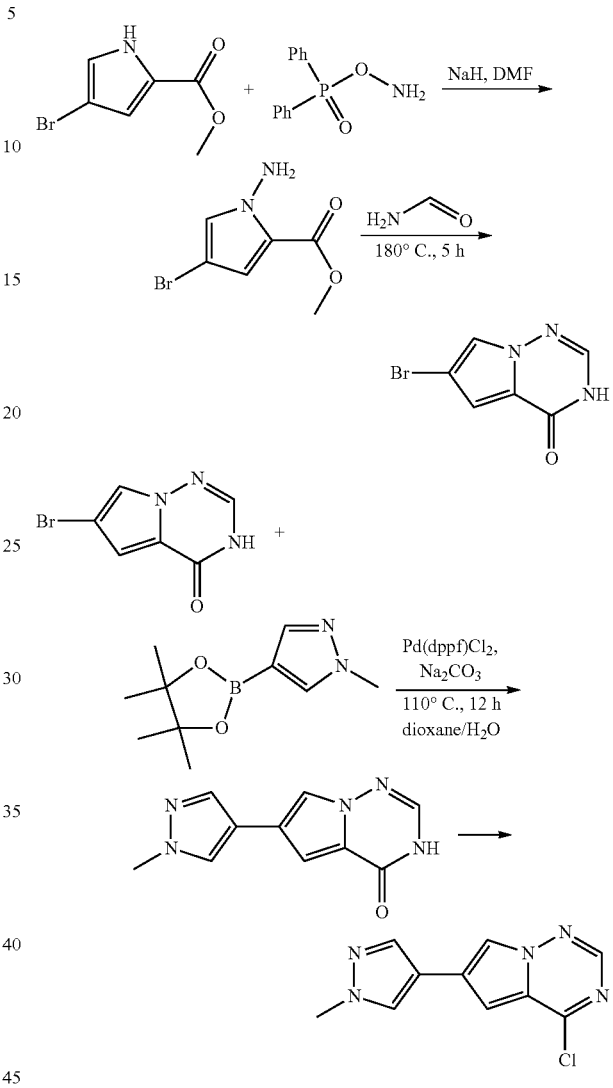

Synthesis of O-(diphenylphosphoryl)hydroxylamine

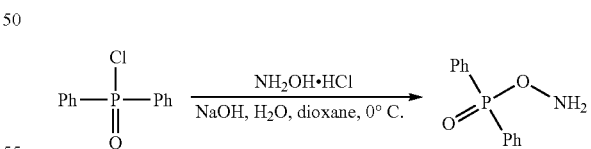

To a solution of hydroxylamine hydrochloride (7.3 g, 106 mmol, 2.5 eq) in water (12 mL) and dioxane (12 mL) was added a solution of NaOH (4.07 g, 102 mmol, 2.4 eq) in water (12 mL), and the mixture was cooled to −5° C. in an ice/salt bath. A solution of diphenylphosphinic chloride (10 g, 42 mmol, 1 eq) in dioxane (12 mL), precooled to below 10° C., was rapidly added to the above solution in an ice/salt bath under vigorous stirring. After completion of the addition, the mixture was stirred for additional 5 minutes in an ice/salt bath, then diluted with ice water (150 mL) and filtered. The filtration cake was washed with ice water, and lyophilized to give o-(diphenylphosphoryl)hydroxylamine (6.0 g, yield 61%) as a white solid. MS (ES+) requires: 233. found 234 [M+H]+; purity: 75%.

Synthesis of 1-amino-4-bromo-1H-pyrrole-2-carboxylic acid methyl ester

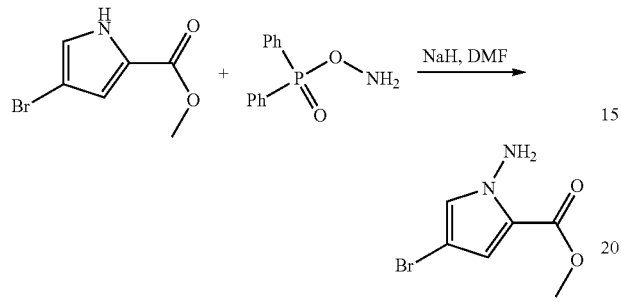

To a solution of 4-bromo-1H-pyrrole-2-carboxylic acid methyl ester (3.5 g, 17.2 mmol, 1 eq) in DMF (120 mL) was added NaH (0.82 g, 20.6 mmol, 1.2 eq) at 0° C., and the mixture was stirred at 0° C. for 1 h, followed by the addition of o-(diphenylphosphinyl)-hydroxylamine (6 g, 25.8 mmol). The reaction mixture was stirred for another 1 h, then neutralized with 20% NH4Cl solution, and extracted with EA. The combined organic layers were washed with water and brine, dried over sodium sulfate, filtered, and concentrated by evaporation. The residue was purified by column chromatography on silica gel (PE/EA=4:1) to give 1-amino-4-bromo-1H-pyrrole-2-carboxylic acid methyl ester (2.9 g, yield 77%) as a light yellow solid. MS (ES+) requires: 218, 220. found 219, 221 [M+H]+; purity: 97%.

Synthesis of 6-bromo-3H-pyrrolo[2,1-f][1,2,4]triazin-4-one

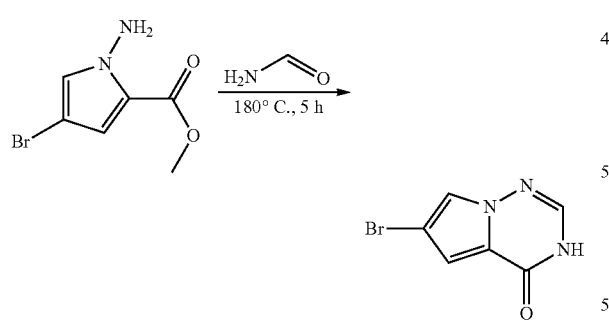

A solution of 1-amino-4-bromo-1H-pyrrole-2-carboxylic acid methyl ester (2.9 g, 13.2 mmol) in formamide (12 mL) was heated at 180° C. for 5 hrs. The mixture was diluted with ethyl acetate (300 mL), and then washed with water (100 mL*2), brine (100 mL*3). The organic layer was dried over sodium sulfate, filtered and concentrated under reduced pressure. The resulting solid was washed with PE/EA (4:1, 50 mL) to give 6-bromo-3H-pyrrolo[2,1-f][1,2,4]triazin-4-one (1.4 g, yield 50%) as yellow solid. MS (ES+) requires: 213, 215. found 214, 216 [M+H]+; purity: 92%.

Synthesis of 6-(1-methyl-1H-pyrazol-4-yl) pyrrolo[1,2-f][1,2,4]triazin-4(3H)-one

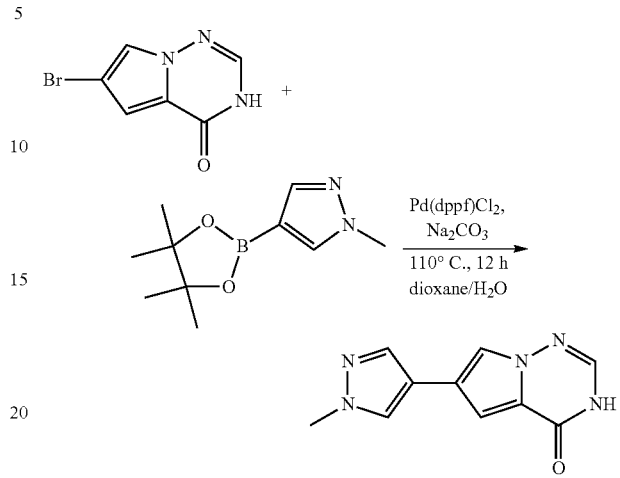

A mixture of 6-bromo-3H-pyrrolo[2,1-f][1,2,4]triazin-4-one (2.15 g, 10 mmol), 1-methyl-4-(4,4,5,5-tetramethyl-1,3,2-dioxaborolan-2-yl)-1H-pyrazole (4.2 g, 20 mmol), Cs2CO3 (9.8 g, 30 mmol), PdCl2dppf (814 mg, 1 mmol), water (15 mL), ethanol (15 mL) and dioxane (70 mL) in a 250 mL flask was degassed with N2 for 10 min, and then heated at 120° C. under N2 atmosphere overnight. The mixture was cooled to RT, followed by the addition of silica gel (~50 g). The residue was subjected to a silica gel column and eluted with DCM:MeOH (20:0-20:1) to afford 6-(1-methyl-1H-pyrazol-4-yl)pyrrolo[1,2-f][1,2,4]triazin-4(3H)-one (600 mg, 28% yield) as a yellow solid. MS (ES+) requires: 215. found 216.1 [M+H]+; purity: 90%.

Synthesis of 4-chloro-6-(1-methyl-1H-pyrazol-4-yl) pyrrolo[1,2-f][1,2,4]triazine

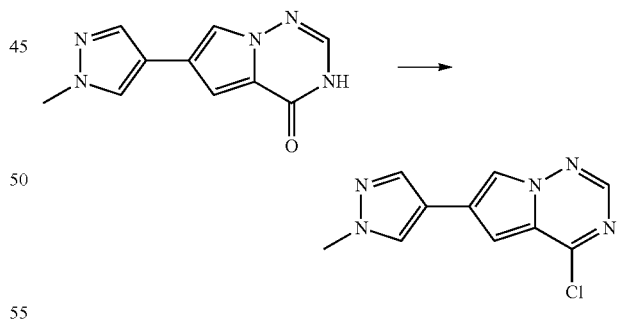

6-(1-methyl-1H-pyrazol-4-yl)pyrrolo[1,2-f][1,2,4]triazin-4(3H)-one (600 mg, 2.8 mmol) was treated with phosphorus oxychloride (20 mL) under reflux for 3 hours. The mixture was cooled to RT, concentrated under reduced pressure and the residue was diluted with ice water (100 mL). The mixture was extracted with dichloromethane (50 mL*4), and the combined organic layers were dried by MgSO4, filtered, concentrated to give 4-chloro-6-(1-methyl-1H-pyrazol-4-yl)pyrrolo[1,2-f][1,2,4]triazine (600 mg, 92% yield) as a brown solid. MS (ES+) requires: 233, 235. found 234, 236 [M+H]+; purity: 90%.

Synthesis of tert-butyl 3-(4-methylbenzylcarbamoyl)azetidine-1-carboxylate

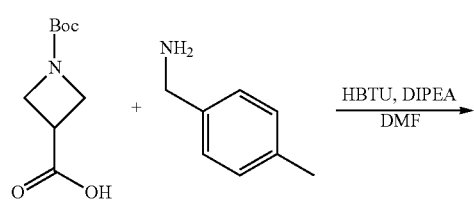

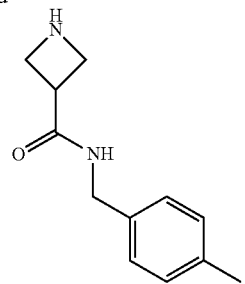

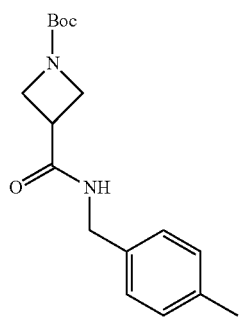

A mixture of 1-(tert-butoxycarbonyl)azetidine-3-carboxylic acid (400 mg, 1.99 mmol), p-tolylmethanamine (340 mg, 1.99 mmol), HBTU (907 mg, 2.39 mmol) and diisopropylethylamine (1.03 g, 7.96 mmol) in N,N-dimethylformamide (10 mL) was stirred at RT overnight. LCMS and TLC indicated completion of the reaction. After quenched with water (50 mL), the reaction mixture was extracted with ethyl acetate (3×50 mL). The organic layers were separated, combined, washed with water (50 mL×2) and brine (50 mL×3), dried over sodium sulfate, filtered and concentrated. The crude residue was purified by silica gel chromatography (petroleum ether:ethyl acetate=4:1) to afford the title compound as a colorless oil (450 mg, yield: 74%). MS (ES+) $C_{17}H_{24}N_2O_3$ requires: 304. found: 249 [M+H-56]$^+$.

Synthesis of N-(4-methylbenzyl)azetidine-3-carboxamide

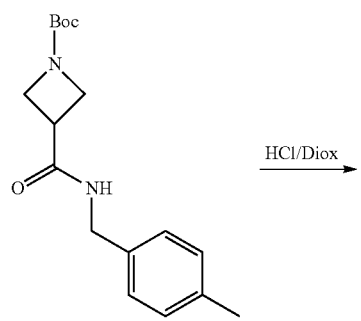

A mixture of tert-butyl 3-(4-methylbenzylcarbamoyl)azetidine-1-carboxylate (400 mg, 1.32 mmol) in HCl/dioxane (10 mL) was stirred at RT overnight. The reaction mixture was concentrated under reduced pressure to afford the title compound (250 mg, crude) as a yellow solid, which was directly used into the next step without further purification. MS (ES+) $C_{12}H_{16}N_2O$ requires: 204. found: 205 [M+H]$^+$.

Synthesis of 1-(6-(1-methyl-1H-pyrazol-4-yl)pyrrolo[1,2-f][1,2,4]triazin-4-yl)-N-(4-methylbenzyl)azetidine-3-carboxamide

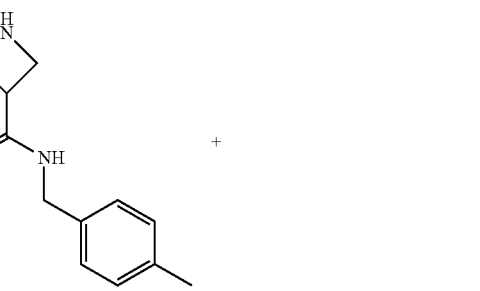

A mixture of N-(4-cyanophenyl)azetidine-3-carboxamide (86 mg, 0.43 mmol), 4-chloro-6-(1-methyl-1H-pyrazol-4-yl)pyrrolo[1,2-f][1,2,4]triazine (100 mg, 0.43 mmol) and diisopropylethylamine (211 mg, 1.72 mmol) in dioxane (5 mL) was stirred at RT overnight. LCMS and TLC indicated completion of the reaction. The reaction mixture was concentrated under reduced pressure to afford a residue, which was purified by Prep-HPLC to give the title compound (18.4 mg, 11%) as a white solid. MS (ES+) $C_{22}H_{23}N_7O$ requires: 401. found: 402 $[M+H]^+$.

Synthesis of (S)—N-((1-(6-(1-methyl-1H-pyrazol-4-yl)pyrrolo[1,2-f][1,2,4]triazin-4-yl)azetidin-3-yl)methyl)-1-p-tolylethanamine (Compound 10)

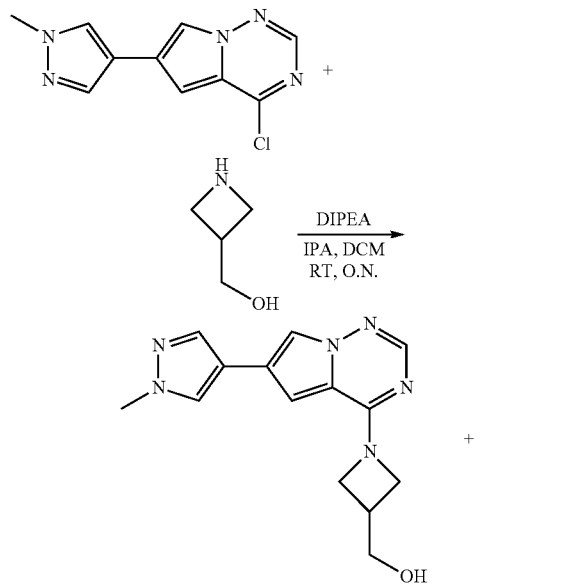

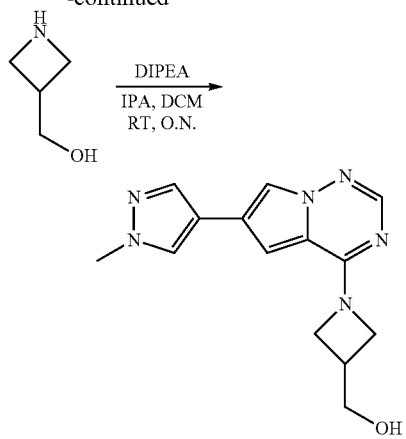

To a solution of 4-chloro-6-(1-methyl-1H-pyrazol-4-yl)pyrrolo[1,2-f][1,2,4]triazine (1.0 g, 4.3 mmol) and azetidin-3-ylmethanol (370 mg, 4.3 mmol) in a mixed solvent of dichloromethane (20 mL) and isopropanol (5 mL) was added diisopropylethylamine (1.7 g, 12.9 mmol) at RT. After that, the resultant solution was stirred at RT overnight. The formed precipitate was collected via filtration to give the title compound (1.0 g, 84%) as a gray solid. MS (ES+) $C_{14}H_{16}N_6O$ requires: 284. found: 285 $[M+H]^+$.

Synthesis of (S)—N-((1-(6-(1-methyl-1H-pyrazol-4-yl)pyrrolo[1,2-f][1,2,4]triazin-4-yl)azetidin-3-yl)methyl)-1-p-tolylethanamine

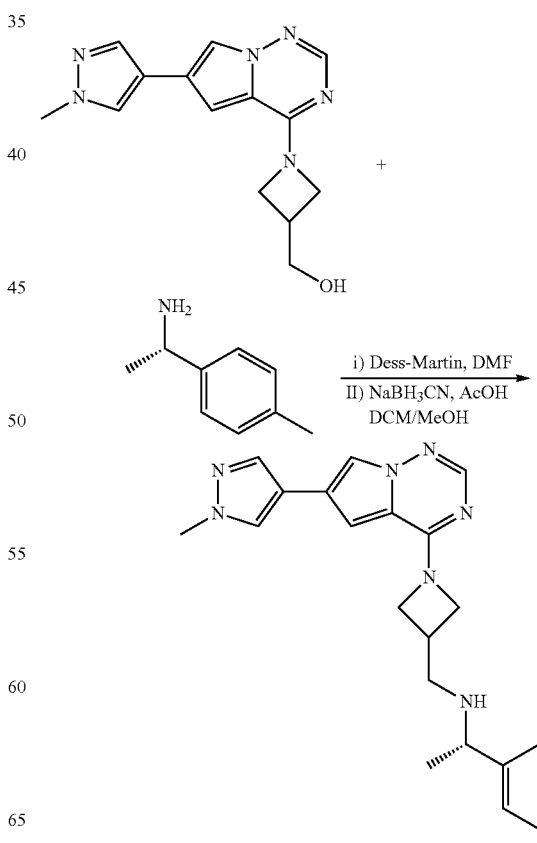

Synthesis of (1-(6-(1-methyl-1H-pyrazol-4-yl)pyrrolo[1,2-f][1,2,4]triazin-4-yl)azetidin-3-yl)methanol

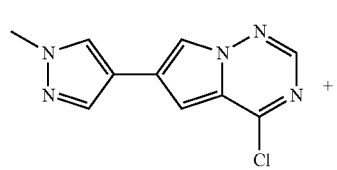

A solution of (1-(6-(1-methyl-1H-pyrazol-4-yl)pyrrolo[1,2-f][1,2,4]triazin-4-yl)azetidin-3-yl)methanol (200 mg, 0.7 mmol) and Dess-Martin reagent (597 mg, 1.4 mmol) in anhydrous N,N-dimethylformamide (5 mL) was stirred at RT for 2 hours. After that, to this mixture was added (S)-1-p-tolylethanamine (149 mg, 1.1 mmol), acetic acid (0.5 mL), dichloromethane (5 mL) and methanol (5 mL) at RT. The resultant mixture was stirred at RT for 5 mins, followed by the addition of sodium cyanoborohydride (88 mg, 1.4 mmol), and the mixture was stirred at RT for overnight. The mixture was concentrated under reduced pressure, and the residue was purified by Prep-HPLC to afford the title compound (50 mg, 18%) as a white solid. MS (ES+) $C_{23}H_{27}N_7$ requires: 401. found: 402 $[M+H]^+$.

Synthetic Protocol 2

Synthetic Protocol 2 is shown above. Pyrrolotriazine (1) can be substituted with azetidines (2 or 6) under nucleophilic aromatic substitution reaction conditions using an amine base such as diisopropylethylamine (DIPEA) or triethylamine (TEA) in a polar solvent such as dioxane to provide the piperazine-substituted pyrrolotriazine (3 or 7). Pyrrolotriazine (3) can also be achieved via an amide bond coupling reaction with amine (8). Azetidine (2) can be synthesized by reaction of A via an amide bond coupling to generate intermediate B followed by deprotection. Pyrrolotriazine (3 or 7) can be coupled (LG typically Cl, Br, I) to a boron, tin or zinc aryl, heteroaryl, alkenyl, alkyl reagent (2) via a palladium-mediated coupling reaction, e.g., Suzuki, Stille, Negishi coupling, to provide the pyrrolotriazine (5 or 9). Pyrrolotriazine (5) can also be achieved via an amide bond coupling reaction with amine (8).

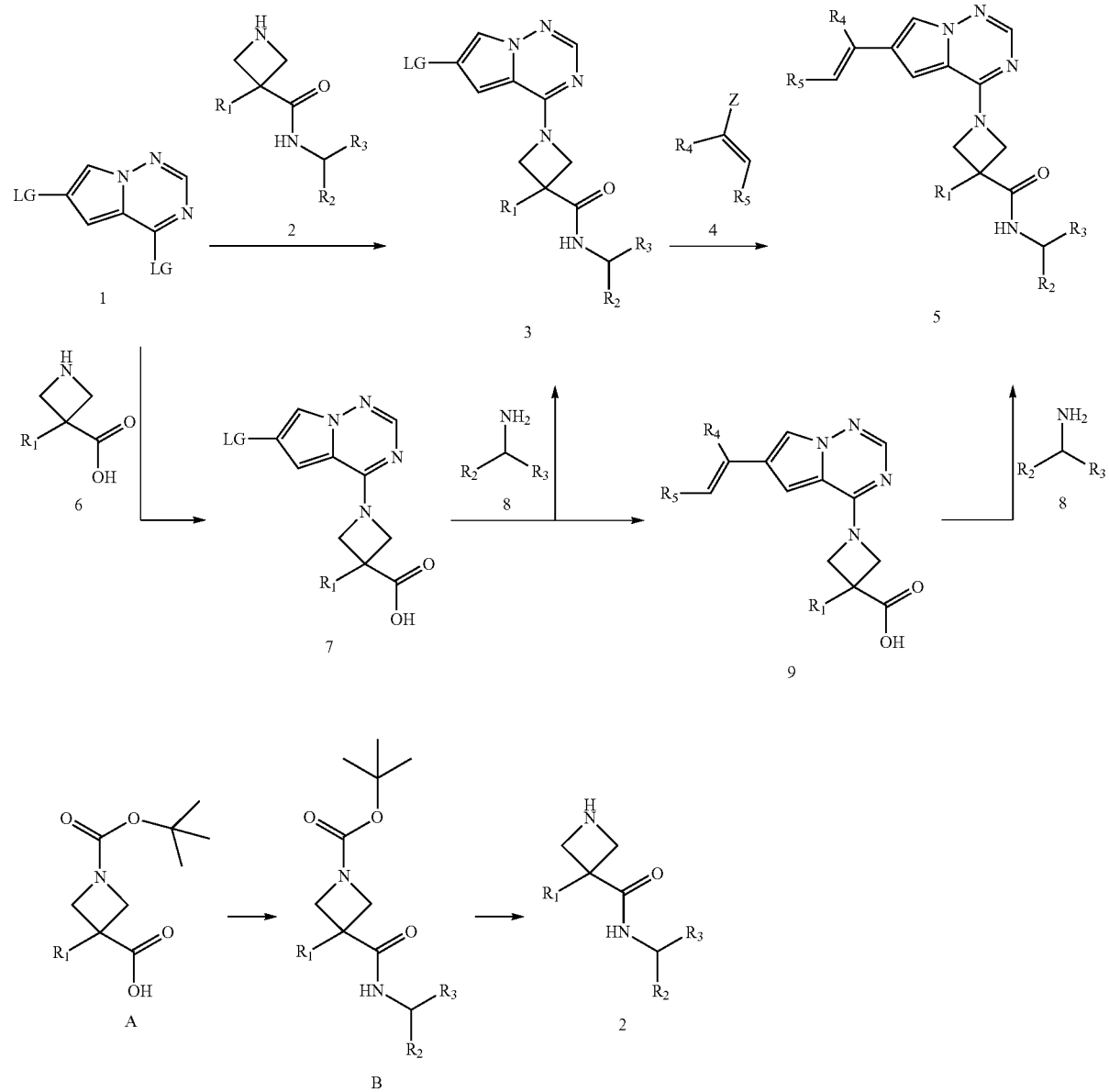

LG = halogen (e.g. chloro)
Z = B or Sn or Zn (substituted)

As shown below, Compounds 42, 173, 184, and 221 were prepared using synthetic protocol 2.

Synthesis of 1-(6-(1-(cyclopropanecarbonyl)-1,2,3,6-tetrahydropyridin-4-yl)pyrrolo[2,1-f][1,2,4]triazin-4-yl)-N-(4-methylbenzyl)azetidine-3-carboxamide (Compound 173)

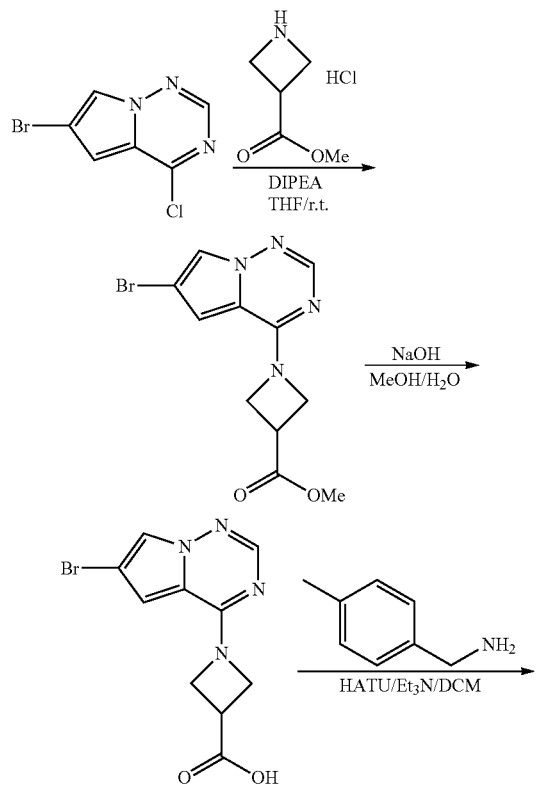

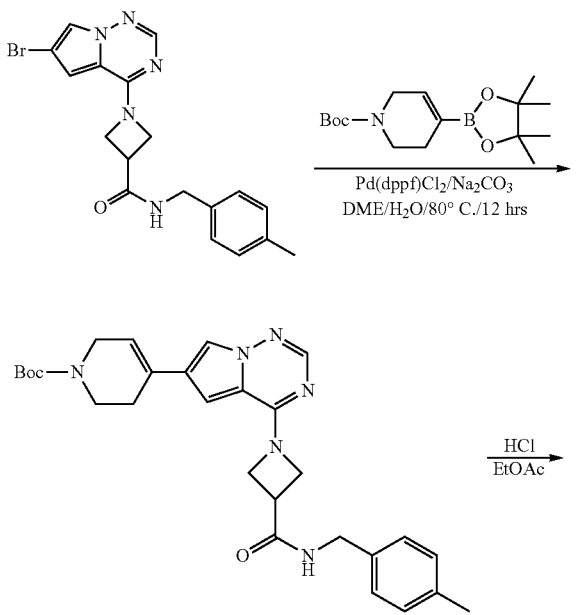

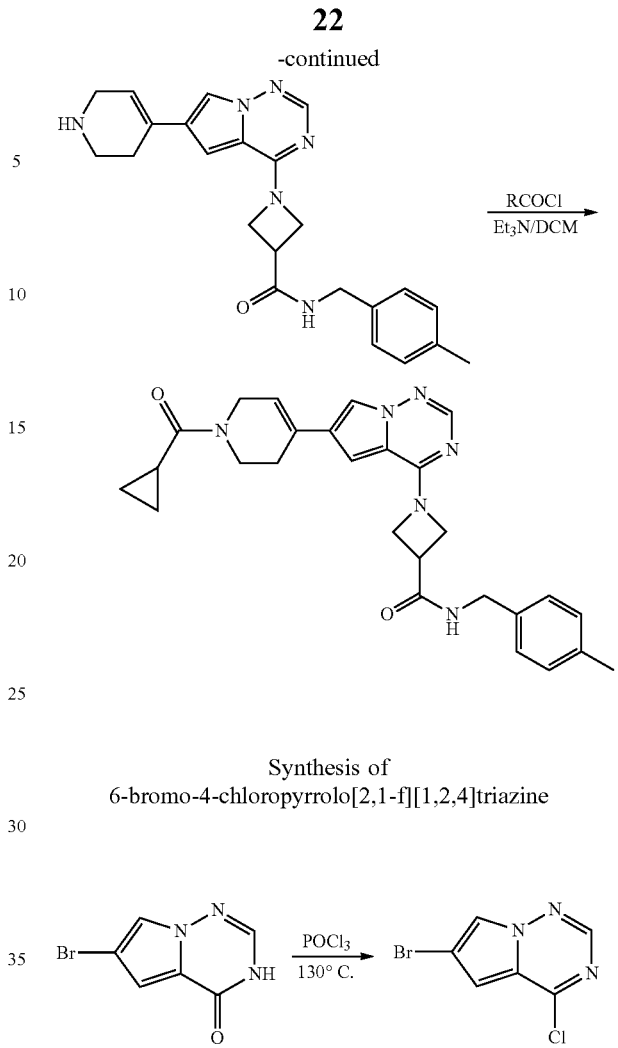

Synthesis of 6-bromo-4-chloropyrrolo[2,1-f][1,2,4]triazine

A solution of 6-bromopyrrolo[2,1-f][1,2,4]triazin-4(3H)-one (15.0 g, 46.9 mmol) in POCl$_3$ (150 mL) was heated to 130° C. for 3 hrs. The solvent was evaporated. The residue was cooled to 0° C. and dissolved with 20% aq. NaHCO$_3$ (200 mL), extracted with EtOAc (200 mL*3). The organic layer was dried over Na$_2$SO$_4$ and concentrated to give 6-bromo-4-chloropyrrolo[2,1-f][1,2,4]triazine (13 g, yield: 79.8%) as a brown solid.

Synthesis of methyl 1-(6-bromopyrrolo[2,1-f][1,2,4]triazin-4-yl)azetidine-3-carboxylate

Synthesis of 1-(6-bromopyrrolo[2,1-f][1,2,4]triazin-4-yl)-N-(4-methylbenzyl)azetidine-3-carboxamide

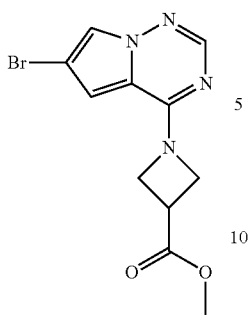

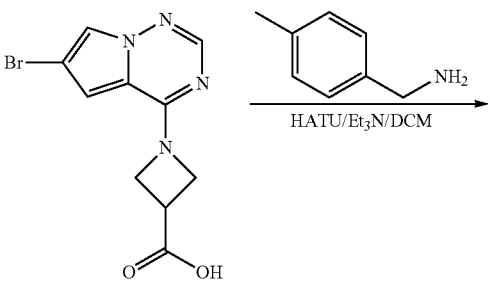

A mixture of 6-bromo-4-chloropyrrolo[2,1-f][1,2,4]triazine (5.0 g, 21.7 mmol), methyl azetidine-3-carboxylate hydrochloride (3.29 g, 21.7 mmol) and DIPEA (14.0 g, 109 mmol) in DCM (50 mL) was stirred at 26° C. for 16 hrs. The mixture was washed with brine (25 mL). The organic layer was dried over Na₂SO₄ and concentrated to give the desired product methyl 1-(6-bromopyrrolo[2,1-f][1,2,4]triazin-4-yl)azetidine-3-carboxylate (5.0 g, yield: 74.2%). ¹H-NMR (400 MHz, DMSO-d₆) δ ppm 7.88 (s, 1H), 7.84 (s, 1H), 6.84 (s, 1H), 4.73-4.24 (m, 4H), 3.76-3.70 (m, 1H), 3.68 (s, 3H).

Synthesis of 1-(6-bromopyrrolo[2,1-f][1,2,4]triazin-4-yl)azetidine-3-carboxylic acid

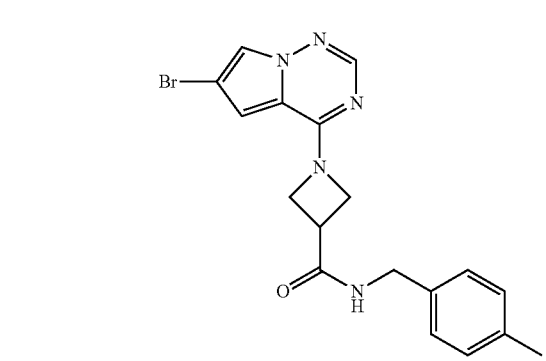

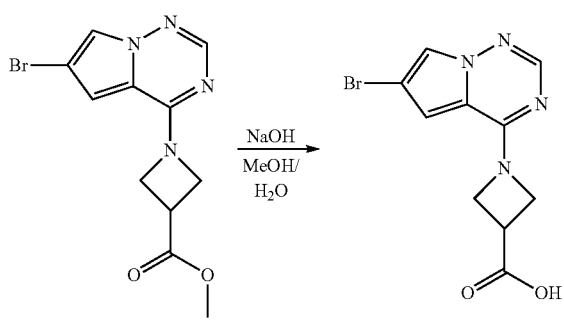

A mixture of methyl 1-(6-bromopyrrolo[2,1-f][1,2,4]triazin-4-yl)azetidine-3-carboxylate (4.0 g, 12.9 mmol) and NaOH (1.03 g, 25.8 mmol) in MeOH—H₂O (50 mL, 4:1) was stirred at 26° C. for 16 hrs. The solvent was concentrated to remove MeOH. The residue was adjusted pH to 5 with 4N aq. HCl. The solid was filtered and dried in vacuo to give the desired product 1-(6-bromopyrrolo[2,1-f][1,2,4]triazin-4-yl)azetidine-3-carboxylic acid (3.5 g, yield: 91.6%). ¹H-NMR (400 MHz, DMSO-d₆) δ ppm 7.89 (s, 1H), 7.85 (s, 1H), 6.87 (s, 1H), 4.72-4.58 (m, 2H), 4.36-4.03 (m, 2H), 3.65-3.61 (m, 1H).

To the mixture of 1-(6-bromopyrrolo[2,1-f][1,2,4]triazin-4-yl)azetidine-3-carboxylic acid (3.5 g, 11.8 mmol) and Et₃N (5.97 g, 59.1 mmol) in DCM (50 mL) was added HATU (5.38 g, 14.2 mmol) at 25° C. After being stirred for 15 mins, p-tolylmethanamine (1.43 g, 11.8 mmol) was added to the reaction at 25° C. The reaction mixture was stirred at 25° C. for 16 hrs. After LCMS showed the reaction was complete, the reaction was diluted with DCM and washed with brine. The organic layer was dried over Na₂SO₄ and concentrated to give the title compound (3.0 g, yield: 63.6%) as a white solid.

Synthesis of tert-butyl 4-(4-(3-((4-methylbenzyl)carbamoyl)azetidin-1-yl)pyrrolo[2,1-f][1,2,4]triazin-6-yl)-3,6-dihydropyridine-1(2H)-carboxylate

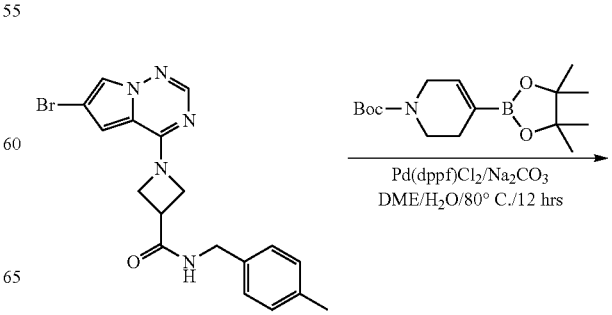

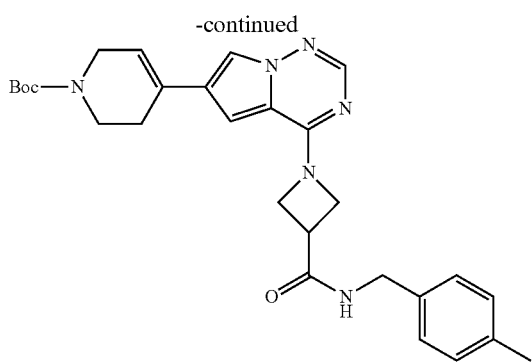

To a mixture of 1-(6-bromopyrrolo[2,1-f][1,2,4]triazin-4-yl)-N-(4-methylbenzyl)azetidine-3-carboxamide (400 mg, 1 mmol) in DME/H$_2$O (12 mL, 5:1) was added the boronic ester (450 mg, 1.5 mmol), Na$_2$CO$_3$ (348 mg, 3 mmol) and Pd(dppf)Cl$_2$ (37 mg, 0.05 mmol) at 25° C. under N$_2$. The mixture was heated to 80° C. for 12 hrs. The mixture was filtered and concentrated to afford crude tert-butyl 4-(4-(3-((4-methylbenzyl)carbamoyl)azetidin-1-yl)pyrrolo[2,1-f][1,2,4]triazin-6-yl)-3,6-dihydropyridine-1(2H)-carboxylate (300 mg) as a brown oil. This material was used without further purification.

Synthesis of N-(4-methylbenzyl)-1-(6-(1,2,3,6-tetra-hydropyridin-4-yl)pyrrolo[2,1-f][1,2,4]triazin-4-yl)azetidine-3-carboxamide

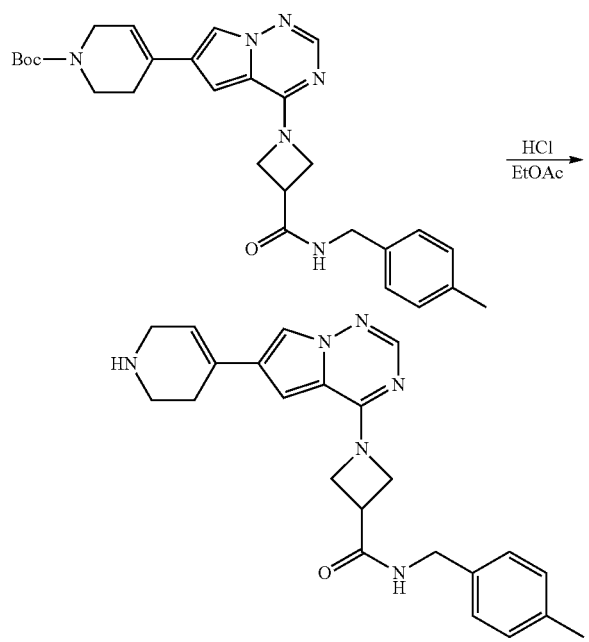

To a solution of tert-butyl 4-(4-(3-((4-methylbenzyl)carbamoyl)azetidin-1-yl)pyrrolo[2,1-f][1,2,4]triazin-6-yl)-3,6-dihydropyridine-1(2H)-carboxylate (300 mg, 0.6 mmol) in EtOAc (10 mL) was added HCl/EtOAc (10 mL, 4 M) at 25° C. The reaction was stirred at 25° C. for 4 hrs. The solid was filtered and dried in vacuo to give crude N-(4-methylbenzyl)-1-(6-(1,2,3,6-tetrahydropyridin-4-yl)pyrrolo[2,1-f][1,2,4]triazin-4-yl)azetidine-3-carboxamide (100 mg, yield: 41.7%) as a brown solid.

Synthesis of 1-(6-(1-(cyclopropanecarbonyl)-1,2,3,6-tetrahydropyridin-4-yl)pyrrolo[2,1-f][1,2,4]triazin-4-yl)-N-(4-methylbenzyl)azetidine-3-carboxamide (Compound 173)

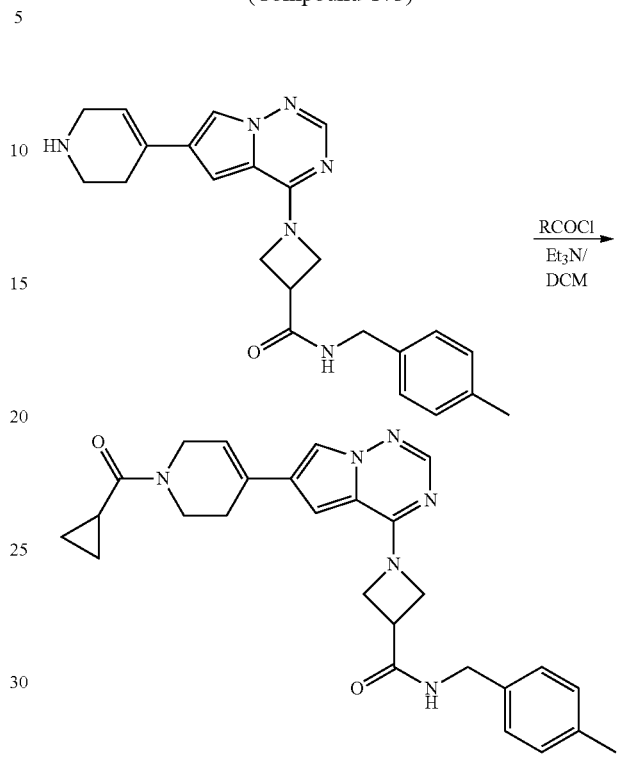

To a mixture of N-(4-methylbenzyl)-1-(6-(1,2,3,6-tetrahydropyridin-4-yl)pyrrolo[2,1-f][1,2,4]triazin-4-yl)azetidine-3-carboxamide (100 mg, 0.248 mmol, crude) and Et$_3$N (75 mg, 0.744 mmol) in DCM (20 mL) was added cyclopropanecarbonyl chloride (26 mg, 0.248 mmol) at 0° C. The reaction mixture was stirred at 25° C. for 2 hrs. After LCMS showed the reaction was complete, the reaction mixture was concentrated. The residue was purified by prep-HPLC to give the title compound (25 mg, yield: 21.2%) as a white solid. MS Calcd.: 470.6, MS Found: 471.3 ([M+1]$^+$).

Synthesis of 1-(6-(4-(2-hydroxy-2-methylpropoxy)phenyl)pyrrolo[1,2-f][1,2,4]triazin-4-yl)-N-(4-methylbenzyl)azetidine-3-carboxamide (Compound 221)

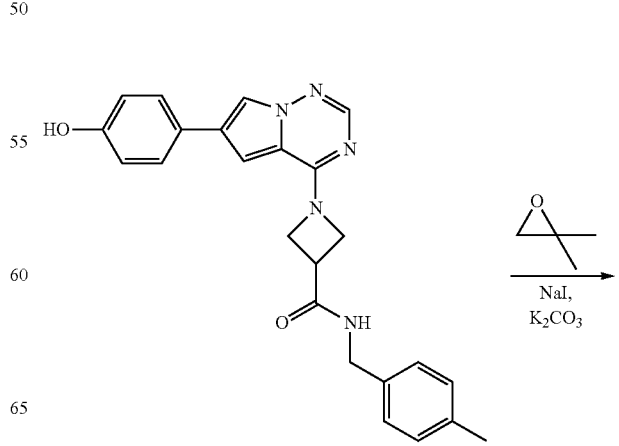

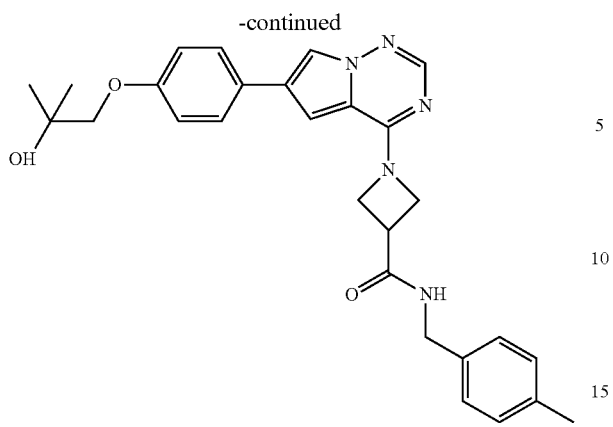

A mixture of (1-(6-(4-hydroxyphenyl)pyrrolo[1,2-f][1,2,4]triazin-4-yl)-N-(4-methylbenzyl)azetidine-3-carboxamide (50 mg, 0.12 mmol), 2,2-dimethyloxirane (345 mg, 4.8 mmol), sodium iodide (72 mg, 0.48 mmol) and potassium carbonate (33 mg, 0.24 mmol) in N,N-dimethylformamide (0.5 mL) was stirred at 110° C. overnight. The reaction mixture was cooled to RT and concentrated. The residue was purified by Prep-HPLC to give the title compound: (2.3 mg, 4%) as a white solid. MS (ES+) $C_{26}H_{30}N_8O_2$ requires: 485. found: 486 [M+H]+.

Synthesis of 1-(6-(4-fluoro-3-(2-hydroxypropan-2-yl)phenyl)pyrrolo[2,1-f][1,2,4]triazin-4-yl)-N-(4-methylbenzyl)azetidine-3-carboxamide (Compound 184)

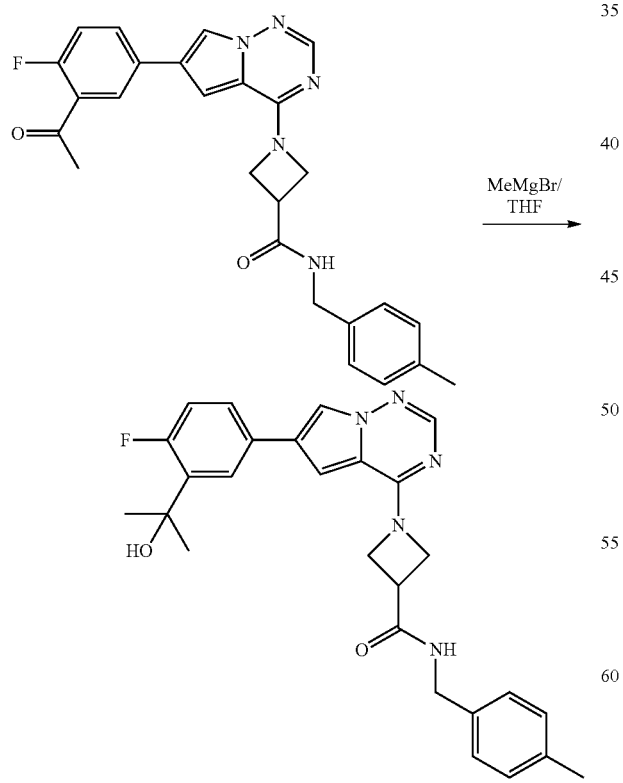

To a solution of 1-(6-(3-acetyl-4-fluorophenyl)pyrrolo[2,1-f][1,2,4]triazin-4-yl)-N-(4-methylbenzyl)azetidine-3-carboxamide (80 mg, 0.175 mmol) in THF (3.00 mL) was added MeMgBr (0.26 mL, 0.53 mmol, 2 M) dropwise at 0° C., then the solution was stirred at 25° C. for 2 hrs under $N_2$ atmosphere, after the starting material was consumed completely which was detected by LCMS, the reaction was quenched with saturated $NH_4Cl$ (5 mL), and extracted with EtOAc (5 mL*3), the combined organic layers were dried over $Na_2SO_4$, concentrated in vacuum and purified by prep-HPLC to get the title compound (2.6 mg, yield: 3.14%).

Synthesis of (E)-N-(4-methylbenzyl)-1-(6-(2-(pyridin-2-yl)vinyl)pyrrolo[2,1-f][1,2,4]triazin-4-yl)azetidine-3-carboxamide (Compound 42)

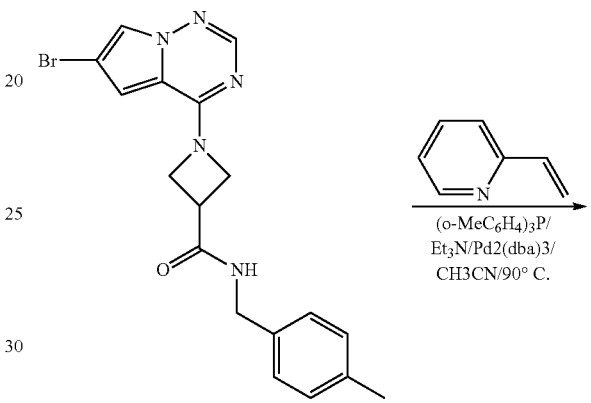

To a mixture of 1-(6-bromopyrrolo[2,1-f][1,2,4]triazin-4-yl)-N-(4-methylbenzyl)azetidine-3-carboxamide (100 mg, 0.250 mmol), 2-vinylpyridine (31.6 mg, 0.300 mmol) and $Et_3N$ (80 mg, 0.750 mmol) in $CH_3CN$ (10 mL) was added $Pd_2(dba)_3$ (11.4 mg, 0.013 mmol) and (o-MeC$_6$H$_4$)$_3$P (7.6 mg, 0.025 mmol) at 20° C. under $N_2$. The reaction mixture was stirred at 90° C. for 16 hrs under $N_2$. The reaction was complete detected by LCMS. The mixture was filtered and the filtrate was concentrated. The crude product was purified by prep-HPLC to give the title compound (15 mg, yield: 14.1%) as a white solid.

Synthetic Protocol 3

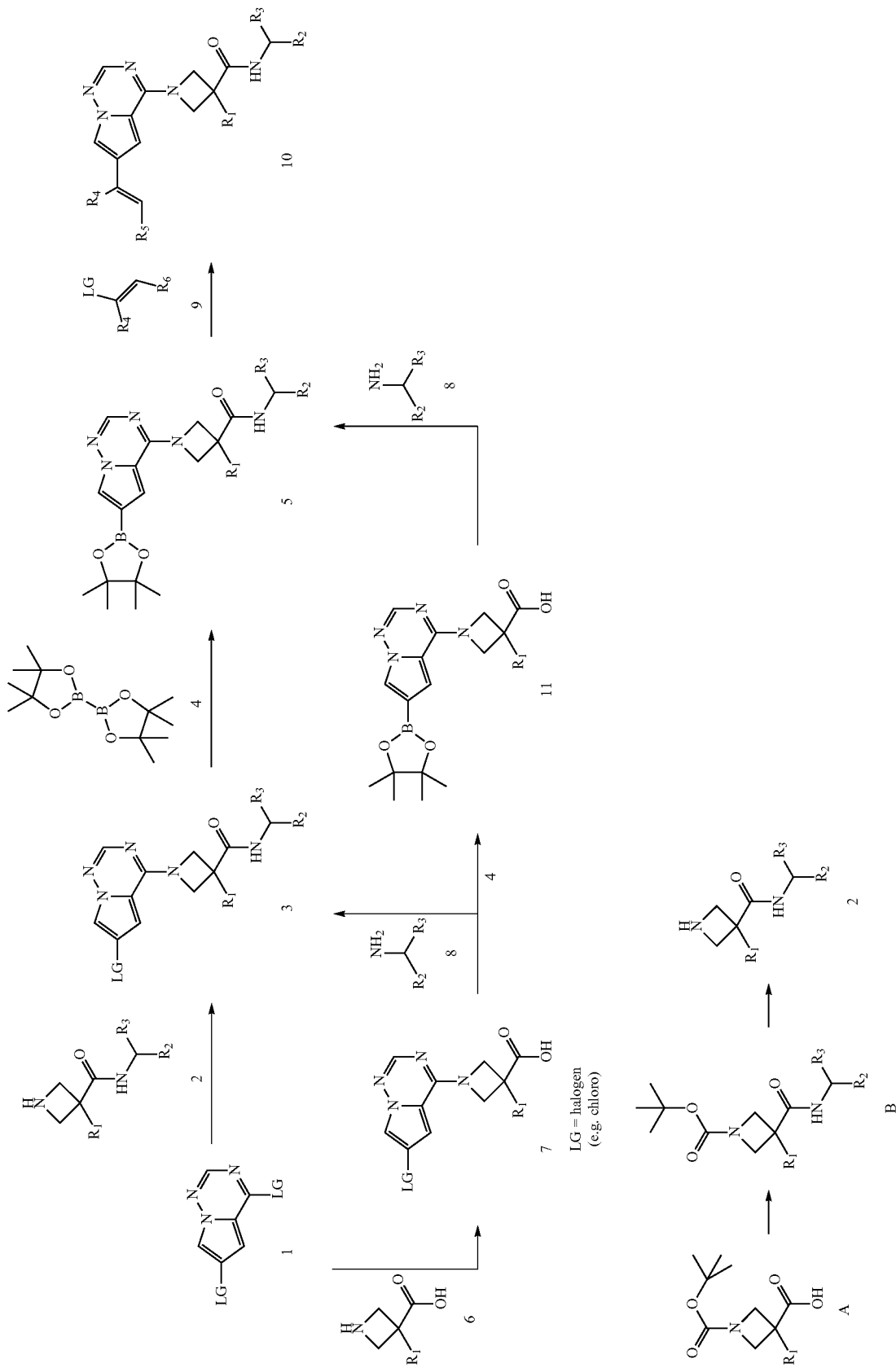

Synthetic Protocol 3 is shown above. Pyrrolotriazine (1) can be substituted with azetidines (2 or 6) under nucleophilic aromatic substitution reaction conditions using an amine base such as diisopropylethylamine (DIPEA) or triethylamine (TEA) in a polar solvent such as dioxane to provide the piperazine-substituted pyrrolotriazine (3 or 7). The leaving group of 3 or 7 can be replaced with a boron-containing group to give 5 or 11. Pyrrolotriazine (5) can also be achieved via an amide bond coupling reaction with amine (8). Azetidine (2) can be synthesized by reaction of A via an amide bond coupling to generate intermediate B followed by deprotection. Pyrrolotriazine (5 or 11) can be coupled (LG typically Cl, Br, I) to an aryl, heteroaryl, alkenyl, alkyl reagent (9) via a palladium-mediated coupling reaction to provide pyrrolotriazine (10).

As shown below, Compounds 148 and 149 were prepared using synthetic protocol 3.

Synthesis of (S)-1-(6-(3-amino-1-methyl-1H-pyrazol-4-yl)pyrrolo[1,2-f][1,2,4]triazin-4-yl)-N-(1-(4-chlorophenyl)propyl)azetidine-3-carboxamide and (S)-1-(6-(5-amino-1-methyl-1H-pyrazol-4-yl)pyrrolo[1,2-f][1,2,4]triazin-4-yl)-N-(1-(4-chlorophenyl)propyl)azetidine-3-carboxamide (Compound 148)

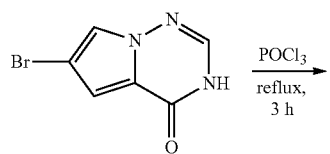

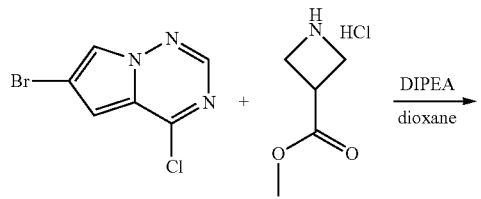

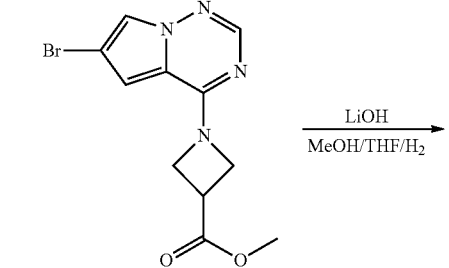

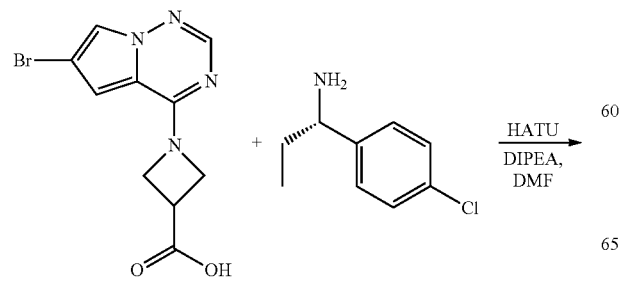

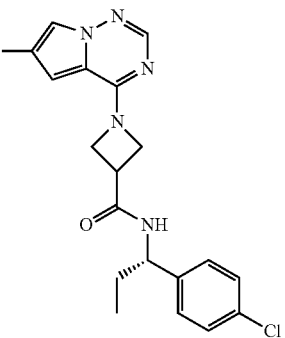

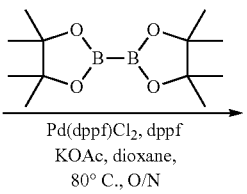

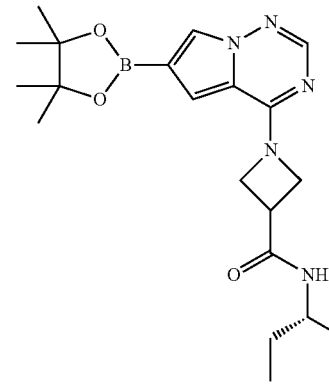

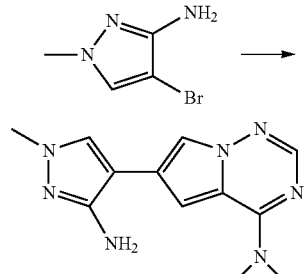

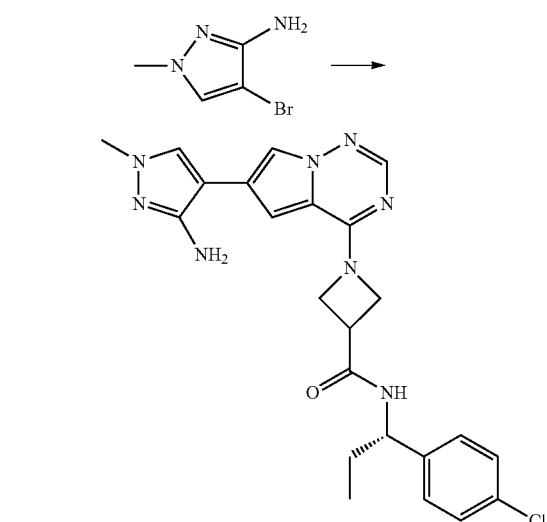

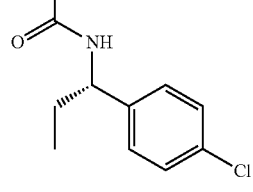

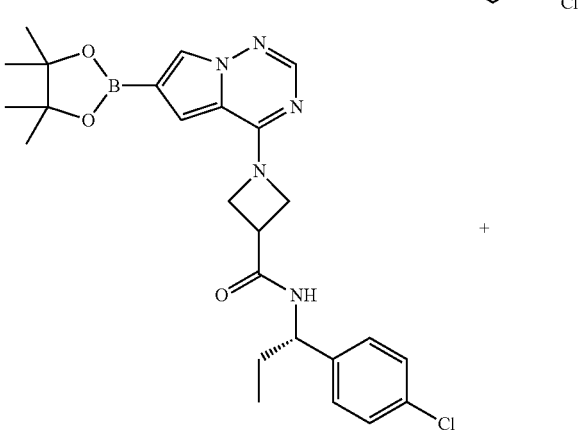

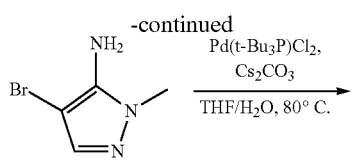

Synthesis of (S)-1-(6-bromopyrrolo[1,2-f][1,2,4]triazin-4-yl)-N-(1-(4-chlorophenyl)propyl)azetidine-3-carboxamide

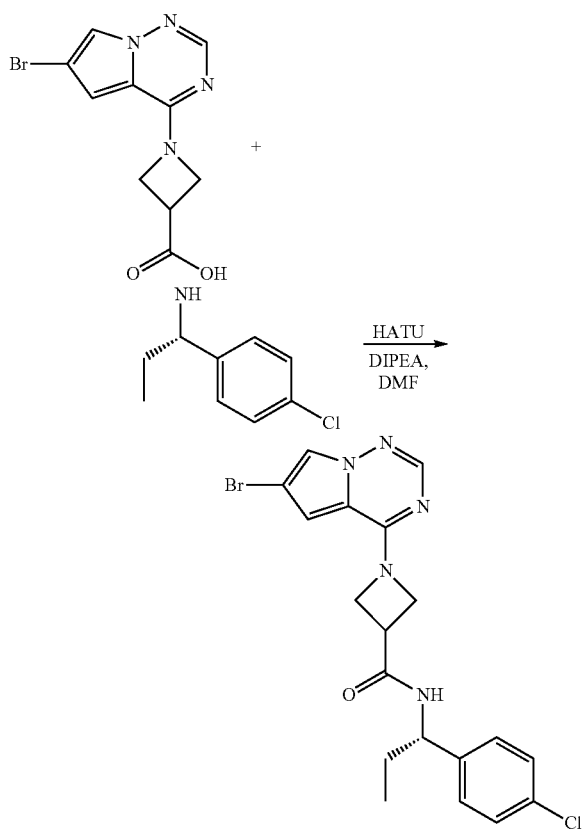

A mixture of 1-(6-bromopyrrolo[1,2-f][1,2,4]triazin-4-yl)azetidine-3-carboxylic acid (950 mg, 3.2 mmol), (S)-1-(4-chlorophenyl)propan-1-amine (718 mg, 3.5 mmol) and HATU (1.44 g, 3.8 mmol) and diisopropylethylamine (490 mg, 3.8 mmol) in N,N-dimethylformamide (20 mL) was stirred at RT overnight. The reaction was quenched with water (100 mL), filtered to afford the title compound (1 g, 70%) as a white solid. MS (ES+) $C_{19}H_{19}BrClN_5O$ requires: 447. found: 448 [M+H]$^+$.

Synthesis of (S)—N-(1-(4-chlorophenyl)propyl)-1-(6-(4,4,5,5-tetramethyl-1,3,2-dioxaborolan-2-yl)pyrrolo[1,2-f][1,2,4]triazin-4-yl)azetidine-3-carboxamide

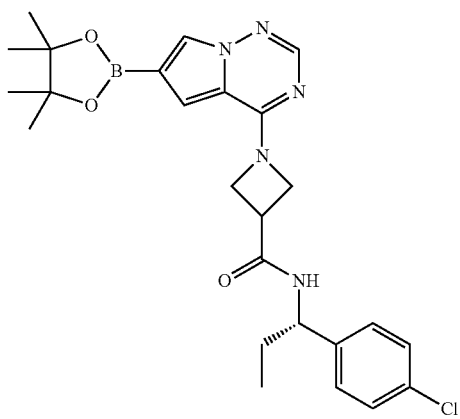

A mixture of (S)-1-(6-bromopyrrolo[1,2-f][1,2,4]triazin-4-yl)-N-(1-(4-chlorophenyl)propyl)azetidine-3-carboxamide (500 mg, 1.1 mmol), 4,4,4',4',5,5,5',5'-octamethyl-2,2'-bi(1,3,2-dioxaborolane) (425 mg, 1.7 mmol), Pd(dppf)Cl$_2$ (164 mg, 0.2 mmol), dppf (150 mg) and potassium acetate (220 mg, 2.2 mmol) in dioxane (15 mL) was degassed with N$_2$ for three times and then heated at 80° C. overnight. The reaction mixture was cooled to RT and directly concentrated. The residue was purified by silica gel column (dichloromethane:methanol=50:1) to the title compound (300 mg, 54%) as a white solid. MS (ES+) $C_{25}H_{31}BClN_5O_3$ requires: 495. found: 496 [M+H]$^+$.

35
Synthesis of (S)-1-(6-(3-amino-1-methyl-1H-pyrazol-4-yl)pyrrolo[1,2-f][1,2,4]triazin-4-yl)-N-(1-(4-chlorophenyl)propyl)azetidine-3-carboxamide (Compound 148)

36
Synthesis of (S)-1-(6-(5-amino-1-methyl-1H-pyrazol-4-yl)pyrrolo[1,2-f][1,2,4]triazin-4-yl)-N-(1-(4-chlorophenyl)propyl)azetidine-3-carboxamide (Compound 149)

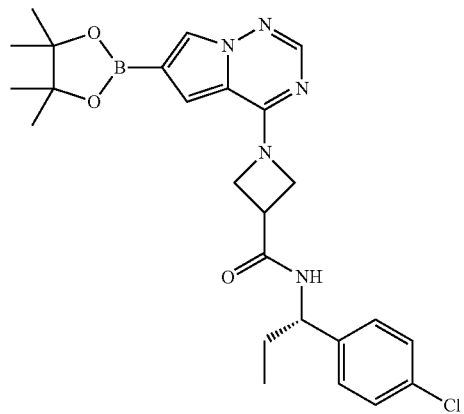

+

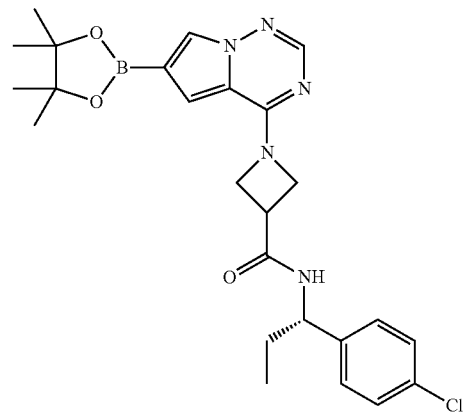

+

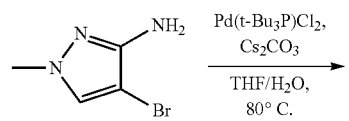

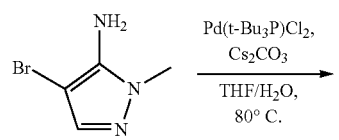

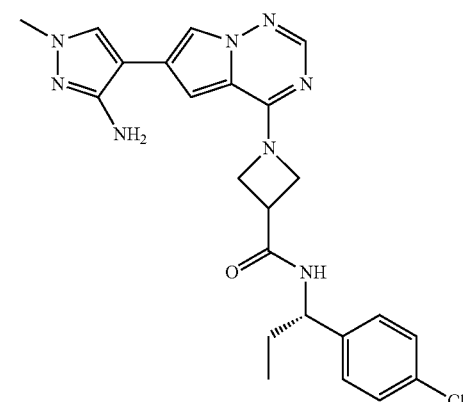

A mixture of (S)—N-(1-(4-chlorophenyl)propyl)-1-(6-(4,4,5,5-tetramethyl-1,3,2-dioxaborolan-2-yl)pyrrolo[1,2-f][1,2,4]triazin-4-yl)azetidine-3-carboxamide (100 mg, 0.57 mmol), 4-bromo-1-methyl-1H-pyrazol-3-amine (40 mg, 0.57 mmol), Pd(t-Bu$_3$P)Cl$_2$ (9 mg, 0.025 mmol) and cesium carbonate (73 mg, 0.57 mmol) in THF/H$_2$O (4:1, 10 mL) was degassed with nitrogen for three times and heated at 80° C. for 3 hrs. The reaction mixture was cooled to RT and concentrated. The residue was purified by Prep-HPLC to give the title compound (24.3 mg, 9%) as a white solid. MS (ES+) C$_{23}$H$_{25}$ClN$_8$O requires: 464. found: 465 [M+H]$^+$.

A mixture of (S)—N-(1-(4-chlorophenyl)propyl)-1-(6-(4,4,5,5-tetramethyl-1,3,2-dioxaborolan-2-yl)pyrrolo[1,2-f][1,2,4]triazin-4-yl)azetidine-3-carboxamide (100 mg, 0.57 mmol), 4-bromo-1-methyl-1H-pyrazol-5-amine (40 mg, 0.57 mmol), Pd(t-Bu$_3$P)Cl$_2$ (9 mg, 0.025 mmol) and cesium carbonate (73 mg, 0.57 mmol) in THF/H$_2$O (4:1, 10 mL) was degassed with nitrogen for three times and was heated at 80° C. for 3 h. The reaction mixture was cooled to RT and concentrated. The residue was purified by Prep-HPLC to give the title compound (30.5 mg, 12%) as a white solid. MS (ES+) C$_{23}$H$_{25}$ClN$_8$O requires: 464. found: 465 [M+H]$^+$.

Synthesis of Selected Intermediates

Synthesis of 2-methyl-1-(4-(4,4,5,5-tetramethyl-1,3,2-dioxaborolan-2-yl)-1H-pyrazol-1-yl)propan-2-ol

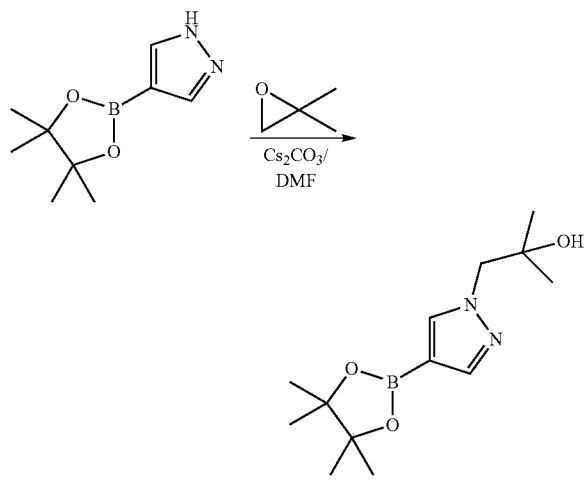

To the mixture of 4-(4,4,5,5-tetramethyl-1,3,2-dioxaborolan-2-yl)-1H-pyrazole (1.94 g, 10 mmol) and 2,2-dimethyloxirane (1.08 g, 15 mmol) in DMF (17 mL) was added $Cs_2CO_3$ (6.52 g, 20 mmol) at 25° C. The reaction was heated at 120° C. for 0.5 hr in a microwave reactor. After the reaction was complete which was detected by LCMS, the mixture was filtered and the filtrate was concentrated. The crude product was purified by flash silica gel chromatography to give the title compound (1.82 g, yield: 68.4%) as a white solid.

Synthesis of (S)-3-(4-iodo-1H-pyrazol-1-yl)-2-methylbutan-2-ol and (R)-3-(4-iodo-1H-pyrazol-1-yl)-2-methylbutan-2-ol

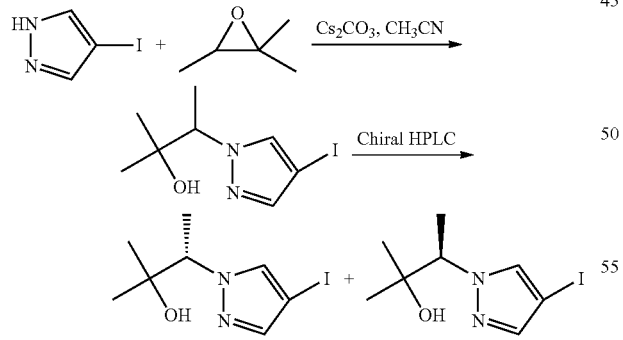

To a solution of 4-iodo-1H-pyrazole (1 g, 5.1 mmol) and 2,2,3-trimethyloxirane (1.3 g, 15.4 mmol) in acetonitrile (5 mL) was added cesium carbonate (2.0 g, 6.2 mmol), and the resultant mixture was heated at 120° C. under microwave for 3 hrs. The reaction mixture was cooled to RT and directly concentrated. The residue was purified by Prep-HPLC to give the title compound (600 mg, 42%) as a white solid. MS (ES+) requires: 280. found: 281 [M+H]$^+$.

The above racemate was separated by Chiral-HPLC to afford the desired enantiomers (peak 1, 250 mg, ee: 100%), (peak 2, 250 mg, ee: 99%).

Synthesis of (2S,3R)-3-(4-iodo-1H-pyrazol-1-yl)butan-2-ol and (2R,3S)-3-(4-iodo-1H-pyrazol-1-yl)butan-2-ol

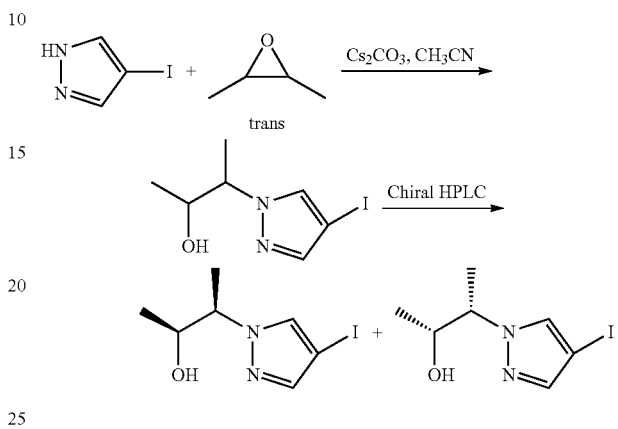

To a solution of 4-iodo-1H-pyrazole (1 g, 5.1 mmol) and trans-2,3-dimethyloxirane (1.1 g, 15.6 mmol) in acetonitrile (3 mL) was added cesium carbonate (2.0 g, 6.2 mmol). The mixture was heated at 120° C. under microwave for 3 hrs. The reaction mixture was cooled to RT and concentrated. The residue was purified by Prep-HPLC to give the title compound (600 mg, 43%) as a white solid. MS (ES+) $C_7H_{11}IN_2O$ requires: 266. found: 267 [M+H]$^+$.

The above racemate was separated by Chiral-HPLC to afford the desired enantiomer (peak 1, 250 mg, ee: 98%), (peak 2, 250 mg, ee: 99%).

Synthesis of (R)-1,1,1-trifluoro-3-(4-iodo-1H-pyrazol-1-yl)propan-2-ol and (S)-1,1,1-trifluoro-3-(4-iodo-1H-pyrazol-1-yl)propan-2-ol

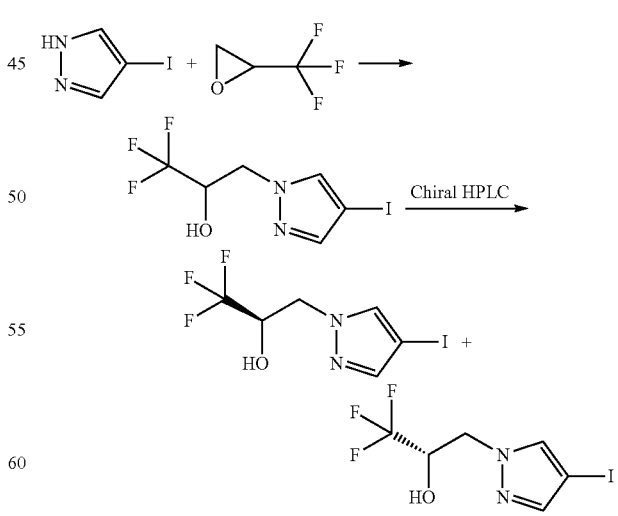

To a solution of 4-iodo-1H-pyrazole (1 g, 5.1 mmol) and 2-(trifluoromethyl)oxirane (700 mg, 6.2 mmol) in a acetonitrile (5 mL) was added cesium carbonate (2.0 g, 6.2 mmol). The mixture was at 120° C. under microwave for 3 hrs. The reaction mixture was cooled to RT and concentrated. The residue was purified by silica gel column (dichloromethane:methanol=70:1) to give the title compound (1.4 g, 88%) as a white solid. MS (ES+) C$_6$H$_6$F$_3$IN$_2$O requires: 306. found: 307 [M+H]$^+$.

The above racemate (800 mg) was separated by Chiral-HPLC to afford the desired enantiomers (peak 1, 280 mg, ee: 99%), (peak 2, 300 mg, ee: 99%).

Synthesis of 2-methyl-4-(4-(4,4,5,5-tetramethyl-1,3,2-dioxaborolan-2-yl)-1H-pyrazol-1-yl)butan-2-ol

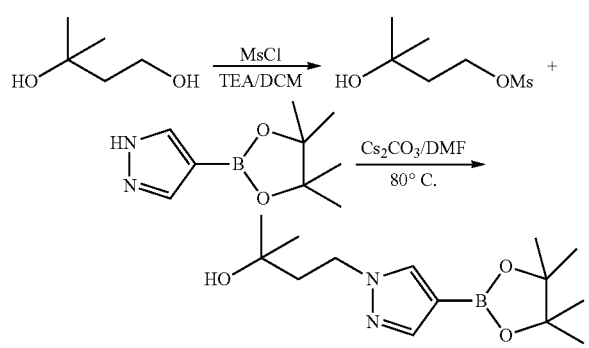

Synthesis of 3-hydroxy-3-methylbutyl methanesulfonate

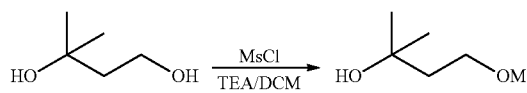

3-Methylbutane-1,3-diol (3.83 g, 36.8 mmol) was dissolved in dichloromethane (150 ml), followed by the addition of triethylamine (6.66 mL) and methanesulfonyl chloride (3.13 mL) at 0° C. After stirring at RT for 7.5 hrs, the reaction was quenched by ethyl acetate and water, and the organic layer was dried over anhydrous sodium sulfate. The solvent was distilled off under reduced pressure to obtain the title compound as a colorless oil (4.79 g, 72%).

Synthesis of 2-methyl-4-(4-(4,4,5,5-tetramethyl-1,3,2-dioxaborolan-2-yl)-1H-pyrazol-1-yl)butan-2-ol

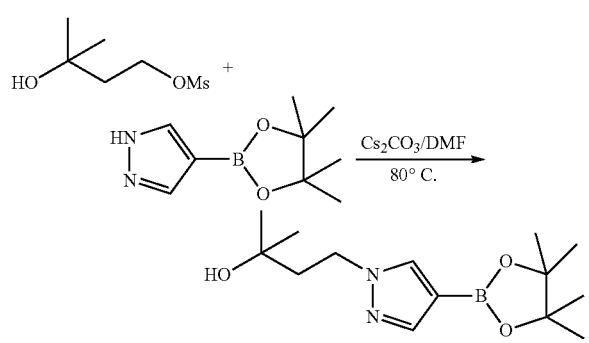

A mixture of 4-(4,4,5,5-tetramethyl-1,3,2-dioxaborolan-2-yl)-1H-pyrazole (500 mg, 2.58 mmol), 3-hydroxy-3-methylbutyl methanesulfonate (938 mg, 5.16 mmol) and cesium carbonate (1.68 g, 5.16 mmol) in N,N-dimethylformamide (10 mL) was heated at 80° C. overnight. LCMS and TLC indicated the completion of the reaction. The reaction mixture was cooled to RT and concentrated to give a residue, which was purified by silica gel chromatography (petroleum ether: ethyl acetate=1:1) to afford the title compound as a colorless oil (350 mg, 49%). MS (ES+) C$_{14}$H$_{25}$BN$_2$O$_3$ requires: 280. found: 281 [M+H]$^+$.

Synthesis of (R)-4-(4-bromophenyl)-2,2-dimethyl-1,3-dioxolane and (S)-4-(4-bromophenyl)-2,2-dimethyl-1,3-dioxolane

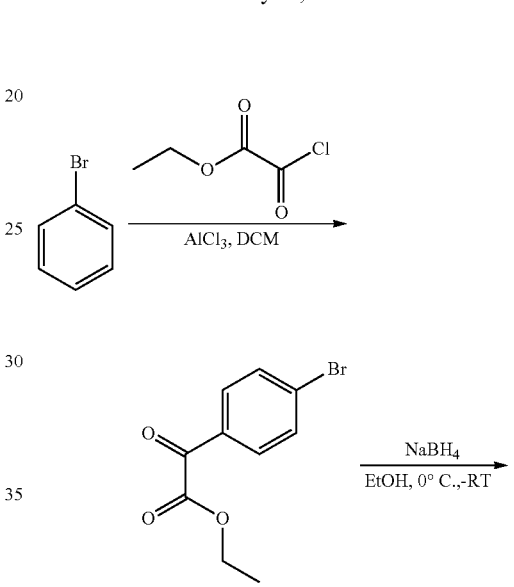

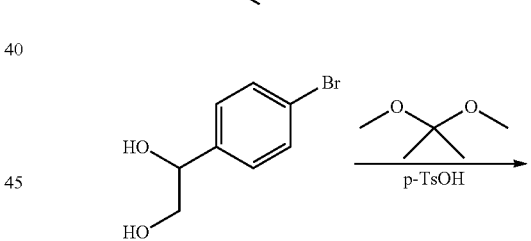

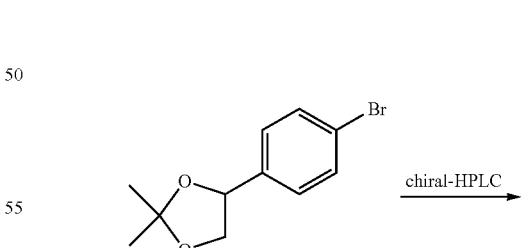

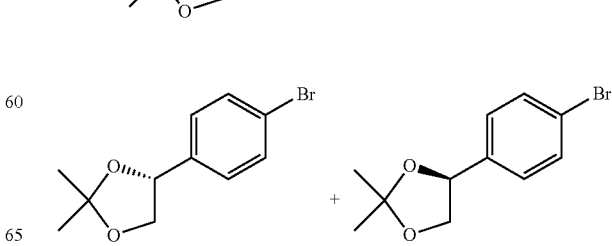

Synthesis of ethyl 2-(4-bromophenyl)-2-oxoacetate

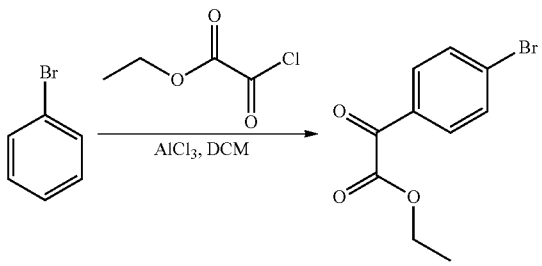

To a stirred mixture of bromobenzene (0.7 mL, 6.5 mmol) and ethyl 2-chloro-2-oxoacetate (0.7 mL, 6.5 mmol) in dichloromethane (12 mL) was added aluminum trichloride (1.7 g, 12.5 mmol) at 0° C. The reaction was warmed to RT slowly and stirred at RT for 18 h. After poured into conc. hydrochloric acid at 0° C., the mixture was extracted with dichloromethane (3×100 mL). The combined organic layers were washed with brine (100 mL), dried over anhydrous sodium sulfate and filtered and concentrated under reduced pressure. The resultant oily matter was purified by silica gel column chromatography (ethyl acetate:petroleum ether=1:20) to afford the title compound (1.0 g, 60%) as a yellow oil. MS (ES+) $C_{10}H_9BrO_3$ requires: 256. found: 257, 259 $[M+H]^+$.

Synthesis of 1-(4-bromophenyl)ethane-1,2-diol

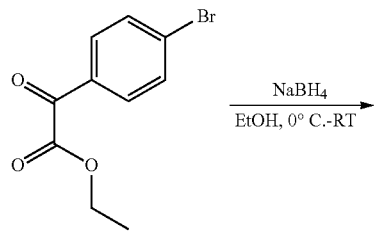

To a solution of ethyl 2-(4-bromophenyl)-2-oxoacetate (1.0 g, 4.0 mmol) in ethanol (20 mL) was added sodium borohydride (380 mg, 10.0 mmol) at 0° C., and the mixture was stirred at RT for 12 h. The reaction was quenched with propan-2-one (10 mL) and concentrated under reduced pressure. The resultant was purified by silica gel column chromatography (dichloromethane:methanol=10:1) to afford the title compound (700 mg, 81%) as a white solid. MS (ES+) $C_8H_9BrO_2$ requires: 216. found: 217, 219 $[M+H]^+$.

Synthesis of (R)-4-(4-bromophenyl)-2,2-dimethyl-1,3-dioxolane and (S)-4-(4-bromophenyl)-2,2-dimethyl-1,3-dioxolane

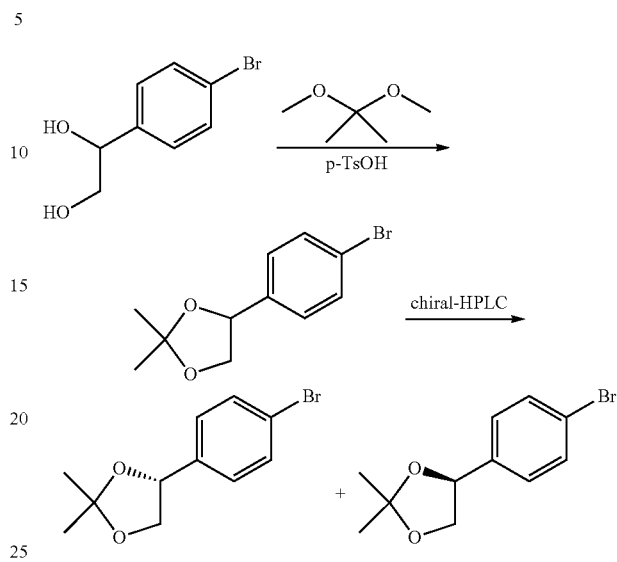

To a solution of 1-(4-bromophenyl)ethane-1,2-diol (700 mg, 3.2 mmol) and 2,2-dimethoxypropane (666 mg, 6.4 mmol) in propan-2-one (10 mL) was added 4-methylbenzenesulfonic acid (110 mg, 0.64 mmol), and the reaction mixture was stirred at RT overnight. The mixture was concentrated under reduced pressure. The residue was purified by silica gel column chromatography (ethyl acetate:petroleum ether=1:10) to afford the title compound (500 mg, 61%) as a light yellow oil. MS (ES+) $C_{11}H_{13}BrO_2$ requires: 256. found: 257, 259 $[M+H]^+$.

Then chiral-HPLC purification to afford Peak 1 (180 mg, 36%), Peak 2 (150 mg, 30%).

Synthesis of 2-(4-(4,4,5,5-tetramethyl-1,3,2-dioxaborolan-2-yl)phenyl)propan-2-ol

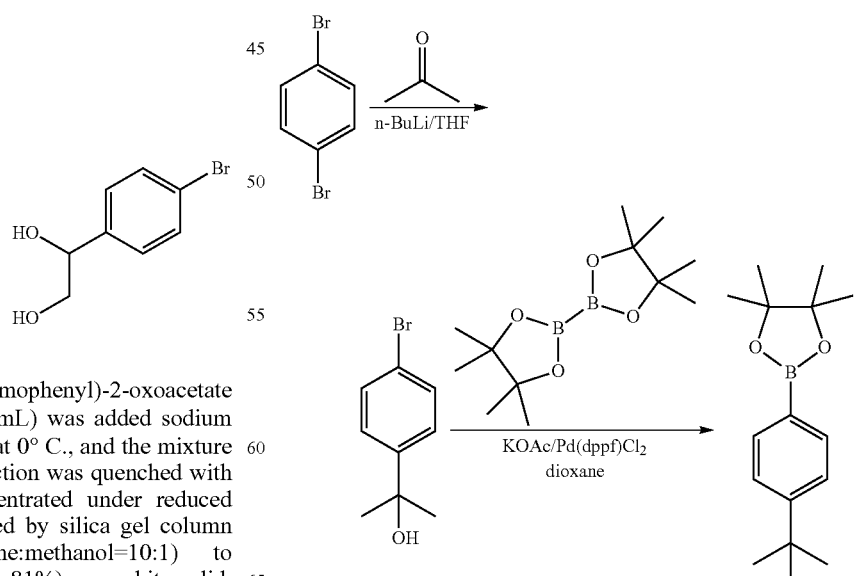

Synthesis of 2-(4-bromophenyl)propan-2-ol

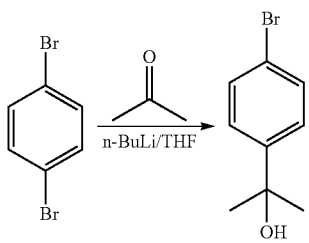

To the mixture of 1,4-dibromobenzene (5.2 g, 22.0 mmol) in THF (50 mL) was added dropwise n-BuLi (8.9 mL, 22.0 mmol, 2.5 M) at −60° C. The resulting mixture was stirred at −60° C. for 1 hr, then a mixture of acetone (3.8 g, 65.5 mmol) in THF (10 mL) was added dropwise at −60° C. After addition, the mixture was allowed to 20° C. slowly. After 1 hr, TLC (PE) showed the starting material was consumed completely. The reaction was quenched by sat. NH$_4$Cl (50 mL). The mixture was extracted with EtOAc (50 mL*3). The combined organic layers were dried over Na$_2$SO$_4$ and filtered. After concentration, the residue was purified by MPLC to give the title compound (3.0 g, yield: 63.8%) as a yellow oil.

Synthesis of 2-(4-(4,4,5,5-tetramethyl-1,3,2-dioxaborolan-2-yl)phenyl)propan-2-ol

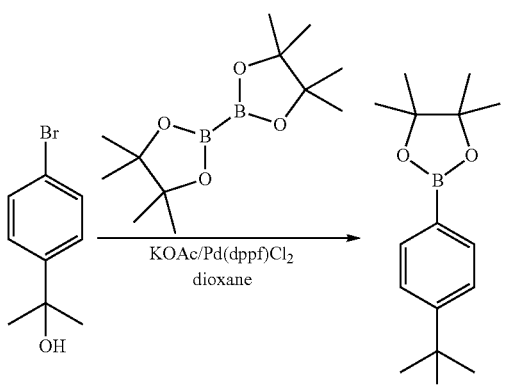

A mixture of 2-(4-bromophenyl)propan-2-ol (2.80 g, 13.0 mmol), 4,4,4',4',5,5,5',5'-octamethyl-2,2'-bi(1,3,2-dioxaborolane) (3.30 g, 13.0 mmol), AcOK (2.60 g, 26.0 mmol) and Pd(dppf)Cl$_2$ (476 mg, 0.65 mmol) in dioxane (60 mL) was stirred at 80° C. for 2 hrs under N$_2$. After HPLC and TLC (PE:EtOAc=3:1) showed the reaction was complete, the mixture was concentrated and purified by MPLC to give the title compound (2.00 g, yield: 58.8%) as a white solid.

Synthesis of pyrrolidin-1-yl(4-(4,4,5,5-tetramethyl-1,3,2-dioxaborolan-2-yl)phenyl)methanone

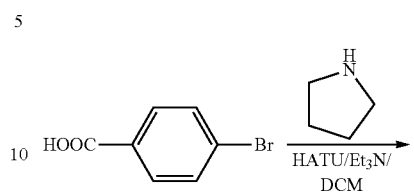

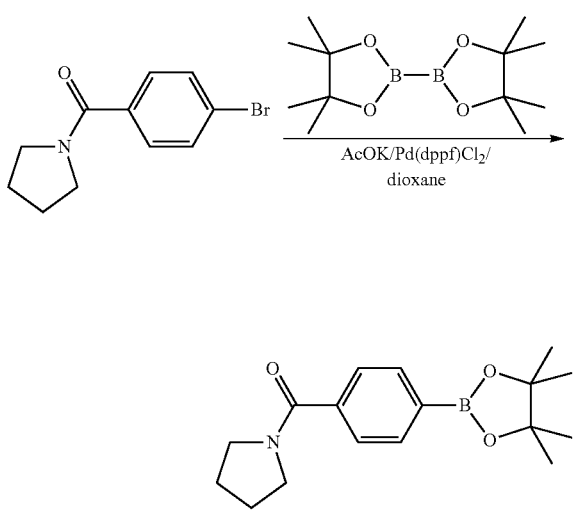

Synthesis of (4-bromophenyl)(pyrrolidin-1-yl)methanone

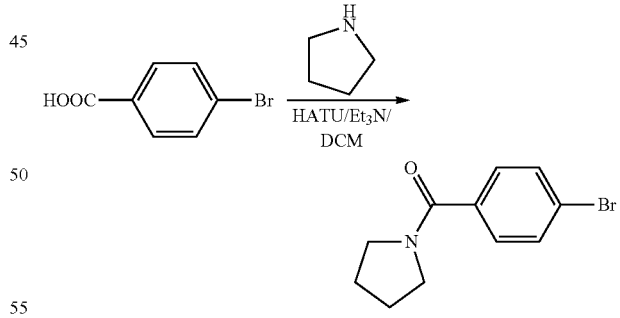

To a stirred mixture of 4-bromobenzoic acid (2.00 g, 10.0 mol) and Et$_3$N (3.03 g, 30.0 mmol) in DCM (30 mL) was added HATU (4.18 g, 11.0 mmol) at 30° C. After 15 mins, pyrrolidine (972 mg, 12.0 mmol) was added into the mixture, which was stirred at 30° C. for 16 hrs. After LCMS and TLC (PE:EtOAc=2:1) showed the reaction was complete, the mixture was concentrated and purified by column chromatography on silica gel (PE:EtOAc=1:0~20:1~10:1~5:1~3:1) to give the title compound (2.20 g, yield: 86.9%) as a white solid.

Synthesis of pyrrolidin-1-yl(4-(4,4,5,5-tetramethyl-1,3,2-dioxaborolan-2-yl)phenyl)methanone

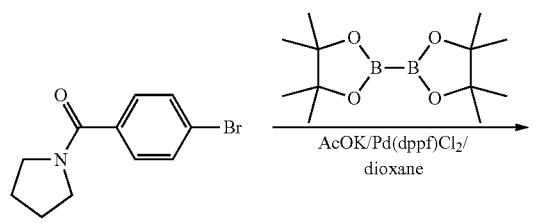

A mixture of (4-bromophenyl)(pyrrolidin-1-yl)methanone (2.20 g, 8.70 mmol), 4,4,4',4',5,5,5',5'-octamethyl-2,2'-bi(1,3,2-dioxaborolane) (2.43 g, 9.57 mmol), AcOK (1.17 g, 17.4 mmol) and Pd(dppf)Cl$_2$ (110 mg) in dioxane (20 mL) was stirred at 100° C. for 16 hrs under N$_2$. After LCMS and TLC (PE:EtOAc=2:1) showed the reaction was complete, the mixture was concentrated and purified by column chromatography on silica gel (PE:EtOAc=1:0~50:1~20:1~10:1~5:1~3:1) to give the title compound (2.15 g, yield: 83.4%) as a white solid.

Synthesis of (4-cyclopropylphenyl)boronic acid

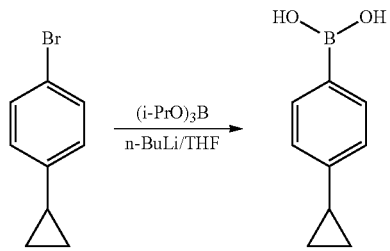 [SMILES: "(i-PrO)3B" ; Brc1ccc(C2CC2)cc1 ; "n-BuLi/THF" ; OB(O)c1ccc(C2CC2)cc1]

To a mixture of 1-bromo-4-cyclopropylbenzene (4.00 g, 20.3 mmol) in THF (50 mL) was added dropwise n-BuLi (9.7 mL, 2.5 M, 24.4 mmol) at −78° C. After addition, the resulting mixture was stirred at −78° C. for 1 hr. Then (i-PrO)$_3$B (7.63 g, 40.6 mmol) was added at −78° C. After stirring for 30 min, the resulting mixture was stirred at 20° C. for 16 hrs. TLC (PE) showed the reaction was complete. The reaction was quenched by 1 M of aq. HCl (50 mL), the mixture was extracted with EtOAc (50 mL*3). The combined organics were dried over Na2SO4 and concentrated. The residue was purified by column chromatography on silica gel (PE:EtOAc=20/1 to 3/1) to give the title compound (800 mg, yield: 24.3%) as a white solid.

Synthesis of 4-bromo-1-(tert-butoxy)-2-fluorobenzene

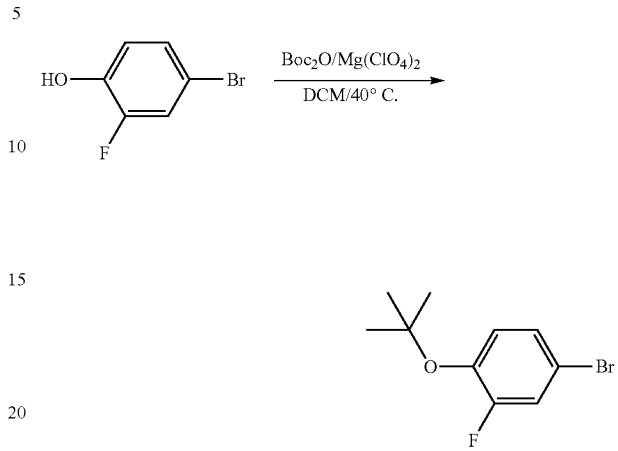

To a mixture of 4-bromo-2-fluorophenol (19.1 g, 0.1 mol) and Mg(ClO$_4$)$_2$ (2.23 g, 0.01 mol) in DCM (50 mL) was added Boc$_2$O (43.6 g, 0.2 mol) at 25° C. The reaction was heated at 40° C. for 1 hr. Then 1 eq. of Boc$_2$O (21.8 g, 0.1 mol) was added to the reaction. The reaction was heated at 40° C. for 12 hrs. The solution was concentrated and purified by silica gel chromatography (PE) to give the title compound (15.0 g, yield: 60.7%) as a colorless oil.

Synthesis of 1-bromo-4-(tert-pentyloxy)benzene

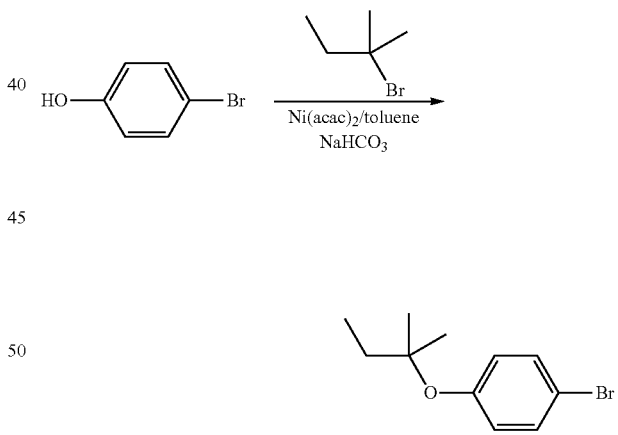

To a mixture of Ni(acac)$_2$ (150 mg, 0.58 mmol) in toluene (50 mL) was heated at 120° C. for 8 hrs. Then 4-bromophenol (1.73 g, 10 mmol) and 2-bromo-2-methylbutane (4.50 g, 30 mmol), NaHCO$_3$ (1.68 g, 20 mmol) was added to the reaction mixture. The reaction was heated at 60° C. for 16 hrs. The starting materials wasn't consumed, but a new point was detected by TLC. The mixture was extracted with EtOAc (30 mL), washed with aq. NaOH (20 mL) and brine (20 mL). The organic layer was dried over Na$_2$SO$_4$ and concentrated. The residue was purified by prep-TLC (PE) to give the title compound (150 mg, yield: 6.17%) as a colorless oil.

Synthesis of 1-(tert-butoxycarbonyl)-3-hydroxyazetidine-3-carboxylic acid

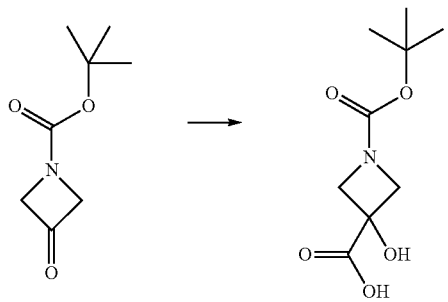

Synthesis of tert-butyl 3-cyano-3-((trimethylsilyl)oxy)azetidine-1-carboxylate

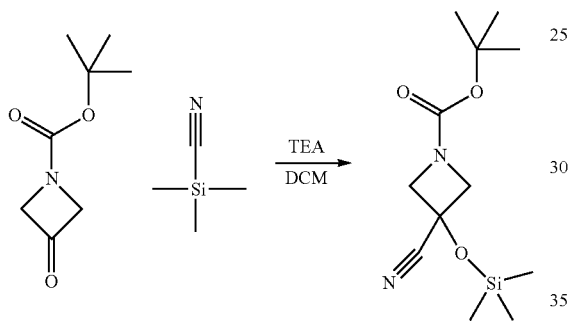

tert-butyl 3-oxoazetidine-1-carboxylate (500 mg, 2.9 mmole) was dissolved in 5 mL DCM and triethylamine (0.41 mL, 2.9 mmole) was added followed by TMS-cyanide (1.1 mL, 8.8 mmole) and the reaction mixture was stirred at room temperature overnight. The reaction mixture was diluted with DCM and washed with saturated sodium bicarbonate solution. The organic layer was dried over sodium sulfate and filtered and evaporated to give tert-butyl 3-cyano-3-((trimethylsilyl)oxy)azetidine-1-carboxylate in crude form which was used directly in the next step without further purification.

Synthesis of 1-(tert-butoxycarbonyl)-3-hydroxyazetidine-3-carboxylic acid

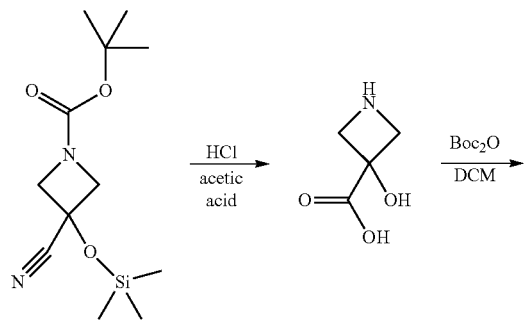

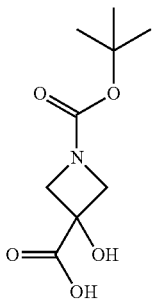

tert-butyl 3-cyano-3-((trimethylsilyl)oxy)azetidine-1-carboxylate (0.79 g, 2.9 mmole) was dissolved in a mixture of acetic acid (4.4 mL) and concentrated hydrochloric acid (3.4 mL) and heated to 100° C. for 2 hours. The solvent was evaporated exhaustively and then co-evaporated (×3) with toluene. The resulting residue was triturated with ether/hexane and filtered to give the desired product in crude form as a yellow semisolid. This material was suspended in 10 mL DCM and diisopropylamine (1.1 mL, 6.4 mmole) was added followed by di-tert-butyl dicarbonate (956 mg, 4.4 mmole) was added and stirred at room temperature overnight. The reaction mixture was diluted with DCM and partition with water. The aqueous layer was brought to pH ~3 with 1M HCl and then extracted 4 times with DCM. The combined organics were dried over sodium sulfate and filtered and evaporated to give 320 mg (50%) of 1-(tert-butoxycarbonyl)-3-hydroxyazetidine-3-carboxylic acid as a white solid.

Synthesis of tert-butyl 3-(N-(4-methylbenzyl)sulfamoyl)azetidine-1-carboxylate

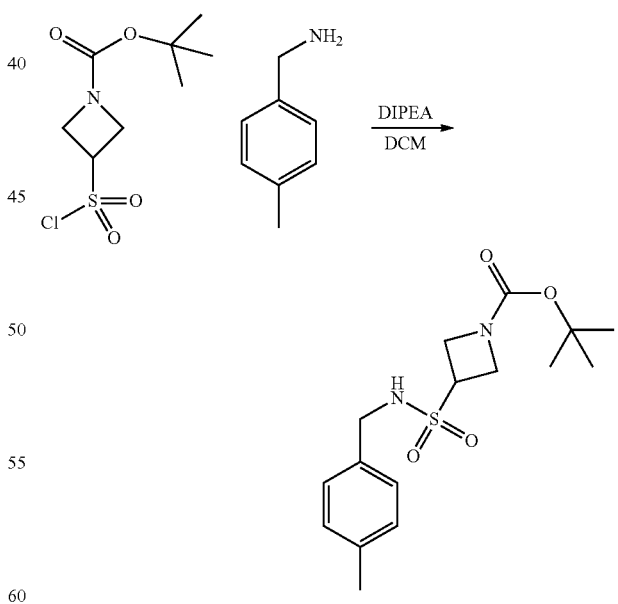

tert-butyl 3-(chlorosulfonyl)azetidine-1-carboxylate (40 mg, 0.16 mmole) dissolved in 0.5 mL pyridine and 4-methylbenzylamine (24 uL, 0.19 mmole) added and stirred at room temperature overnight. Solvent evaporated exhaustively and then triturated the resulting residue with water. The resulting suspension filtered and washed with water and suction dried to give 25 mg (47%) of tert-butyl 3-(N-(4-methylbenzyl)sulfamoyl)azetidine-1-carboxylate as a pale yellow solid.

Synthesis of 4-cyclopropylbenzaldehyde

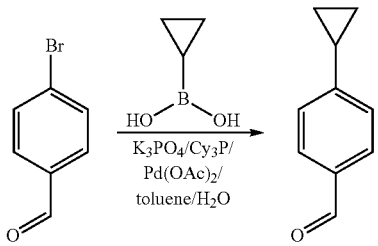

To a mixture of 4-bromobenzaldehyde (13.5 g, 0.0734 mol), cyclopropylboronic acid (6.3 g, 0.0734 mol), K₃PO₄.3H₂O (33.3 g, 0.147 mol) and PCy₃ (20.5 g, 0.0734 mol) in toluene/H₂O (180 mL, 5:1) was added Pd(OAc)₂ (500 mg) under N₂. The reaction was heated at 80° C. for 15 hrs under N₂. The reaction was complete detected by LCMS. Toluene and H₂O were removed by vacuum. The crude product was purified by column chromatography on silica gel (eluted with PE:EtOAc=20:1) to give the title compound (5.0 g, yield: 93.2%) as a yellow oil. $^1$H-NMR (400 MHz, CDCl₃) δ ppm 9.94 (s, 1H), 7.76 (d, 2H, J=7.6 Hz), 7.18 (d, 2H, J=7.6 Hz), 2.00-1.94 (m, 1H), 1.11-1.07 (m, 2H), 0.82-0.80 (m, 2H).

Synthesis of (S,E)-N-(4-cyclopropylbenzylidene)-2-methylpropane-2-sulfinamide

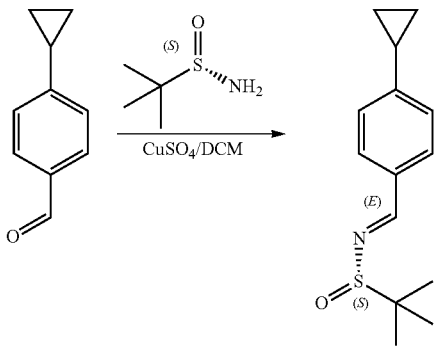

To a mixture of 4-cyclopropylbenzaldehyde (5.0 g, 0.0685 mol) and CuSO₄ (21.9 g, 0.137 mol) in dry DCM (200 mL) was added (S)-2-methylpropane-2-sulfinamide (16.6 g, 0.137 mol). The reaction mixture was stirred at 40° C. for 24 hrs. The reaction was complete detected by LCMS. The mixture was filtered and the filtrate was concentrated to give crude product. PE was added to the mixture, and the mixture was cooled to −78° C., filtered and the filtrate was concentrated to give crude product. EtOAc (150 mL) was added the mixture, and then the mixture was washed by H₂O (200 mL*2), brine (150 mL*2), then the organics was dried by vacuum to give product (6 g, yield: 70.3%) as a yellow oil.

Synthesis of (S)—N—((S)-1-(4-cyclopropylphenyl)propyl)-2-methylpropane-2-sulfinamide

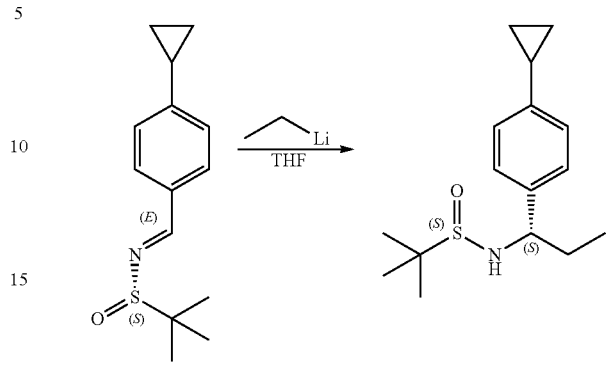

To a mixture of (S,E)-N-(4-cyclopropylbenzylidene)-2-methylpropane-2-sulfinamide (1.0 g, 4.02 mmol) in THF (20 mL) cooled to −78° C. was added ethyllithium (0.290 mg, 8.03 mmol) dropwise under N₂. The reaction mixture was stirred at 29° C. for 15 hrs under N₂. The reaction was complete detected by LCMS. The reaction was quenched with aq. NH₄Cl (10 mL) and extracted with 50 mL of EtOAc carefully. The organic layer was separated and concentrated to give crude product. The crude product was purified by column chromatography on silica gel (eluted with PE:EtOAc=20:1) to give product (1.05 g, yield: 93.8%) as a yellow oil.

Synthesis of (S)-1-(4-cyclopropylphenyl)propan-1-amine

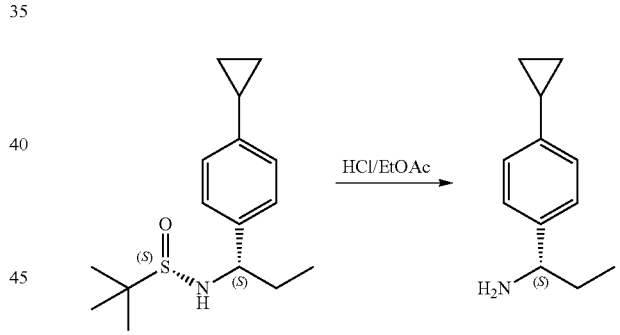

A mixture of (S)—N—((S)-1-(4-cyclopropylphenyl)propyl)-2-methylpropane-2-sulfinamide (1.05 g, 3.76 mmol) in HCl/EtOAc (4 M, 50 mL) was stirred at 25° C. for 5 hrs. The reaction was complete detected by TLC (PE:EtOAc=1:2, R$_f$=0). The reaction mixture was filtered and the filter cake was washed with EtOAc (5 mL), dried in vacuum to give the title compound (0.64 g, yield: 97.1%) as a white solid.

Synthesis of methyl 2-(2,4-dichlorophenyl)acetate

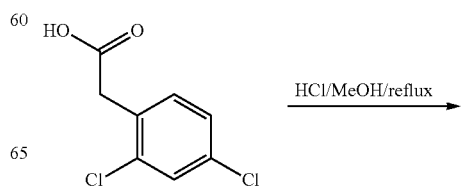

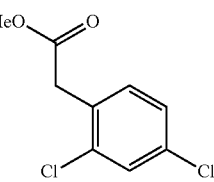

2-(2,4-Dichlorophenyl)acetic acid (1.0 g, 4.9 mmol) in MeOH (20 mL) saturated with HCl gas was stirred at 60° C. for 1 hr. After the starting material was consumed completely detected by TLC, the solution was concentrated in vacuum to get the title compound (0.9 g, 84.1%) as yellow oil.

Synthesis of methyl 2-(2,4-dichlorophenyl)propanoate

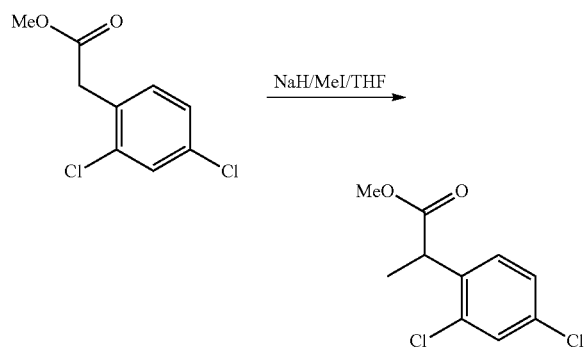

To the mixture of methyl 2-(2,4-dichlorophenyl)acetate (0.5 g, 2.29 mmol) in THF (10 mL) was added NaH (0.12 g, 2.98 mmol) at 0° C. portionwise, then the mixture was stirred at 25° C. for 0.5 hr, then to the mixture was added MeI (0.42 g, 2.98 mmol) dropwise, the mixture was stirred at 25° C. for 2 hrs. After the starting material was consumed completely detected by TLC, the mixture was quenched by H$_2$O (10 mL), extracted with EtOAc (10 mL*3). The organics were dried over Na$_2$SO$_4$ and concentrated in vacuum to get the title compound (0.3 g, yield: 50.8%) as yellow oil.

Synthesis of 2-(2,4-dichlorophenyl)propanoic acid

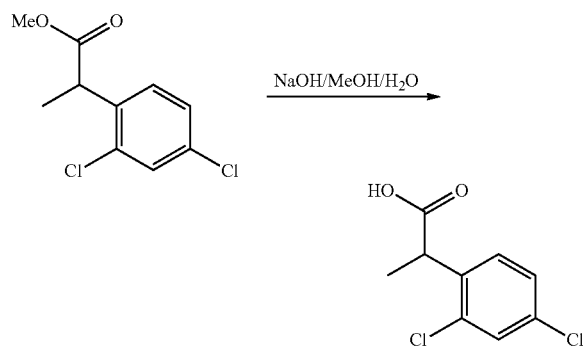

To the mixture of methyl 2-(2,4-dichlorophenyl)propanoate (0.5 g, 2.15 mmol) in MeOH (10 mL) and H$_2$O (5 mL) was added NaOH (0.17 g, 4.30 mmol), then the mixture was stirred at 25° C. for 3 hrs. After the starting material was consumed completely detected by TLC, the organic solvent was evaporated in vacuum and the aqueous phase was acidified with diluted aq. HCl to pH=5, the aqueous phase was extracted with EtOAc (10 mL*4), the organic layers were dried over Na$_2$SO$_4$ and concentrated to get the title compound (0.3 g, yield: 63.8%) as yellow oil.

Synthesis of 2-(2,4-dichlorophenyl)-2-hydroxyacetic acid

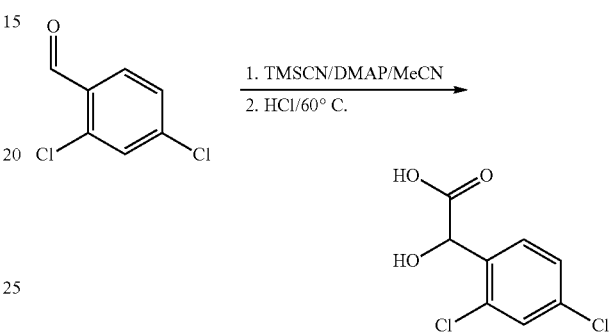

To the mixture of 2,4-dichlorobenzaldehyde (1.0 g, 5.75 mmol) in CH$_3$CN (30 mL) was added TMSCN (0.68 g, 6.90 mmol), DMAP (50 mg), then the mixture was stirred at 25° C. for 8 hrs, then the mixture was concentrated in vacuum and dissolved in HCl (30 mL, 6 M), the mixture was stirred at 70° C. for 4 hrs, then the solution was concentrated in vacuum to get the title compound as crude product (0.4 g).

Indications

The compounds described herein can be useful for treating conditions associated with aberrant Kit activity. Activating mutations in Kit are found in multiple indications, including systemic mastocytosis, GIST (gastrointestinal stromal tumors), AML (acute myeloid leukemia), melanoma, and seminoma.

Mastocytosis refers to a group of disorders characterized by excessive mast cell accumulation in one tissue, or in multiple tissues. Mastocytosis is subdivided into two groups of disorders: (1) cutaneous mastocytosis (CM) describes forms that are limited to the skin; and (2) systemic mastocytosis (SM) describes forms in which mast cells infiltrate extracutaneous organs, with or without skin involvement. SM is further subdivided into four forms: indolent (ISM), smoldering (SSM), aggressive (ASM), SM with associated hemotologic non-mast cell lineage disease (SM-AHNMD), and mast cell leukemia (MCL).

Diagnosis of systemic mastocytosis is based on histological and cytological study of bone marrow showing infiltration by mast cells of frequently atypical morphology, which frequently abnormally express non-mast cell markers (CD25 and/or CD2). An elevated level of serum tryptase above 20 ng/mL or the presence of an activating mutation of Kit can confirm the diagnosis.

Activating mutations at the D816 position are found in the vast majority of mastocytosis cases, with the most common mutations being D816V and D816H, and D816Y. The D816V mutation is found in the activation loop of the kinase domain, and leads to constitutive activation.

The compounds described herein may also be useful to treat GIST. Complete surgical resection remains the principal treatment of choice for patients with a primary GIST. Surgery is effective in approximately 50% of patients with GIST. Of the remaining patients, tumor recurrence is frequent. Primary treatment with a Kit inhibitor such as imatinib has also been shown to be sufficient for initial treatment. However, resistance to imatinib occurs within months through somatic mutation. These secondary imatinib resistant mutations are most frequently located on exon 11, 13, 14, 17 or 18. Sunitinib is the standard of care second line treatment for most imatinib resistant tumors and is effective for those containing mutations in exons 11, 13 and 14. However, secondary kit mutations in exons 17 and 18 are resistant to sunitinib treatment and furthermore, tumors containing tertiary resistance mutations in exon 17 and 18 emerge several months after sunitinib treatment. Regorafenib has shown promising results in a phase 3 clinical trial of imatinib, sunitinib resistant GISTs with activity against several exon 17 and 18 mutations, with the exception of the D816 mutant which remains refractory to all treatments. Regorafenib has been approved for 3rd line GIST treatment.

The compounds described herein may also be useful in treating AML. Some AML patients harbor Kit mutations as well, with the majority of these mutations at the D816 position.

In addition, mutations in Kit have been linked to Ewing's sarcoma, DLBCL (diffuse large B cell lymphoma), dysgerminoma, MDS (myelodysplastic syndrome), NKTCL (nasal NK/T-cell lymphoma), and CMML (chronic myelomonocytic leukemia).

Pharmaceutical Compositions

While it is possible for a compound disclosed herein to be administered alone, it is preferable to administer the compound as a pharmaceutical formulation, where the compound is combined with one or more pharmaceutically acceptable excipients or carriers. The compounds disclosed herein may be formulated for administration in any convenient way for use in human or veterinary medicine. In certain embodiments, the compound included in the pharmaceutical preparation may be active itself, or may be a prodrug, e.g., capable of being converted to an active compound in a physiological setting.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Examples of pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; (21) cyclodextrins such as Captisol®; and (22) other non-toxic compatible substances employed in pharmaceutical formulations.

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Solid dosage forms (e.g., capsules, tablets, pills, dragees, powders, granules and the like) can include one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents.

Liquid dosage forms can include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

When the compounds disclosed herein are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The formulations can be administered topically, orally, transdermally, rectally, vaginally, parentally, intranasally, intrapulmonary, intraocularly, intravenously, intramuscularly, intraarterially, intrathecally, intracapsularly, intradermally, intraperitoneally, subcutaneously, subcuticularly, or by inhalation.

Dosages

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound disclosed herein employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound that is the lowest dose effective to produce a therapeutic effect. Such an effective dose will generally depend upon the factors described above. Generally, intravenous, intracerebroventricular and subcutaneous doses of the compounds of this invention for a patient will range from about 0.0001 to about 100 mg per kilogram of body weight per day. If desired, the effective daily dose of the active compound may be administered as two, three, four, five, six or more sub-doses administered separately at appropriate intervals throughout the day, optionally, in unit dosage forms. In some embodiments, the dose will be 1-20, or 5-10 mg per kilogram of body weight, administed twice daily.

EXAMPLES

The following examples are intended to be illustrative, and are not meant in any way to be limiting.

NMR and LC MS data for compounds disclosed herein are shown below.

| Compound Number | Synthetic Method | $^1$H MR | LC/MS M + 1 |
|---|---|---|---|
| 1 | 1 | $^1$H NMR (400 MHz, DMSO-$d_6$) δ 8.67 (t, J = 5.9 Hz, 1H), 8.01 (s, 1H), 7.92 (t, J = 1.2 Hz, 1H), 7.85-7.72 (m, 2H), 7.40-7.20 (m, 5H), 6.89 (d, J = 0.9 Hz, 1H), 4.79-4.53 (m, 3H), 4.45-4.15 (m, 4H), 3.84 (s, 3H), 3.70-3.59 (m, 1H) | 388 |
| 2 | 1 | $^1$H-NMR (400 MHz, DMSO-$d_6$) δ ppm 12.81 (s, 1H), 8.61 (t, 1H, J = 6.0 Hz), 8.07 (s, 1H), 7.94 (d, 1H, J = 1.2 Hz), 7.85 (s, 1H), 7.79 (s, 1H), 7.16 (d, 2H, J = 8.0 Hz), 7.12 (d, 2H, J = 8.0 Hz), 6.90 (d, 1H, J = 1.2 Hz), 4.70-4.17 (m, 6H), 3.66-3.61 (m, 1H), 2.27 (s, 3H) | 388 |
| 3 | 2 | $^1$H NMR (500 MHz, DMSO-d6) δ 8.00 (s, 1H), 7.88 (d, J = 1.6 Hz, 1H), 7.76 (d, J = 0.8 Hz, 1H), 7.76 (s, 1H), 7.23 (d, J = 7.7 Hz, 2H), 7.11 (d, J = 7.7 Hz, 2H), 6.82 (d, J = 1.7 Hz, 1H), 4.60 (s, 1H), 4.32-4.15 (m, 2H), 3.84 (m, 4H), 3.68 (s, 2H), 2.92 (m, 1H), 2.75 (d, J = 7.1 Hz, 2H), 2.27 (s, 3H). | 388 |
| 4 | 2 | $^1$H-NMR (400 MHz, DMSO-$d_6$) δ ppm 8.66 (br.s, 1H), 8.20 (s, 1H), 7.82 (s, 1H), 7.79 (d, 2H, J = 7.6 Hz), 7.40 (t, 2H, J = 7.6 Hz), 7.24-7.20 (m, 1H), 7.17-7.12 (m, 5H), 4.27 (br.s, 2H), 2.27 (s, 3H) | 398 |
| 5 | 2 | $^1$H-NMR (500 MHz, CDCl$_3$) δ ppm 7.87 (s, 1H), 7.71 (d, 2H, J = 8.5 Hz), 7.67-7.65 (m, 4H), 7.53 (s, 1H), 7.46-7.43 (m, 1H), 6.59 (s, 1H), 4.68 (br, 4H), 3.94 (s, 3H), 3.72-3.68 (m, 1H) | 399 |
| 6 | 1 | $^1$H-NMR (500 MHz, CDCl$_3$) δ ppm 7.84 (s, 1H), 7.66 (s, 1H), 7.63 (d, 1H, J = 1.0 Hz), 7.53 (s, 1H), 7.19 (d, 2H, J = 8.5 Hz), 7.16 (d, 2H, J = 8.0 Hz), 6.58 (s, 1H), 5.85 (br. s., 1H), 4.61 (br. s., 4H), 4.46 (d, 2H, J = 5.0 Hz), 3.94 (s, 3H), 3.53-3.49 (m, 1H), 2.34 (s, 3H) | 402 |
| 7 | 1 | $^1$H-NMR (500 MHz, DMSO-$d_6$) δ ppm 8.84 (d, 1H, J = 7.0 Hz), 8.02 (s, 1H), 7.93 (d, 1H, J = 1.5 Hz), 7.81(s, 1H), 7.80 (s, 1H), 7.16 (d, 2H, J = 7.0 Hz), 7.11 (d, 2H, J = 7.5 Hz), 6.89 (d, 1H, J = 1.5 Hz), 4.85-4.10 (m, 5H), 3.84 (s, 3H), 3.41 (s, 2H), 2.27 (s, 3H) | 402 |
| 8 | 3 | $^1$H-NMR (400 MHz, DMSO-$d_6$) δ ppm 8.63 (t, 1H, J = 5.6 Hz), 8.07 (d, 1H, J = 1.2 Hz), 7.88 (s, 1H), 7.40 (d, 1H, J = 2.0 Hz), 7.15 (d, 2H, J = 8.0 Hz), 7.12 (d, 2H, J = 8.4 Hz), | 402 |

| Compound Number | Synthetic Method | $^1$H MR | LC/MS M + 1 |
|---|---|---|---|
| | | 6.94 (d, 1H, J = 1.2 Hz), 6.53 (d, 1H, J = 2.0 Hz), 4.80-4.57 (m, 2H), 4.42-4.14 (m, 4H), 3.95 (s, 3H), 3.66-3.55 (m, 1H), 2.26 (s, 3H) | |
| 9 | 2 | $^1$H NMR (400 MHz, DMSO-d$_6$) δ 8.59 (t, J = 5.9 Hz, 1H), 7.83 (d, J = 1.5 Hz, 1H), 7.79 (s, 1H), 7.57 (d, J = 1.3 Hz, 1H), 7.43 (d, J = 1.3 Hz, 1H), 7.20-7.09 (m, 3H), 6.86 (d, J = 1.6 Hz, 1H), 4.64 (m, 2H), 4.27 (m, 4H), 3.66 (m, 4H), 2.27 (s, 3H) | 402 |
| 10 | 1 | $^1$H-NMR (400 MHz, CDCl$_3$) δ ppm 7.81 (s, 1H), 7.67 (s, 1H), 7.60 (d, 1H, J = 1.6 Hz), 7.53 (s, 1H), 7.22-7.14 (m, 4H), 6.54 (d, 1H, J = 1.6 Hz), 4.60 (br s, 1H), 4.34-4.19 (m, 2H), 3.94-3.91 (m, 4H), 3.75 (q, 1H, J = 6.4 Hz), 2.87-2.82 (m, 2H), 2.75-2.70 (m, 1H), 2.33 (s, 3H), 1.36 (d, 3H, J = 6.8 Hz) | 402 |
| 11 | 1 | $^1$H-NMR (400 MHz, DMSO-d$_6$) δ ppm 8.01 (s, 1H), 7.88 (d, 1H, J = 1.2 Hz), 7.77 (s, 1H), 7.75 (s, 1H), 7.23 (d, 2H, J = 8.0 Hz), 7.11 (d, 2H, J = 8.0 Hz), 6.82 (s, 1H), 4.58 (br. s., 1H), 4.19 (br. s., 2H), 3.84 (s, 3H), 3.79 (br. s., 1H), 3.70-3.62 (m, 1H), 2.92-2.81 (m, 1H), 2.72-2.61 (m, 1H), 2.26 (br., s., 4 H), 1.24 (d, 3H, J = 6.4 Hz) | 402 |
| 12 | 2 | $^1$H NMR (400 MHz, DMSO-d$_6$) δ 8.58 (t, J = 5.8 Hz, 1H), 7.88-7.73 (m, 2H), 7.25-7.06 (m, 4H), 6.79 (d, J = 1.8 Hz, 1H), 6.24 (s, 1H), 4.96-3.94 (m, 8H), 3.79 (t, J = 5.4 Hz, 2H), 3.60 (t, J = 8.1 Hz, 1H), 2.40 (s, 2H), 2.26 (s, 3H) | 404 |
| 13 | 2 | $^1$H NMR (400 MHz, DMSO-d$_6$) δ 8.66 (t, J = 5.9 Hz, 1H), 8.00 (s, 1H), 7.92 (d, J = 1.6 Hz, 1H), 7.82-7.73 (m, 2H), 7.37-7.27 (m, 2H), 7.20-7.13 (m, 2H), 6.88 (d, J = 1.6 Hz, 1H), 4.78-4.50 (m, 2H), 4.32 (d, J = 5.8 Hz, 4H), 3.84 (s, 3H) | 406 |
| 14 | 1 | $^1$H-NMR (400 MHz, DMSO-d$_6$) δ ppm 8.72 (t, 1H, J = 5.6 Hz), 8.01 (s, 1H), 7.92 (d, 1H, J = 1.2 Hz), 7.80 (s, 1H), 7.79 (s, 1H), 6.89 (d, 1H, J = 1.6 Hz), 6.76 (d, 1H, J = 3.2 Hz), 6.63 (dd, 1H, J = 1.2, 3.2 Hz), 4.78-4.09 (m, 6H), 3.84 (s, 3H), 3.62-3.55 (m, 1H), 2.39 (s, 3H) | 408 |
| 15 | 1 | $^1$H-NMR (400 MHz, DMSO-d$_6$) δ ppm 8.73 (t, 1H, J = 5.6 Hz), 8.01 (s, 1H), 7.92 (d, 1H, J = 1.6 Hz), 7.80 (s, 1H), 7.79 (s, 1H), 6.96 (s, 1H), 6.89 (d, 1H, J = 1.6 Hz), 6.81 (s, 1H), 4.69-4.60 (m, 2H), 4.43 (d, 2H, J = 6.0 Hz), 4.38-4.19 (m, 2H), 3.84 (s, 3H), 3.63-3.56 (m, 1H), 2.16 (s, 3H) | 408 |
| 16 | 1 | $^1$H-NMR (400 MHz, DMSO-d$_6$) δ ppm 10.34 (s, 1H), 8.00 (s, 1H), 7.93 (s, 1H), 7.81 (s, 1H), 7.78 (s, 1H), 7.66 (d, 2H, J = 8.8 Hz), 7.39 (d, 2H, J = 8.8 Hz), 6.90 (d, 1H, J = 1.2 Hz), 4.75-4.69 (m, 2H), 4.39-4.28 (m, 2H), 3.83 (s, 3H), 3.82-3.73 (m, 1H) | 408 |
| 17 | 2 | $^1$H NMR (400 MHz, DMSO-d$_6$) δ 10.62 (s, 1H), 7.91 (s, 1H), 7.88-7.76 (m, 5H), 6.79 (d, J = 1.7 Hz, 1H), 4.89-4.62 (m, 2H), 4.54-4.18 (m, 3H), 3.76 (s, 3H), 2.31 (s, 3H) | 413 |
| 18 | 2 | $^1$H NMR (400 MHz, DMSO-d$_6$) δ 10.60 (s, 1H), 7.85-7.76 (m, 5H), 7.64 (s, 1H), 6.78 (d, J = 1.7 Hz, 1H), 4.87-4.62 (m, 2H), 4.48-4.23 (m, 2H), 3.87-3.78 (m, 1H), 3.75 (s, 3H), 2.39 (s, 3H) | 413 |
| 19 | 2 | $^1$H NMR (400 MHz, DMSO-d6) δ 10.53 (s, 1H), 7.99 (s, 1H), 7.92 (d, J = 1.6 Hz, 1H), 7.80 (s, 1H), 7.77 (d, J = 0.8 Hz, 1H), 7.74-7.69 (m, 2H), 7.61 (dd, J = 8.6, 2.0 Hz, 1H), 6.89 (d, J = 1.6 Hz, 1H), 4.83-4.58 (m, 2H), 4.48-4.26 (m, 2H), 3.83 (s, 4H), 2.44 (s, 3H). | 413 |
| 20 | 1 | $^1$H-NMR (400 MHz, DMSO-d$_6$) δ ppm 10.36 (s, 1H), 8.00 (s, 1H), 7.93 (s, 1H), 7.86-7.78 (m, 6H), 6.88 (s, 1H), 4.93 (br. s., 1H), 4.50-4.41 (m, 2H), 4.07-3.98 (br. s., 1H), 3.83 (s, 3H), 1.59 (s, 3H) | 413 |
| 21 | 2 | $^1$H-NMR (400 MHz, DMSO-d$_6$) δ ppm 8.62 (t, 1H, J = 6.0 Hz), 8.37 (d, 1H, J = 1.6 Hz), 8.06 (d, 1H, J = 1.6 Hz), 7.80 (s, 1H), 7.78 (dd, 1H, J = 8.8, 2.4 Hz), 7.17 (d, 2H, J = 8.4 Hz), 7.13 (d, 2H, J = 8.4 Hz), 6.99 (d, 1H, J = 1.2 Hz), 6.47 (d, 1H, J = 8.4 Hz), 5.96 (s, 2H), 4.75-4.62 (m, 2H), 4.34-4.17 (m, 4H), 3.64-3.60 (m, 1H), 2.28 (s, 3H) | 414 |
| 22 | 2 | $^1$H-NMR (400 MHz, DMSO-d$_6$) δ ppm 8.58 (br.s, 1H), 8.17 (s, 1H), 7.84-7.81 (m, 3H), 7.22-7.09 (m, 7H), 4.73-4.26 (m, 3H), 3.62 (br.s, 1H), 2.26 (s, 3H) | 416 |
| 23 | 1 | $^1$H-NMR (500 MHz, CDCl$_3$) δ ppm 7.86 (s, 1H), 7.68 (s, 1H), 7.65 (d, 1H, J = 1.0 Hz), 7.55 (s, 1H), 7.25 (d, 2H, J = 8.0 Hz), 7.20 (d, 2H, J = 8.5 Hz), 6.58 (s, 1H), 5.76 (d, 1H, J = 7.5 Hz), 5.21-5.15 (m, 1H), 4.65-4.63 (br, 4H), 3.96 (s, 3H), 3.52-3.46 (m, 1H), 2.37 (s, 3H), 1.55 (d, 3H, J = 6.5 Hz) | 416 |
| 24 | 2 | $^1$H NMR (400 MHz, DMSO-d6) δ 8.59 (t, J = 5.9 Hz, 1H), 7.81 (d, 1H, J = 1.6 Hz, 1H), 7.80 (s, 1H), 7.64 (s, 1H), 7.21- | 416 |

-continued

| Compound Number | Synthetic Method | ¹H NMR | LC/MS M + 1 |
|---|---|---|---|
| | | 7.08 (m, 4H), 6.77 (d, J = 1.7 Hz, 1H), 4.78-4.53 (m, 2H), 4.39-4.13 (m, 4H), 3.75 (s, 3H), 3.61 (ddd, J = 14.3, 8.7, 5.6 Hz, 1H), 2.38 (s, 3H), 2.26 (s, 3H) | |
| 25 | 2 | ¹H NMR (400 MHz, DMSO-d6) δ 8.58 (t, J = 5.8 Hz, 1H), 7.90 (s, 1H), 7.80 (s, 1H), 7.77 (d, J = 1.6 Hz, 1H), 7.21-7.08 (m, 4H), 6.76 (d, J = 1.7 Hz, 1H), 4.73-4.53 (m, 2H), 4.27 (d, J = 5.8 Hz, 4H), 3.75 (s, 3H), 3.65-3.57 (m, 1H), 2.29 (s, 3H), 2.27 (s, 3H). | 416 |
| 26 | 1 | ¹H NMR (400 MHz, DMSO-d$_6$) δ ppm 8.54 (t, 1H, J = 6.0 Hz), 8.00 (s, 1H), 7.91 (d, 1H, J = 1.6 Hz), 7.79 (s, 1H), 7.77 (s, 1H), 7.15 (d, 2H, J = 8.4 Hz), 7.12 (d, 2H, J = 8.0 Hz), 6.86 (d, 1H, J = 1.6 Hz), 4.81-4.78 (br, 1H), 4.35-4.31 (br, 2H), 4.28 (d, 2H, J = 5.6 Hz), 3.98-3.95 (br, 1H), 3.83 (s, 3H), 2.26 (s, 3H), 1.59 (s, 3H) | 416 |
| 27 | 2 | ¹H-NMR (400 MHz, DMSO-d$_6$) δ ppm 12.24-12.20 (br, 1H), 8.62 (t, 1H, J = 5.6 Hz), 7.83 (s, 1H), 7.73 (s, 1H), 7.18-7.14 (m, 4H), 6.66 (s, 1H), 4.73-4.61 (m, 2H), 4.34-4.21 (m, 2H), 4.28 (d, 2H, J = 5.6 Hz), 3.64-3.60 (m, 1H), 2.27 (s, 9H) | 416 |
| 28 | 1 | ¹H-NMR (400 MHz, DMSO-d$_6$) δ ppm 8.60 (t, 1H, J = 6.0 Hz), 8.01 (s, 1H), 7.98 (s, 1H), 7.85 (s, 1H), 7.78 (s, 1H), 7.19-7.14 (m, 4H), 6.98 (s, 1H), 4.28 (d, 2H, J = 5.6 Hz), 3.83 (s, 3H), 3.67-3.60 (m, 1H), 2.56 (q, 2H, J = 7.6 Hz), 1.14 (t, 3H, J = 7.6 Hz) | 416 |
| 29 | 3 | ¹H NMR (400 MHz, DMSO-d6) δ 8.58 (t, J = 5.9 Hz, 1H), 7.85 (d, J = 1.6 Hz, 1H), 7.77 (s, 1H), 7.70 (s, 1H), 7.19-7.09 (m, 4H), 6.78 (d, J = 1.7 Hz, 1H), 4.68 (m, 4H), 4.27 (m, 3H), 3.60 (s, 3H), 2.27 (s, 3H) | 417 |
| 30 | 3 | ¹H-NMR (400 MHz, DMSO-d$_6$) δ ppm 8.63 (br. s., 1H), 7.92 (br. s., 1H), 7.78 (br. s., 1H), 7.48 (br. s., 1H), 7.16 (br. s., 4H), 6.78 (br. s., 1H), 5.35 (br. s., 2H), 4.93-4.43 (m, 2H), 4.43-3.99 (m, 4H), 3.68-3.51 (m, 4H), 2.28 (s, 3H) | 417 |
| 31 | 1 | ¹H-NMR (400 MHz, DMSO-d$_6$) δ ppm 8.57 (d, 1H, J = 8.0 Hz), 8.00 (s, 1H), 7.90 (d, 1H, J = 1.2 Hz), 7.78, 7.77 (s, s, 2H), 7.35-7.31 (m, 4H), 7.25-7.22 (m, 1H), 6.87 (s, 1H), 4.93-4.88 (m, 2H), 4.71-4.22 (m, 4H), 3.83 (s, 3H), 3.71-3.67 (m, 1H), 3.57 (br. s., 2H) | 418 |
| 32 | 1 | ¹H-NMR (400 MHz, DMSO-d$_6$) δ ppm 8.57 (t, 1H, J = 5.6 Hz), 8.00 (s, 1H), 7.91 (s, 1H), 7.79 (s, 1H), 7.78 (s, 1H), 7.21 (d, 2H, J = 8.4 Hz), 6.89 (d, 2H, J = 8.8 Hz), 6.88 (s, 1H), 4.83-4.45 (m, 2H), 4.44-4.02 (m, 2H), 4.26 (d, 2H, J = 5.6 Hz), 3.84 (s, 3H), 3.73 (s, 3H), 3.66-3.55 (m, 1H) | 418 |
| 33 | 2 | ¹H-NMR (400 MHz, CD$_3$OD) δ ppm 8.10 (s, 1H), 7.92 (s, 1H), 7.28-6.94 (m, 7H), 6.94 (s, 1H), 4.68-4.61 (m, 3H), 4.38 (s, 2H), 3.79 (br.s, 1H), 2.30 (s, 3H), 2.25 (s, 3H) | 418 |
| 34 | 2 | ¹H-NMR (400 MHz, CD$_3$OD) δ ppm 8.64 (br.s, 1H), 8.05 (s, 1H), 7.91 (s, 1H), 7.22-7.13 (m, 5H), 6.73 (s, 1H), 4.65 (br.s, 4H), 4.40-4.39 (m, 2H), 3.78 (br.s, 1H), 2.48 (s, 3H), 2.31 (s, 3H) | 418 |
| 35 | 2 | ¹H NMR (400 MHz, DMSO-d6) δ 8.59 (d, J = 7.9 Hz, 1H), 8.00 (s, 1H), 7.91 (d, J = 1.6 Hz, 1H), 7.78 (d, J = 3.6 Hz, 1H), 7.43-7.30 (m, 2H), 7.21-7.09 (m, 2H), 6.87 (d, J = 2.1 Hz, 1H), 5.04-4.92 (m, 2H), 4.75-4.46 (m, 1H), 4.46-4.04 (m, 2H), 3.84 (s, 3H), 3.68-3.55 (m, 2H), 1.37 (d, J = 7.0 Hz, 3H). | 420 |
| 36 | 1 | ¹H NMR (400 MHz, DMSO-d6) δ 8.59 (t, J = 5.8 Hz, 1H), 7.99 (s, 1H), 7.91 (d, J = 1.6 Hz, 1H), 7.78 (d, J = 1.0 Hz, 1H), 7.77 (d, J = 0.8 Hz, 1H), 7.22 (t, J = 8.0 Hz, 1H), 7.04-6.94 (m, 2H), 6.87 (d, J = 1.6 Hz, 1H), 4.72-4.49 (m, 2H), 4.38-4.12 (m, 4H), 3.83 (s, 3H), 3.61 (m, 1H), 2.28 (s, 3H). | 420 |
| 37 | 1 | ¹H NMR (400 MHz, DMSO-d6) δ 8.64 (t, J = 5.9 Hz, 1H), 7.99 (s, 1H), 7.91 (d, J = 1.6 Hz, 1H), 7.78 (d, J = 1.8 Hz, 1H), 7.77 (t, J = 1.1 Hz, 1H), 7.22 (t, J = 7.9 Hz, 1H), 7.06-6.96 (m, 2H), 6.87 (d, J = 1.7 Hz, 1H), 4.74-4.52 (m, 2H), 4.39-4.13 (m, 4H), 3.83 (s, 3H), 3.67-3.58 (m, 1H), 2.19 (s, 3H). | 420 |
| 38 | 1 | ¹H-NMR (400 MHz, CDCl$_3$) δ ppm 7.86 (s, 1H), 7.67 (d, 2H, J = 9.6 Hz), 7.54 (s, 1H), 7.34 (d, 2H, J = 6.8 Hz), 7.28-7.24 (m, 2H), 6.59 (s, 1H), 5.93 (br. s., 1H), 4.64 (br. s., 3H), 4.49 (br. s., 2H), 3.96 (s, 3H), 3.56-3.53 (m, 1H), 1.64 (br. s., 1H). | 422 |
| 39 | 1 | ¹H-NMR (400 MHz, DMSO-d$_6$) δ ppm 8.85 (d, 1H, J = 6.8 Hz), 7.99 (s, 1H), 7.89 (s, 1H), 7.77 (d, 2H, J = 8.0 Hz), 7.35 (d, 2H, J = 8.0 Hz), 7.28 (d, 2H, J = 8.4 Hz), 6.85 (s, 1H), 4.66 (d, 1H, J = 6.0 Hz), 3.82 (s, 3H), 3.45 (s, 2H) | 422 |

-continued

| Compound Number | Synthetic Method | ¹H MR | LC/MS M + 1 |
|---|---|---|---|
| 40 | 1 | ¹H NMR (500 MHz, DMSO-d6) δ 8.63 (t, J = 5.8 Hz, 1H), 7.99 (s, 1H), 7.90 (d, J = 1.6 Hz, 1H), 7.77 (d, J = 7.9 Hz, 2H), 7.39 (td, J = 8.7, 6.7 Hz, 1H), 7.22 (ddd, J = 10.4, 9.4, 2.6 Hz, 1H), 7.11-7.03 (m, 1H), 6.86 (d, J = 1.7 Hz, 1H), 4.82-4.48 (m, 2H), 4.44-4.05 (m, 3H), 3.83 (s, 3H), 3.68-3.56 (m, 1H). | 424 |
| 41 | 1 | | 425 |
| 42 | 2 | ¹H-NMR (400 MHz, DMSO-d₆) δ ppm 8.60-8.59 (m, 1H), 8.52 (d, 1H, J = 4.4 Hz), 7.97 (s, 1H), 7.80 (s, 1H), 7.74 (t, 1H, J = 8.0 Hz), 7.63 (d, 1H, J = 16.0 Hz), 7.40 (d, 1H, J = 8.0 Hz), 7.22-7.13 (m, 6H), 7.03 (s, 1H), 4.27 (d, 2H, J = 5.2 Hz), 3.65-3.58 (m, 1H), 2.26 (s, 3H) | 425 |
| 43 | 2 | ¹H-NMR (400 MHz, DMSO-d₆) δ ppm 10.62 (s, 1H), 8.11 (s, 1H), 7.93 (d, 1H, J = 1.2 Hz), 7.83-7.78 (m, 5H), 6.91 (d, 1H, J = 1.2 Hz), 4.65-4.43 (m, 5H), 3.85-3.81 (m, 1H), 1.42 (d, 6H, J = 6.4 Hz) | 427 |
| 44 | 1 | ¹H-NMR (400 MHz, DMSO-d₆ + CD₃OD) δ ppm 10.85 (s, 1H), 8.71 (d, 1H, J = 6.4 Hz), 7.98 (s, 1H), 7.88 (s, 1H), 7.76 (d, 2H, J = 5.2 Hz), 7.54 (d, 1H, J = 8.0 Hz), 7.33 (d, 1H, J = 8.4 Hz), 7.19 (s, 1H), 7.07-7.03 (m, 1H), 6.98-6.96 (m, 1H), 6.84 (s, 1H), 4.70 (d, 1H, J = 6.0 Hz), 3.82 (s, 3H), 3.54 (s, 2H). | 427 |
| 45 | 1 | | 428 |
| 46 | 2 | ¹H-NMR (400 MHz, DMSO-d₆) δ ppm 8.61 (t, 1H, J = 5.6 Hz), 8.22 (d, 1H, J = 1.6 Hz), 7.83 (s, 1H), 7.38-7.35 (m, 2H), 7.30-7.26 (m, 1H), 7.17-7.12 (m, 5H), 6.82-6.80 (m, 1H), 4.70-4.67 (br, 2H), 4.31-4.25 (m, 2H), 4.27 (d, 2H, J = 5.6 Hz), 3.81 (s, 3H), 3.65-3.60 (m, 1H), 2.27 (s, 3H) | 428 |
| 47 | 2 | ¹H NMR (500 MHz, DMSO-d6) δ 8.59 (t, J = 5.9 Hz, 1H), 8.11 (s, 1H), 7.91 (d, J = 1.6 Hz, 1H), 7.77 (d, J = 6.1 Hz, 2H), 7.18-7.10 (m, 4H), 6.89 (d, J = 1.6 Hz, 1H), 4.60 (m, 2H) 4.27 (m, 2H), 4.19 (m, 2H), 3.73-3.57 (m, 2H), 2.27 (s, 3H), 1.06-0.99 (m, 2H), 1.00-0.93 (m, 2H) | |
| 48 | 1 | ¹H NMR (300 MHz, DMSO-d6) δ 8.60 (t, J = 5.8 Hz, 1H), 8.01 (s, 1H), 7.92 (d, J = 1.6 Hz, 1H), 7.84-7.75 (m, 2H), 7.15 (d, J = 8.1 Hz, 2H), 7.10-6.99 (m, 2H), 6.89 (d, J = 1.7 Hz, 1H), 4.61 (s, 2H), 4.50-4.10 (m, 4H), 3.84 (s, 3H), 3.70-3.54 (m, 1H), 1.97-1.81 (m, 1H), 0.97-0.86 (m, 2H), 0.69-0.58 (m, 2H). | 428 |
| 49 | 2 | ¹H NMR (300 MHz, DMSO-d6) δ 8.62 (t, J = 5.9 Hz, 1H), 7.83 (d, J = 1.5 Hz, 1H), 7.81 (s, 2H), 7.22-7.09 (m, 4H), 6.78 (d, J = 1.7 Hz, 1H), 4.64 (s, 4H), 4.29 (d, J = 5.8 Hz, 2H), 4.08 (t, J = 7.2 Hz, 2H), 3.63 (td, J = 9.1, 8.5, 4.4 Hz, 1H), 3.03 (t, J = 7.3 Hz, 2H), 2.62 (q, J = 7.3 Hz, 2H), 2.28 (s, 3H) | 428 |
| 50 | 2 | ¹H-NMR (400 MHz, DMSO-d₆) δ ppm 8.65-8.62 (m, 2H), 8.23 (d, 1H, J = 1.2 Hz), 8.13 (dd, 1H, J = 8.4, 2.4 Hz), 7.84 (s, 1H), 7.18-7.14 (m, 5H), 6.86 (d, 1H, J = 8.8 Hz), 4.86-4.55 (m, 2H), 4.45-4.09 (m, 4H), 3.87 (s, 3H), 3.67-3.58 (m, 1H), 2.28 (s, 3H) | 429 |
| 51 | 2 | ¹H NMR (400 MHz, DMSO-d6) δ 8.59 (t, J = 6.2 Hz, 1H), 8.27 (d, J = 3.0 Hz, 1H), 8.16 (d, J = 1.6 Hz, 1H), 7.90-7.79 (m, 2H), 7.41 (dd, J = 8.7, 3.0 Hz, 1H), 7.22-7.08 (m, 5H), 4.77 (br.s, 1H), 4.65 (br.s, 1H), 4.42-4.16 (m, 4H), 3.84 (s, 3H), 3.68-3.57 (m, 1H), 2.27 (s, 3H). | 429 |
| 52 | 3 | ¹H-NMR (400 MHz, DMSO-d₆) δ ppm 8.62 (br. s., 1H), 8.23 (s, 1H), 8.06 (s, 1H), 7.90 (d, 1H, J = 9.6 Hz), 7.81 (s, 1H), 7.15 (br.s., 4H), 7.01 (s, 1H), 6.44 (d, 1H, J = 9.2 Hz), 4.67-4.63 (m, 2H), 4.34-4.19 (m, 4 H), 3.62 (br. s., 1H), 3.47 (s, 3H), 2.27 (s, 3H) | 429 |
| 53 | 1 | ¹H-NMR (400 MHz, DMSO-d₆) δ ppm 8.29 (d, 1H, J = 8.4 Hz), 8.02 (s, 1H), 7.93 (d, 1H, J = 1.2 Hz), 7.81(s, 1H), 7.80 (s, 1H), 7.25-7.19 (m, 4H), 6.91 (br. s., 1H), 5.26-5.23 (m, 1H), 5.10 (br. s., 1H), 4.71 (br. s., 2H), 4.46-4.27 (m, 3H), 3.85 (s, 3H), 3.82-3.78 (m, 1H), 3.09 (dd, 1H, J = 16.0, 4.8 Hz), 2.82 (d, 1H, J = 16.0 Hz) | 430 |
| 54 | 2 | ¹H-NMR (400 MHz, DMSO-d₆) δ ppm 8.60 (t, 1H, J = 6.0 Hz), 8.11 (s, 1H), 7.91 (d, 1H, J = 1.6 Hz), 7.78 (d, 2H, J = 2.0 Hz), 7.16 (d, 2H, J = 8.4 Hz), 7.13 (d, 2H, J = 8.4 Hz), 6.90 (d, 1H, J = 1.6 Hz), 4.70-4.19 (m, 7H), 3.64-3.60 (m, 1H), 2.27 (s, 3H), 1.43 (d, 6H, J = 6.4 Hz) | 430 |
| 55 | 1 | ¹H NMR (400 MHz, DMSO-d₆) δ 8.53 (q, J = 5.3, 4.6 Hz, 1H), 8.00 (s, 1H), 7.90 (d, J = 1.5 Hz, 1H), 7.78 (d, J = 3.6 Hz, 2H), 7.13 (q, J = 8.1 Hz, 4H), 6.88 (d, J = 1.7 Hz, 1H), 4.75 (s, 1H), 4.28 (d, J = 5.9 Hz, 3H), 3.98 (s, 1H), 3.83 (s, | 430 |

-continued

| Compound Number | Synthetic Method | ¹H MR | LC/MS M + 1 |
|---|---|---|---|
| | | 3H), 3.03 (s, 1H), 2.25 (s, 3H), 1.99 (q, J = 7.4 Hz, 2H), 0.83 (t, J = 7.3 Hz, 3H) | |
| 56 | 1 | ¹H-NMR (400 MHz, CDCl$_3$) δ ppm 7.92 (br.s, 1H), 7.78 (s, 1H), 7.70 (s, 1H), 7.58 (s, 1H), 7.16 (br.s, 4H), 6.90 (s, 1H), 5.10 (br.s., 2H), 4.85-4.83 (m, 2H), 4.58 (br.s, 1H), 3.97 (s, 3H), 3.63 (br.s, 1H), 2.33 (s, 3H), 1.86-1.79 (m, 2H), 0.89 (t, 3H, J = 7.2 Hz) | 430 |
| 57 | 1 | ¹H NMR (400 MHz, DMSO-d$_6$) δ 8.80 (t, J = 5.9 Hz, 1H), 8.38 (s, 1H), 8.08-7.68 (m, 4H), 7.26-6.96 (m, 4H), 6.85 (d, J = 1.6 Hz, 1H), 6.59 (s, 1H), 4.82-3.96 (m, 6H), 3.83 (s, 3H), 3.04 (s, 4H), 2.26 (s, 3H) | 431 |
| 58 | 2 | 1H-NMR (400 MHz, DMSO-d6) δ ppm 8.59 (d, 1H, J = 7.6 Hz), 8.36 (d, 1H, J = 1.6 Hz), 8.04 (d, 1H, J = 1.2 Hz), 7.79-7.75 (m, 2H), 7.35 (dd, 2H, J = 8.4, 5.6 Hz), 7.17-7.12 (m, 2H), 6.97 (s, 1H), 6.45 (d, 1H, J = 8.4 Hz), 5.95 (s, 2H), 5.01-4.93 (m, 1H), 4.71-4.56 (m, 2H), 4.32-4.12 (m, 2H), 3.64-3.57 (m, 1H), 1.37 (d, 3H, J = 7.2 Hz) | 432 |
| 59 | 1 | ¹H NMR (400 MHz, DMSO-d$_6$) δ 8.47 (t, J = 5.9 Hz, 1H), 8.01 (s, 1H), 7.91 (d, J = 1.6 Hz, 1H), 7.78 (d, J = 3.0 Hz, 1H), 7.19-7.08 (m, 4H), 6.87 (d, J = 1.6 Hz, 1H), 5.39 (t, J = 5.3 Hz, 1H), 4.70 (s, 1H), 4.49 (d, J = 9.1 Hz, 1H), 4.29 (d, J = 5.8 Hz, 2H), 4.16 (s, 1H), 3.83 (s, 3H), 3.79 (d, J = 5.4 Hz, 2H), 2.25 (s, 3H) | 432 |
| 60 | 1 | ¹H NMR (400 MHz, DMSO-d$_6$) δ 8.78 (s, 1H), 8.11-7.67 (m, 4H), 7.24-7.03 (m, 4H), 6.94 (d, J = 1.7 Hz, 1H), 4.92-4.14 (m, 6H), 3.83 (s, 3H), 3.32 (s, 3H), 2.26 (s, 3H) | 432 |
| 61 | 2 | ¹H-NMR (400 MHz, DMSO-d$_6$) δ ppm 8.59 (t, 1H, J = 5.6 Hz), 8.23 (d, 1H, J = 1.2 Hz), 7.83-7.81 (m, 3H), 7.42 (d, 2H, J = 8.8 Hz), 7.16-7.11 (m, 5H), 4.27 (br.s, 2H), 3.65-3.60 (m, 1H), 2.26 (s, 3H). | 432 |
| 62 | 2 | ¹H-NMR (400 MHz, DMSO-d$_6$) δ ppm 8.60-8.57 (m, 1H), 8.27 (s, 1H), 7.91 (s, 1H), 7.82 (s, 1H), 7.75 (d, 1H, J = 7.6 Hz), 7.38 (t, 1H, J = 8.0 Hz), 7.26 (d, 1H, J = 7.6 Hz), 7.16-7.11 (m, 4H), 4.75-4.67 (m, 2H), 4.33-4.26 (m, 5H), 3.65-3.54 (m, 1H), 2.26 (s, 3H) | 432 |
| 63 | 2 | ¹H NMR (400 MHz, DMSO-d$_6$) δ 8.58 (t, J = 5.9 Hz, 1H), 7.89 (d, J = 1.7 Hz, 1H), 7.86 (s, 1H), 7.20-7.05 (m, 4H), 6.73 (d, J = 1.7 Hz, 1H), 4.79-4.56 (m, 2H), 4.27 (m, 4H), 3.61 (tt, J = 8.7, 5.7 Hz, 1H), 2.59 (s, 3H), 2.42 (s, 3H), 2.26 (s, 3H) | 433 |
| 64 | 1 | ¹H-NMR (400 MHz, DMSO-d$_6$) δ ppm 8.41 (d, 1H, J = 7.6 Hz), 8.00 (s, 1H), 7.91 (s, 1H), 7.79 (s, 1H), 7.77 (s, 1H), 7.37-7.33 (m, 2H), 7.16-7.12 (m, 2H), 6.85 (s, 1H), 4.98-4.95 (m, 1H), 4.78 (br. s., 1H), 4.31 (br. s., 2H), 3.99 (br. s., 1H), 3.83 (s, 3H), 1.58 (s, 3H), 1.37 (d, 3H, J = 7.2 Hz) | 434 |
| 65 | 2 | ¹H-NMR (400 MHz, DMSO-d$_6$) δ ppm 8.59 (d, 1H, J = 8.0 Hz), 7.91 (s, 1H), 7.81 (s, 1H), 7.78 (d, 1H, J = 2.0 Hz), 7.38-7.34 (m, 2H), 7.18-7.13 (m, 2H), 6.76 (s, 1H), 5.00-4.96 (m, 1H), 4.78-4.12 (m, 4H), 3.76 (s, 3H), 3.63-3.60 (m, 1H), 2.30 (s, 3H), 1.37 (d, 3H, J = 7.2 Hz) | 434 |
| 66 | 2 | ¹H-NMR (400 MHz, CD$_3$OD) δ ppm 8.02 (s, 1H), 7.92 (br.s, 1H), 7.86 (br.s, 1H), 7.79 (br.s, 1H), 7.35-7.32 (m, 2H), 7.25-7.21 (m, 1H), 7.05 (t, 2H, J = 8.4 Hz), 4.73-4.59 (m, 2H), 3.90 (s, 3H), 3.85-3.81 (m, 1H), 1.84-1.79 (m, 2H), 0.92 (t, 3H, J = 6.8 Hz) | 434 |
| 67 | 2 | ¹H NMR (400 MHz, DMSO-d6) δ 8.83-8.70 (m, 2H), 7.89-7.74 (m, 2H), 7.13 (qd, J = 8.7, 2.6 Hz, 4H), 6.92-6.81 (m, 1H), 6.25 (d, J = 2.7 Hz, 1H), 4.79 (br.s, 1H), 4.64 (br.s, 1H), 4.44-4.14 (m, 6H), 3.79 (dd, J = 6.4, 4.2 Hz, 2H), 2.41 (d, J = 6.0 Hz, 2H), 2.25 (s, 3H) - methoxy peak buried under water signal | 434 |
| 68 | 3 | ¹H-NMR (400 MHz, DMSO-d$_6$) δ 8.58 (d, 1H, J = 8.0 Hz), 7.85 (s, 1H), 7.77 (s, 1H), 7.70 (s, 1H), 7.35 (dd, J = 5.6, 8.0 Hz, 2H), 7.17-7.12 (m, 2H), 6.77 (s, 1H), 4.99-4.95 (m, 1H), 4.79-4.03 (m, 6H), 3.63-3.56 (m, 4H), 1.37 (d, 3H, J = 6.8 Hz) | 435 |
| 69 | 2 | ¹H NMR (400 MHz, DMSO-d$_6$) δ 8.76 (t, J = 6.0 Hz, 1H), 8.00 (s, 1H), 7.92 (d, J = 1.6 Hz, 1H), 7.86-7.76 (m, 2H), 7.71 (d, J = 8.0 Hz, 2H), 7.51 (d, J = 7.9 Hz, 2H), 6.88 (d, J = 1.7 Hz, 1H), 4.80-4.53 (m, 2H), 4.46-4.18 (m, 4H), 3.84 (s, 3H), 3.71-3.61 (m, 1H). | 436 |
| 70 | 1 | 1H-NMR (400 MHz, DMSO-d6) δ ppm 8.61 (t, J = 5.2 Hz, 1H), 8.00 (s, 1H), 7.91 (d, 1H, J = 1.2 Hz), 7.79 (s, 1H), 7.77 (s, 1H), 7.38 (d, 2H, J = 8.8 Hz), 7.28 (d, 2H, J = 8.4 Hz), 6.86 (d, 1H, J = 1.2 Hz), 4.79 (br. s, 1H), 4.33-4.29 (m, 4H), 3.97 (br. s., 1H), 3.83 (s, 3H), 1.60 (s, 3H) | 436 |

| Compound Number | Synthetic Method | $^1$H MR | LC/MS M + 1 |
|---|---|---|---|
| 71 | 1 | $^1$H-NMR (400 MHz, DMSO-$d_6$) δ ppm 8.78 (d, 1H, J = 6.8 Hz), 7.98 (s, 1H), 7.88 (s, 1H), 7.76 (d, 1H, J = 4.0 Hz), 7.37-7.31 (m, 4H), 6.85 (s, 1H), 4.65 (br.s, 1H), 3.82 (s, 3H), 3.63-3.58 (m, 1H), 1.33 (d, 3H, J = 7.2 Hz) | 436 |
| 72 | 2 | $^1$H-NMR (400 MHz, DMSO-$d_6$) δ ppm 12.80 (br. s., 1H), 8.57 (d, 1H, J = 8.4 Hz), 8.05 (br. s., 1H), 7.93 (d, 1H, J = 1.6 Hz), 7.85 (br. s., 1H), 7.78 (s, 1H), 7.39 (d, 2H, J = 8.8 Hz), 7.32 (d, 2H, J = 9.6 Hz), 6.89 (s, 1H), 4.76-4.51 (m, 3H), 4.50-4.07 (m, 2H), 3.66-3.61 (m, 1H), 1.69-1.64 (m, 2H), 0.83 (t, 3H, J = 7.2 Hz) | 436 |
| 73 | 1 | $^1$H-NMR (400 MHz, DMSO-$d_6$) δ ppm 8.01 (s, 1H), 7.88 (d, 1H, J = 1.2 Hz), 7.77 (s, 1H), 7.75 (s, 1H), 7.40-7.33 (m, 4H), 6.81 (d, 1H, J = 1.2 Hz), 4.57 (br. s., 1H), 4.18 (br. s., 2H), 3.90-3.71 (m, 4H), 3.48-3.45 (m, 1H), 2.92-2.81 (m, 1H), 2.65-2.60 (m, 1H), 2.33 (br. s., 1H), 1.72-1.63 (m, 1H), 1.52-1.43 (m, 1H), 0.73 (t, 3H, J = 7.2 Hz) | 436 |
| 74 | 2 | $^1$H-NMR (400 MHz, CDCl$_3$ + CD$_3$OD) δ ppm 7.82 (d, 2H, J = 11.2 Hz), 7.48 (d, 2H, J = 8.0 Hz), 7.21-7.18 (m, 4H), 7.11 (d, 2H, J = 7.6 Hz), 6.76 (s, 1H), 6.24 (br.s, 1H), 4.46 (d, 2H, J = 4.4 Hz), 2.35 (s, 3H), 1.36-1.32 (m, 1H), 1.00-0.98 (m, 2H), 0.73-0.72 (m, 2H) | 438 |
| 75 | 2 | $^1$H-NMR (400 MHz, DMSO-$d_6$) δ ppm 8.67 (br. s., 1H), 8.55 (s, 1H), 8.47 (s, 1H), 8.20 (d, J = 9.6 Hz, 1H), 8.10 (d, J = 9.6 Hz, 1H), 7.89 (s, 1H), 7.47 (s, 1H), 7.19-7.14 (m, 4H), 4.80-4.72 (m, 2H), 4.48-4.24 (m, 4H), 3.68-3.35 (m, 1H), 2.28 (s, 3H) | 440 |
| 76 | 1 | $^1$H NMR (500 MHz, DMSO-d6) δ 8.66 (t, J = 5.8 Hz, 1H), 7.99 (s, 1H), 7.90 (d, J = 1.6 Hz, 1H), 7.81-7.74 (m, 2H), 7.46-7.33 (m, 2H), 7.28 (dd, J = 8.3, 2.1 Hz, 1H), 6.86 (d, J = 1.7 Hz, 1H), 4.63 (d, J = 50.3 Hz, 2H), 4.42-4.09 (m, 4H), 3.83 (s, 3H), 3.67-3.57 (m, 1H). | 440 |
| 77 | 1 | $^1$H-NMR (400 MHz, DMSO-$d_6$) δ ppm 8.86 (d, 1H, J = 6.4 Hz), 7.99 (s, 1H), 7.90 (s, 1H), 7.76 (d, 2H, J = 6.4 Hz), 7.38-7.34 (m, 2H), 7.23 (d, 1H, J = 8.0 Hz), 6.86 (s, 1H), 4.81 (br.s, 1H), 4.68 (br.s, 1H), 4.46-4.07 (m, 3H), 3.81 (s, 3H), 3.51 (s, 2H) | 440 |
| 78 | 1 | $^1$H-NMR (400 MHz, CD$_3$OD) δ ppm 8.05 (d, 1H, J = 1.2 Hz), 7.94 (s, 1H), 7.89 (s, 1H), 7.81 (s, 1H), 7.68 (d, 2H, J = 8.4 Hz), 7.48 (d, 2H, J = 8.8 Hz), 7.27 (s, 1H), 5.00 (br.s, 2H), 4.72-4.69 (m, 2H), 3.99-3.93 (m, 1H), 3.90 (s, 3H), 1.70 (s, 6H) | 441 |
| 79 | 2 | $^1$H NMR (400 MHz, DMSO-$d_6$) δ 8.59 (s, 1H), 8.16 (d, J = 0.8 Hz, 1H), 7.91 (d, J = 1.6 Hz, 1H), 7.87-7.66 (m, 2H), 7.23-7.04 (m, 4H), 6.90 (d, J = 1.6 Hz, 1H), 4.94-4.01 (m, 7H), 3.62 (tt, J = 8.7, 5.6 Hz, 1H), 2.46-2.31 (m, 4H), 2.27 (s, 3H), 1.93-1.67 (m, 2H) | 442 |
| 80 | 2 | $^1$H-NMR (400 MHz, DMSO-$d_6$) δ ppm 8.61 (t, 1H, J = 6.0 Hz), 8.54 (d, 1H, J = 2.4 Hz), 8.10 (d, 1H, J = 2.0 Hz), 7.90 (dd, 1H, J = 2.4, 8.8 Hz), 7.80 (s, 1H), 7.16 (d, 2H, J = 8.4 Hz), 7.12 (d, 2H, J = 8.0 Hz), 7.02 (d, 1H, J = 1.6 Hz), 7.66 (d, 1H, J = 8.8 Hz), 4.74-4.21 (m, 6H), 3.65-3.58 (m, 1H), 3.03 (s, 6H), 2.27 (s, 3H) | 442 |
| 81 | 3 | $^1$H-NMR (400 MHz, DMSO-$d_6$) δ ppm 10.64 (s, 1H), 8.01 (s, 1H), 7.95 (d, 1H, J = 1.2 Hz), 7.79-7.84 (m, 6H), 6.91 (d, 1H, J = 1.2 Hz), 4.95 (d, 1H, J = 4.4 Hz), 4.21-4.84 (m, 4H), 3.98 (s, 3H), 3.83 (dd, 1H, J = 2.8 Hz), 1.04 (d, 3H, J = 5.6 Hz) | 443 |
| 82 | 2 | $^1$H-NMR (400 MHz, CD$_3$OD) δ ppm 8.43 (s, 1H), 8.17 (d, 1H, J = 5.6 Hz), 7.91 (s, 1H), 7.54-7.47 (m, 2H), 7.42 (s, 1H), 7.20-7.12 (m, 4H), 5.07 (d, 1H, J = 7.2 Hz), 4.66 (br.s, 1H), 4.57 (d, 1H, J = 8.8 Hz), 4.39 (s, 2H), 4.24 (br.s, 1H), 4.08 (s, 3H), 2.30 (s, 3H), 1.72 (s, 3H) | 443 |
| 83 | 1 | | 444 |
| 84 | 1 | $^1$H-NMR (400 MHz, DMSO-$d_6$) δ ppm 8.60 (t, 1H, J = 5.6 Hz), 8.0 (s, 1H), 7.91 (d, 1H, J = 1.6 Hz), 7.79 (s, 1H), 7.78 (s, 1H), 7.35 (d, 2H, J = 8.4 Hz), 7.20 (d, 2H, J = 8.0 Hz), 6.88 (d, 1H, J = 1.2 Hz), 4.71-4.62 (m, 2H), 4.41-4.20 (m, 4H), 3.83 (s, 3H), 3.66-3.57 (m, 1H), 1.26 (s, 9H) | 444 |
| 85 | 2 | $^1$H NMR (400 MHz, DMSO-d6) δ 8.63 (t, J = 5.9 Hz, 1H), 8.22 (d, J = 0.8 Hz, 1H), 7.96 (d, J = 1.6 Hz, 1H), 7.82 (d, J = 0.8 Hz, 1H), 7.81 (s, 1H), 7.24-7.11 (m, 4H), 6.95 (d, J = 1.6 Hz, 1H), 4.80-4.55 (m, 2H), 4.34 (m, 4H), 3.71-3.60 (m, 1H), 2.30 (s, 3H), 1.56 (s, 9H). | 444 |
| 86 | 1 | $^1$H NMR (400 MHz, DMSO-$d_6$) δ 8.52 (t, J = 5.9 Hz, 1H), 8.01 (s, 1H), 7.93 (d, J = 1.6 Hz, 1H), 7.81 (s, 1H), 7.77 (d, J = 0.8 Hz, 1H), 7.52 (s, 2H), 7.31-7.00 (m, 4H), 6.86 | 445 |

| Compound Number | Synthetic Method | ¹H NMR | LC/MS M + 1 |
|---|---|---|---|
| | | (d, J = 1.7 Hz, 1H), 4.83 (s, 2H), 4.46 (s, 2H), 4.30 (d, J = 5.8 Hz, 2H), 3.83 (s, 3H), 2.25 (s, 3H) | |
| 87 | 2 | ¹H-NMR (400 MHz, CD$_3$OD) δ ppm 8.00 (d, 1H, J = 8.0 Hz), 7.91 (s, 1H), 7.25-7.14 (m, 5H), 6.30 (br.s, 1H), 4.39 (s, 2H), 4.21 (d, 2H, J = 2.0 Hz), 3.81-3.73 (m, 3H), 2.66-2.52 (m, 2H), 2.31 (s, 3H), 2.16 (d, 3H, J = 15.2 Hz) | 445 |
| 88 | 1 | ¹H NMR (400 MHz, DMSO-d$_6$) δ 8.95 (s, 1H), 7.99 (s, 1H), 7.96-7.91 (m, 1H), 7.82 (s, 1H), 7.76 (s, 1H), 7.22-7.09 (m, 4H), 6.81 (s, 1H), 4.76 (s, 1H), 4.55 (s, 1H), 4.32 (d, J = 5.7 Hz, 3H), 4.19 (s, 1H), 3.83 (s, 3H), 2.99 (s, 2H), 2.26 (s, 3H). | 445 |
| 89 | 2 | ¹H NMR (400 MHz, DMSO-d$_6$) δ 8.58 (t, J = 6.0 Hz, 1H), 7.86 (d, J = 1.6 Hz, 1H), 7.80 (s, 1H), 7.77 (s, 1H), 7.23-6.98 (m, 4H), 6.80 (d, J = 1.7 Hz, 1H), 4.94-3.98 (m, 8H), 3.73-3.56 (m, 1H), 2.27 (s, 3H), 1.35 (d, J = 6.6 Hz, 6H) | 445 |
| 90 | 1 | ¹H NMR (400 MHz, DMSO-d6) δ 8.52 (d, J = 8.4 Hz, 1H), 7.99 (s, 1H), 7.89 (d, J = 1.6 Hz, 1H), 7.77, 7.76 (2 closely spaced singlets, 2H), 7.18 (d, J = 7.7 Hz, 2H), 7.12 (d, J = 7.8 Hz, 2H), 6.86 (s, 1H), 4.91 (td, J = 8.4, 6.0 Hz, 1H), 4.77-3.97 (m, 6H), 3.82 (s, 3H), 3.66-3.55 (m, 1H), 2.26 (s, 3H), 1.72 (dp, J = 20.0, 6.5 Hz, 2H). | 445 |
| 91 | 2 | ¹H-NMR (400 MHz, DMSO-d$_6$) δ ppm 8.60 (t, 1H, J = 5.6 Hz), 8.07 (s, 1H), 7.82-7.79 (m, 2H), 7.16 (d, 2H, J = 8.0 Hz), 7.13 (d, 2H, J = 7.6 Hz), 7.08 (s, 1H), 7.0 (dd, 1H, J = 2.4, 11.2 Hz), 6.82 (ddd, 1H, J = 2.4, 8.4, 16.8 Hz), 4.75-4.65 (m, 2H), 4.35-4.21 (m, 4H), 3.91 (s, 3H), 3.64-3.61 (m, 1H), 2.27 (s, 3H) | 446 |
| 92 | 2 | ¹H-NMR (400 MHz, DMSO-d$_6$) δ ppm 8.61 (br. s., 1H), 8.19 (s, 1H), 7.82 (s, 1H), 7.71 (d, 1H, J = 12.8 Hz), 7.58 (d, 1H, J = 8.8 Hz), 7.16-7.11 (m, 6H), 4.74-4.63 (m, 2H), 4.28-4.18 (m, 4H), 3.85 (s, 3H), 3.62 (br. s., 1H), 2.27 (s, 3H) | 446 |
| 93 | 3 | ¹H-NMR (400 MHz, DMSO-d$_6$) δ ppm 8.60 (t, 1H, J = 5.6 Hz), 8.01 (s, 1H), 7.92 (t, 1H, J = 1.6 Hz), 7.79 (d, 2H, J = 2.8 Hz), 7.15 (d, 2H, J = 8.0 Hz), 7.12 (d, 2H, J = 8.0 Hz), 6.89 (d, 1H, J = 1.2 Hz), 4.94 (d, 1H, J = 4.4 Hz), 4.69-4.20 (m, 6H), 3.98 (s, 3H), 3.63-3.59 (m, 1H), 2.28 (s, 3H), 1.04 (d, 3H, J = 5.2 Hz) | 446 |
| 94 | 2 | ¹H NMR (400 MHz, DMSO-d6) δ 8.49 (d, J = 8.3 Hz, 1H), 7.99 (s, 1H), 7.90 (d, J = 1.6 Hz, 1H), 7.77 (two closely spaced peaks, 2H), 7.18 (d, J = 8.1 Hz, 2H), 7.12 (d, J = 7.9 Hz, 2H), 6.86 (s, 1H), 4.92 (q, J = 8.6, 8.2 Hz, 1H), 4.75-4.07 (m, 6H), 3.83 (s, 3H), 3.60 (ddd, J = 14.4, 8.8, 5.6 Hz, 1H), 2.26 (s, 3H), 1.81 (dtd, J = 25.1, 13.6, 7.0 Hz, 2H)-one peak is partially buried under water signal. | 446 |
| 95 | 2 | ¹H-NMR (400 MHz, DMSO-d$_6$) δ ppm 8.60 (d, 1H, J = 8.0 Hz), 8.11 (s, 1H), 7.91 (d, 1H, J = 1.6 Hz), 7.78 (d, 2H, J = 1.6 Hz), 7.38-7.35 (m, 2H), 7.19-7.13 (m, 2H), 6.89 (s, 1H), 5.00-4.96 (m, 1H), 4.75-4.22 (m, 4H), 3.64-3.60 (m, 1H), 1.44 (d, 6H, J = 6.8 Hz), 1.38 (d, 3H, J = 7.2 Hz) | 448 |
| 96 | 1 | ¹H-NMR (400 MHz, DMSO-d$_6$ + CD$_3$OD) δ ppm 7.97 (s, 1H), 7.86 (s, 1H), 7.74 (d, 2H, J = 4.8 Hz), 7.66 (d, 1H, J = 7.2 Hz), 7.38-7.33 (m, 4H), 6.80 (s, 1H), 4.80-4.71 (m, 1H), 4.35 (br.s, 2H), 3.82 (s, 3H), 1.36 (d, 2H, J = 2.4 Hz), 0.98 (s, 2H). | 448 |
| 97 | 1 | ¹H NMR (400 MHz, DMSO-d$_6$) δ 8.53 (d, J = 8.1 Hz, 1H), 8.00 (s, 1H), 7.91 (d, J = 1.6 Hz, 1H), 7.82-7.75 (m, 2H), 7.32 (d, J = 1.6 Hz, 1H), 7.24 (d, J = 1.2 Hz, 2H), 6.89 (d, J = 1.6 Hz, 1H), 5.30 (q, J = 7.9 Hz, 1H), 4.66-4.24 (m, 4H), 3.84 (s, 3H), 3.59 (tt, J = 8.6, 5.7 Hz, 1H), 3.00-2.75 (m, 2H), 2.42 (m, 1H), 1.83 (m, 1H) | 448 |
| 98 | 3 | ¹H-NMR (400 MHz, CD$_3$OD) δ ppm 7.94 (br.s, 1H), 7.79 (s, 1H), 7.76 (d, 1H, J = 2.0 Hz), 7.71 (s, 1H), 7.37-7.34 (m, 2H), 7.05 (t, 2H, J = 8.4 Hz), 6.85 (s, 1H), 5.06-5.03 (m, 1H), 4.24 (t, 2H, J = 6.4 Hz), 3.90 (t, 2H, J = 6.4 Hz), 3.69-3.63 (m, 1H), 1.47 (d, 3H, J = 6.8 Hz) | 450 |
| 99 | 1 | ¹H NMR (400 MHz, DMSO-d6) δ 8.55 (d, J = 8.2 Hz, 1H), 7.99 (s, 1H), 7.90 (d, J = 1.6 Hz, 1H), 7.77 (d, J = 3.3 Hz, 2H), 7.43-7.36 (m, 2H), 7.36-7.27 (m, 2H), 6.86 (s, 1H), 4.73 (q, J = 7.6 Hz, 1H), 4.61-4.05 (m, 4H), 3.83 (s, 3H), 3.63 (tt, J = 8.7, 5.7 Hz, 1H), 1.68 (p, J = 7.3 Hz, 2H), 0.83 (t, J = 7.3 Hz, 3H). | 450 |
| 100 | 2 | ¹H NMR (300 MHz, DMSO-d6) δ 8.46 (d, J = 7.8 Hz, 1H), 8.01 (s, 1H), 7.92 (d, J = 1.6 Hz, 1H), 7.79 (d, J = 5.7 Hz, 2H), 7.43-7.31 (m, 4H), 6.86 (d, J = 1.7 Hz, 1H), 4.97 (q, J = 7.1 Hz, 1H), 4.47-3.91 (m, 4H), 3.84 (s, 3H), 1.59 (s, 3H), 1.38 (d, J = 7.0 Hz, 3H). | 450 |

| Compound Number | Synthetic Method | ¹H MR | LC/MS M + 1 |
|---|---|---|---|
| 101 | 2 | ¹H NMR (400 MHz, DMSO-d6) δ 8.42 (d, J = 8.4 Hz, 1H), 7.98 (s, 1H), 7.92 (s, 1H), 7.78 (d, J = 9.1 Hz, 2H), 7.38 (s, 4H), 7.09 (s, 1H), 6.89 (d, J = 4.5 Hz, 1H), 4.99 (m, 1H), 4.80 (d, J = 39.7 Hz, 1H), 4.50-4.31 (m, 2H), 4.14-4.03 (m, 1H), 3.83 (s, 3H), 1.41 (d, J = 7.0 Hz, 3H). | 452 |
| 102 | 1 | ¹H-NMR (400 MHz, DMSO-d₆) δ ppm 8.89 (t, 1H, J = 6.4 Hz), 8.00 (s, 1H), 7.95 (d, 1H, J = 1.2 Hz), 7.82 (s, 1H), 7.78 (s, 1H), 7.39-7.37 (m, 2H), 7.31-7.29 (d, 2H, J = 8.4 Hz), 6.94 (d, 1H, J = 1.6 Hz), 4.81, 4.64 (br. s., 2H), 4.34, 4.24 (br. s., 2H), 4.32 (d, 2H, J = 6.0 Hz), 3.84 (s, 3H), 3.33 (s, 3H) | 452 |
| 103 | 1 | ¹H-NMR (400 MHz, DMSO-d₆) δ ppm 8.61 (d, 1H, J = 6.8 Hz), 8.00 (s, 1H), 7.92 (s, 1H), 7.79 (br. s., 2H), 7.49-7.35 (m, 4H), 6.88 (s, 1H), 4.98-4.91 (m, 2H), 4.70-4.10 (m, 4H), 3.84 (s, 3H), 3.69 (br. s., 1H), 3.57 (br. s., 2H) | 452 |
| 104 | 1 | ¹H-NMR (400 MHz, DMSO-d₆) δ ppm 10.33 (s, 1H), 8.00 (s, 1H), 7.92 (d, 1H, J = 1.5 Hz), 7.81 (s, 1H), 7.78 (s, 1H), 7.60 (d, 2H, J = 8.8 Hz), 7.50 (d, 2H, J = 9.2 Hz), 6.89 (d, 1H, J = 1.6 Hz), 4.75-4.28 (m, 4H), 3.83 (s, 3H), 3.80-3.74 (m, 1H) | 453 |
| 105 | 2 | ¹H NMR (400 MHz, DMSO-d6) δ 8.61 (t, J = 5.9 Hz, 1H), 8.49 (s, 1H), 8.30 (d, J = 1.7 Hz, 1H), 8.00 (s, 1H), 7.92 (dd, J = 7.9, 1.5 Hz, 1H), 7.84 (s, 1H), 7.64 (d, J = 7.9 Hz, 1H), 7.23 (d, J = 1.7 Hz, 1H), 7.20-7.09 (m, 4H), 4.84-4.64 (m, 2H), 4.43-4.16 (m, 6H), 3.63 (m, 1H), 2.27 (s, 3H). | 453 |
| 106 | 2 | ¹H-NMR (400 MHz, DMSO-d₆) δ ppm 10.59 (s, 1H), 8.09 (s, 1H), 7.82-7.77 (m, 4H), 7.66 (d, 2H, J = 8.8 Hz), 7.02 (s, 1H), 6.90 (d, 2H, J = 8.8 Hz), 4.80-4.70 (m, 2H), 4.64-4.58 (m, 1H), 4.41-4.32 (m, 2H), 3.83-3.80 (m, 1H), 1.24 (d, 6H, J = 5.6 Hz) | 453 |
| 107 | 2 | ¹H-NMR (400 MHz, DMSO-d₆) δ ppm 10.60 (s, 1H), 8.15 (s, 1H), 7.83-7.77 (m, 4H), 7.68 (d, 2H, J = 8.4 Hz), 7.44 (d, 2H, J = 8.0 Hz), 7.08 (s, 1H), 4.96 (s, 1H), 4.80-4.70 (m, 2H), 4.42-4.30 (m, 2H), 3.82-3.81 (m, 1H), 1.41 (s, 6H) | 453 |
| 108 | 2 | ¹H NMR (400 MHz, DMSO-d6) δ ppm 8.60 (t, J = 5.9 Hz, 1H), 8.15 (d, J = 1.7 Hz, 1H), 7.81 (s, 1H), 7.68 (d, J = 8.3 Hz, 2H), 7.29 (d, J = 8.3 Hz, 2H), 7.21-7.10 (m, 4H), 7.07 (d, J = 1.8 Hz, 1H), 4.84-4.58 (m, 2H), 4.28 (d, J = 5.8 Hz, 4H), 3.63 (m, 1H), 2.27 (s, 3H), 0.93 (d, J = 15.0 Hz, 4H). | 454 |
| 109 | 2 | ¹H-NMR (400 MHz, CDCl₃) δ ppm 7.89 (d, 2H, J = 9.6 Hz), 7.48 (d, 2H, J = 8.4 Hz), 7.18-7.07 (m, 7H), 6.87 (br.s, 1H), 5.16 (br.s, 1H), 4.96 (br.s, 1H), 4.82 (br.s, 1H), 4.69 (br.s, 1H), 4.42 (br.s, 2H), 3.77-3.76 (m, 1H), 3.75-3.71 (m, 1H), 2.29 (s, 3H), 0.80 (d, 4H, J = 6.0 Hz) | 454 |
| 110 | 2 | ¹H NMR (300 MHz, DMSO-d₆) δ 8.61 (t, J = 5.7 Hz, 1H), 8.01 (s, 1H), 7.93 (d, J = 1.6 Hz, 1H), 7.83-7.74 (m, 2H), 7.49-7.23 (m, 3H), 6.87 (d, J = 1.7 Hz, 1H), 4.92-4.65 (m, 2H), 4.49-4.25 (m, 4H), 4.06-3.93 (m, 1H), 3.84 (s, 3H), 1.60 (s, 3H) | 454 |
| 111 | 2 |  | 455 |
| 112 | 2 | ¹H NMR (400 MHz, DMSO-d6) δ 8.76 (t, J = 6.0 Hz, 1H), 8.00 (s, 1H), 7.92 (d, J = 1.6 Hz, 1H), 7.86-7.76 (m, 2H), 7.71 (d, J = 8.0 Hz, 2H), 7.51 (d, J = 7.9 Hz, 2H), 6.88 (d, J = 1.7 Hz, 1H), 4.80-4.53 (m, 2H), 4.46-4.18 (m, 4H), 3.84 (s, 3H), 3.71-3.61 (m, 1H). | 456 |
| 113 | 2 | ¹H-NMR (400 MHz, DMSO-d₆) δ ppm 8.59 (t, 1H, J = 6.0 Hz), 8.09 (s, 1H), 7.80 (s, 1H), 7.31 (d, 1H, J = 2.4 Hz), 7.23 (d, 1H, J = 2.0 Hz), 7.17-7.12 (m, 4H), 7.02 (s, 1H), 6.85 (d, 1H, J = 8.4 Hz), 4.29-4.27 (m, 4H), 4.25 (s, 2H), 3.64-3.56 (m, 1H), 2.27 (s, 3H) | 456 |
| 114 | 2 | ¹H-NMR (400 MHz, CD₃OD) δ ppm 8.69 (d, 1H, J = 7.6 Hz), 8.14 (s, 1H), 7.86 (s, 1H), 7.56 (d, 2H, J = 7.6 Hz), 7.39-7.35 (m, 3H), 7.11-7.03 (m, 4H), 5.09-5.04 (m, 1H), 4.98-4.92 (m, 2H), 4.60-4.46 (m, 2H), 3.78-3.76 (m, 1H), 1.93-1.90 (m, 1H), 1.48 (d, 3H, J = 6.8 Hz), 0.99-0.97 (m, 2H), 0.70-0.68 (m, 2H) | 456 |
| 115 | 2 | ¹H-NMR (400 MHz, DMSO-d₆) δ ppm 8.60 (t, 1H, J = 5.6 Hz), 8.10 (d, 1H, J = 0.8 Hz), 7.81 (s, 1H), 7.68 (d, 2H, J = 8.8 Hz), 7.16 (d, 2H, J = 8.8 Hz), 7.13 (d, 2H, J = 8.80 Hz), 7.02 (s, 1H), 8.92 (d, 2H, J = 8.8 Hz), 4.75-4.19 (m, 7H), 3.66-3.59 (m, 1H), 2.27 (s, 3H), 1.27 (d, 6H, J = 6.0 Hz) | 456 |
| 116 | 2 | ¹H NMR (400 MHz, DMSO-d6) δ 8.60 (t, J = 5.9 Hz, 1H), 8.17 (d, J = 1.6 Hz, 1H), 7.85-7.78 (m, 2H), 7.59 (dt, J = 7.4, 1.5 Hz, 1H), 7.39-7.25 (m, 2H), 7.20-7.04 (m, 5H), 4.99 (s, 1H), 4.68 (s, 2H), 4.28 (d, J = 5.8 Hz, 2H), 4.21 (s, 1H), 3.69-3.57 (m, 1H), 2.27 (s, 3H), 1.46 (s, 6H) | 456 |

-continued

| Compound Number | Synthetic Method | $^1$H MR | LC/MS M + 1 |
|---|---|---|---|
| 117 | 2 | $^1$H NMR (400 MHz, DMSO-d$_6$) δ 8.60 (t, J = 5.9 Hz, 1H), 8.15 (d, J = 1.6 Hz, 1H), 7.8 (s, 1H), 7.74-7.66 (m, 2H), 7.49-7.42 (m, 2H), 7.20-7.09 (m, 4H), 7.07 (d, J = 1.7 Hz, 1H), 4.98 (s, 1H), 4.76 (s, 1H), 4.67 (s, 2H), 4.35 (s, 1H), 4.28 (d, J = 5.8 Hz, 2H), 4.22 (s, 1H), 3.68-3.56 (m, 1H), 2.27 (s, 3H), 1.43 (s, 6H) | |
| 118 | 2 | $^1$H-NMR (400 MHz, CDCl$_3$ + CD$_3$OD) δ ppm 7.75 (s, 1H), 7.70 (s, 1H), 7.48-7.43 (m, 4H), 7.13-7.08 (m, 4H), 6.71 (s, 1H), 4.76 (br.s, 1H), 3.47 (s, 2H), 2.27 (s, 3H), 1.52 (s, 6H) | 456 |
| 119 | 1 | $^1$H-NMR (400 MHz, CDCl$_3$) δ ppm 7.76 (s, 1H), 7.59 (s, 1H), 7.55 (s, 1H), 7.45 (s, 1H), 7.10 (d, 2H, J = 7.6 Hz), 6.99 (d, 2H, J = 8.0 Hz), 6.48 (s, 1H), 5.60 (d, 1H, J = 8.4 Hz), 4.82 (d, 1H, J = 7.6 Hz), 4.51 (br.s, 4H), 3.87 (s, 3H), 3.40 (d, 1H, J = 8.4 Hz), 1.82-1.73 (m, 3H), 0.89 (d, 2H, J = 7.2 Hz), 0.83 (t, 3H, J = 7.2 Hz), 0.61 (d, 3H, J = 4.4 Hz) | 456 |
| 120 | 1 | $^1$H NMR (500 MHz, DMSO-d6) δ 8.68 (t, J = 5.8 Hz, 1H), 7.99 (s, 1H), 7.91 (d, J = 1.6 Hz, 1H), 7.82-7.74 (m, 2H), 7.61 (d, J = 2.1 Hz, 1H), 7.43 (dd, J = 8.3, 2.1 Hz, 1H), 7.38 (d, J = 8.4 Hz, 1H), 6.87 (d, J = 1.6 Hz, 1H), 4.65 (d, J = 47.0 Hz, 2H), 4.41-4.14 (m, 3H), 3.83 (s, 3H), 3.72-3.61 (m, 2H). | 456 |
| 121 | 1 | $^1$H-NMR (400 MHz, DMSO-d$_6$) δ ppm 8.84 (d, 1H, J = 6.0 Hz), 8.00 (s, 1H), 7.94 (s, 1H), 7.82 (s, 1H), 7.78 (s, 1H), 7.57 (s, 1H), 7.39 (s, 2H), 6.93 (s, 1H), 4.69 (br.s, 1H), 3.82 (s, 3H), 3.70-3.63(m, 6H). | 456 |
| 122 | 3 | $^1$H-NMR (400 MHz, DMSO-d$_6$) δ ppm 8.62 (t, 1H, J = 5.8 Hz), 8.13 (s, 1H), 7.92 (s, 1H), 7.80 (s, 2H), 7.16 (d, 2H, J = 8.0 Hz), 7.13 (d, 2H, J = 8.0 Hz), 6.90 (d, 1H, J = 1.6 Hz), 4.80-4.49 (m, 3H), 4.35-4.20 (m, 4H), 3.68-3.58 (m, 1H), 3.18-3.10 (m, 1H), 3.07-2.99 (m, 1H), 2.98-2.91 (m, 1H), 2.89-2.79 (m, 1H), 2.28 (s, 3H), 2.23-2.12 (m, 1H), 2.06-1.96 (m, 1H) | 457 |
| 123 | 1 | $^1$H NMR (400 MHz, DMSO-d6) δ 10.40 (s, 1H), 8.01 (s, 1H), 7.94 (d, J = 1.6 Hz, 1H), 7.82 (s, 1H), 7.79 (d, J = 0.8 Hz, 1H), 7.78-7.72 (m, 2H), 7.35 (d, J = 8.6 Hz, 2H), 6.91 (d, J = 1.6 Hz, 1H), 4.84-4.63 (br.m, 2H), 4.48-4.24 (br.m, 2H), 3.84 (s, 4H). | 458 |
| 124 | 2 | $^1$H-NMR (400 MHz, CD$_3$OD) δ ppm 8.65 (d, 1H, J = 7.6 Hz), 7.87 (s, 1H), 7.83 (s, 1H), 7.37-7.34 (m, 2H), 7.07-7.03 (m, 3H), 6.22 (br.s, 1H), 5.07-5.04 (m, 1H), 4.58 (br.s, 4H), 4.10 (s, 2H), 3.73 (br.s, 1H), 3.72 (s, 3H), 3.69-3.68 (m, 2H), 2.51 (br.s, 2H), 1.47 (d, 2H, J = 6.8 Hz). | 458 |
| 125 | 2 | $^1$H NMR (400 MHz, DMSO-d$_6$) δ 8.60 (t, J = 5.9 Hz, 1H), 8.16 (d, J = 1.6 Hz, 1H), 7.82 (d, J = 1.2 Hz, 1H), 7.76-7.66 (m, 2H), 7.33 (d, J = 8.0 Hz, 2H), 7.22-7.11 (m, 4H), 7.08 (d, J = 1.7 Hz, 1H), 5.20 (d, J = 4.3 Hz, 1H), 4.90-4.01 (m, 7H), 3.71-3.55 (m, 1H), 3.43 (t, J = 5.9 Hz, 2H), 2.27 (s, 3H) | 458 |
| 126 | 2 | $^1$H NMR (300 MHz, DMSO-d$_6$) δ 8.61 (t, J = 5.9 Hz, 1H), 7.89-7.73 (m, 2H), 7.27-7.07 (m, 4H), 6.82 (d, J = 1.9 Hz, 1H), 6.22 (d, J = 4.2 Hz, 1H), 4.65 (m, 2H), 4.41-4.04 (m, 6H), 3.64 (m, 3H), 2.45-2.34 (m, 2H), 2.28 (s, 3H), 1.08-0.94 (m, 3H) | 459 |
| 127 | 2 | $^1$H NMR (400 MHz, DMSO-d6) δ 8.59 (q, J = 5.1 Hz, 1H), 7.96-7.77 (m, 2H), 7.23-7.05 (m, 4H), 6.81 (dd, J = 26.1, 1.7 Hz, 1H), 6.41-6.30 (m, 1H), 4.65 (br.d, J = 36.3 Hz, 2H), 4.27 (m, 6H), 3.58 (ddd, J = 20.0, 10.8, 4.5 Hz, 3H), 2.41 (m, 2H), 2.27 (m, 4H), 2.19 (br.s, 1H), 1.01 (td, J = 7.4, 4.2 Hz, 3H). | 459 |
| 128 | 1 | $^1$H NMR (400 MHz, DMSO-d$_6$) δ 8.70 (t, J = 5.8 Hz, 1H), 8.02 (s, 1H), 7.91 (d, J = 1.6 Hz, 1H), 7.78 (d, J = 0.9 Hz, 2H), 7.29-7.01 (m, 4H), 6.89 (d, J = 1.6 Hz, 1H), 5.03-3.91 (m, 6H), 3.83 (s, 3H), 2.91 (d, J = 23.4 Hz, 2H), 2.26 (s, 3H), 2.17 (s, 6H) | |
| 129 | 2 | $^1$H NMR (300 MHz, DMSO-d6) δ 8.44 (d, J = 7.8 Hz, 1H), 7.81 (m, 3H), 7.44-7.28 (m, 2H), 7.23-7.08 (m, 2H), 6.74 (d, J = 1.7 Hz, 1H), 4.97 (m, 1H), 4.78 (s, 1H), 4.36 (d, J = 4.2 Hz, 2H), 4.07 (t, J = 7.2 Hz, 3H), 3.03 (t, J = 7.3 Hz, 2H), 2.60 (m, 2H), 1.59 (s, 3H), 1.39 (d, J = 7.0 Hz, 3H). | 460 |
| 130 | 2 | $^1$H-NMR (400 MHz, DMSO-d$_6$) δ ppm 8.61 (t, 1H, J = 5.6 Hz), 7.99 (s, 1H), 7.94 (s, 1H), 7.79 (d, 2H, J = 2.0 Hz), 7.15 (d, 2H, J = 8.0 Hz), 7.12 (d, 2H, J = 8.0 Hz), 6.90 (s, 1H), 4.72-4.18 (m, 7H), 3.99 (s, 2H), 3.63-3.60 (m, 1H), 2.27 (s, 3H), 1.07 (s, 6H) | 460 |

| Compound Number | Synthetic Method | ¹H MR | LC/MS M + 1 |
|---|---|---|---|
| 131 | 2 | ¹H-NMR (400 MHz, CD₃OD) δ ppm 8.11 (s, 1H), 8.01 (s, 1H), 7.91 (s, 1H), 7.85 (s, 1H), 7.32 (s, 1H), 7.20-7.12 (m, 4H), 4.76-4.74 (m, 1H), 4.11 (s, 2H), 3.53 (s, 2H), 2.30 (s, 3H), 1.19 (s, 6H) | 460 |
| 132 | 3 | ¹H-NMR (400 MHz, CD₃OD) δ ppm 8.63 (br.s, 1H), 8.13 (s, 1H), 8.02 (s, 1H), 7.84 (d, 2H, J = 3.6 Hz), 7.23-7.13 (m, 5H), 4.39 (d, 2H, J = 4.8 Hz), 3.75 (s, 3H), 2.31 (s, 3H), 1.58 (s, 6H) | 460 |
| 133 | 2 | ¹H NMR (400 MHz, DMSO-d₆) δ 8.86 (t, J = 5.8 Hz, 1H), 7.85 (d, J = 1.6 Hz, 1H), 7.77 (s, 1H), 7.69 (s, 1H), 7.31-6.84 (m, 4H), 6.76 (d, J = 1.7 Hz, 1H), 4.70 (m, 3H), 4.47 (s, 1H), 4.28 (m, 3H), 4.10 (s, 1H), 3.60 (s, 3H), 3.31 (s, 5H), 3.01 (s, 2H), 2.32 (s, 3H), 2.26 (s, 3H) | 460 |
| 134 | 2 | ¹H NMR (400 MHz, DMSO-d₆) δ 8.58 (t, J = 5.9 Hz, 1H), 7.87-7.72 (m, 2H), 7.22-7.06 (m, 4H), 6.80 (d, J = 1.7 Hz, 1H), 6.20 (s, 1H), 4.74-4.49 (m, 2H), 4.36-4.13 (m, 4H), 4.02 (br.s, 2H), 3.59 (m, 6H), 2.46-2.40 (m, 2H), 2.27 (s, 3H) | 461 |
| 135 | 2 |  | 461 |
| 136 | 2 | ¹H-NMR (400 MHz, DMSO-d₆) δ ppm 8.60 (d, 1H, J = 8.0 Hz), 8.28 (s, 1H), 7.95 (d, 2H, J = 1.6 Hz), 7.80 (s, 1H), 7.38-7.35 (m, 2H), 7.18-7.14 (m, 2H), 6.94 (s, 1H), 5.57-5.54 (m, 1H), 5.00-4.87 (m, 5H), 4.72-4.16 (m, 4H), 3.64-3.61 (m, 1H), 1.38 (d, 3H, J = 7.2 Hz) | 462 |
| 137 | 2 | ¹H NMR (400 MHz, DMSO-d6) δ 8.58 (d, J = 7.8 Hz, 1H), 8.18 (s, 1H), 7.92 (d, J = 1.6 Hz, 1H), 7.78 (d, J = 5.8 Hz, 2H), 7.39-7.29 (m, 2H), 7.20-7.09 (m, 2H), 6.90 (d, J = 1.8 Hz, 1H), 4.97 (m, 1H), 4.74-4.06 (m, 4H), 3.61 (tt, J = 8.7, 5.6 Hz, 1H), 1.53 (s, 9H), 1.36 (d, J = 6.9 Hz, 3H). | 462 |
| 138 | 1 | ¹H-NMR (400 MHz, CDCl₃) δ ppm 7.74-7.72 (m, 3H), 7.58 (s, 1H) 7.55-7.40 (m, 1H) 7.24-7.15 (m, 4H), 6.95 (d, 1H, J = 5.6 Hz), 5.03-4.75 (m, 2H), 4.71-4.73 (m, 1H), 4.59-4.50 (m, 1H), 4.23-4.15 (m, 1H) 3.93 (s, 3H), 3.80-3.68 (m, 1H), 1.09 (br.s, 1H), 0.53 (br.s, 2H), 0.31-0.25 (m, 2H) | 462 |
| 139 | 2 | ¹H-NMR (400 MHz, DMSO-d₆) δ ppm 8.57 (d, 1H, J = 8.4 Hz), 8.37 (s, 1H), 8.05 (s, 1H), 7.83-7.72 (m, 2H), 7.39 (d, 2H, J = 8.4 Hz), 7.33 (d, 2H, J = 8.4 Hz), 6.98 (s, 1H), 6.46 (d, 1H, J = 8.4 Hz), 5.96-5.91 (m, 2H), 4.78-4.50 (m, 3H), 4.50-4.00 (m, 2H), 3.70-3.65 (m, 1H), 1.74-1.62 (m, 2H), 0.85 (t, 3H, J = 7.2 Hz) | 462 |
| 140 | 2 | ¹H-NMR (400 MHz, CD₃OD) δ ppm 7.92 (s, 1H), 7.78 (s, 2H), 7.72 (s, 1H), 7.35-7.32 (m, 2H), 7.06 (t, 2H, J = 8.8 Hz), 6.86 (d, 1H, J = 2.0 Hz), 4.40 (s, 2H), 4.10 (s, 2H), 3.69-3.66 (m, 1H), 1.19 (s, 6H) | 464 |
| 141 | 2 | ¹H-NMR (400 MHz, CD₃OD) δ ppm 8.70 (d, 1H, J = 7.6 Hz), 8.06 (s, 1H), 7.99 (s, 1H), 7.88 (s, 1H), 7.84 (s, 1H), 7.38-7.35 (m, 2H), 7.27 (br.s, 1H), 7.06 (t, 2H, J = 8.8 Hz), 5.08-5.05 (m, 1H), 4.95-4.90 (m, 2H), 4.63-4.48 (m, 2H), 4.33-4.30 (m, 2H), 3.76-3.74 (m, 3H), 3.04 (s, 3H), 1.48 (d, 3H, J = 6.4 Hz) | 464 |
| 142 | 3 | ¹H-NMR (400 MHz, CD₃OD) δ ppm 8.72 (d, 1H, J = 8.0 Hz), 8.07 (s, 1H), 8.00 (br.s, 1H), 7.90-7.84 (m, 2H), 7.38-7.35 (m, 2H), 7.27 (d, 1H, J = 8.0 Hz), 7.05 (t, 2H, J = 8.8 Hz), 5.09-5.04 (m, 1H), 4.97-4.93 (m, 2H), 4.66-4.64 (m, 2H), 4.15-4.07 (m, 3H), 3.81-3.78 (m, 1H), 1.48 (d, 3H, J = 4.0 Hz), 1.18 (d, 3H, J = 5.6 Hz) | 464 |
| 143 | 1 | ¹H-NMR (400 MHz, DMSO-d₆) δ ppm 8.32 (d, 1H, J = 8.4 Hz), 8.02 (s, 1H), 7.93 (s, 1H), 7.81 (s, 1H), 7.79 (s, 1H), 7.32 (s, 1H), 7.25 (s, 1H), 7.18 (s, 1H), 6.90 (br. s., 1H), 5.24-5.19 (m, 2H), 4.75-4.70 (m, 2H), 4.47-4.45 (m, 1H), 4.32-4.27 (m, 2H), 3.85 (s, 3H), 3.81-3.77 (m, 1H), 3.07 (dd, 1H, J = 16.8, 4.8 Hz), 2.81 (d, 1H, J = 16.0 Hz) | 464 |
| 144 | 2 | ¹H NMR (300 MHz, DMSO-d6) δ 8.40 (d, J = 8.1 Hz, 1H), 8.01 (s, 1H), 7.92 (d, J = 1.6 Hz, 1H), 7.79 (d, J = 4.7 Hz, 2H), 7.47-7.25 (m, 4H), 6.86 (d, J = 1.7 Hz, 1H), 4.73 (m, 1H), 4.48-3.94 (m, 4H), 3.84 (s, 3H), 1.71 (qd, J = 7.4, 3.7 Hz, 2H), 1.59 (s, 3H), 0.87 (t, J = 7.3 Hz, 3H). | 464 |
| 145 | 2 | ¹H NMR (300 MHz, DMSO-d6) δ 8.72 (t, J = 5.9 Hz, 1H), 8.38-8.31 (m, 1H), 8.01 (s, 1H), 7.92 (d, J = 1.6 Hz, 1H), 7.82-7.76 (m, 2H), 7.59 (ddd, J = 8.1, 2.3, 0.9 Hz, 1H), 7.21 (d, J = 8.0 Hz, 1H), 6.89 (d, J = 1.7 Hz, 1H), 4.73-4.19 (m, 7H), 3.84 (s, 3H), 3.74-3.62 (m, 1H), 2.28 (s, 3H). | 464 |
| 146 | 2 | ¹H-NMR (400 MHz, CD₃OD) δ ppm 7.96 (s, 1H), 7.75 (s, 2H), 7.70 (s, 1H), 7.32 (s, 4H), 6.85 (s, 1H), 5.06-5.01 (m, | 464 |

| Compound Number | Synthetic Method | $^1$H MR | LC/MS M + 1 |
|---|---|---|---|
| | | 1H), 4.54-4.49 (m, 2H), 3.68-3.65 (m, 1H), 1.51 (d, 6H, J = 6.8 Hz), 1.46 (d, 3H, J = 6.8 Hz) | |
| 147 | 2 | $^1$H NMR (400 MHz, DMSO-d$_6$) δ 8.60 (t, J = 5.9 Hz, 1H), 8.22 (d, J = 1.6 Hz, 1H), 7.90-7.77 (m, 3H), 7.54-7.48 (m, 2H), 7.23-7.04 (m, 5H), 4.82-4.63 (m, 2H), 4.40-4.19 (m, 4H), 3.67-3.58 (m, 1H), 2.27 (s, 3H), 1.70 (s, 6H) | 465 |
| 148 | 3 | $^1$H-NMR (400 MHz, DMSO-d$_6$) δ ppm 8.57 (d, 1H, J = 8.4 Hz), 7.86 (d, 1H, J = 1.6 Hz), 7.77 (s, 1H), 7.71 (s, 1H), 7.39 (d, 2H, J = 8.8 Hz), 7.33 (d, 2H, J = 8.4 Hz), 6.78 (s, 1H), 4.83-4.50 (m, 5H), 4.45-4.01 (m, 2H), 3.64-3.58 (m, 1H), 3.61 (s, 3H), 1.73-1.63 (m, 2H), 0.84 (t, J = 7.6 Hz, 3H) | 465 |
| 149 | 3 | $^1$H-NMR (400 MHz, DMSO-d$_6$) δ ppm 8.57 (d, 1H, J = 8.0 Hz), 7.91 (d, 1H, J = 1.2 Hz), 7.77 (s, 1H), 7.47 (s, 1H), 7.39 (d, 2H, J = 8.8 Hz), 7.33 (d, 2H, J = 8.4 Hz), 6.77 (s, 1H), 5.35-5.32 (m, 2H), 4.83-4.45 (m, 3H), 4.44-3.40 (m, 2H), 3.66-3.60 (m, 1H), 3.57 (s, 3H), 1.74-1.63 (m, 2H), 0.84 (t, J = 7.2 Hz, 3H) | 465 |
| 150 | | $^1$H NMR (500 MHz, DMSO-d$_6$) δ 8.68 (d, J = 8.2 Hz, 1H), 8.15 (s, 1H), 7.99 (s, 1H), 7.90 (d, J = 1.6 Hz, 1H), 7.77 (d, J = 5.3 Hz, 2H), 7.42-7.33 (m, 4H), 6.86 (s, 1H), 5.07 (q, J = 7.4 Hz, 1H), 4.0-4.9 (m, 4H), 4.58 (s, 1H), 4.34 (s, 2H), 3.83 (s, 3H), 3.72-3.59 (m, 1H), 3.62-3.44 (m, 3H), 3.25 (s, 3H), 3.18-3.09 (m, 1H) | |
| 151 | 2 | $^1$H NMR (300 MHz, DMSO-d6) δ 8.60 (d, J = 8.1 Hz, 1H), 8.00 (s, 1H), 7.91 (d, J = 1.5 Hz, 1H), 7.78 (d, J = 2.2 Hz, 2H), 7.45-7.37 (m, 2H), 7.37-7.29 (m, 2H), 6.87 (d, J = 1.8 Hz, 1H), 4.96 (q, J = 7.7 Hz, 2H), 4.80-4.31 (m, 5H), 3.84 (s, 3H), 3.70-3.54 (m, 1H), 1.94-1.70 (m, 3H). | 466 |
| 152 | 1 | $^1$H-NMR (400 MHz, DMSO-d$_6$) δ ppm 8.76 (br. s., 1H), 8.01 (s, 1H), , 7.96 (s, 1H), 7.82 (s, 1H), 7.79 (s, 1H), 7.39 (br. s., 4H), 6.94 (s, 1H), 5.03-5.00 (m, 1H), 4.98-4.10 (m, 4H), 3.84 (s, 3H), 3.30 (s, 3H), 1.42 (d, 3H, J = 6.8 Hz) | 466 |
| 153 | 1 | $^1$H-NMR (400 MHz, DMSO-d$_6$) δ ppm 8.69 (t, 1H, J = 6.0 Hz), 7.99 (s, 1H), 7.91 (d, 1H, J = 1.2 Hz), 7.78 (d, 2H, J = 2.4 Hz), 7.52 (d, 2H, J = 8.8 Hz), 7.23 (d, 2H, J = 8.4 Hz), 6.87 (d, 1H, J = 1.2 Hz), 4.69-4.19 (m, 6H), 3.83 (s, 3H), 3.66-3.62 (m, 1H) | 466 |
| 154 | 2 | $^1$H NMR (400 MHz, DMSO-d6) δ 8.53 (t, J = 6.0 Hz, 1H), 8.49 (s, 1H), 8.30 (d, J = 1.7 Hz, 1H), 8.00 (s, 1H), 7.91 (dd, J = 7.9, 1.5 Hz, 1H), 7.84 (s, 1H), 7.64 (d, J = 7.9 Hz, 1H), 7.20 (d, J = 1.7 Hz, 1H), 7.19-7.09 (m, 4H), 4.87 (br.s, 1H), 4.39 (m, 4H), 4.28 (d, J = 5.8 Hz, 2H), 4.00 (br.s, 1H), 2.26 (s, 3H), 1.60 (s, 3H). | 467 |
| 155 | 2 | $^1$H-NMR (400 MHz, CD$_3$OD) δ ppm 8.08 (s, 1H), 7.85 (s, 1H), 7.57-7.54 (m, 2H), 7.23-7.11 (m, 5H), 6.91 (d, 1H, J = 8.0 Hz), 5.03 (br.s, 1H), 4.70 (br.s, 1H), 4.56 (br.s, 1H), 4.39 (s, 2H), 4.24 (br.s, 1H), 3.77 (s, 2H), 2.29 (s, 3H), 1.72 (s, 3H) | 467 |
| 156 | 2 | $^1$H-NMR (400 MHz, DMSO-d$_6$) δ ppm 10.61 (s, 1H), 8.13 (d, 1H, J = 1.2 Hz), 7.82-7.77 (m, 5H), 7.68 (d, 2H, J = 8.4 Hz), 7.06 (d, 1H, J = 1.2 Hz), 6.96 (d, 2H, J = 8.4 Hz), 4.80-4.70 (m, 2H), 4.40-4.30 (m, 2H), 3.84-3.80 (m, 1H), 1.29 (s, 9H) | 467 |
| 157 | 2 | $^1$H NMR (400 MHz, DMSO-d6) δ 8.60 (t, J = 5.9 Hz, 1H), 8.14 (d, J = 1.7 Hz, 1H), 7.81 (s, 1H), 7.72-7.62 (m, 2H), 7.34-7.25 (m, 2H), 7.21-7.09 (m, 4H), 7.06 (d, J = 1.7 Hz, 1H), 4.81-4.60 (m, 3H), 4.42-4.18 (m, 4H), 3.69-3.56 (m, 1H), 3.53 (d, J = 5.7 Hz, 2H), 2.27 (s, 3H), 0.87-0.80 (m, 2H), 0.73 (t, J = 3.0 Hz, 2H). | 468 |
| 158 | 3 | $^1$H-NMR (400 MHz, CDCl$_3$) δ ppm 7.89 (s, 1H), 7.84 (s, 1H), 7.53-7.48 (m, 4H), 7.19-7.09 (m, 4H), 6.87 (s, 1H), 5.96 (br.s, 1H), 4.70 (t, 2H, J = 8.8 Hz), 4.39 (d, 2H, J = 5.2 Hz), 3.49-3.47 (m, 1H), 2.53-2.49 (m, 2H), 2.37-2.30 (m, 3H), 2.28 (s, 3H), 2.00-1.97 (m, 2H) | 468 |
| 159 | 2 | $^1$H NMR (400 MHz, DMSO-d$_6$) δ 8.59 (t, J = 5.9 Hz, 1H), 8.12 (d, J = 1.7 Hz, 1H), 7.28-7.09 (m, 8H), 7.05 (d, J = 1.7 Hz, 1H), 4.74 (s, 1H), 4.65 (s, 2H), 3.61 (ddd, J = 14.4, 8.8, 5.7 Hz, 1H), 2.98 (s, 2H), 2.27 (s, 3H), 1.41 (s, 6H) | 468 |
| 160 | 2 | $^1$H NMR (400 MHz, DMSO-d$_6$) δ 8.59 (t, J = 5.9 Hz, 1H), 8.05 (d, J = 1.7 Hz, 1H), 7.80 (s, 1H), 7.61 (d, J = 1.9 Hz, 1H), 7.60-7.46 (m, 1H), 7.20-7.09 (m, 4H), 7.00 (d, J = 1.7 Hz, 1H), 6.80-6.66 (m, 1H), 4.74 (s, 1H), 4.65 (s, 1H), 3.62 (ddd, J = 14.4, 8.7, 5.8 Hz, 1H), 3.02 (s, 2H), 2.27 (s, 3H), 1.41 (s, 6H) | 468 |

-continued

| Compound Number | Synthetic Method | ¹H MR | LC/MS M + 1 |
|---|---|---|---|
| 161 | 1 | ¹H-NMR (400 MHz, DMSO-d$_6$) δ ppm 8.61 (d, 1H, J = 8.0 Hz), 7.97 (s, 1H), 7.88 (s, 1H), 7.76 (d, 2H, J = 4.4 Hz), 7.39-7.35 (m, 2H), 7.30-7.27 (m, 1H), 6.84 (s, 1H), 4.97-4.91 (m, 1H), 3.81 (s, 3H), 3.66-3.59 (m, 1H), 1.73-1.61 (m, 2H), 0.84 (t, 3H, J = 7.2 Hz) | 468 |
| 162 | 2 | ¹H-NMR (400 MHz, DMSO-d$_6$) δ ppm 8.64 (t, 1H, J = 5.6 Hz), 8.29 (d, 1H, J = 1.2 Hz), 7.88-7.85 (m, 3H), 7.42 (d, 2H, J = 8.4 Hz), 7.20-7.13 (m, 5H), 4.83-4.60 (m, 2H), 4.42-4.15 (m, 4H), 3.68-3.58 (m, 1H), 2.97 (s, 6H), 2.28 (s, 3H) | 469 |
| 163 | 2 | ¹H NMR (300 MHz, DMSO-d$_6$) δ 8.53 (t, J = 5.8 Hz, 1H), 7.79 (d, J = 1.6 Hz, 1H), 7.72 (s, 1H), 7.64 (s, 1H), 7.39-7.17 (m, 1H), 7.11 (t, J = 8.9 Hz, 1H), 6.71 (d, J = 1.7 Hz, 1H), 4.64 (s, 2H), 4.31 (d, J = 5.7 Hz, 2H), 3.92 (s, 3H), 3.54 (s, 2H), 1.54 (s, 3H). | 469 |
| 164 | 3 | ¹H-NMR (400 MHz, DMSO-d$_6$) δ ppm 8.59 (br.s, 1H), 8.19 (s, 1H), 7.81-7.79 (m, 3H), 7.58 (d, 2H, J = 8.0 Hz), 7.16-7.11 (m, 5H), 6.32 (s, 1H), 4.76 (d, 2H, J = 6.4 Hz), 4.68 (s, 2H, J = 6.0 Hz), 4.26 (br.s, 2H), 2.26 (s, 3H) | 470 |
| 165 | 2 | ¹H-NMR (400 MHz, DMSO-d$_6$) δ ppm 8.63 (t, 1H, J = 5.6 Hz), 8.15 (d, 1H, J = 1.6 Hz), 7.83 (s, 1H), 7.70 (d, 2H, J = 8.4 Hz), 7.17 (d, 2H, J = 8.4 Hz), 7.14 (d, 2H, J = 8.4 Hz), 7.07 (d, J = 1.6 Hz, 1H), 6.98 (d, 2H, J = 8.4 Hz), 4.81-4.60 (m, 2H), 4.42-4.15 (m, 4H), 3.66-3.59 (m, 1H), 2.28 (s, 3H), 1.31 (s, 9H) | 470 |
| 166 | 2 | ¹H-NMR (400 MHz, DMSO-d$_6$) δ ppm 8.53 (t, J = 5.6 Hz, 1H), 8.90 (s, 1H), 7.81 (s, 1H), 7.67 (d, 2H, J = 8.8 Hz), 7.14 (d, 2H, J = 8.4 Hz), 7.11 (d, 2H, J = 8.4 Hz), 6.99 (s, 1H), 6.91 (d, 2H, J = 8.8 Hz), 4.84 (br. s., 1H), 4.66-4.60 (m, 1H), 4.37 (br. s., 2H), 4.28 (d, 2H, J = 5.6 Hz), 3.98 (br. s., 1H), 2.26 (s, 3H), 1.60 (s, 3H), 1.26 (d, 6H, J = 6.0 Hz) | 470 |
| 167 | 2 | ¹H NMR (400 MHz, DMSO-d6) δ ppm 8.60 (t, J = 5.9 Hz, 1H), 8.19 (d, J = 1.6 Hz, 1H), 7.82 (d, J = 0.9 Hz, 1H), 7.54-7.45 (m, 1H), 7.39-7.33 (m, 1H), 7.27 (t, J = 7.9 Hz, 1H), 7.20-7.05 (m, 5H), 6.86 (ddd, J = 8.2, 2.1, 1.1 Hz, 1H), 4.72 (s, 2H), 4.39-4.17 (m, 4H), 3.63 (m, 1H), 2.27 (s, 3H), 1.32 (s, 9H). | 470 |
| 168 | 2 | ¹H-NMR (400 MHz, CDCl$_3$) δ ppm 7.88 (s, 1H), 7.85 (d, 1H, J = 1.2 Hz), 7.53 (s, 4H), 7.22-7.11 (m, 4H), 6.86 (d, 1H, J = 1.2 Hz), 6.29 (br.s 1H), 4.45 (d, 2H, J = 5.6 Hz), 4.30 (d, 2H, J = 4.0 Hz), 2.33 (s, 3H), 1.71 (s, 3H), 1.61 (s, 6H) | 470 |
| 169 | 3 | ¹H-NMR (400 MHz, CDCl$_3$) δ ppm 7.87 (s, 1H), 7.84 (s, 1H), 7.57 (d, 2H, J = 8.4 Hz), 7.47 (d, 2H, J = 8.4 Hz), 7.22-7.17 (m, 4H), 6.78 (d, 1H, J = 1.6 Hz), 5.82 (br.s, 1H), 4.62 (br.s, 4H), 4.48 (d, 2H, J = 6.0 Hz), 3.55-3.48 (m, 1H), 2.36 (s, 3H) 1.93-1.83 (m, 2H), 1.59 (s, 3H), 0.85 (t, 3H, J = 7.6 Hz) | 470 |
| 170 | 2 | ¹H-NMR (400 MHz, DMSO-d$_6$) δ ppm 8.54 (d, 1H, J = 8.0 Hz), 8.16 (s, 1H), 7.82 (s, 1H), 7.70 (d, 2H, J = 8.0 Hz), 7.46 (d, 2H, J = 8.4 Hz), 7.21 (d, 2H, J = 8.0 Hz), 7.14 (d, 2H, J = 7.6 Hz), 7.07 (s, 1H), 5.00 (s, 1H), 4.97-4.91 (m, 1H), 4.75-4.58 (m, 2H), 4.35-4.13 (m, 2H), 3.60-3.59 (m, 1H), 2.27 (s, 3H), 1.43 (s, 6H), 1.36 (d, 3H, J = 6.8 Hz) | 470 |
| 171 | 1 | ¹H NMR (400 MHz, DMSO-d$_6$) δ 8.85 (t, J = 6.1 Hz, 1H), 8.07-7.67 (m, 4H), 7.50-7.12 (m, 3H), 6.94 (d, J = 1.6 Hz, 1H), 4.36 (d, J = 6.0 Hz, 6H), 3.83 (s, 3H), 3.33 (s, 3H) | 470 |
| 172 | 1 | ¹H-NMR (400 MHz, CD$_3$OD) δ ppm 8.08 (s, 1H), 7.96 (s, 1H), 7.90 (s, 1H), 7.82 (s, 1H), 7.47-7.45 (m, 2H), 7.34 (dd, 1H, J = 8.4, 2.4 Hz), 7.30 (s, 1H), 5.09 (br.s, 1H), 4.70 (br.s, 2H), 4.49 (br.s, 2H), 4.14-4.13 (m, 1H), 3.91 (s, 3H), 1.49 (d, 3H, J = 7.6 Hz) | 470 |
| 173 | 2 | ¹H-NMR (400 MHz, DMSO-d$_6$) δ ppm 8.00 (d, 1H, J = 8.0 Hz), 7.91 (s, 1H), 7.25-7.14 (m, 5H), 6.30 (br.s, 1H), 4.39 (s, 2H), 4.21 (d, 2H, J = 2.0 Hz), 3.81-3.73 (m, 3H), 2.66-2.52 (m, 2H), 2.31 (s, 3H), 2.16 (d, 3H, J = 15.2 Hz) | 471 |
| 174 | 2 | ¹H-NMR (400 MHz, CD$_3$OD) δ ppm 8.69 (d, 1H, J = 8.0 Hz), 8.12 (s, 1H), 7.87 (s, 1H), 7.64 (d, 2H, J = 8.0 Hz), 7.39-7.30 (m, 3H), 7.10-7.04 (m, 4H), 5.09-5.00 (m, 1H), 4.65-4.48 (m, 4H), 3.81-3.76 (m, 1H), 1.48 (d, 3H, J = 6.8 Hz), 0.81-0.79 (m, 2H), 0.72-0.70 (m, 2H) | 472 |
| 175 | 2 | ¹H-NMR (400 MHz, DMSO-d$_6$) δ ppm 8.63 (t, 1H, J = 6.0 Hz), 8.16 (s, 1H), 7.85 (s, 1H), 7.72 (d, 2H, J = 8.8 Hz), 7.17 (d, 2H, J = 8.8 Hz), 7.14 (d, 2H, J = 8.8 Hz), 7.10 (s, 1H), 6.96 (d, 2H, J = 8.8 Hz), 4.78-4.67 (m, 2H), 4.38- | 472 |

| Compound Number | Synthetic Method | ¹H MR | LC/MS M + 1 |
|---|---|---|---|
| | | 4.22 (m, 4H), 4.13-4.10 (m, 2H), 3.68-3.60 (m, 3H), 3.32 (s, 3H), 2.28 (s, 3H) | |
| 176 | 2 | ¹H-NMR (400 MHz, DMSO-d$_6$) δ ppm 8.64 (t, 1H, J = 5.6 Hz), 8.08 (s, 1H), 7.94 (d, 1H, J = 1.2 Hz), 7.84 (s, 1H), 7.80 (s, 1H), 7.16 (d, 2H, J = 8.4 Hz), 7.13 (d, 2H, J = 8.4 Hz), 6.90 (d, 1H, J = 1.2 Hz), 4.79-4.50 (m, 4H), 4.41-4.12 (m, 8H), 3.69-3.56 (m, 1H), 2.28 (s, 3H), 1.15 (s, 3H) | 472 |
| 177 | 1 | ¹H-NMR (400 MHz, CD$_3$OD) δ ppm 8.10 (s, 1H), 7.96 (s, 1H), 7.92 (s, 1H), 7.83 (s, 1H), 7.51-7.48 (m, 2H), 7.37-7.33 (m, 2H), 5.51 (s, 1H), 5.14 (br.s, 1H), 4.96-4.94 (m, 3H), 4.58 (br.s, 1H), 3.92 (s, 3H) | 472 |
| 178 | 1 | ¹H-NMR (400 MHz, DMSO-d$_6$) δ ppm 10.62 (s, 1H), 8.41 (s, 1H), 8.07 (d, 2H, J = 8.4 Hz), 7.91-7.88 (m, 2H), 7.83-7.78 (m, 4H), 7.32 (s, 1H), 4.85-4.75 (m, 2H), 4.46-4.35 (m, 2H), 3.85-3.83 (m, 1H), 3.21 (s, 3H) | 473 |
| 179 | 2 | ¹H-NMR (400 MHz, CDCl$_3$) δ ppm 7.89 (s, 1H), 7.71 (d, 1H, J = 8.4 Hz), 7.18-7.09 (m, 4H), 6.99 (br.s, 1H), 6.91 (s, 1H), 6.20-6.02 (m, 1H), 5.26 (d, 1H, J = 8.4 Hz), 4.52 (br.s, 1H), 4.42-4.40 (m, 3H), 4.26 (br.s, 1H), 4.15 (br.s, 1H), 3.85 (br.s, 1H), 3.70 (br.s, 1H), 2.52-2.40 (m, 4H), 2.32 (s, 3H), 1.72 (s, 3H), 1.21-1.18 (m, 3H) | 473 |
| 180 | 2 | ¹H-NMR (400 MHz, CD$_3$OD) δ ppm 8.67 (d, 1H, J = 7.6 Hz), 8.03 (s, 1H), 7.82 (s, 1H), 7.38-7.35 (m, 2H), 7.18-7.15 (m, 3H), 7.08-7.03 (m, 2H), 6.84 (d, 2H, J = 8.4 Hz), 5.08-5.03 (m, 3H), 4.26 (m, 4H), 3.78-3.72 (m, 1H), 1.48 (d, 3H, J = 7.2 Hz) | 474 |
| 181 | 2 | ¹H-NMR (400 MHz, DMSO-d$_6$) δ ppm 8.59 (d, 1H, J = 8.0 Hz), 8.10 (d, 1H, J = 1.6 Hz), 7.81 (s, 1H), 7.69 (d, 2H, J = 9.2 Hz), 7.38-7.35 (m, 2H), 7.18-7.13 (m, 2H), 7.02 (s, 1H), 6.93 (d, 2H, J = 8.8 Hz), 5.02-4.95 (m, 1H), 4.82-4.56 (m, 3H), 4.42-4.13 (m, 2H), 3.63-3.61 (m, 1H), 1.38 (d, 3H, J = 7.2 Hz), 1.28 (d, 6H, J = 6.0 Hz) | 474 |
| 182 | 2 | ¹H-NMR (400 MHz, CD$_3$OD) δ 8.29 (s, 1H), 7.93 (s, 1H), 7.70 (br.s, 1H), 7.56-7.54 (m, 1H), 7.50-7.48 (m, 1H), 7.36-7.35 (m, 3H), 7.08-7.04 (m, 3H), 5.11-5.02 (m, 4H), 4.64 (br.s, 1H), 3.81 (s, 1H), 1.54-1.48 (m, 6H), 1.34 (s, 3H) | 474 |
| 183 | 2 | ¹H-NMR (400 MHz, DMSO-d$_6$) δ ppm 8.64 (t, 1H, J = 5.6 Hz), 8.11 (s, 1H), 7.80 (s, 1H), 7.67 (d, 2H, J = 8.4 Hz), 7.32-7.29 (m, 2H), 7.14 (t, 2H, J = 8.8 Hz), 7.03 (s, 1H), 6.96 (d, 2H, J = 8.4 Hz), 4.74-4.65 (m, 2H), 4.30 (d, 2H, J = 5.6 Hz), 4.30-4.20 (m, 2H), 3.65-3.55 (m, 1H), 1.29 (s, 9H) | 474 |
| 184 | 3 | ¹H-NMR (400 MHz, CD$_3$OD) δ ppm 7.93-7.89 (m, 2H), 7.75 (s, 1H), 7.63-7.58 (m, 1H), 7.20-7.13 (m, 4H), 7.06-7.05 (m, 1H), 6.99 (s, 1H), 4.38 (s, 2H), 3.70-3.67 (m, 1H), 2.31 (s, 3H), 1.61 (s, 6H) | 474 |
| 185 | 2 | ¹H NMR (400 MHz, DMSO-d6) δ 8.58 (t, J = 5.9 Hz, 1H), 7.82-7.75 (m, 2H), 7.19-7.08 (m, 4H), 6.79 (d, J = 1.7 Hz, 1H), 6.19 (d, J = 3.3 Hz, 1H), 4.63 (m, 2H), 4.27 (m, 4H), 3.79 (m, 2H), 3.60 (m, 1H), 2.75 (s, 6H), 2.26 (s, 3H) - one set of protons mostly obscured by DMSO peak. | 474 |
| 186 | 3 | ¹H-NMR (400 MHz, DMSO-d$_6$) δ ppm 8.62 (t, 1H, J = 5.6 Hz), 7.96 (s, 2H), 7.80 (s, 2H), 7.17 (d, 2H, J = 8.0 Hz), 7.14 (d, 2H, J = 8.0 Hz), 6.92 (s, 1H), 4.70-4.62 (m, 2H), 4.34 (br. s., 1H), 4.29 (d, 2H, J = 5.2 Hz), 4.21 (br. s., 1H), 4.11 (s, 2H), 3.66-3.59 (m, 1H), 3.19 (s, 3H), 2.28 (s, 3H), 1.09 (s, 6H). | 474 |
| 187 | 2 | ¹H-NMR (400 MHz, DMSO-d$_6$) δ ppm 8.53 (d, 1H, J = 8.0 Hz), 8.00 (s, 1H), 7.94 (d, 1H, J = 2.0 Hz), 7.80 (s, 1H), 7.79 (s, 1H), 7.20 (d, 2H, J = 8.0 Hz), 7.13 (d, 2H, J = 8.0 Hz), 6.90 (s, 1H), 4.97-4.91 (m, 1H), 4.73 (s, 1H), 4.73-3.99 (m, 4H), 3.99 (s, 2H), 3.64-3.58 (m, 1H), 2.27 (s, 3H), 1.35 (d, 3H, J = 6.8 Hz), 1.08 (s, 6H) | 474 |
| 188 | 2 | ¹H-NMR (400 MHz, CD$_3$OD) δ ppm 7.90 (s, 1H), 7.85 (s, 1H), 7.25-7.12 (m, 5H), 6.24 (br.s, 1H), 4.38 (s, 2H), 4.18-4.11 (m, 4H), 3.77-3.68 (m, 3H), 2.52 (br.s, 2H), 2.31 (s, 3H), 1.28 (t, 3H, J = 7.2 Hz) | 475 |
| 189 | 2 | ¹H-NMR (400 MHz, CDCl$_3$) δ ppm 7.77 (s, 1H), 7.65 (s, 1H), 7.18-7.16 (m, 1H), 7.09-7.03 (m, 4H), 6.87 (s, 1H), 6.04 (br.s, 1H), 5.20 (d, 1H, J = 9.2 Hz), 4.77 (d, 1H, J = 10.0 Hz), 4.48 (d, 1H, J = 9.6 Hz), 4.34-4.32 (m, 3H), 4.06 (br.s, 2H), 3.68 (s, 3H), 3.64 (d, 2H, J = 6.0 Hz), 2.40 (br.s, 2H), 2.24 (s, 3H), 1.65 (s, 3H) | 475 |
| 190 | 1 | ¹H-NMR (400 MHz, DMSO-d$_6$) δ ppm 8.65 (t, 1H, J = 5.6 Hz), 8.40 (d, 1H, J = 1.2 Hz), 8.09 (d, 2H, J = 8.8 Hz), 7.90 (d, 2H, J = 8.4 Hz), 7.87 (s, 1H), 7.29 (d, 1H, J = 0.4 Hz), 7.17 (d, 2H, J = 8.0 Hz), 7.14 (d, 2H, J = 8.0 Hz), | 476 |

| Compound Number | Synthetic Method | $^1$H MR | LC/MS M + 1 |
|---|---|---|---|
| | | 4.87-4.61 (m, 2H), 4.42-4.16 (m, 4H), 3.68-3.59 (m, 1H), 3.24 (s, 3H), 2.28 (s, 3H) | |
| 191 | 2 | $^1$H-NMR (400 MHz, DMSO-d$_6$) δ ppm 8.58 (d, 1H, J = 8.0 Hz), 8.22 (s, 1H), 8.05 (s, 1H), 7.89 (d, 1H, J = 9.2 Hz), 7.80 (s, 1H), 7.39 (d, 2H, J = 8.4 Hz), 7.32 (d, 2H, J = 8.0 Hz), 6.99 (s, 1H), 6.44 (d, 1H, J = 9.6 Hz), 4.76-4.52 (m, 3H), 4.50-4.00 (m, 2H), 3.66-3.63 (m, 1H), 3.46 (s, 3H), 1.70-1.66 (m, 2H), 0.85-0.82 (m, 3H) | 477 |
| 192 | 2 | $^1$H-NMR (400 MHz, CD$_3$OD) δ ppm 8.71 (d, 1H, J = 7.2 Hz), 8.07 (s, 1H), 8.01 (br.s, 1H), 7.89 (s, 1H), 7.85 (br.s, 1H), 7.39-7.35 (m, 2H), 7.28 (br.s, 1H), 7.06 (t, 2H, J = 7.2 Hz), 5.09-5.07 (m, 1H), 4.94 (br.s, 1H), 4.67-4.49 (m, 3H), 4.11 (s, 2H), 3.80-3.78 (m, 1H), 1.48 (d, 3H, J = 7.2 Hz), 1.19 (s, 6H) | 478 |
| 193 | 2 | $^1$H-NMR (400 MHz, CD$_3$OD) δ ppm 7.92 (s, 1H), 7.78 (s, 2H), 7.72 (s, 1H), 7.24 (t, 1H, J = 8.0 Hz), 6.98-6.91 (m, 2H), 6.87 (s, 1H), 4.43 (s, 2H), 4.10 (s, 2H), 3.71-3.65 (m, 1H), 2.33 (s, 3H), 1.19 (s, 6H) | 478 |
| 194 | 3 | $^1$H-NMR (400 MHz, CD$_3$OD) δ ppm 8.71 (d, 1H, J = 7.6 Hz), 8.15 (s, 1H), 8.12 (s, 1H), 7.90 (s, 1H), 7.86 (s, 1H), 7.39-7.35 (m, 3H), 7.06 (t, 2H, J = 8.4 Hz), 5.13-5.04 (m, 2H), 4.68-4.62 (m, 2H), 4.51 (br.s, 1H), 3.82-3.79 (m, 1H), 3.76 (s, 3H), 1.56 (s, 6H), 1.48 (d, 3H, J = 6.8 Hz) | 478 |
| 195 | 3 | $^1$H-NMR (400 MHz, CD$_3$OD) δ ppm 8.69 (d, 1H, J = 7.2 Hz), 8.05 (s, 1H), 7.99 (br.s, 1H), 7.87 (s, 1H), 7.84 (s, 1H), 7.38-7.35 (m, 2H), 7.24 (br.s, 1H), 7.06 (t, 2H, J = 8.8 Hz), 5.09-5.05 (m, 1H), 5.04-4.89 (m, 2H), 4.81-4.40 (m, 2H), 4.21-4.16 (m, 1H), 4.10-4.04 (m, 1H), 3.86 (br.s, 1H), 3.79-3.76 (m, 1H), 1.49-1.47 (m, 5H), 1.03-0.98 (m, 3H) | 478 |
| 196 | 3 | $^1$H-NMR (400 MHz, CDCl$_3$) δ ppm 7.84 (br.s, 1H), 7.74 (s, 1H), 7.65 (s, 1H), 7.60 (s, 1H), 6.99-6.94 (m, 2H), 6.86 (s, 1H), 6.50 (s, 1H), 6.37 (s, 1H), 5.04 (br.s, 2H), 4.70 (br.s, 3H), 4.26-4.25 (m, 1H), 4.12-4.10 (m, 1H), 3.55 (br.s, 1H), 1.49 (d, 3H, J = 6.8 Hz), 1.44 (d, 3H, J = 6.8 Hz), 1.11 (d, 3H, J = 6.8 Hz) | 478 |
| 197 | 2 | $^1$H-NMR (400 MHz, CD$_3$OD) δ ppm 7.95 (s, 1H), 7.74-7.73 (m, 2H), 7.68 (s, 1H), 7.33-7.28 (m, 4H), 6.81 (s, 1H), 4.81-4.77 (m, 2H), 4.57-4.50 (m, 4H), 3.70-3.66 (m, 1H), 1.82-1.78 (m, 2H), 1.50 (d, 6H, J = 6.8 Hz), 0.92 (t, 3H, J = 7.6 Hz) | 478 |
| 198 | 2 | $^1$H-NMR (400 MHz, CDCl$_3$) δ ppm 7.77 (br.s, 1H), 7.73 (s, 1H), 7.65 (br.s, 1H), 7.60 (s, 1H), 7.36-7.12 (m, 5H), 6.91 (s, 1H), 5.16 (br.s, 1H), 4.96 (br.s, 1H), 4.83-4.74 (m, 1H), 4.51-4.45 (m, 2H), 4.35 (br.s, 1H), 1.64 (d, 3H, J = 19.6 Hz), 1.48 (d, 6H, J = 6.8 Hz), 1.40 (d, 3H, J = 5.6 Hz) | 478 |
| 199 | 2 | $^1$H-NMR (400 MHz, CD$_3$OD) δ ppm 8.65 (d, 1H, J = 7.6 Hz), 7.87 (s, 1H), 7.83 (s, 1H), 7.37-7.34 (m, 2H), 7.07-7.03 (m, 3H), 6.22 (br.s, 2H), 5.07-5.04 (m, 1H), 4.58 (br.s, 4H), 4.10 (s, 2H), 3.73 (br.s, 1H), 3.72 (s, 3H), 3.69-3.68 (m, 2H), 2.51 (br.s, 2H), 1.47 (d, 2H, J = 6.8 Hz) | 479 |
| 200 | 2 | $^1$H-NMR (400 MHz, CDCl$_3$) δ ppm 7.87 (s, 1H), 7.75 (s, 1H), 7.25 (br.s, 2H), 7.03 (t, 2H, J = 8.4 Hz), 6.96 (s, 1H), 6.14 (br.s, 1H), 5.29 (d, 1H, J = 7.6 Hz), 4.88 (br.s, 1H), 4.59-4.42 (m, 4H), 4.16 (br.s, 2H), 3.77 (s, 3H), 3.72 (br.s, 2H), 2.49 (br.s, 2H), 1.75 (s, 3H) | 479 |
| 201 | 2 | $^1$H NMR (400 MHz, DMSO-d6) δ 8.57 (d, J = 8.1 Hz, 1H), 7.90 (s, 1H), 7.83-7.70 (m, 2H), 7.42-7.34 (m, 2H), 7.31 (d, J = 8.4 Hz, 2H), 6.74 (s, 1H), 4.99-4.90 (m, 1H), 4.78-4.00 (m, 6H), 3.75 (s, 3H), 3.60 (td, J = 8.5, 4.2 Hz, 1H), 2.29 (s, 3H), 1.91-1.72 (m, 2H) - one peak partially obscured by water signal. | 480 |
| 202 | 2 | $^1$H NMR (400 MHz, DMSO-d6) δ 8.41 (d, J = 8.0 Hz, 1H), 7.99 (s, 1H), 7.90 (d, J = 1.6 Hz, 1H), 7.78 (d, J = 7.4 Hz, 2H), 7.42-7.35 (m, 2H), 7.32 (d, J = 8.5 Hz, 2H), 6.84 (d, J = 1.7 Hz, 1H), 5.00-4.89 (m, 1H), 4.76 (br.s, 1H), 4.57 (t, J = 4.9 Hz, 1H), 4.30 (br.s, 2H), 3.99 (br.s, 1H), 3.83 (s, 3H), 1.97-1.83 (m, 1H), 1.85-1.72 (m, 1H), 1.57 (s, 3H) - one peak partially obscured by water signal. | 480 |
| 203 | 1 | $^1$H NMR (400 MHz, DMSO-d$_6$) δ 8.70 (d, J = 8.5 Hz, 1H), 7.99 (s, 1H), 7.93 (d, J = 1.6 Hz, 1H), 7.79 (d, J = 12.8 Hz, 2H), 7.37 (s, 4H), 6.92 (s, 1H), 5.00-3.90 (m, 5H), 3.83 (s, 3H), 3.28 (s, 3H), 1.76 (ddt, J = 40.6, 13.7, 6.7 Hz, 2H), 0.86 (t, J = 7.3 Hz, 3H) | 480 |
| 204 | 2 | $^1$H-NMR (400 MHz, CD$_3$OD) δ ppm 7.92 (s, 1H), 7.78 (s, 2H), 7.72 (s, 1H), 7.35-7.29 (m, 4H), 6.87 (s, 1H), 4.41 (s, 2H), 4.10 (s, 2H), 3.68-3.67 (m, 1H), 1.19 (s, 6H) | 480 |

| Compound Number | Synthetic Method | $^1$H MR | LC/MS M + 1 |
|---|---|---|---|
| 205 | 2 | $^1$H-NMR (400 MHz, CD$_3$OD) δ ppm 7.93 (s, 1H), 7.78 (s, 1H), 7.75 (s, 1H), 7.34-7.28 (m, 4H), 6.85 (s, 1H), 4.23 (t, 2H, J = 5.2 Hz), 3.89 (t, 2H, J = 5.2 Hz), 3.69-3.65 (m, 1H), 1.81 (t, 2H, J = 7.6 Hz), 0.92 (t, 3H, J = 7.6 Hz) | 480 |
| 206 | 3 | $^1$H-NMR (400 MHz, CDCl$_3$) δ ppm 7.79 (s, 1H), 7.74 (s, 1H), 7.59 (d, 2H, J = 8.8 Hz), 7.51 (d, 2H, J = 8.8 Hz), 7.14-7.09 (m, 4H), 6.67 (s, 1H), 5.73 (br.s, 1H), 4.40 (d, 2H, J = 5.6 Hz), 3.83 (t, 2H, J = 6.8 Hz), 3.49-3.43 (m, 1H), 3.10-3.05 (m, 1H), 2.57 (t, 2H, J = 8.0 Hz), 2.23 (s, 3H), 2.14-2.12 (m, 2H) | 481 |
| 207 | 2 | $^1$H NMR (400 MHz, DMSO-d6) δ 8.59 (t, J = 5.9 Hz, 1H), 7.83 (d, J = 1.6 Hz, 1H), 7.80 (s, 1H), 7.19-7.06 (m, 4H), 6.84 (d, J = 1.7 Hz, 1H), 6.25 (m, 1H), 4.76-4.54 (m, 2H), 4.40-4.15 (m, 4H), 3.87-3.77 (m, 2H), 3.61 (ddd, J = 14.3, 8.7, 5.7 Hz, 1H), 2.92 (s, 3H), 2.56 (br.s, 2H), 2.27 (s, 3H). | 481 |
| 208 | 2 | $^1$H-NMR (400 MHz, DMSO-d$_6$) δ ppm 8.61 (t, 1H, J = 5.8 Hz), 8.25 (d, 1H, J = 1.5 Hz), 7.92 (d, 2H, J = 8.7 Hz), 7.84 (s, 1H), 7.37 (d, 2H, J = 8.3 Hz), 7.21-7.08 (m, 5H), 4.76-4.67 (m, 2H), 4.40-4.14 (m, 4H), 3.69-3.55 (m, 1H), 2.27 (s, 3H) | 482 |
| 209 | 2 | $^1$H-NMR (400 MHz, CD$_3$OD) δ ppm 7.92 (s, 1H), 7.78 (s, 2H), 7.72 (s, 1H), 7.44-7.40 (m, 1H), 6.98-6.92 (m, 2H), 6.86 (d, 1H, J = 1.2 Hz), 4.45 (s, 2H), 4.10 (s, 2H), 3.71-3.63 (m, 1H), 1.19 (s, 6H) | 482 |
| 210 | 3 | $^1$H-NMR (400 MHz, CDCl$_3$) δ ppm 7.78 (s, 1H), 7.77 (s, 1H), 7.50 (s, 4H), 7.14-7.08 (m, 4H), 6.74 (s, 1H), 5.88 (br.s, 1H), 4.59 (br.s, 1H), 4.40 (d, 2H, J = 5.2 Hz), 3.49-3.48 (m, 1H), 2.27 (s, 3H), 1.46 (s, 3H), 1.23-1.18 (m, 1H), 0.50-0.37 (m, 4H) | 482 |
| 211 | 3 | $^1$H-NMR (400 MHz, CD$_3$OD) δ ppm 7.93 (s, 1H), 7.74 (s, 1H), 7.64 (d, 2H, J = 8.4 Hz), 7.50 (d, 2H, J = 8.4 Hz), 7.20-7.13 (m, 4H), 7.01 (s, 1H), 4.38 (s, 2H), 3.69-3.68 (m, 1H), 2.31 (s, 3H), 2.02-1.84 (m, 8H) | 482 |
| 212 | 2 | $^1$H NMR (400 MHz, DMSO-d6) δ 8.84-8.75 (m, 1H), 8.50 (s, 1H), 8.34 (d, J = 1.9 Hz, 1H), 8.01 (s, 1H), 7.97-7.91 (m, 1H), 7.87 (d, J = 1.4 Hz, 1H), 7.65 (d, J = 7.7 Hz, 1H), 7.30 (d, J = 1.9 Hz, 1H), 7.22-7.06 (m, 3H), 4.89 (d, J = 9.5 Hz, 1H), 4.72 (d, J = 10.1 Hz, 1H), 4.40 (m, 3H), 4.30 (m, 3H), 2.26 (s, 3H). | 483 |
| 213 | 3 | $^1$H-NMR (400 MHz, CD$_3$OD) δ ppm 7.95 (s, 1H), 7.74 (s, 1H), 7.69 (d, 2H, J = 8.4 Hz), 7.53 (d, 2H, J = 8.4 Hz), 7.20-7.13 (m, 4H), 7.03 (s, 1H), 4.38 (s, 2H), 4.18-4.11 (m, 1H), 3.96-3.88 (m, 2H), 2.46-2.38 (m, 1H), 2.31 (s, 3H) | 484 |
| 214 | 2 | $^1$H-NMR (400 MHz, CDCl$_3$) δ ppm 7.93 (s, 1H), 7.86 (s, 1H), 7.46 (d, 2H, J = 8.4 Hz), 7.18-7.12 (m, 4H), 7.04 (d, 2H, J = 8.4 Hz), 6.96 (s, 1H), 6.62 (br.s, 1H), 4.44-4.38 (m, 4H), 2.32 (s, 3H), 1.72 (s, 3H), 1.38 (s, 9H) | 484 |
| 215 | 2 | $^1$H-NMR (400 MHz, CDCl$_3$) δ ppm 7.86 (s, 1H), 7.78 (d, 1H, J = 1.6 Hz), 7.48 (d, 2H, J = 8.8 Hz), 7.23 (d, 2H, J = 8.4 Hz), 7.18 (d, 2H, J = 8.0 Hz), 7.03 (d, 2H, J = 8.4 Hz), 6.71 (d, 1H, J = 1.2 Hz), 5.72 (d, 1H, J = 7.6 Hz), 5.20-5.12 (m, 1H), 4.64-4.59 (m, 4H), 3.50-3.43 (m, 1H), 2.36 (s, 3H), 1.54 (d, 3H, J = 6.8 Hz), 1.38 (s, 9H) | 484 |
| 216 | 3 | $^1$H-NMR (400 MHz, CD$_3$OD) δ ppm 8.87 (s, 1H), 7.73 (s, 1H), 7.58 (d, 2H, J = 8.4 Hz), 7.20-7.13 (m, 4H), 7.00 (d, 2H, J = 8.4 Hz), 6.96 (s, 1H), 4.38 (s, 2H), 3.71-3.66 (m, 1H), 2.30 (s, 3H), 1.73-1.67 (m, 2H), 1.28 (s, 6H), 2.31 (t, 3H, J = 7.2 Hz) | 484 |
| 217 | 2 | $^1$H-NMR (400 MHz, DMSO-d$_6$) δ ppm 8.59 (t, 1H, J = 5.6 Hz), 8.11 (s, 1H), 7.80 (s, 1H), 7.67 (d, 2H, J = 8.4 Hz), 7.19-7.14 (m, 4H), 7.04 (s, 1H), 6.96 (d, 2H, J = 8.8 Hz), 4.73-4.64 (m, 2H), 4.28-4.27 (m, 4H), 3.65-3.55 (m, 1H), 2.57-2.55 (m, 2H), 1.29 (s, 9H), 1.14 (t, 3H, J = 7.6 Hz) | 484 |
| 218 | 2 | $^1$H-NMR (400 MHz, DMSO-d$_6$) δ ppm 8.56 (d, 1H, J = 7.6 Hz), 8.25 (d, 1H, J = 0.8 Hz), 7.85-7.83 (m, 3H), 7.40 (d, 2H, J = 7.6 Hz), 7.33-7.31 (m, 4H), 7.25-7.21 (m, 1H), 7.16 (s, 1H), 4.95-4.90 (m, 2H), 4.77-4.58 (m, 2H), 4.35-4.12 (m, 2H), 3.75-3.70 (m, 1H), 3.59-3.56 (m, 2H), 2.96 (br. s., 6H) | 485 |
| 219 | 2 | $^1$H-NMR (500 MHz, DMSO-d$_6$) δ ppm 8.57 (d, 1H, J = 8.0 Hz), 8.26 (s, 1H), 7.86-7.84 (m, 3H), 7.41 (d, 2H, J = 7.5 Hz), 7.33-7.30 (m, 4H), 7.26-7.22 (m, 1H), 7.17 (s, 1H), 4.94-4.90 (m, 2H), 4.77-4.50 (m, 2H), 4.45-4.36 (m, 2H), 3.75-3.69 (m, 1H), 3.61-3.32 (m, 2H), 2.97 (br. s., 6H) | 485 |

-continued

| Compound Number | Synthetic Method | ¹H MR | LC/MS M + 1 |
|---|---|---|---|
| 220 | 3 | ¹H-NMR (400 MHz, CDCl₃) δ ppm 7.93 (s, 1H), 7.73 (s, 1H), 7.69-7.64 (m, 2H), 7.38-7.34 (m, 2H), 7.08-7.02 (m, 3H), 5.07 (br.s, 2H), 5.05 (br.s, 1H), 4.58 (br.s, 2H), 3.69-3.66 (m, 1H), 2.54-2.51 (m, 2H), 2.40-2.33 (m, 2H), 2.03-2.00 (m, 1H), 1.75-1.70 (m, 1H), 1.47 (d, 3H, J = 7.2 Hz) | 486 |
| 221 | 3 | ¹H-NMR (400 MHz, DMSO-d₆) δ ppm 8.62 (t, 1H, J = 5.6 Hz), 8.11 (d, 1H, J = 1.6 Hz), 7.81 (s, 1H), 7.70 (d, 2H, J = 8.4 Hz), 7.16 (d, 2H, J = 7.6 Hz), 7.12 (d, 2H, J = 8.0 Hz), 7.03 (d, 1H, J = 1.2 Hz), 6.94 (d, 2H, J = 8.8 Hz), 4.83-4.64 (m, 3H), 4.42-4.11 (m, 4H), 3.72 (s, 2H), 3.66-3.56 (m, 1H), 2.27 (s, 3H), 1.20 (s, 6H) | 486 |
| 222 | 2 | ¹H-NMR (400 MHz, CDCl₃) δ ppm 7.89 (s, 1H), 7.85 (d, 1H, J = 1.6 Hz), 7.58 (d, 2H, J = 8.8 Hz), 7.53 (d, 2H, J = 8.8 Hz), 7.21 (d, 2H, J = 8.4 Hz), 7.18 (d, 2H, J = 8.4 Hz), 6.81-6.79 (m, 2H), 5.05-4.48 (m, 4H), 5.49 (d, 2H, J = 5.6 Hz), 3.48 (s, 3H), 2.37 (s, 3H), 1.63 (s, 6H) | 486 |
| 223 | 2 | ¹H-NMR (400 MHz, DMSO-d₆) δ ppm 8.67-8.54 (m, 1H), 8.00 (s, 1H), 7.93 (d, 1H, J = 1.2 Hz), 7.80 (s, 1H), 7.78 (s, 1H), 7.17-7.14 (m, 4H), 6.90 (d, 1H, J = 1.2 Hz), 4.80-4.49 (m, 2H), 4.48-4.37 (m, 1H), 4.28-4.25 (m, 2H), 4.23-4.13 (m, 1H), 4.09-4.06 (m, 2H), 3.72-3.68 (m, 2H), 3.65-3.55 (m, 1H), 3.41-3.36 (m, 2H), 2.77-2.70 (m, 1H), 2.67-2.56 (m, 2H), 2.39-2.33 (m, 1H), 2.27 (s, 3H) | 487 |
| 224 | 2 | ¹H NMR (400 MHz, DMSO-d₆) δ 8.58 (t, J = 5.9 Hz, 1H), 7.84-7.75 (m, 2H), 7.20-7.08 (m, 4H), 6.79 (d, J = 1.7 Hz, 1H), 6.21 (t, J = 3.5 Hz, 1H), 4.64 (m, 2H), 4.42-4.05 (m, 8H), 3.73 (t, J = 5.6 Hz, 2H), 3.60 (m, 1H), 2.26 (s, 3H), 1.21 (s, 9H) | 487 |
| 225 | 2 | ¹H NMR (300 MHz, DMSO-d6) δ 8.44 (d, J = 7.8 Hz, 1H), 8.17 (d, J = 1.6 Hz, 1H), 7.83 (s, 1H), 7.70 (d, J = 8.3 Hz, 2H), 7.51-7.43 (m, 2H), 7.41-7.32 (m, 2H), 7.20-7.10 (m, 2H), 7.05 (d, J = 1.7 Hz, 1H), 4.99 (m, 2H), 4.84 (br.s, 1H), 4.43-4.31 (m, 2H), 4.00 (br.s, 1H), 1.60 (s, 3H), 1.44 (s, 6H), 1.39 (d, J = 7.0 Hz, 3H). | 488 |
| 226 | 3 | ¹H-NMR (400 MHz, CDCl₃) δ ppm 7.96 (s, 1H), 7.88 (s, 1H), 7.29 (s, 1H), 7.22-7.09 (m, 6H), 6.97 (s, 1H), 6.33 (br.s, 1H), 4.83 (br.s, 1H), 4.45 (br.s, 2H), 3.62 (br.s, 1H), 2.32 (s, 3H), 1.39 (s, 9H) | 488 |
| 227 | 3 | ¹H-NMR (400 MHz, CDCl₃) δ ppm 7.92 (s, 1H), 7.79 (s, 1H), 7.26-7.20 (m, 6H), 7.18-7.13 (m, 1H), 6.75 (s, 1H), 5.87 (br.s, 1H), 4.68 (br.s, 1H), 4.49 (d, 2H, J = 5.6 Hz), 3.58-3.52 (m, 1H), 2.37 (s, 3H), 1.43 (s, 9H) | 488 |
| 228 | 3 | ¹H-NMR (400 MHz, CD₃OD) δ ppm 7.91 (s, 1H), 7.72 (s, 1H), 7.62 (d, 2H, J = 7.6 Hz), 7.45 (d, 2H, J = 8.4 Hz), 7.38-7.34 (m, 2H), 7.05 (t, 2H, J = 8.4 Hz), 6.99 (s, 1H), 5.06-5.05 (m, 1H), 4.90 (br.s, 2H), 4.44 (br.s, 2H), 3.69-3.66 (m, 1H), 1.85-1.79 (m, 2H), 1.52 (s, 3H), 1.47 (d, 3H, J = 6.8 Hz), 0.79 (t, 3H, J = 7.6 Hz) | 488 |
| 229 | 2 | ¹H NMR (400 MHz, DMSO-d6) δ 8.58 (t, J = 5.8 Hz, 1H), 7.86-7.73 (m, 2H), 7.20-7.08 (m, 4H), 6.79 (d, J = 1.7 Hz, 1H), 6.19 (br.s, 1H), 4.87-4.74 (m, 1H), 4.71-4.54 (m, 2H), 4.37-4.15 (m, 4H), 4.00 (br.s, 2H), 3.65-3.52 (m, 3H), 2.43 (br.s, 2H), 2.27 (s, 3H), 1.19 (d, J = 6.2 Hz, 6H). | 489 |
| 230 | 2 | ¹H-NMR (400 MHz, DMSO-d₆) δ ppm 8.58 (d, 1H, J = 7.2 Hz), 8.06 (s, 1H), 7.92 (d, 1H, J = 1.6 Hz), 7.81 (s, 1H), 7.78 (s, 2H), 7.37-7.34 (m, 2H), 7.17-7.12 (m, 2H), 6.88 (s, 1H), 4.99-4.95 (m, 1H), 4.73-4.59 (m, 4H), 4.32-4.22 (m, 6H), 3.63-3.59 (m, 1H), 1.36 (d, 3H, J = 7.2 Hz), 1.14 (s, 3H) | 490 |
| 231 | 2 | ¹H NMR (400 MHz, DMSO-d₆) δ ppm 8.77 (t, J = 6.3 Hz, 1H), 8.15-7.66 (m, 4H), 7.30-7.06 (m, 4H), 6.96 (d, J = 1.7 Hz, 1H), 5.02-4.07 (m, 7H), 3.99 (s, 2H), 2.26 (s, 3H), 1.07 (s, 6H) | 490 |
| 232 | 1 | ¹H-NMR (400 MHz, DMSO-d₆) δ ppm 8.56 (t, J = 6.0 Hz, 1H), 8.41 (s, 1H), 8.08 (d, 2H, J = 8.4 Hz), 7.89 (d, 2H, J = 8.4 Hz), 7.87 (s, 1H), 7.28 (s, 1H), 7.17-7.09 (m, 4H), 4.90 (br. s., 1H), 4.41 (br. s., 2H), 4.29 (d, 2H, J = 5.6 Hz), 4.03 (br. s., 1H), 3.22 (s, 3H), 2.26 (s, 3H), 1.61 (s, 3H) | 490 |
| 233 | 2 | ¹H-NMR (400 MHz, DMSO-d₆) δ ppm 8.66 (t, 1H, J = 6.0 Hz), 8.11 (d, 1H, J = 1.2 Hz), 7.80 (s, 1H), 7.67 (d, 2H, J = 8.4 Hz), 7.37 (d, 2H, J = 8.0 Hz), 7.28 (d, 2H, J = 8.4 Hz), 7.03 (d, 1H, J = 1.2 Hz), 6.96 (d, 2H, J = 8.4 Hz), 4.73-4.64 (m, 2H), 4.30 (d, 2H, J = 5.6 Hz), 4.30-4.20 (m, 2H), 3.64-3.61 (m, 1H), 1.29 (s, 9H) | 490 |
| 234 | 2 | ¹H NMR (300 MHz, DMSO-d6) δ 8.41 (d, J = 8.2 Hz, 1H), 7.81 (m, 3H), 7.44-7.29 (m, 4H), 6.74 (d, J = 1.7 Hz, | 490 |

| Compound Number | Synthetic Method | ¹H MR | LC/MS M + 1 |
|---|---|---|---|
| | | 1H), 4.92-4.57 (m, 2H), 4.34 (s, 2H), 4.07 (t, J = 7.2 Hz, 3H), 3.03 (t, J = 7.3 Hz, 2H), 2.61 (q, J = 7.3 Hz, 2H), 1.73 (mbr., 2H), 1.59 (s, 3H), 0.87 (t, J = 7.2 Hz, 3H). | |
| 235 | 2 | ¹H-NMR (400 MHz, DMSO-d₆) δ ppm 8.77 (t, 1H, J = 6.0 Hz), 7.83 (d, 2H, J = 1.6 Hz), 7.81 (s, 1H), 7.15 (d, 2H, J = 8.0 Hz), 7.11 (d, 2H, J = 8.0 Hz), 6.87 (d, 1H, J = 1.6 Hz), 6.21 (br. s., 1H), 4.79 (br. s., 1H), 4.64 (br. s., 1H), 4.37-4.22 (m, 2H), 4.28 (d, 2H, J = 5.6 Hz), 4.02 (s, 2H), 3.62 (s, 3H), 3.57 (t, 2H, J = 6.0 Hz), 3.32 (s, 3H), 2.45 (s, 2H), 2.26 (s, 3H) | 491 |
| 236 | 2 | ¹H NMR (400 MHz, DMSO-d6) δ 8.39 (d, J = 7.9 Hz, 1H), 7.87-7.72 (m, 2H), 7.40-7.27 (m, 2H), 7.20-7.07 (m, 2H), 6.76 (d, J = 2.8 Hz, 1H), 6.20 (d, J = 4.7 Hz, 1H), 5.02-4.89 (m, 1H), 4.76 (s, 1H), 4.32 (br.s, 2H), 4.14-4.03 (m, 2H), 3.95 (br.s, 1H), 3.70-3.54 (m, 2H), 2.43-2.28 (m, 3H), 1.56 (s, 3H), 1.37 (d, J = 7.0 Hz, 3H), 0.99 (q, J = 7.2 Hz, 3H). | 491 |
| 237 | 2 | ¹H-NMR (400 MHz, DMSO-d₆) δ ppm 8.64-8.62 (m, 1H), 8.11 (s, 1H), 7.80 (s, 1H), 7.67 (d, 2H, J = 8.4 Hz), 7.40-7.38 (m, 1H), 7.23-7.18 (m, 1H), 7.08-7.03 (m, 2H), 6.95 (d, 2H, J = 8.4 Hz), 4.73-4.63 (m, 2H), 4.32 (d, 2H, J = 5.2 Hz), 4.29-4.19 (m, 2H), 3.64-3.59 (m, 1H), 1.29 (s, 9H) | 492 |
| 238 | 3 | ¹H-NMR (400 MHz, DMSO-d₆) δ ppm 8.60 (d, 1H, J = 8.0 Hz), 8.04 (s, 1H), 7.93 (d, 1H, J = 1.6 Hz), 7.77 (s, 1H), 7.16 (s, 1H), 7.37-7.33 (m, 2H), 7.16-7.12 (m, 2H), 6.89 (s, 1H), 5.00-4.93 (m, 1H), 4.68-4.53 (m, 3H), 4.33 (br. s., 1H), 4.20-4.15 (m, 2H), 3.63-3.59 (m, 1H), 1.44 (d, 3H, J = 7.2 Hz), 1.35 (d, 3H, J = 7.2 Hz), 1.04 (s, 3H), 0.99 (s, 3H) | 492 |
| 239 | 3 | ¹H-NMR (400 MHz, DMSO-d₆) δ ppm 8.60 (d, 1H, J = 8.0 Hz), 8.04 (s, 1H), 7.93 (d, 1H, J = 1.6 Hz), 7.78 (s, 1H), 7.77 (s, 1H), 7.37-7.34 (m, 2H), 7.17-7.12 (m, 2H), 6.90 (s, 1H), 5.00-4.93 (m, 1H), 4.67-4.53 (m, 3H), 4.33 (br. s., 1H), 4.20-4.15 (m, 2H), 3.66-3.56 (m, 1H), 1.44 (d, 3H, J = 7.2 Hz), 1.35 (d, 3H, J = 7.2 Hz), 1.04 (s, 3H), 0.99 (s, 3H) | 492 |
| 240 | 2 | ¹H NMR (400 MHz, DMSO-d6) δ 8.57 (d, J = 8.1 Hz, 1H), 7.79 (m, 3H), 7.43-7.34 (m, 2H), 7.34-7.27 (m, 2H), 6.74 (s, 1H), 4.95 (m, 1H), 4.54 (m, 5H), 4.05 (t, J = 7.3 Hz, 2H), 3.60 (ddd, J = 14.4, 8.8, 5.7 Hz, 1H), 3.41 (dt, J = 11.3, 5.9 Hz, 1H), 3.01 (t, J = 7.3 Hz, 2H), 2.58 (m, 2H), 1.93-1.70 (m, 2H). | 492 |
| 241 | 2 | ¹H-NMR (400 MHz, DMSO-d₆) δ ppm 8.58 (d, 1H, J = 8.0 Hz), 8.29 (s, 1H), 7.96 (s, 1H), 7.95 (s, 1H), 7.80 (s, 1H), 7.39 (d, 2H, J = 8.8 Hz), 7.33 (d, 2H, J = 8.8 Hz), 6.94 (s, 1H), 5.57-5.54 (m, 1H), 4.96-4.87 (m, 4H), 4.75-4.00 (m, 5H), 3.68-3.64 (m, 1H), 1.71-1.66 (m, 2H), 0.85(t, 3H, J = 7.2 Hz) | 492 |
| 242 | 2 | ¹H-NMR (400 MHz, CDCl₃) δ ppm 7.92 (s, 1H), 7.75 (s, 1H), 7.68 (s, 1H), 7.60 (s, 1H), 7.31-7.29 (m, 2H), 7.24-7.22 (m, 2H), 6.83 (s, 1H), 4.81 (q, 1H, J = 8.0 Hz), 4.56-4.50 (m, 1H), 4.42 (br.s, 2H), 1.86-1.78 (m, 2H), 1.71 (br.s, 3H), 1.55 (d, 6H, J = 6.4 Hz), 0.90 (t, 3H, J = 7.2 Hz) | 492 |
| 243 | 1 | ¹H NMR (400 MHz, DMSO-d₆) δ 8.90 (d, J = 8.0 Hz, 1H), 7.99 (s, 1H), 7.90 (d, J = 1.6 Hz, 1H), 7.77 (d, J = 5.4 Hz, 2H), 7.41-7.27 (m, 4H), 6.84 (d, J = 1.8 Hz, 1H), 4.72 (dq, J = 19.4, 10.5, 8.9 Hz, 2H), 4.45 (d, J = 9.0 Hz, 1H), 4.11 (s, 1H), 3.83 (s, 3H), 3.00 (s, 2H), 2.32 (s, 3H), 1.70 (p, J = 7.3 Hz, 2H), 0.85 (t, J = 7.3 Hz, 3H) | 493 |
| 244 | 3 | ¹H-NMR (400 MHz, CDCl₃) δ ppm 7.71-7.67 (m, 4H), 7.11-7.09 (m, 2H), 6.96-6.85 (m, 3H), 4.97 (br.s, 1H), 4.79-4.47 (m, 4H), 4.29-4.14 (m, 3H), 3.65 (s, 1H), 3.55 (s, 1H), 3.33 (s, 3H), 1.40 (d, 3H, J = 6.8 Hz) | 494 |
| 245 | 1 | ¹H-NMR (400 MHz, DMSO-d₆) δ ppm 8.58 (d, 1H, J = 8.0 Hz), 8.36 (s, 1H), 8.05 (d, 2H, J = 8.0 Hz), 7.89-7.84 (m, 3H), 7.34-7.33 (m, 2H), 7.25 (s, 1H), 7.14 (t, 2H, J = 8.8 Hz), 5.00-4.96 (m, 1H), 4.76-4.72 (m, 2H), 4.36-4.31 (m, 2H), 3.65-3.60 (m, 1H), 3.21 (s, 3H), 1.35 (d, 3H, J = 7.2 Hz) | 494 |
| 246 | 2 | ¹H-NMR (400 MHz, CDCl₃) δ ppm 7.98 (s, 1H), 7.90 (s, 1H), 7.59-7.53 (m, 3H), 7.33-7.29 (m, 1H), 7.14-7.09 (m, 3H) 6.96 (br.s, 1H), 5.19 (br.s, 1H), 5.04 (br.s, 1H), 4.85 (br.s, 1H), 4.70 (br.s, 1H), 4.51 (br.s, 2H), 3.74-3.71 (m, 1H), 1.63 (s, 6H) | 494 |
| 247 | 2 | ¹H NMR (400 MHz, DMSO-d6) δ 8.52 (d, J = 8.1 Hz, 1H), 7.99 (s, 1H), 7.90 (d, J = 1.6 Hz, 1H), 7.78 (s, 1H), | 494 |

| Compound Number | Synthetic Method | ¹H MR | LC/MS M + 1 |
|---|---|---|---|
| | | 7.77 (d, J = 0.8 Hz, 1H), 7.43-7.34 (m, 2H), 7.34-7.26 (m, 2H), 6.85 (d, J = 1.7 Hz, 1H), 5.07-5.02 (m, 1H), 4.74-4.47 (m, 2H), 4.41 (s, 1H), 4.19 (s, 2H), 3.83 (s, 3H), 3.58 (ddd, J = 14.4, 8.7, 5.6 Hz, 1H), 1.89 (dd, J = 14.3, 9.1 Hz, 1H), 1.70 (dd, J = 14.3, 3.5 Hz, 1H), 1.09 (2 very closely spaced singlets, 6H). | |
| 248 | 3 | ¹H-NMR (400 MHz, CD$_3$OD) δ ppm 8.71 (d, 1H, J = 8.0 Hz), 8.07 (s, 1H), 7.99 (br.s, 1H), 7.88 (s, 1H), 7.85 (s, 1H), 7.35-7.25 (m, 5H), 5.00-4.98 (m, 1H), 4.82-4.60 (m, 4H), 4.16-4.07 (m, 3H), 3.84-3.79 (m, 1H), 1.87-1.78 (m, 2H), 1.18 (d, 3H, J = 5.6 Hz), 0.93 (t, 3H, J = 7.2 Hz) | 494 |
| 249 | 2 | ¹H-NMR (400 MHz, CD$_3$OD) δ ppm 8.69 (d, 1H, J = 8.0 Hz), 8.10 (s, 1H), 8.00 (s, 1H), 7.90 (s, 1H), 7.84 (s, 1H), 7.35-7.30 (m, 5H), 4.96-4.90 (m, 3H), 4.67-4.48 (m, 2H), 4.35-4.30 (m, 2H), 3.85-3.80 (m, 1H), 3.76-3.74 (m, 2H), 3.32 (s, 3H), 1.85-1.80 (m, 2H), 0.93 (t, 3H, J = 7.2 Hz) | 494 |
| 250 | 2 | ¹H-NMR (400 MHz, DMSO-d$_6$) δ ppm 8.62 (d, 1H, J = 7.6 Hz), 8.00 (s, 1H), 7.94 (d, 1H, J = 1.2 Hz), 7.80 (s, 1H), 7.79 (s, 1H), 7.39 (d, 2H, J = 8.8 Hz), 7.34 (d, 2H, J = 8.4 Hz), 6.90 (s, 1H), 4.98-4.94 (m, 1H), 4.74 (s, 1H), 4.73-3.99 (m, 4H), 4.00 (s, 2H), 3.64-3.58 (m, 1H), 1.36 (d, 3H, J = 7.2 Hz), 1.08 (s, 6H) | 494 |
| 251 | 3 | ¹H-NMR (400 MHz, DMSO-d$_6$) δ ppm 8.57 (d, 1H, J = 8.4 Hz), 8.01 (s, 1H), 7.93 (d, 1H, J = 1.6 Hz), 7.80 (s, 1H), 7.79 (s, 1H), 7.39 (d, 2H, J = 8.4 Hz), 7.32 (d, 2H, J = 8.8 Hz), 6.89 (s, 1H), 4.95 (d, 1H, J = 4.4 Hz), 4.79-4.08 (m, 5H), 3.97 (s, 3H), 3.69-3.59 (m, 1H), 1.77-1.62 (m, 2H), 1.04 (d, 3H, J = 5.6 Hz), 0.85 (t, 3H, J = 7.2 Hz) | 494 |
| 252 | 2 | ¹H-NMR (400 MHz, CDCl$_3$) δ ppm 7.79 (s, 1H), 7.75 (s, 1H), 7.54-7.48 (m, 4H), 7.14-7.08 (m, 4H), 6.67 (s, 1H), 5.96 (br.s, 1H), 4.39 (d, 2H, J = 5.6 Hz), 3.60-3.56 (m, 2H), 3.44-3.42 (m, 3H), 2.28 (s, 3H), 1.92-1.81 (m, 4H) | 495 |
| 253 | 2 | ¹H-NMR (400 MHz, CDCl$_3$) δ ppm 7.92 (s, 1H), 7.88 (s, 1H), 7.62 (d, 2H, J = 8.0 Hz), 7.53 (d, 2H, J = 8.0 Hz), 7.11-7.05 (m, 5H), 6.96 (br.s, 1H), 4.44-4.149 (m, 10H), 2.35-2.28 (m, 2H), 2.25 (s, 3H), 1.67 (s, 3H) | 495 |
| 254 | 3 | ¹H-NMR (400 MHz, CDCl$_3$) δ ppm 7.78 (s, 1H), 7.75 (d, 1H, J = 1.2 Hz), 7.59 (d, 2H, J = 8.8 Hz), 7.50 (d, 2H, J = 8.8 Hz), 7.13-7.08 (m, 4H), 6.71 (s, 1H), 5.95 (br.s, 1H), 4.40 (d, 2H, J = 5.6 Hz), 4.19 (br.s, 1H), 3.83 (t, 2H, J = 7.2 Hz), 2.56 (t, 2H, J = 8.4 Hz), 2.27 (s, 3H), 2.20-2.05 (m, 2H), 1.64 (br.s, 3H) | 495 |
| 255 | 2 | ¹H-NMR (400 MHz, CDCl$_3$) δ ppm 7.85 (s, 1H), 7.60 (s, 1H), 7.36-7.27 (m, 2H), 7.25-7.16 (m, 2H), 6.66 (s, 1H), 6.53 (br.s, 1H), 6.05 (br.s, 1H), 4.45 (d, 2H, J = 5.2 Hz), 4.29 (d, 2H, J = 9.2 Hz), 4.12 (br.s, 2H), 3.74 (s, 3H), 3.69 (br.s, 2H), 2.47 (br.s, 2H), 1.71 (s, 3H) | 495 |
| 256 | 2 | | 496 |
| 257 | 1 | ¹H-NMR (400 MHz, DMSO-d$_6$) δ ppm 8.90 (t, 1H, J = 6.0 Hz), 8.00 (s, 1H), 7.95 (d, 1H, J = 1.6 Hz), 7.82 (s, 1H), 7.78 (d, 1H, J = 1.2 Hz), 7.53-7.50 (m, 2H), 7.25-7.23 (m, 2H), 6.95 (d, 1H, J = 1.6 Hz), 4.80, 4.65 (br. s., 2H), 4.36, 4.22 (br. s., 2H), 4.30 (d, 2H, J = 6.4 Hz), 3.84 (s, 3H), 3.31 (s, 3H) | 497 |
| 258 | 2 | ¹H-NMR (400 MHz, CDCl$_3$) δ ppm 7.85 (s, 1H), 7.61 (s, 1H), 7.31-7.21 (m, 1H), 6.85 (br.s, 1H), 6.82-6.66 (m, 3H), 6.02 (br.s, 1H), 4.41 (d, 2H, J = 4.0 Hz), 4.36 (br.s, 2H), 4.06 (br.s, 2H), 3.68 (s, 3H), 3.63 (br.s, 2H), 2.40 (br.s, 2H), 1.65 (s, 3H) | 497 |
| 259 | 2 | ¹H-NMR (400 MHz, CD$_3$OD) δ ppm 7.92 (s, 1H), 7.78 (s, 2H), 7.72 (s, 1H), 7.38 (t, 1H, J = 8.0 Hz), 7.21-7.19 (m, 2H), 6.87 (s, 1H), 4.45 (s, 2H), 4.10 (s, 2H), 3.73-3.64 (m, 1H), 1.19 (s, 6H) | 498 |
| 260 | 3 | ¹H-NMR (400 MHz, CDCl$_3$) δ ppm 7.83 (s, 1H), 7.75 (s, 1H), 7.59-7.57 (m, 2H), 7.51-7.49 (m, 2H), 7.27-7.25 (m, 2H), 6.99-6.95 (m, 2H), 6.74 (s, 1H), 6.18 (d, 1H, J = 6.8 Hz), 5.09-5.06 (m, 1H), 4.54 (br.s, 2H), 3.85-3.82 (m, 3H), 2.56 (t, 2H, J = 8.0 Hz), 2.15-2.13 (m, 2H), 1.45 (d, 3H, J = 6.4 Hz) | 499 |
| 261 | 2 | ¹H-NMR (400 MHz, CD$_3$OD) δ 8.27 (s, 1H), 7.89 (s, 1H), 7.82 (d, 2H, J = 7.6 Hz), 7.68 (d, 2H, J = 8.0 Hz), 7.42 (s, 1H), 7.38-7.35 (m, 2H), 7.08-7.03 (m, 2H), 5.07-5.03 (m, 3H), 4.64 (br.s, 2H), 4.42-4.40 (m, 2H), 4.23-4.19 (m, 2H), 3.79-3.78 (m, 1H), 2.42-2.36 (m, 2H), 1.47 (d, 3H, J = 7.2 Hz) | 499 |
| 262 | 2 | ¹H-NMR (400 MHz, CD$_3$OD) δ ppm 8.69 (d, 1H, J = 6.8 Hz), 7.88 (s, 2H), 7.38-7.34 (m, 2H), 7.08-7.03 (m, 2H), | 499 |

-continued

| Compound Number | Synthetic Method | ¹H MR | LC/MS M + 1 |
|---|---|---|---|
| | | 5.06 (br.s, 1H), 4.90 (br.s, 2H), 3.93 (s, 1H), 3.78 (br.s, 2H) , 3.49 (s, 1H), 3.34 (s, 1H), 2.92 (s, 3H), 2.62 (br.s, 1H), 1.47 (d, 3H, J = 7.2 Hz) | |
| 263 | 2 | ¹H-NMR (400 MHz, CDCl₃) δ ppm 7.79 (s, 1H), 7.51 (s, 1H), 7.25 (t, 1H, J = 8.0 Hz), 7.05 (t, 2H, J = 7.2 Hz), 6.50 (s, 1H), 5.99 (br.s, 2H), 4.55 (br.s, 4H), 4.44 (d, 2H, J = 6.0 Hz), 4.05 (br.s, 2H), 3.67 (s, 3H), 3.62 (br.s, 2H), 3.46-3.43 (m, 1H), 2.41 (br.s, 2H) | 499 |
| 264 | 2 | ¹H-NMR (400 MHz, DMSO-d₆) δ ppm 8.80 (t, 1H, J = 6.0 Hz), 8.16 (s, 1H), 7.84 (s, 1H), 7.70 (d, 2H, J = 8.4 Hz), 7.17-7.11 (m, 5H), 6.98 (d, 2H, J = 8.4 Hz), 4.85 (br. s., 1H), 4.70 (br. s., 1H), 4.29-4.23 (m, 4H), 3.33 (s, 3H), 2.26 (s, 3H), 1.30 (s, 9H) | 500 |
| 265 | 2 | ¹H NMR (400 MHz, DMSO-d6) δ 8.58 (t, J = 5.9 Hz, 1H), 7.86-7.70 (m, 2H), 7.19-7.07 (m, 4H), 6.79 (d, J = 1.7 Hz, 1H), 6.22-6.15 (m, 1H), 4.74-4.52 (m, 2H), 4.23 (m, 4H), 3.83 (dt, J = 5.3, 2.6 Hz, 2H), 3.65-3.54 (m, 1H), 3.36 (t, J = 5.6 Hz, 2H), 2.26 (s, 3H), 1.74 (m, 4H)-one peak partially hidden by water signal. | 500 |
| 266 | 2 | ¹H-NMR (400 MHz, DMSO-d₆) δ ppm 8.56 (d, 1H, J = 8.0 Hz), 7.81 (s, 1H), 7.79 (d, 1H, J = 8.0 Hz), 7.38 (d, 2H, J = 8.0 Hz), 7.31 (d, 2H, J = 8.0 Hz), 6.79 (s, 1H), 6.09 (s, 1H), 4.94 (q, 1H, J = 8.0 Hz), 4.80-4.43 (m, 2H), 4.53 (t, 1H, J = 4.0 Hz), 4.42-4.02 (br m, 2H), 3.63-3.55 (m, 1H), 3.43-3.29 (m, 2H), 2.74-2.57 (m, 4H), 2.20-2.08 (m, 2H), 1.90-1.71 (m, 2H) | 502 |
| 267 | 2 | ¹H NMR (300 MHz, DMSO-d6) δ 8.61 (t, J = 5.9 Hz, 1H), 7.80 (d, J = 4.8 Hz, 2H), 7.15 (d, J = 2.0 Hz, 4H), 6.81 (d, J = 1.7 Hz, 1H), 6.20 (s, 1H), 4.78-4.49 (m, 2H), 4.28 (m, 4H), 3.98 (s, 2H), 3.60 (d, J = 5.6 Hz, 1H), 3.58-3.47 (m, 2H), 2.28 (s, 3H), 1.42 (s, 9H). | 503 |
| 268 | 2 | ¹H NMR (400 MHz, DMSO-d₆) δ 9.07-8.68 (m, 1H), 8.10-7.58 (m, 4H), 7.25-6.96 (m, 4H), 6.84 (d, J = 1.7 Hz, 1H), 4.71 (m, 2H), 4.53 (s, 1H), 4.31 (d, J = 5.9 Hz, 3H), 4.17 (s, 1H), 3.99 (s, 2H), 3.19 (s, 2H), 2.41 (s, 3H), 2.26 (s, 3H), 1.07 (s, 6H) | 503 |
| 269 | 2 | ¹H-NMR (400 MHz, DMSO-d₆) δ ppm 8.52 (d, 1H, J = 8.4 Hz), 8.06 (s, 1H), 7.78 (s, 1H), 7.65 (d, 2H, J = 8.4 Hz), 7.38-7.30 (m, 4H), 6.98 (s, 1H), 6.89 (d, 2H, J = 8.4 Hz), 4.75-4.71 (m, 1H), 4.64-4.58 (m, 1H), 4.50-4.05 (m, 4H), 3.65-3.55 (m, 1H), 1.67 (q, 2H, J = 7.2 Hz), 1.25 (d, 6H, J = 6.0 Hz), 0.83 (t, 3H, J = 7.2 Hz) | 504 |
| 270 | 2 | ¹H-NMR (400 MHz, DMSO-d₆) δ ppm 8.56 (d, 1H, J = 8.4 Hz), 8.19 (s, 1H), 7.85 (s, 1H), 7.69 (d, 2H, J = 7.6 Hz), 7.45 (d, 1H, J = 8.4 Hz), 7.39-7.31 (m, 4H), 7.13 (s, 1H), 4.76-4.70 (m, 1H), 4.37-4.14 (m, 4H), 3.65-3.60 (m, 1H), 1.70-1.64 (m, 2H), 1.42 (s, 6H), 0.84 (t, 3H, J = 7.2 Hz) | 504 |
| 271 | 2 | ¹H-NMR (400 MHz, CD₃OD) δ ppm 7.87 (s, 1H), 7.72 (s, 1H), 7.58 (d, 2H, J = 8.0 Hz), 7.32 (s, 4H), 7.01 (d, 2H, J = 8.4 Hz), 6.94 (s, 1H), 5.06-5.01 (m, 1H), 3.71-3.64 (m, 1H), 1.46 (d, 3H, J = 6.8 Hz), 1.35 (s, 9H) | 504 |
| 272 | 2 | ¹H NMR (300 MHz, DMSO-d6) δ 8.63 (t, J = 5.8 Hz, 1H), 8.23 (d, J = 1.6 Hz, 1H), 7.89-7.76 (m, 2H), 7.46 (d, J = 8.0 Hz, 2H), 7.24-7.09 (m, 4H), 4.72 (d, J = 26.2 Hz, 2H), 4.50-4.13 (m, 4H), 3.64 (dd, J = 10.1, 5.3 Hz, 1H), 2.28 (s, 2H), 1.39-1.29 (m, 2H), 1.15 (d, J = 5.2 Hz, 2H). | 506 |
| 273 | 3 | ¹H-NMR (400 MHz, CD₃OD) δ ppm 7.90 (s, 1H), 7.72 (s, 1H), 7.47-7.40 (m, 1H), 7.37-7.34 (m, 3H), 7.10-7.03 (3H, m), 6.96 (s, 1H), 5.08-5.03 (m, 1H), 4.90 (br.s, 2H), 4.58 (br.s, 2H), 3.69-3.66 (m, 1H), 1.47 (d, J = 6.8 Hz), 1.36 (s, 9H) | 506 |
| 274 | 1 | ¹H-NMR (400 MHz, DMSO-d₆) δ ppm 8.81 (t, 1H, J = 5.6 Hz), 8.42 (d, 1H, J = 1.6 Hz), 8.08 (d, 2H, J = 8.4 Hz), 7.90 (d, 2H, J = 8.4 Hz), 7.89 (s, 1H), 7.34 (d, 1H, J = 1.6 Hz), 7.16 (d, 2H, J = 8.0 Hz), 7.11 (d, 2H, J = 8.0 Hz), 4.91-4.88 (m, 1H), 4.74-4.71 (m, 1H), 4.42-4.26 (m, 4H), 3.34 (s, 3H), 3.23 (s, 3H), 2.26 (s, 3H) | 506 |
| 275 | 3 | ¹H-NMR (400 MHz, DMSO-d₆) δ ppm 8.59 (d, 1H, J = 8.4 Hz), 8.17 (s, 1H), 7.82 (s, 1H), 7.72 (d, 2H, J = 7.6 Hz), 7.39 (d, 2H, J = 8.0 Hz), 7.34-7.32 (m, 4H), 7.09 (s, 1H), 5.23 (d, 1H, J = 4.4 Hz), 4.76-4.71 (m, 3H), 4.55-4.52 (m, 1H), 4.32-4.10 (br, 2H), 3.68-3.64 (m, 1H), 3.44-3.41 (m, 2H), 3.34-3.33 (m, 1H), 1.71-1.65 (m, 2H), 0.85 (t, 3H, J = 7.2 Hz) | 506 |
| 276 | 3 | ¹H-NMR (400 MHz, DMSO-d₆) δ ppm 8.58 (d, 1H, J = 8.0 Hz), 8.18 (s, 1H), 7.82 (s, 1H), 7.73 (d, 2H, J = 6.4 Hz), 7.41-7.33 (m, 6H), 7.09 (s, 1H), 5.23 (s, 1H), 4.75- | 506 |

-continued

| Compound Number | Synthetic Method | $^1$H MR | LC/MS M + 1 |
|---|---|---|---|
| | | 4.72 (m, 3H), 4.56-4.52 (m, 2H), 4.40-4.00 (br, 2H), 3.65 (br. s, 1H), 3.43 (br. s., 1H), 3.34-3.31 (m, 1H), 1.72-1.68 (m, 2H), 0.85 (s, 3H) | |
| 277 | 2 | $^1$H-NMR (400 MHz, DMSO-$d_6$) δ ppm 10.31 (s, 1H), 8.15 (s, 1H), 7.83 (s, 1H), 7.68 (d, 2H, J = 8.4 Hz), 7.60 (d, 2H, J = 9.2 Hz), 7.49 (d, 2H, J = 8.8 Hz), 7.44 (d, 2H, J = 8.4 Hz), 7.08 (s, 1H), 4.98 (s, 1H), 4.80-4.70 (m, 2H), 4.41-4.29 (m, 2H), 3.80-3.75 (m, 1H), 1.42 (s, 6H) | 507 |
| 278 | 3 | $^1$H-NMR (400 MHz, DMSO-$d_6$) δ ppm 8.57 (d, 1H, J = 8.4 Hz), 8.16 (s, 1H), 7.93 (s, 1H), 7.81 (s, 1H), 7.77 (s, 1H), 7.39 (d, 2H, J = 8.4 Hz), 7.32 (d, 2H, J = 8.4 Hz), 6.91 (s, 1H), 4.74-4.00 (m, 5H), 3.70-3.56 (m, 1H), 2.83 (s, 2H), 1.70-1.62 (m, 2H), 1.47 (s, 6H), 0.83 (t, 3H, J = 7.2 Hz) | 507 |
| 279 | 2 | $^1$H NMR (300 MHz, DMSO-d6) δ 8.45 (d, J = 7.8 Hz, 1H), 8.40 (d, J = 1.6 Hz, 1H), 8.08 (d, J = 8.4 Hz, 2H), 7.96-7.84 (m, 3H), 7.42-7.32 (m, 2H), 7.30-7.22 (m, 1H), 7.22-7.09 (m, 2H), 4.98 (m, 1H), 4.88 (d, J = 9.1 Hz, 1H), 4.49-4.29 (m, 2H), 4.02 (br.s, 1H), 3.23 (s, 3H), 1.60 (s, 3H), 1.39 (d, J = 7.0 Hz, 3H). | 508 |
| 280 | 2 | $^1$H NMR (300 MHz, DMSO-$d_6$) δ 8.62 (t, J = 5.8 Hz, 1H), 8.19 (d, J = 1.7 Hz, 1H), 7.86 (s, 1H), 7.75-7.66 (m, 2H), 7.52-7.24 (m, 5H), 7.13-7.03 (m, 1H), 4.98-4.76 (m, 2H), 4.49-4.30 (m, 4H), 4.07-3.94 (m, 1H), 1.61 (s, 3H), 1.44 (s, 6H) | 508 |
| 281 | 2 | $^1$H-NMR (400 MHz, DMSO-$d_6$) δ ppm 8.55 (d, 1H, J = 7.6 Hz), 8.05 (s, 1H), 8.01 (s, 1H), 7.88 (s, 1H), 7.80 (s, 1H), 7.38-7.30 (m, 4H), 7.06 (br.s, 1H), 4.75-4.70 (m, 1H), 3.98 (s, 2H), 3.70-3.60 (m, 1H), 1.70-1.64 (m, 2H), 1.06 (s, 6H), 0.83 (t, 3H, J = 7.2 Hz) | 508 |
| 282 | 3 | $^1$H-NMR (400 MHz, DMSO-$d_6$) δ ppm 8.58 (d, 1H, J = 8.4 Hz), 8.02 (s, 1H), 7.93 (d, 1H, J = 1.6 Hz), 7.80 (s, 1H), 7.79 (s, 1H), 7.39 (d, 2H, J = 8.4 Hz), 7.33 (d, 2H, J = 8.4 Hz), 6.89 (s, 1H), 4.92 (d, 1H, J = 5.2 Hz), 4.81-4.45 (m, 3H), 4.44-3.92 (m, 4H), 3.79-3.69 (m, 1H), 3.68-3.58 (m, 1H), 1.74-1.60 (m, 2H), 1.45-1.21 (m, 2H), 0.89 (t, 3H, J = 7.2 Hz), 0.85 (t, 3H, J = 7.2 Hz) | 508 |
| 283 | 3 | $^1$H-NMR (400 MHz, DMSO-$d_6$) δ ppm 8.62 (d, 1H, J = 8.4 Hz), 8.18 (s, 1H), 8.04 (s, 1H), 7.88 (s, 1H), 7.83 (s, 1H), 7.40 (d, 2H, J = 8.4 Hz), 7.33 (d, 2H, J = 8.0 Hz), 7.07 (s, 1H), 4.77-4.71 (m, 1H), 4.67-4.10 (m, 5H), 3.70-3.66 (m, 1H), 3.58 (s, 2H), 1.71-1.67 (m, 2H), 1.48 (s, 6H), 0.85 (t, 3H, J = 7.2 Hz) | 508 |
| 284 | 3 | $^1$H-NMR (400 MHz, DMSO-$d_6$) δ ppm 8.58 (d, 1H, J = 8.4 Hz), 8.06 (s, 1H), 7.91 (d, 1H, J = 1.6 Hz), 7.78 (s, 1H), 7.77 (s, 1H), 7.38 (d, 2H, J = 8.4 Hz), 7.31 (d, 2H, J = 8.4 Hz), 6.88 (s, 1H), 4.97 (d, 1H, J = 5.2 Hz), 4.76-4.54 (m, 3H), 4.35-4.30 (br, 1H), 4.18-4.04 (m, 2H), 3.82-3.78 (m, 1H), 3.67-3.60 (m, 1H), 1.69-1.66 (m, 2H), 1.44 (d, 3H, J = 7.2 Hz), 0.87 (d, 3H, J = 6.0 Hz), 0.83 (t, 3H, J = 7.2 Hz) | 508 |
| 285 | 3 | $^1$H-NMR (400 MHz, DMSO-$d_6$) δ ppm 8.57 (d, 1H, J = 8.0 Hz), 8.06 (s, 1H), 7.91 (d, 1H, J = 1.6 Hz), 7.78 (s, 1H), 7.77 (s, 1H), 7.38 (d, 2H, J = 8.4 Hz), 7.32 (d, 2H, J = 8.8 Hz), 6.89 (s, 1H), 4.96 (d, 1H, J = 5.6 Hz), 4.76-4.49 (m, 3H), 4.36-4.30 (br, 1H), 4.18-4.03 (m, 2H), 3.82-3.78 (m, 1H), 3.65-3.61 (m, 1H), 1.71-1.64 (m, 2H), 1.44 (d, 3H, J = 6.8 Hz), 0.87 (d, 6H, J = 6.8 Hz), 0.83 (t, 6H, J = 7.2 Hz) | 508 |
| 286 | 2 | $^1$H-NMR (400 MHz, CDCl$_3$) δ ppm 7.80 (s, 1H), 7.53 (s, 1H), 7.31 (d, 2H, J = 8.4 Hz), 7.21 (d, 2H, J = 8.0 Hz), 6.49 (s, 1H), 6.00 (br.s, 1H), 5.77 (d, 1H, J = 7.6 Hz), 4.91-4.85 (m, 1H), 4.75-4.35 (m, 4H), 4.10 (br.s, 2H), 3.73 (s, 3H), 3.67 (br.s, 2H), 3.51-3.43 (m, 1H), 2.47 (br.s, 2H), 1.88-1.79 (m, 2H), 0.90 (t, 3H, J = 7.2 Hz) | 508 |
| 287 | 2 | $^1$H NMR (400 MHz, DMSO-d6) δ 8.60 (t, J = 5.9 Hz, 1H), 8.21 (d, J = 1.7 Hz, 1H), 7.83 (s, 1H), 7.82-7.75 (m, 2H), 7.57 (d, J = 8.1 Hz, 2H), 7.24-7.05 (m, 5H), 6.56 (s, 1H), 4.72 (d, J = 35.9 Hz, 2H), 4.40-4.16 (m, 4H), 3.63 (ddd, J = 14.5, 8.8, 5.8 Hz, 1H), 2.27 (s, 3H), 1.70 (s, 3H). | 510 |
| 288 | 2 | 1H-NMR (400 MHz, CD3OD) δ ppm 8.17 (s, 1H), 7.88 (s, 1H), 7.68 (d, 2H, J = 8.4 Hz), 7.53 (d, 2H, J = 8.0 Hz), 7.47 (s, 1H), 7.36-7.32 (m, 3H), 4.74 (br.s, 1H), 3.75 (s, 2H), 1.54 (s, 6H) | 510 |
| 289 | 2 | $^1$H-NMR (400 MHz, CDCl$_3$) δ ppm 7.92 (s, 1H), 7.66 (s, 1H), 7.31 (d, 1H, J = 8.0 Hz), 7.13-7.07 (m, 2H), 6.85 | 513 |

-continued

| Compound Number | Synthetic Method | ¹H MR | LC/MS M + 1 |
|---|---|---|---|
| | | (br.s, 1H), 6.77 (s, 1H), 6.08 (br.s, 1H), 4.50 (d, 2H, J = 5.2 Hz), 4.38 (d, 2H, J = 9.6 Hz), 4.14 (br.s, 2H), 3.75 (s, 3H), 2.48 (br.s, 2H), 1.72 (s, 3H) | |
| 290 | 2 | ¹H-NMR (400 MHz, DMSO-$d_6$) δ ppm 8.49 (d, 1H, J = 8.0 Hz), 8.11 (s, 1H), 7.80 (s, 1H), 7.68 (d, 2H, J = 8.0 Hz), 7.18 (d, 2H, J = 8.0 Hz), 7.12 (d, 2H, J = 8.0 Hz), 7.03 (s, 1H), 6.96 (d, 2H, J = 8.0 Hz), 4.92 (q, 1H, J = 8.0 Hz), 4.80-4.48 (br m, 2H), 4.48 (t, 1H, J = 4.0 Hz), 4.41-4.04 (br m, 2H), 3.65-3.57 (m, 1H), 3.42-3.27 (m, 2H), 2.26 (s, 3H), 1.93-1.73 (m, 2H), 1.29 (s, 9H) | 514 |
| 291 | 1 | ¹H-NMR (400 MHz, DMSO-$d_6$) δ ppm 8.67 (s, 1H), 8.37 (s, 1H), 8.07-8.05 (m, 2H), 7.90-7.85 (m, 2H), 7.42-7.37 (m, 2H) 7.28-7.26 (m, 2H) , 4.78-4.68 (m, 2H), 4.34-4.33 (m, 2H), 4.20 (br.s, 2H), 3.64 (br.s, 1H), 3.21 (s, 3H) | 514 |
| 292 | 2 | ¹H-NMR (400 MHz, CDCl₃) δ ppm 7.89 (s, 1H), 7.67 (s, 1H), 7.43 (s, 1H), 7.28 (s, 2H), 6.76 (s, 1H), 6.64 (br.s, 1H), 4.62 (br.s, 1H), 4.13 (br.s, 2H), 3.74 (s, 3H), 3.70 (s, 4H), 2.46 (br.s, 2H) | 515 |
| 293 | 3 | ¹H-NMR (400 MHz, CD₃OD) δ ppm 8.62 (d, 1H, J = 7.6 Hz), 7.97 (s, 1H), 7.75 (s, 1H), 7.67 (d, 2H, J = 8.4 Hz), 7.52 (d, 2H, J = 7.6 Hz), 7.34-7.29 (m, 4H), 7.06 (s, 1H), 4.85-4.80 (m, 3H), 4.50-4.40 (m, 2H), 3.73-3.70 (m, 1H), 2.54-2.53 (m, 2H), 2.40-2.33 (m, 2H), 2.02-2.00 (m, 1H), 1.82-1.72 (m, 3H), 0.93 (t, 3H, J = 7.2 Hz) | 516 |
| 294 | 2 | ¹H-NMR (400 MHz, DMSO-$d_6$) δ ppm 8.54 (d, 1H, J = 8.0 Hz), 8.11 (s, 1H), 7.80 (s, 1H), 7.67 (d, 2H, J = 8.4 Hz), 7.39-7.31 (m, 4H), 7.03 (s, 1H), 6.96 (d, 2H, J = 8.4 Hz), 4.76-4.70 (m, 1H), 4.30-4.25 (m, 2H), 4.19-4.10 (m, 2H), 3.66-3.62 (m, 1H), 1.69-1.66 (m, 2H), 1.29 (s, 9H), 0.83 (t, 3H, J = 7.2 Hz) | 518 |
| 295 | 2 | ¹H-NMR (400 MHz, CDCl₃) δ ppm 7.85 (s, 1H), 7.82 (s, 1H), 7.57-7.51 (m, 4H), 7.33-7.20 (m, 4H), 6.75 (s, 1H), 5.78 (d, 1H, J = 7.6 Hz), 4.88 (q, 1H, J = 7.6 Hz), 4.21 (br.s, 2H), 1.89-1.82 (m, 2H), 1.69 (s, 3H), 1.61 (s, 6H), 0.92 (t, 3H, J = 7.6 Hz) | 518 |
| 296 | 2 | ¹H-NMR (400 MHz, CDCl₃) δ ppm 7.78 (s, 1H), 7.72 (s, 1H), 7.40 (d, 2H, J = 8.4 Hz), 7.25 (d, 2H, J = 8.4 Hz), 7.17 (d, 2H, J = 8.4 Hz), 6.95 (d, 2H, J = 8.8 Hz), 6.67 (s, 1H), 5.76 (d, 1H, J = 7.2 Hz), 5.10-5.03 (m, 1H), 4.16 (br.s, 2H), 1.62 (s, 3H), 1.45 (d, 3H, J = 6.8 Hz), 1.30 (s, 9H) | 518 |
| 297 | 3 | ¹H-NMR (400 MHz, CD₃OD) δ ppm 8.60 (d, 1H, J = 8.0 Hz), 7.91 (s, 1H), 7.71 (s, 1H), 7.61 (d, 2H, J = 8.4 Hz), 7.43 (d, 2H, J = 8.4 Hz), 7.34-7.28 (m, 4H), 6.99 (s, 1H), 480-4.78 (m, 3H), 4.50-4.40 (m, 2H), 3.71-3.68 (m, 1H), 1.84-1.77 (m, 4H), 1.51 (s, 3H), 0.92 (t, 3H, J = 7.2 Hz), 0.78 (t, 3H, J = 7.2 Hz) | 518 |
| 298 | 2 | ¹H-NMR (400 MHz, DMSO-$d_6$) δ ppm 8.58 (d, 1H, J = 8.2 Hz), 8.07 (s, 1H), 7.91 (d, 1H, J = 1.2 Hz), 7.78 (s, 2H), 7.40 (d, 2H, J = 8.4 Hz), 7.33 (d, 2H, J = 8.4 Hz), 6.89 (s, 1H), 4.81-3.91 (m, 8H), 3.67-3.64 (m, 1H), 1.91 (t, 2H, J = 8.4 Hz), 1.71-1.65 (m, 2H), 1.13 (s, 6H), 0.85 (t, 3H, J = 7.2 Hz) | 522 |
| 299 | 3 | ¹H-NMR (400 MHz, DMSO-$d_6$) δ ppm 8.59 (d, 1H, J = 8.4 Hz), 8.05 (s, 1H), 7.94 (d, 1H, J = 1.6 Hz), 7.79 (s, 1H), 7.78 (s, 1H), 7.39 (d, 2H, J = 8.4 Hz), 7.33 (d, 2H, J = 8.4 Hz), 6.91 (s, 1H), 4.77-4.53 (m, 4H), 4.38-4.33 (br, 1H), 4.21-4.08 (m, 2H), 3.67-3.62 (m, 1H), 1.72-1.65 (m, 2H), 1.45 (d, 3H, J = 6.8 Hz), 1.05 (s, 3H), 1.0 (s, 3H), 0.85 (t, 3H, J = 7.2 Hz) | 522 |
| 300 | 3 | ¹H-NMR (400 MHz, DMSO-$d_6$) δ ppm 8.59 (d, 1H, J = 8.0 Hz), 8.05 (s, 1H), 7.94 (d, 1H, J = 1.6 Hz), 7.79 (s, 1H), 7.78 (s, 1H), 7.39 (d, 2H, J = 8.8 Hz), 7.33 (d, 2H, J = 8.4 Hz), 6.91 (s, 1H), 4.77-4.51 (m, 4 H), 4.38-4.33 (br, 1H), 4.21-4.07 (m, 2H), 3.66-3.63 (m, 1 H), 1.70-1.65 (m, 2H), 1.45 (d, 3H, J = 6.8 Hz), 1.05 (s, 3H), 1.0 (s, 3H), 0.85 (t, 3H, J = 7.2 Hz) | 522 |
| 301 | 3 | ¹H NMR (400 MHz, DMSO-d6) δ 8.56 (d, J = 8.1 Hz, 1H), 7.83-7.73 (m, 2H), 7.41-7.35 (m, 2H), 7.34-7.27 (m, 2H), 6.79 (s, 1H), 6.20 (s, 1H), 4.94 (m, 1H), 4.78-4.13 (m, 6H), 4.08 (d, J = 12.7 Hz, 2H), 3.68-3.55 (m, 3H), 2.43-2.28 (m, 3H), 1.92-1.69 (m, 2H), 1.00 (m, 3H) - one signal is partially buried under water signal. | 523 |
| 302 | 2 | ¹H-NMR (400 MHz, CD₃OD) δ ppm 7.69 (s, 1H), 7.63 (s, 1H), 7.34-7.28 (m, 4H), 6.16 (s, 1H), 6.13 (br.s, 1H), 4.88-4.76 (m, 4H), 4.55-4.50 (m, 1H), 4.15 (q, 2H, J = 7.2 Hz), | 523 |

| Compound Number | Synthetic Method | ¹H MR | LC/MS M + 1 |
|---|---|---|---|
| | | 4.08 (br.s, 2H), 3.67 (br.s, 3H), 2.49 (br.s, 2H), 1.82-1.78 (m, 2H), 1.27 (t, 3H, J = 7.2 Hz), 0.92 (t, 3H, J = 7.2 Hz) | |
| 303 | 2 | ¹H-NMR (400 MHz, CDCl₃) δ ppm 7.74 (s, 1H), 7.47 (s, 1H), 7.25-7.13 (m, 4H), 6.43 (s, 1H), 5.94 (br.s, 1H), 5.82 (d, 1H, J = 8.0 Hz), 4.83-4.78 (m, 1H), 4.63-4.62 (m, 2H), 4.09 (br.s, 2H), 4.04 (br.s, 2H), 3.67 (s, 3H), 3.61 (br.s, 2H), 2.40 (br.s, 2H), 1.82-1.75 (m, 2H), 1.60 (s, 3H), 0.84 (t, 3H, J = 7.6 Hz) | 523 |
| 304 | 2 | ¹H-NMR (400 MHz, DMSO-d₆) δ ppm 8.44 (d, 1H, J = 8.4 Hz), 8.10 (s, 1H), 7.79 (s, 1H), 7.66 (d, 2H, J = 8.4 Hz), 7.15 (d, 2H, J = 8.0 Hz), 7.01-6.99 (m, 3H), 6.95 (d, 2H, J = 8.4 Hz), 4.70-4.64 (m, 2H), 4.33-4.07 (m, 3H), 3.65-3.55 (m, 1H), 1.87-1.84 (m, 1H), 1.67-1.64 (m, 2H), 1.29 (s, 9H), 0.89 (d, 2H, J = 6.8 Hz), 0.81 (t, 3H, J = 6.8 Hz), 0.63-0.59 (m, 2H) | 524 |
| 305 | 1 | ¹H-NMR (400 MHz, DMSO-d₆) δ ppm 8.55 (d, 1H, J = 8.4 Hz), 8.34 (s, 1H), 8.04 (d, 2H, J = 7.6 Hz), 7.87 (d, 2H, J = 8.0 Hz), 7.82 (s, 1H), 7.37-8.29 (m, 4H), 7.28 (br.s, 1H), 4.73-4.71 (m, 1H), 4.35-4.09 (m, 4H), 3.70-3.60 (m, 1H), 3.19 (s, 3H), 1.68-1.65 (m, 2H), 0.82 (t, 3H, J = 7.2 Hz) | 524 |
| 306 | 3 | ¹H-NMR (400 MHz, DMSO-d₆) δ ppm 8.56 (d, 1H, J = 8.4 Hz), 8.06 (s, 1H), 7.91 (s, 1H), 7.78 (s, 1H), 7.77 (s, 1H), 7.38 (d, 2H, J = 8.8 Hz), 7.32 (d, 2H, J = 8.4 Hz), 6.88 (s, 1H), 4.95 (d, 1H, J = 5.6 Hz), 4.76-4.51(m, 3H), 4.36-4.33 (br, 1H), 4.09-4.03 (m, 2H), 3.82-3.78 (m, 1H), 3.66-3.61(m, 1H), 1.71-1.64 (m, 2H), 1.44 (d, 3H, J = 6.8 Hz), 0.88-0.82 (m, 6H) | 524 |
| 307 | 2 | ¹H-NMR (400 MHz, DMSO-d₆) δ ppm 8.85 (d, 1H, J = 6.8 Hz), 8.11 (s, 1H), 7.81 (s, 1H), 7.68 (d, 2H, J = 8.8 Hz), 7.56 (s, 1H), 7.38 (d, 2H, J = 2.4 Hz), 7.04 (s, 1H), 6.95 (d, 2H, J = 8.4 Hz), 4.70 (d, 1H, J = 6.0 Hz), 3.62 (s, 2H), 1.28 (s, 9H) | 524 |
| 308 | 2 | ¹H-NMR (400 MHz, CDCl₃) δ ppm 7.96 (d, 2H, J = 8.4 Hz), 7.91 (d, 1H, J = 1.2 Hz), 7.88 (s, 1H), 7.75 (d, 2H, J = 8.4 Hz), 7.33-7.29 (m, 1H), 7.14-7.10 (m, 2H), 6.84 (s, 1H), 6.14 (br. s., 1H), 5.00-4.80 (br., 2H), 4.52 (d, 2H, J = 5.2 Hz), 4.25 (br. s., 2H), 3.09 (s, 3H), 1.72 (s, 3H) | 528 |
| 309 | 2 | ¹H-NMR (400 MHz, DMSO-d₆) δ ppm 8.55 (d, 1H, J = 8.4 Hz), 7.90 (s, 1H), 7.86 (s, 1H), 7.36 (d, 2H, J = 1.1 Hz), 7.31 (d, 2H, J = 7.6 Hz), 6.95 (br.s, 1H), 6.26 (br.s, 1H), 4.74-4.70 (m, 1H), 4.40-4.30 (m, 2H), 4.23-4.14 (m, 2H), 3.81 (br.s, 2H), 3.65-3.60 (m, 1H), 3.35-3.34 (m, 2H), 2.90 (s, 3H), 2.55 (br.s, 2H), 1.68-1.65 (m, 2H), 0.82 (t, 3H, J = 7.2 Hz) | 529 |
| 310 | 2 | ¹H-NMR (400 MHz, DMSO-d₆) δ ppm 8.57 (d, 1H, J = 8.0 Hz), 8.12 (s, 1H), 7.80 (s, 1H), 7.68 (d, 2H, J = 8.0 Hz), 7.38 (d, 2H, J = 8.0 Hz), 7.31 (d, 2H, J = 8.0 Hz), 7.03 (br s, 1H), 6.96 (d, 2H, J = 8.0 Hz), 4.99-4.92 (m, 1H), 4.81-4.53 (br m, 2H), 4.53 (t, 1H, J = 4.0 Hz), 4.41-4.04 (br m, 2H), 3.66-3.57 (m, 1H), 3.45-3.29 (m, 2H), 1.91-1.72 (m, 2H), 1.30 (s, 9H) | 534 |
| 311 | 2 | ¹H NMR (400 MHz, DMSO-d6) δ 8.46-8.32 (m, 1H), 7.86-7.74 (m, 2H), 7.42-7.35 (m, 2H), 7.35-7.27 (m, 2H), 6.76 (s, 1H), 6.20 (d, J = 4.6 Hz, 1H), 4.99-4.88 (m, 2H), 4.74 (br.s, 1H), 4.56 (t, J = 4.9 Hz, 1H), 4.33 (m, 2H), 4.08 (d, J = 12.2 Hz, 2H), 3.96 (br.s, 1H), 3.69-3.56 (m, 2H), 2.36 (m, 3H), 1.89 (m, 1H), 1.78 (m, 1H), 1.00 (m, 3H) - one signal partially buried under water peak. | 537 |
| 312 | 2 | ¹H-NMR (400 MHz, DMSO-d₆) δ ppm 8.72 (d, 1H, J = 7.6 Hz), 8.00-7.97 (m, 2H), 7.81 (s, 1H), 7.79 (br. s., 1H), 7.38 (s, 4H), 6.95 (s, 1H), 4.82-4.21 (m, 6H), 3.99 (s, 2H), 3.28 (s, 3H), 1.83-1.67 (m, 2H), 1.07 (s, 6H), 0.85 (t, 3H, J = 6.8 Hz) | 538 |
| 313 | 2 | ¹H-NMR (400 MHz, CDCl₃) δ ppm 7.97 (d, 2H, J = 8.4 Hz), 7.94-7.86 (m, 2H), 7.77 (d, 2H, J = 8.4 Hz), 7.34 (d, 2H, J = 8.4 Hz), 7.24 (d, 2H, J = 8.4 Hz), 6.82 (d, 1H, J = 1.2 Hz), 5.79 (d, 1H, J = 8.4 Hz), 4.93-4.87 (m, 1H), 3.10 (s, 3H), 1.91-1.83 (m, 2H), 1.73 (s, 3H), 0.94 (t, 3H, J = 7.2 Hz) | 538 |

-continued

| Compound Number | Synthetic Method | $^1$H MR | LC/MS M + 1 |
|---|---|---|---|
| 314 | 2 | $^1$H-NMR (400 MHz, DMSO-d$_6$) δ ppm 8.57 (d, 1H, J = 7.6 Hz), 8.11 (s, 1H), 7.94 (s, 1H), 7.87 (s, 1H), 7.78 (s, 1H), 7.40 (d, 2H, J = 8.8 Hz), 7.33 (d, 2H, J = 8.4 Hz), 6.91 (s, 1H), 6.74 (d, 1H, J = 6.0 Hz), 4.75-4.68 (m, 3H), 4.40-4.36 (m, 3H), 4.23-4.18 (m, 2H), 3.66-3.63 (m, 1H), 1.69-1.65 (m, 2H), 0.85 (t, 3H, J = 7.6 Hz) | 548 |
| 315 | 2 | $^1$H-NMR (400 MHz, DMSO-d$_6$) δ ppm 8.58 (d, 1H, J = 8.4 Hz), 8.11 (s, 1H), 7.94 (s, 1H), 7.88 (s, 1H), 7.78 (s, 1H), 7.39 (d, 2H, J = 8.8 Hz), 7.33 (d, 2H, J = 8.8 Hz), 6.91 (s, 1H), 6.75 (s, 1H), 4.74-4.52 (m, 3H), 4.39-4.36 (m, 3H), 4.22-4.16 (m, 1H), 4.06 (br. s., 1H), 3.65-3.62 (m, 1H), 1.69-1.65 (m, 2H), 0.83 (t, 3H, J = 7.6 Hz) | 548 |
| 316 | 2 | $^1$H NMR (400 MHz, DMSO-d6) δ 8.56 (d, J = 8.1 Hz, 1H), 7.83-7.73 (m, 2H), 7.41-7.34 (m, 2H), 7.34-7.27 (m, 2H), 6.78 (s, 1H), 6.18 (s, 1H), 4.94 (q, J = 7.8 Hz, 1H), 4.75-4.03 (m, 6H), 3.96 (br.s, 2H), 3.60 (td, J = 8.7, 4.4 Hz, 1H), 3.51 (t, J = 5.8 Hz, 2H), 2.41 (br.s, 2H), 1.92-1.69 (m, 2H) - one peak partially obscured by water signal. | 567 |
| 317 | 2 | $^1$H NMR (400 MHz, DMSO-d6) δ 8.39 (d, J = 8.0 Hz, 1H), 7.83-7.76 (m, 2H), 7.41-7.35 (m, 2H), 7.35-7.29 (m, 2H), 6.76 (s, 1H), 6.17 (s, 1H), 4.98-4.90 (m, 1H), 4.74 (br.s, 1H), 4.56 (t, J = 4.9 Hz, 1H), 4.30 (br.s, 2H), 3.96 (br.s, 3H), 3.51 (t, J = 5.7 Hz, 2H), 2.42 (br.s, 2H), 1.90 (dt, J = 14.2, 7.1 Hz, 1H), 1.79 (dt, J = 13.5, 6.5 Hz, 1H), 1.56 (s, 3H), 1.41 (s, 9H). | 581 |

Biochemical Activity of Compounds

In order to assess the activity of chemical compounds against the relevant kinase of interest, the Caliper Life-Sciences electrophoretic mobility shift technology platform is used. Fluorescently labeled substrate peptide is incubated in the presence of kinase and ATP so that a reflective proportion of the peptide is phosphorylated. At the end of the reaction, the mix of phosphorylated (product) and non-phosphorylated (substrate) peptides are passed through the microfluidic system of the Caliper EZ Reader 2, under an applied potential difference. The presence of the phosphate group on the product peptide provides a difference in mass and charge between those of the substrate peptide, resulting in a separation of the substrate and product pools in the sample. As the pools pass a LEDS within the instrument, these pools are detected and resolved as separate peaks. The ratio between these peaks therefore reflects the activity of the chemical matter at that concentration in that well, under those conditions.

Kit wild type assay at Km: In each well of a 384-well plate, 0.2 ng/ul final (2 nM) of wild type Kit (Carna Bioscience 08-156) was incubated in a total of 12.5 ul of buffer (100 mM HEPES pH 7.5, 0.015% Brij 35, 10 mM MgCl2, 1 mM DTT) with 1 uM Srctide (5-FAM-GEEPLY-WSFPAKKK-NH2) and 400 uM ATP at 25 C for 90 minutes in the presence or absence of a dosed concentration series of compound (1% DMSO final concentration). The reaction was stopped by the addition of 70 ul of Stop buffer (100 mM HEPES pH 7.5, 0.015% Brij 35, 35 mM EDTA and 0.2% of Coating Reagent 3 (Caliper Lifesciences)). The plate was then read on a Caliper EZReader 2 (protocol settings: −1.9 psi, upstream voltage −700, downstream voltage −3000, post sample sip 35s). Data was normalized to 0% and 100% inhibition controls and the IC50 or EC50 calculated using a 4-parameter fit using GraphPad Prism.

Kit D816V assay at Km: In each well of a 384-well plate, 0.04 ng/ul (0.5 nM) of D816V Kit (Carna Bioscience 08-156) was incubated in a total of 12.5 ul of buffer (100 mM HEPES pH 7.5, 0.015% Brij 35, 10 mM MgCl2, 1 mM DTT) with 1 uM Srctide (5-FAM-GEEPLYWSFPAKKK-NH2) and 15 uM ATP at 25 C for 90 minutes in the presence or absence of a dosed concentration series of compound (1% DMSO final concentration). The reaction was stopped by the addition of 70 ul of Stop buffer (100 mM HEPES pH 7.5, 0.015% Brij 35, 35 mM EDTA and 0.2% of Coating Reagent 3 (Caliper Lifesciences)). The plate was then read on a Caliper EZReader 2 (protocol settings: −1.9 psi, upstream voltage −700, downstream voltage −3000, post sample sip 35s). Data was normalized to 0% and 100% inhibition controls and the IC50 or EC50 calculated using a 4-parameter fit using GraphPad Prism.

The Table below shows the activity of compounds described herein, against wild-type Kit and mutant Kit (the D816V mutant). In the Table below, for D816V activity, the following designations are used: <1.00 nM=A; 1.01-10.0 nM=B; 10.01-100.0 nM=C; >100 nM=D; and ND=not determined. For wild-type Kit activity, the following designations are used: <10 nM=A; 11-100 nM=B; 100-1000 nM=C; >1000 nM=D; and ND=not determined.

| Compound Number | Structure | D816V IC$_{50}$ (nM) | WT IC$_{50}$ (nM) |
|---|---|---|---|
| 1 | 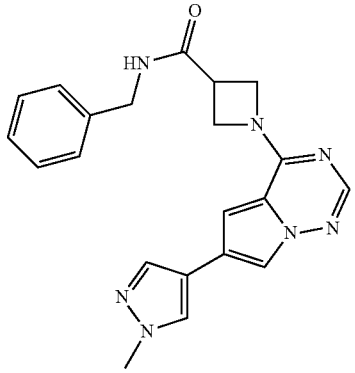 [SMILES: Cn1cc(-c2cc3c(N4CC(C(=O)NCc5ccccc5)C4)ncnn3c2)cn1] | B | C |
| 2 | 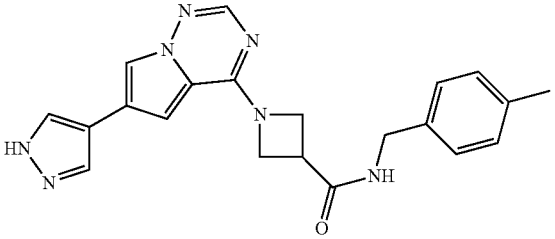 [SMILES: Cc1ccc(CNC(=O)C2CN(c3ncnn4cc(-c5cn[nH]c5)cc34)C2)cc1] | A | C |
| 3 | 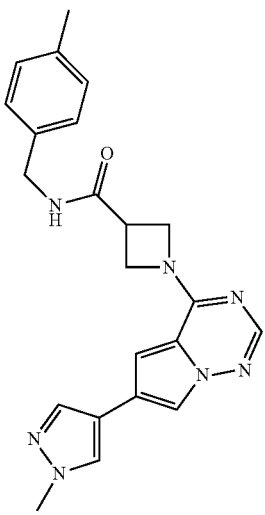 [SMILES: Cc1ccc(CNC(=O)C2CN(c3ncnn4cc(-c5cnn(C)c5)cc34)C2)cc1] | B | C |
| 4 | 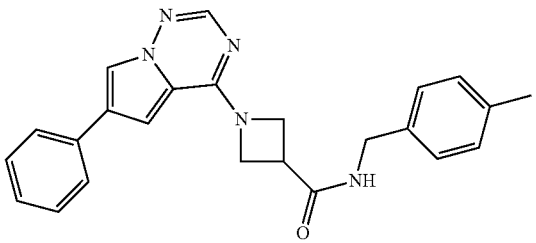 [SMILES: Cc1ccc(CNC(=O)C2CN(c3ncnn4cc(-c5ccccc5)cc34)C2)cc1] | B | C |

| Compound Number | Structure | D816V IC$_{50}$ (nM) | WT IC$_{50}$ (nM) |
|---|---|---|---|
| 5 | 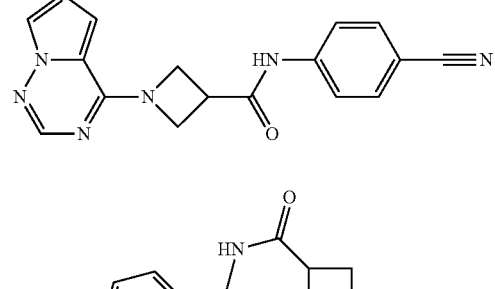 | A | B |
| 6 | 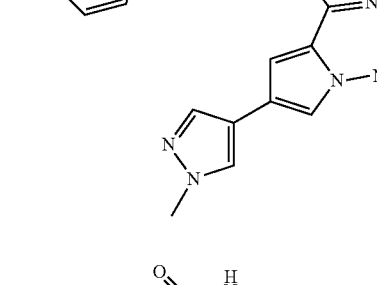 | A | B |
| 7 | 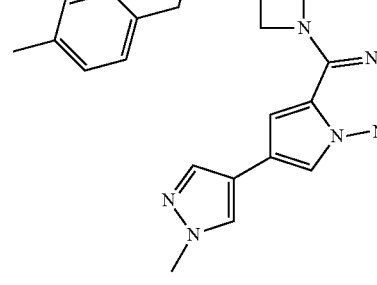 | B | C |
| 8 | 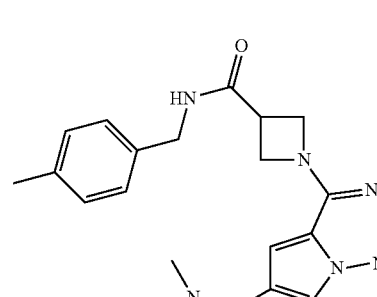 | B | B |

-continued

| Compound Number | Structure | D816V IC$_{50}$ (nM) | WT IC$_{50}$ (nM) |
| --- | --- | --- | --- |
| 9 | 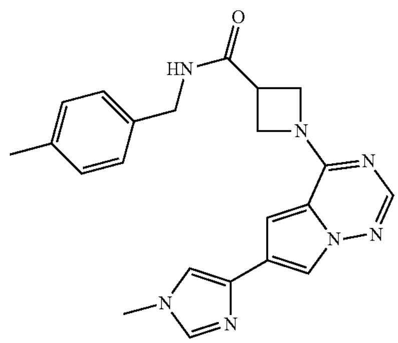 [SMILES: Cc1ccc(CNC(=O)C2CN(c3ncnn4cc(-c5cn(C)cn5)cc34)C2)cc1] | B | C |
| 10 | 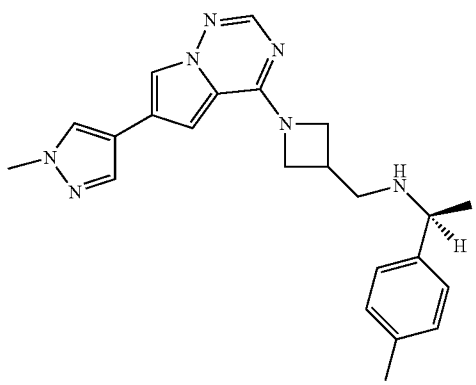 [SMILES: Cc1ccc([C@H](C)NCC2CN(c3ncnn4cc(-c5cnn(C)c5)cc34)C2)cc1] | B | C |
| 11 | 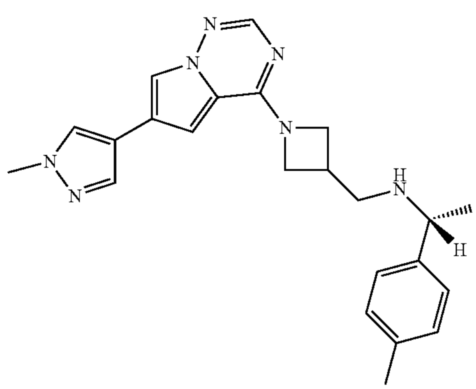 [SMILES: Cc1ccc([C@@H](C)NCC2CN(c3ncnn4cc(-c5cnn(C)c5)cc34)C2)cc1] | B | C |
| 12 | 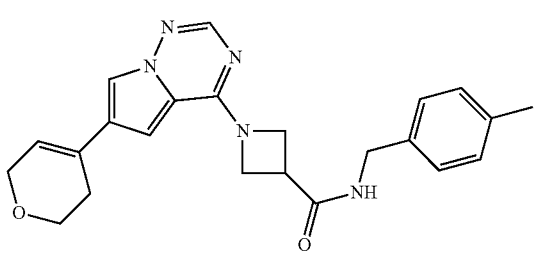 [SMILES: Cc1ccc(CNC(=O)C2CN(c3ncnn4cc(C5=CCOCC5)cc34)C2)cc1] | A | C |

-continued
| Compound Number | Structure | D816V IC$_{50}$ (nM) | WT IC$_{50}$ (nM) |
|---|---|---|---|
| 13 | 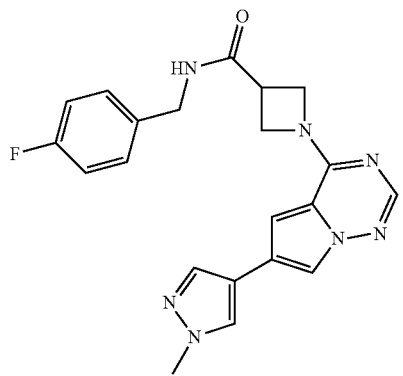 [SMILES: Cn1cc(-c2cc3c(N4CC(C(=O)NCc5ccc(F)cc5)C4)ncnn3c2)cn1] | B | C |
| 14 | 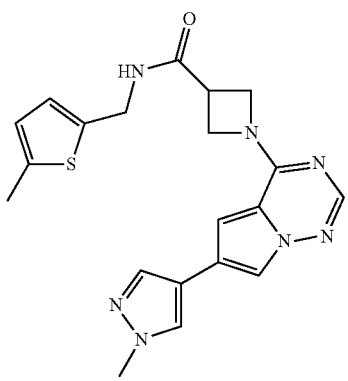 [SMILES: Cc1ccc(CNC(=O)C2CN(c3ncnn4cc(-c5cnn(C)c5)cc34)C2)s1] | A | C |
| 15 | 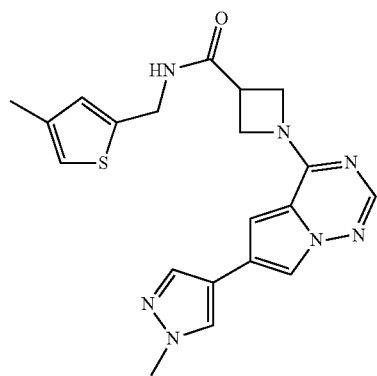 [SMILES: Cc1csc(CNC(=O)C2CN(c3ncnn4cc(-c5cnn(C)c5)cc34)C2)c1] | A | C |

| Compound Number | Structure | D816V IC$_{50}$ (nM) | WT IC$_{50}$ (nM) |
|---|---|---|---|
| 16 | 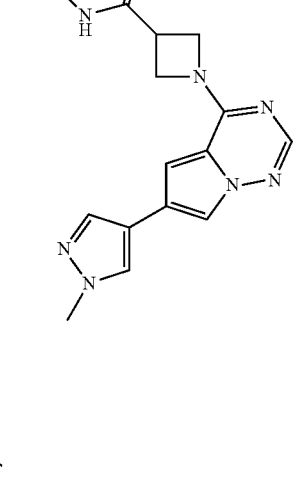 | B | B |
| 17 | 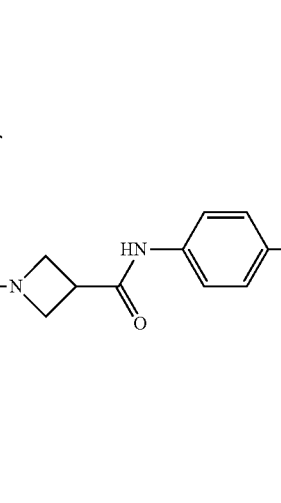 | A | B |
| 18 | 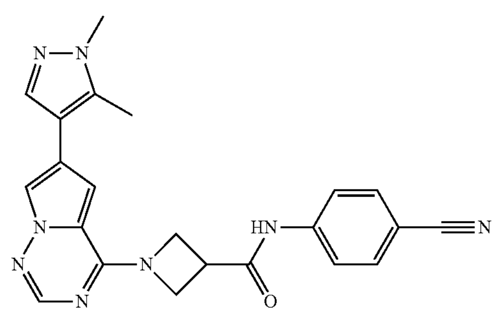 [SMILES: Cc1c(-c2cc3c(N4CC(C(=O)Nc5ccc(C#N)cc5)C4)ncnn3c2)cnn1C] | B | B |
| 19 | 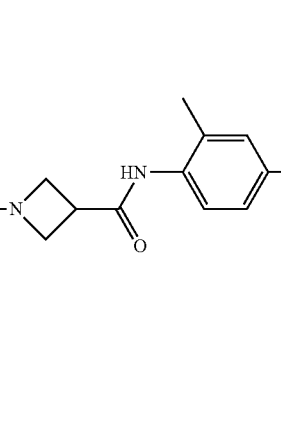 | B | C |

| Compound Number | Structure | D816V IC$_{50}$ (nM) | WT IC$_{50}$ (nM) |
|---|---|---|---|
| 20 | 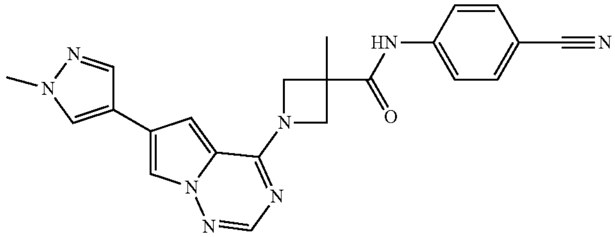 [SMILES: Cn1cc(-c2cc3c(N4CC(C)(C(=O)Nc5ccc(C#N)cc5)C4)ncnn3c2)cn1] | B | C |
| 21 | 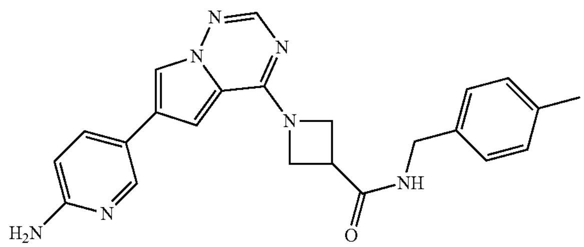 [SMILES: Cc1ccc(CNC(=O)C2CN(c3ncnn4cc(-c5ccc(N)nc5)cc34)C2)cc1] | A | C |
| 22 | 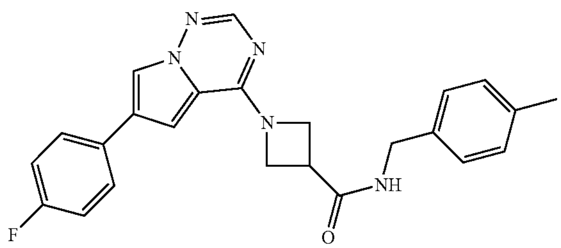 [SMILES: Cc1ccc(CNC(=O)C2CN(c3ncnn4cc(-c5ccc(F)cc5)cc34)C2)cc1] | A | C |
| 23 | 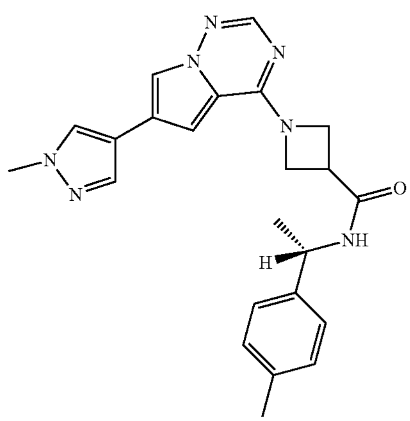 [SMILES: Cc1ccc([C@H](C)NC(=O)C2CN(c3ncnn4cc(-c5cnn(C)c5)cc34)C2)cc1] | A | C |
| 24 | 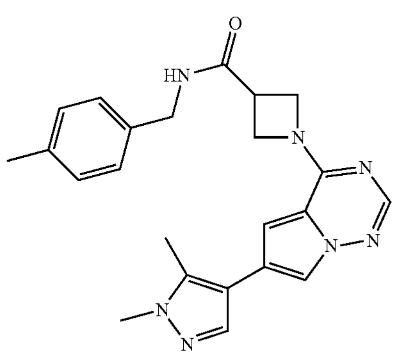 [SMILES: Cc1ccc(CNC(=O)C2CN(c3ncnn4cc(-c5cnn(C)c5C)cc34)C2)cc1] | A | C |

-continued

| Compound Number | Structure | D816V IC$_{50}$ (nM) | WT IC$_{50}$ (nM) |
| --- | --- | --- | --- |
| 25 | 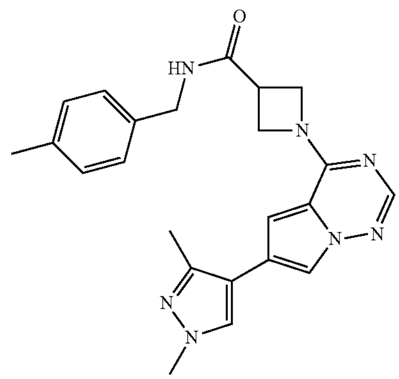 [SMILES: Cc1ccc(CNC(=O)C2CN(c3ncnn4cc(-c5cn(C)nc5C)cc34)C2)cc1] | A | C |
| 26 | 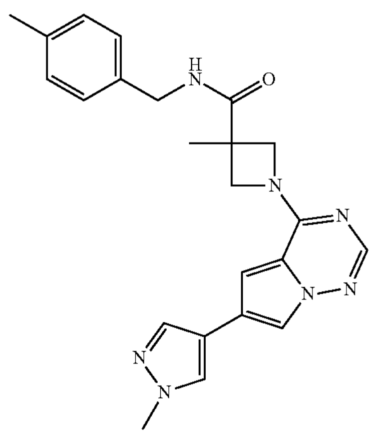 [SMILES: Cc1ccc(CNC(=O)C2(C)CN(c3ncnn4cc(-c5cnn(C)c5)cc34)C2)cc1] | B | C |
| 27 | 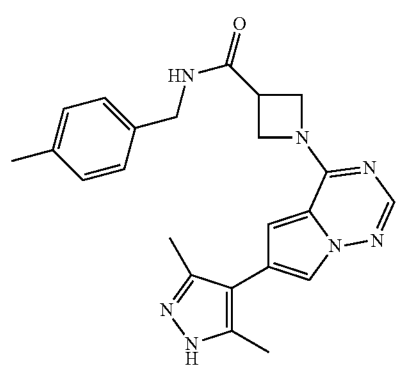 [SMILES: Cc1ccc(CNC(=O)C2CN(c3ncnn4cc(-c5c(C)n[nH]c5C)cc34)C2)cc1] | B | C |
| 28 | 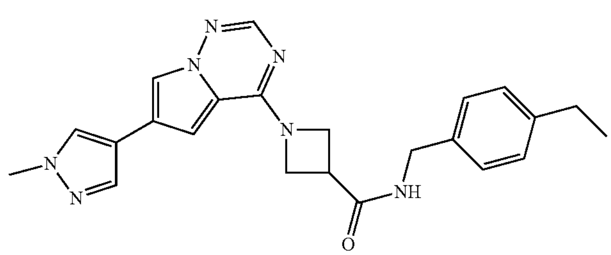 [SMILES: CCc1ccc(CNC(=O)C2CN(c3ncnn4cc(-c5cnn(C)c5)cc34)C2)cc1] | A | B |

-continued
| Compound Number | Structure | D816V IC$_{50}$ (nM) | WT IC$_{50}$ (nM) |
|---|---|---|---|
| 29 | 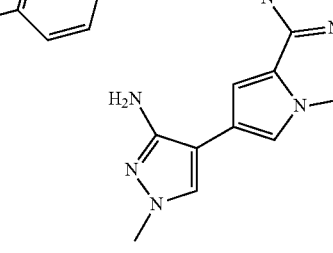 | A | C |
| 30 | 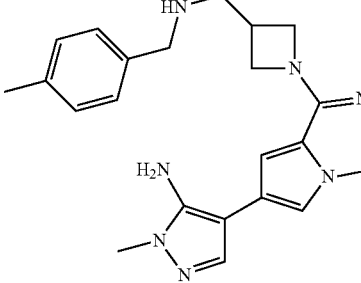 | B | C |
| 31 | 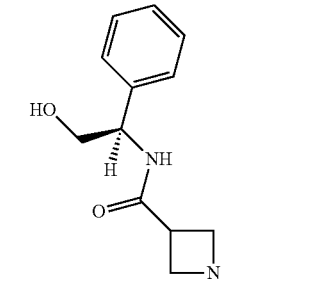 | B | C |
| 32 | 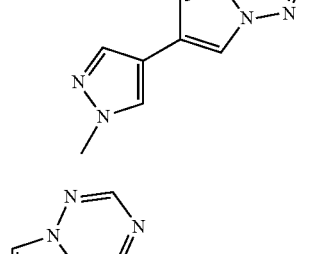 | B | C |

-continued
| Compound Number | Structure | D816V IC₅₀ (nM) | WT IC₅₀ (nM) |
|---|---|---|---|
| 33 | 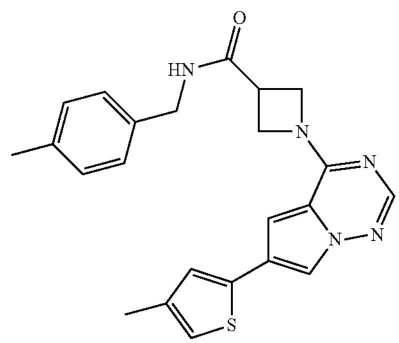 [SMILES: Cc1ccc(CNC(=O)C2CN(c3ncnn4cc(-c5cc(C)cs5)cc34)C2)cc1] | A | C |
| 34 | 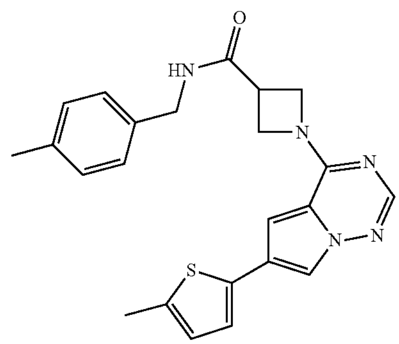 [SMILES: Cc1ccc(CNC(=O)C2CN(c3ncnn4cc(-c5ccc(C)s5)cc34)C2)cc1] | B | C |
| 35 | 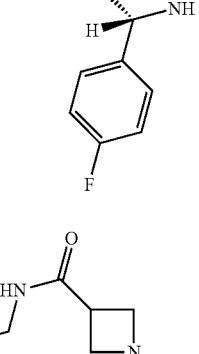 | B | C |
| 36 | 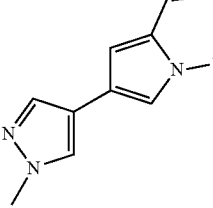 | A | B |

-continued

| Compound Number | Structure | D816V IC$_{50}$ (nM) | WT IC$_{50}$ (nM) |
|---|---|---|---|
| 37 | 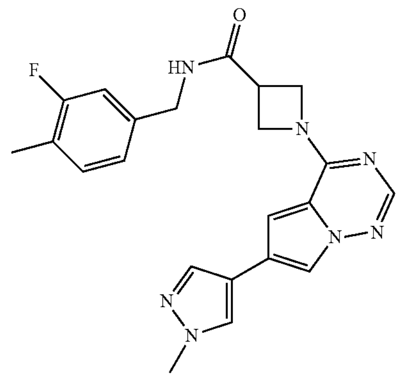 [SMILES: Cc1ccc(CNC(=O)C2CN(c3ncnn4cc(-c5cnn(C)c5)cc34)C2)cc1F] | B | C |
| 38 | 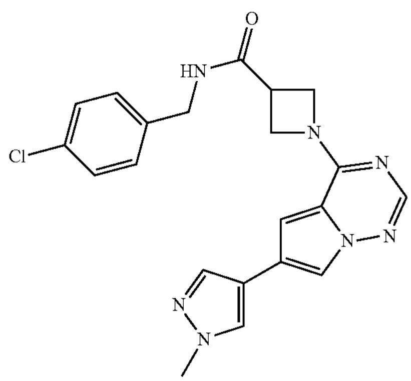 [SMILES: Cn1cc(-c2cc3c(N4CC(C(=O)NCc5ccc(Cl)cc5)C4)ncnn3c2)cn1] | A | C |
| 39 | 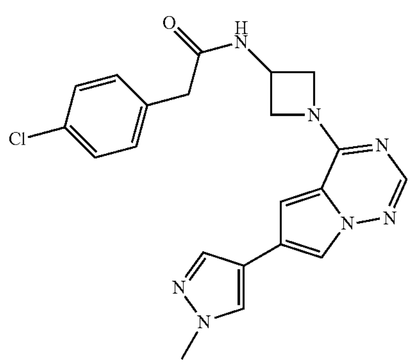 [SMILES: Cn1cc(-c2cc3c(N4CC(NC(=O)Cc5ccc(Cl)cc5)C4)ncnn3c2)cn1] | B | C |
| 40 | 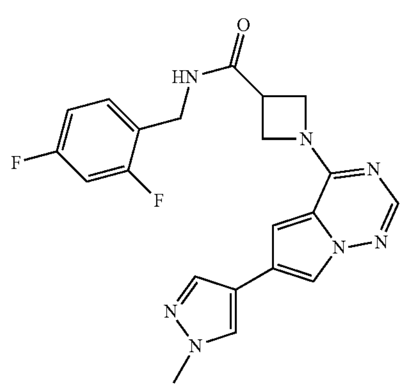 [SMILES: Cn1cc(-c2cc3c(N4CC(C(=O)NCc5ccc(F)cc5F)C4)ncnn3c2)cn1] | B | C |

| Compound Number | Structure | D816V IC$_{50}$ (nM) | WT IC$_{50}$ (nM) |
|---|---|---|---|
| 41 | 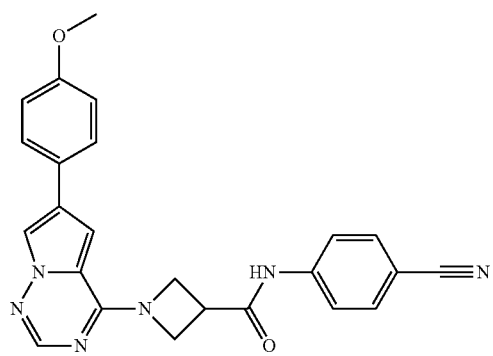 [SMILES: COc1ccc(-c2cc3c(N4CC(C(=O)Nc5ccc(C#N)cc5)C4)ncnn3c2)cc1] | B | C |
| 42 | 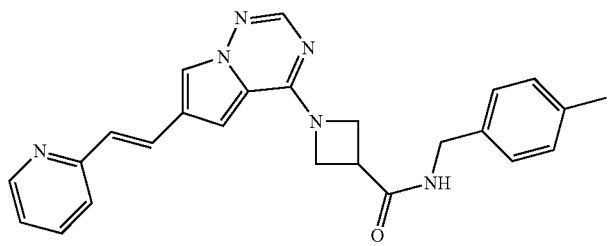 [SMILES: Cc1ccc(CNC(=O)C2CN(c3ncnn4cc(/C=C/c5ccccn5)cc34)C2)cc1] | B | C |
| 43 | 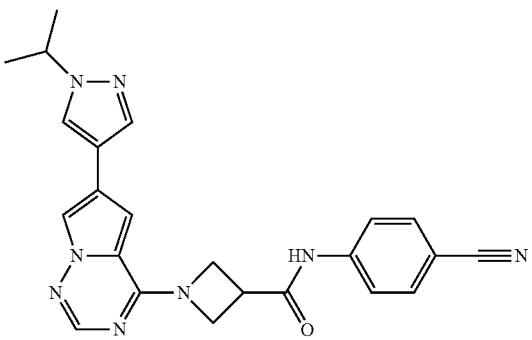 [SMILES: CC(C)n1cc(-c2cc3c(N4CC(C(=O)Nc5ccc(C#N)cc5)C4)ncnn3c2)cn1] | A | B |
| 44 | 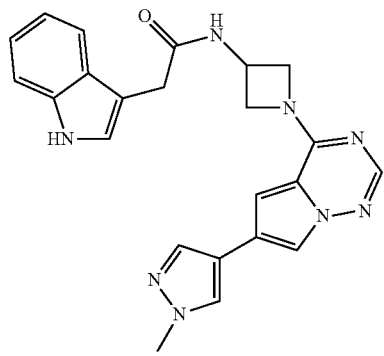 [SMILES: Cn1cc(-c2cc3c(N4CC(NC(=O)Cc5c[nH]c6ccccc56)C4)ncnn3c2)cn1] | B | C |

-continued

| Compound Number | Structure | D816V IC$_{50}$ (nM) | WT IC$_{50}$ (nM) |
|---|---|---|---|
| 45 | 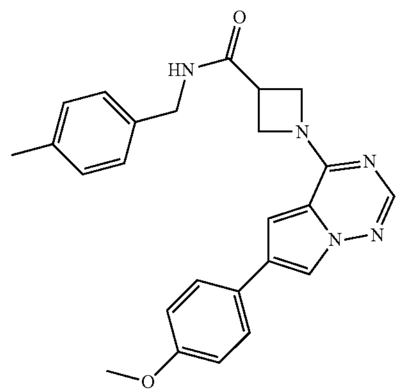 [SMILES: COc1ccc(-c2cc3c(N4CC(C(=O)NCc5ccc(C)cc5)C4)ncnn3c2)cc1] | A | C |
| 46 | 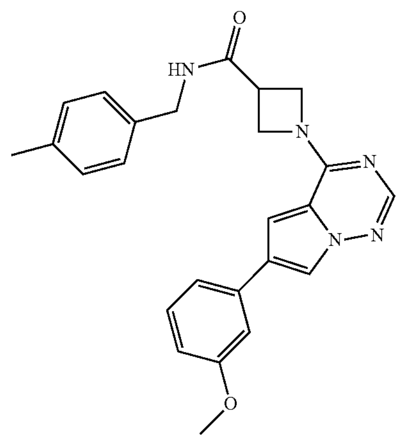 [SMILES: COc1cccc(-c2cc3c(N4CC(C(=O)NCc5ccc(C)cc5)C4)ncnn3c2)c1] | B | C |
| 47 | 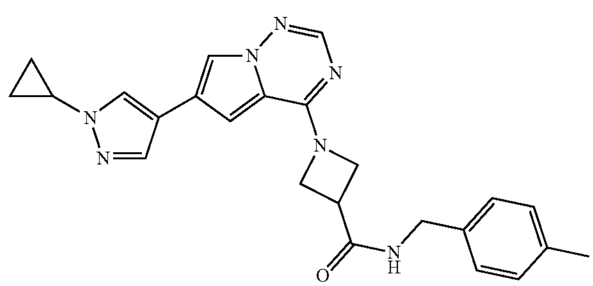 [SMILES: Cc1ccc(CNC(=O)C2CN(c3ncnn4cc(-c5cnn(C6CC6)c5)cc34)C2)cc1] | A | C |
| 48 | 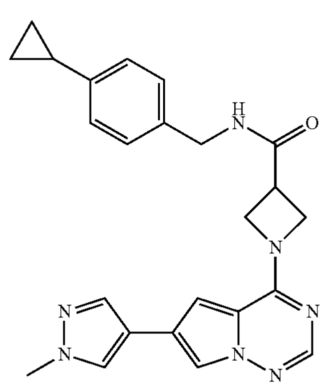 [SMILES: Cn1cc(-c2cc3c(N4CC(C(=O)NCc5ccc(C6CC6)cc5)C4)ncnn3c2)cn1] | A | B |

-continued

| Compound Number | Structure | D816V IC$_{50}$ (nM) | WT IC$_{50}$ (nM) |
|---|---|---|---|
| 49 | 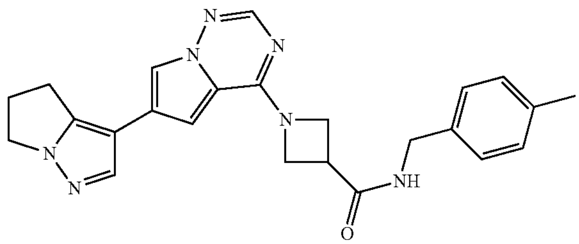 [SMILES: Cc1ccc(CNC(=O)C2CN(c3ncnn4cc(-c5cnn6c5CCC6)cc34)C2)cc1] | A | B |
| 50 | 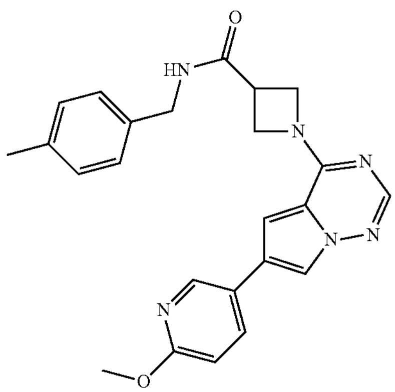 [SMILES: COc1ccc(-c2cc3c(N4CC(C(=O)NCc5ccc(C)cc5)C4)ncnn3c2)cn1] | B | C |
| 51 | 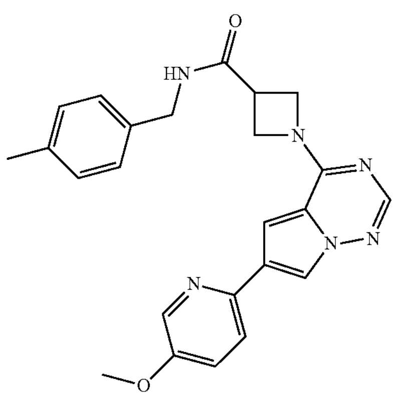 [SMILES: COc1ccc(-c2cc3c(N4CC(C(=O)NCc5ccc(C)cc5)C4)ncnn3c2)nc1] | B | C |
| 52 | 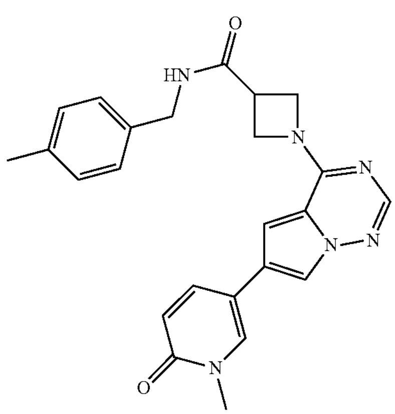 [SMILES: Cc1ccc(CNC(=O)C2CN(c3ncnn4cc(-c5ccc(=O)n(C)c5)cc34)C2)cc1] | A | C |

-continued

| Compound Number | Structure | D816V IC$_{50}$ (nM) | WT IC$_{50}$ (nM) |
|---|---|---|---|
| 53 | 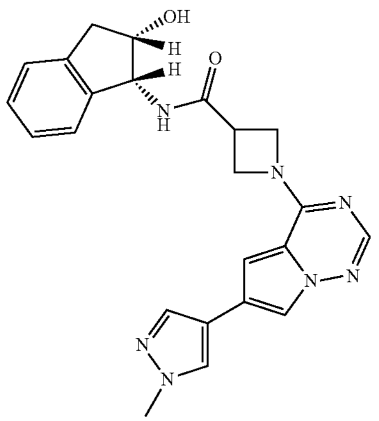 [SMILES: Cn1cc(-c2cc3c(N4CC(C(=O)N[C@@H]5c6ccccc6C[C@@H]5O)C4)ncnn3c2)cn1] | B | C |
| 54 | 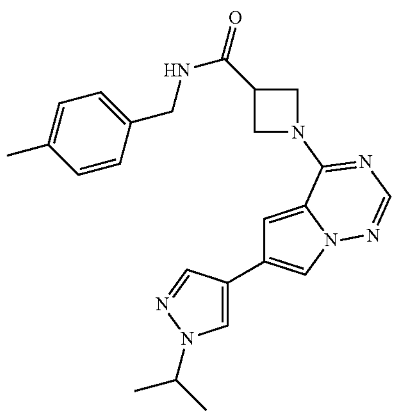 [SMILES: Cc1ccc(CNC(=O)C2CN(c3ncnn4cc(-c5cnn(C(C)C)c5)cc34)C2)cc1] | A | C |
| 55 | 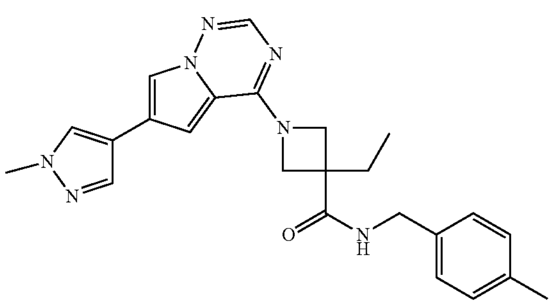 | B | C |
| 56 | 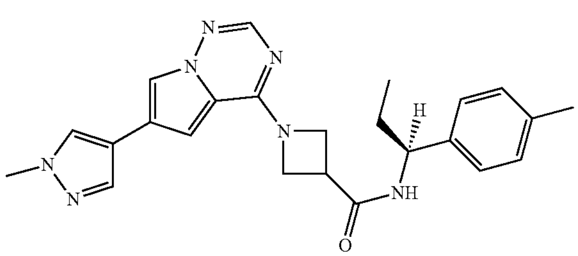 | A | C |

-continued

| Compound Number | Structure | D816V IC$_{50}$ (nM) | WT IC$_{50}$ (nM) |
|---|---|---|---|
| 57 | 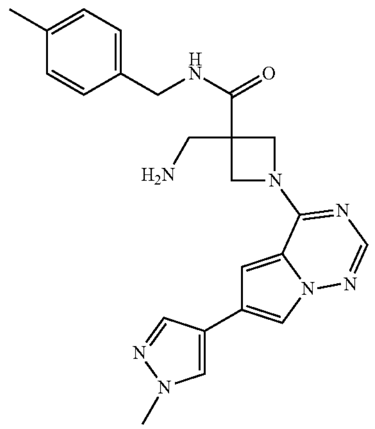 [SMILES: Cc1ccc(CNC(=O)C2(CN)CN(c3ncnn4cc(-c5cnn(C)c5)cc34)C2)cc1] | B | C |
| 58 | 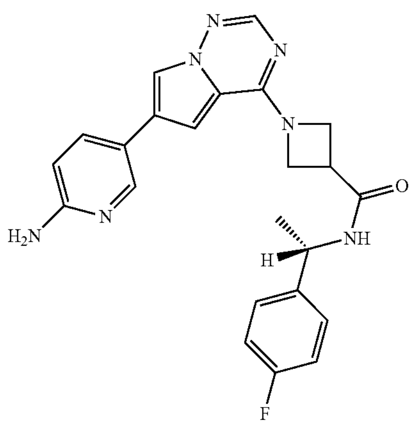 [SMILES: C[C@H](NC(=O)C1CN(c2ncnn3cc(-c4ccc(N)nc4)cc23)C1)c1ccc(F)cc1] | B | C |
| 59 | 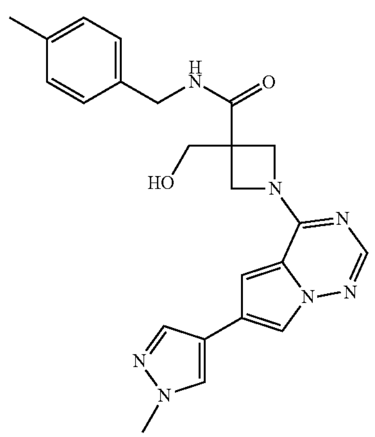 [SMILES: Cc1ccc(CNC(=O)C2(CO)CN(c3ncnn4cc(-c5cnn(C)c5)cc34)C2)cc1] | B | C |
| 60 | 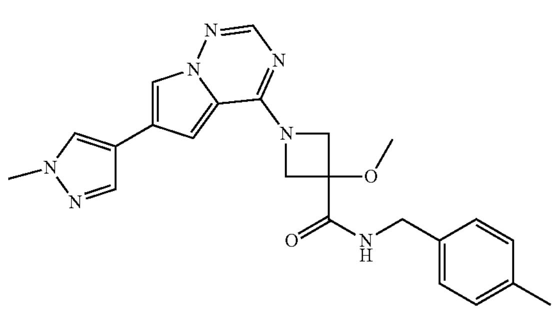 | B | C |

| Compound Number | Structure | D816V IC$_{50}$ (nM) | WT IC$_{50}$ (nM) |
|---|---|---|---|
| 61 | 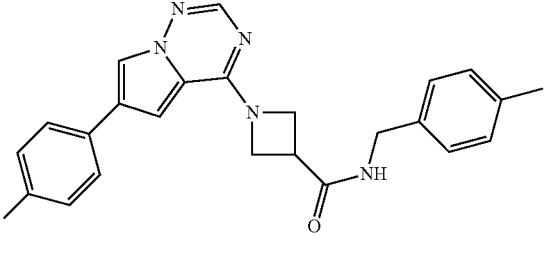 | A | C |
| 62 | 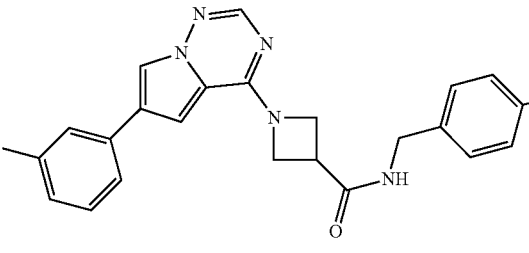 | B | C |
| 63 | 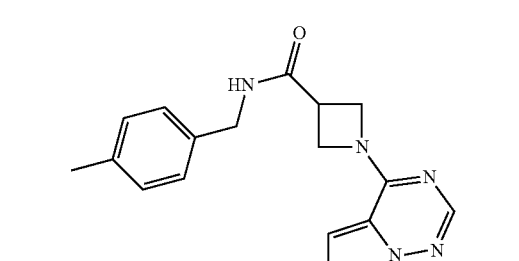 | B | C |
| 64 | 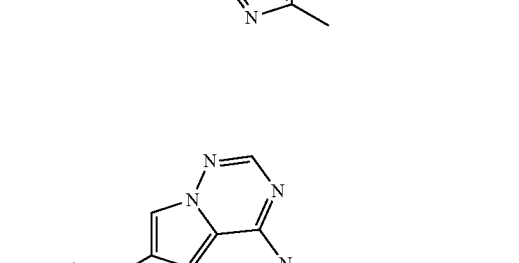 | B | C |

| Compound Number | Structure | D816V IC$_{50}$ (nM) | WT IC$_{50}$ (nM) |
|---|---|---|---|
| 65 | 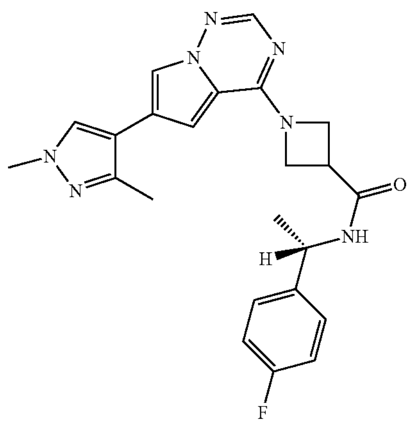 [SMILES: Cc1nn(C)cc1-c1cc2c(N3CC(C(=O)N[C@@H](C)c4ccc(F)cc4)C3)ncnn2c1] | B | C |
| 66 | 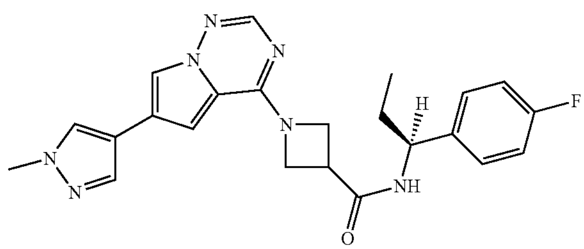 [SMILES: CC[C@H](NC(=O)C1CN(c2ncnn3cc(-c4cnn(C)c4)cc23)C1)c1ccc(F)cc1] | B | C |
| 67 | 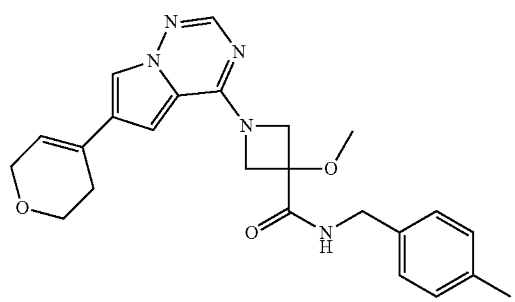 [SMILES: COC1(C(=O)NCc2ccc(C)cc2)CN(c2ncnn3cc(C4=CCOCC4)cc23)C1] | B | C |
| 68 | 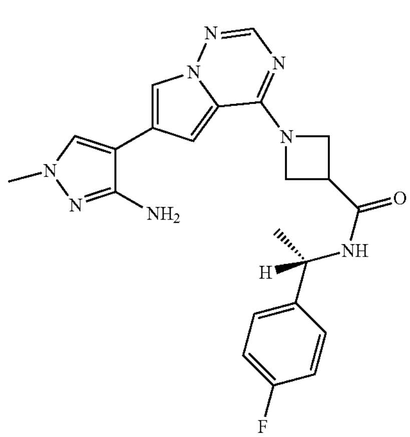 [SMILES: C[C@H](NC(=O)C1CN(c2ncnn3cc(-c4cn(C)nc4N)cc23)C1)c1ccc(F)cc1] | B | C |

| Compound Number | Structure | D816V IC$_{50}$ (nM) | WT IC$_{50}$ (nM) |
|---|---|---|---|
| 69 | 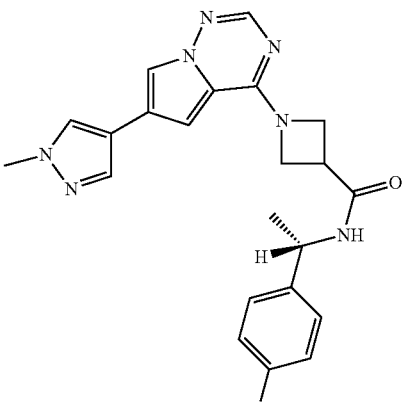 | B | C |
| 70 | 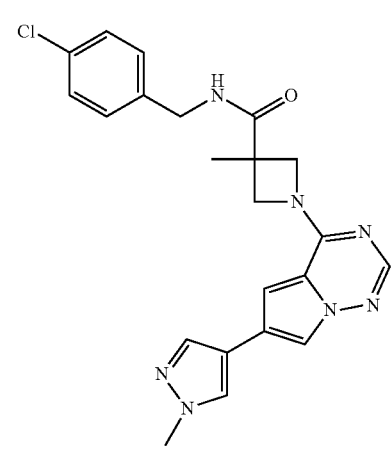 [SMILES: Cn1cc(-c2cc3c(N4CC(C)(C(=O)NCc5ccc(Cl)cc5)C4)ncnn3c2)cn1] | B | C |
| 71 | 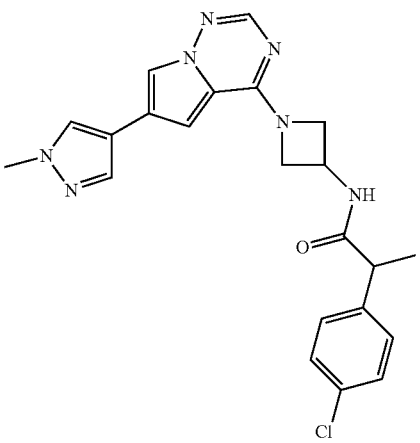 [SMILES: CC(C(=O)NC1CN(c2ncnn3cc(-c4cnn(C)c4)cc23)C1)c1ccc(Cl)cc1] | B | C |
| 72 | 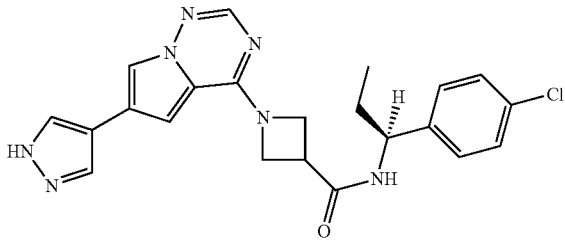 [SMILES: CC[C@H](NC(=O)C1CN(c2ncnn3cc(-c4cn[nH]c4)cc23)C1)c1ccc(Cl)cc1] | A | C |

-continued

| Compound Number | Structure | D816V IC$_{50}$ (nM) | WT IC$_{50}$ (nM) |
|---|---|---|---|
| 73 | 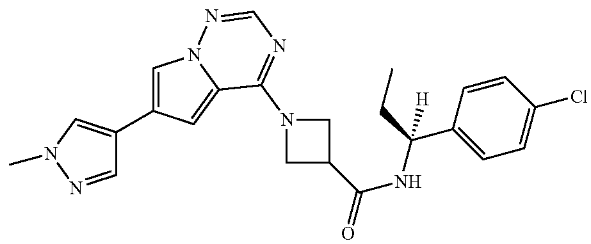 [SMILES: CC[C@H](NC(=O)C1CN(c2ncnn3cc(-c4cnn(C)c4)cc23)C1)c1ccc(Cl)cc1] | B | C |
| 74 | 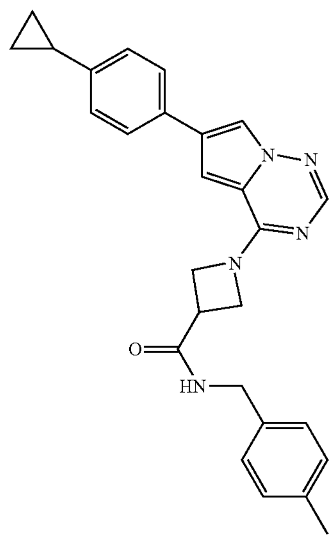 [SMILES: Cc1ccc(CNC(=O)C2CN(c3ncnn4cc(-c5ccc(C6CC6)cc5)cc34)C2)cc1] | A | C |
| 75 | 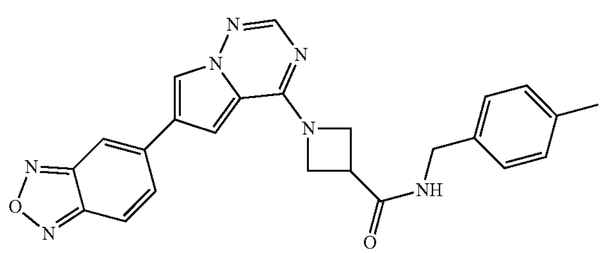 [SMILES: Cc1ccc(CNC(=O)C2CN(c3ncnn4cc(-c5ccc6nonc6c5)cc34)C2)cc1] | B | C |
| 76 | 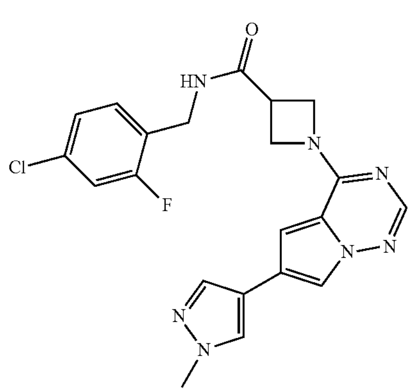 [SMILES: Cn1cc(-c2cc3c(N4CC(C(=O)NCc5ccc(Cl)cc5F)C4)ncnn3c2)cn1] | A | B |

| Compound Number | Structure | D816V IC$_{50}$ (nM) | WT IC$_{50}$ (nM) |
|---|---|---|---|
| 77 | 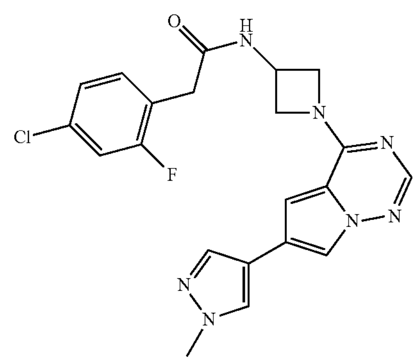 [SMILES: Cn1cc(-c2cc3c(N4CC(NC(=O)Cc5ccc(Cl)cc5F)C4)ncnn3c2)cn1] | A | C |
| 78 | 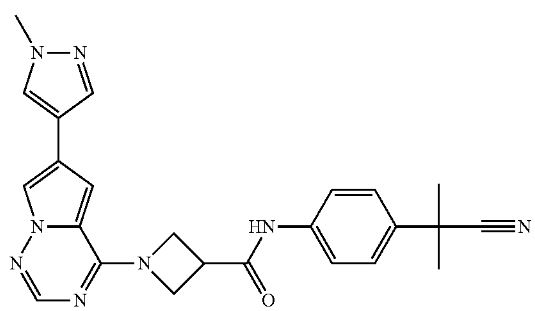 [SMILES: Cn1cc(-c2cc3c(N4CC(C(=O)Nc5ccc(C(C)(C)C#N)cc5)C4)ncnn3c2)cn1] | B | C |
| 79 | 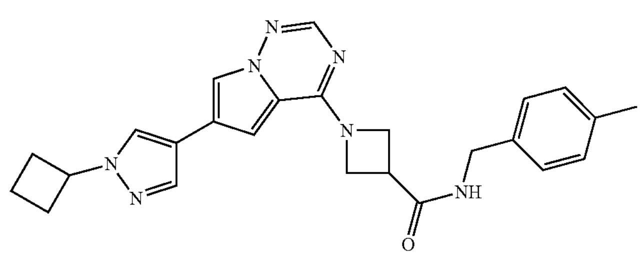 [SMILES: Cc1ccc(CNC(=O)C2CN(c3ncnn4cc(-c5cnn(C6CCC6)c5)cc34)C2)cc1] | A | B |
| 80 | 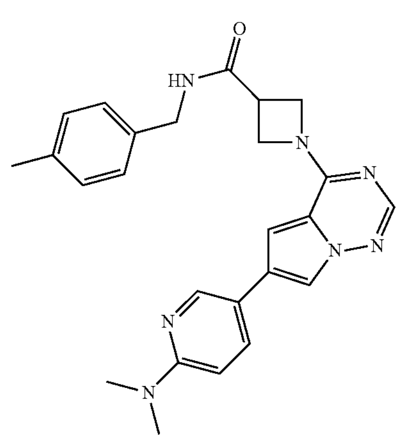 [SMILES: Cc1ccc(CNC(=O)C2CN(c3ncnn4cc(-c5ccc(N(C)C)nc5)cc34)C2)cc1] | A | C |

| Compound Number | Structure | D816V IC$_{50}$ (nM) | WT IC$_{50}$ (nM) |
|---|---|---|---|
| 81 | 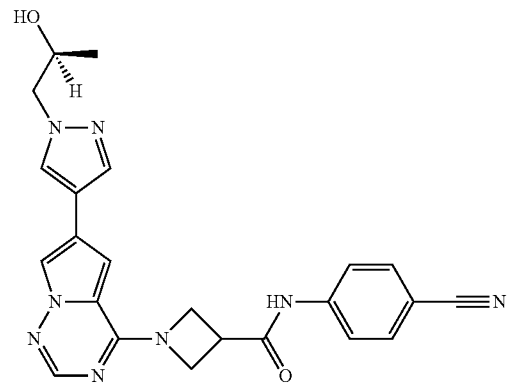 [SMILES: C[C@H](O)Cn1cc(-c2cc3c(N4CC(C(=O)Nc5ccc(C#N)cc5)C4)ncnn3c2)cn1] | B | C |
| 82 | 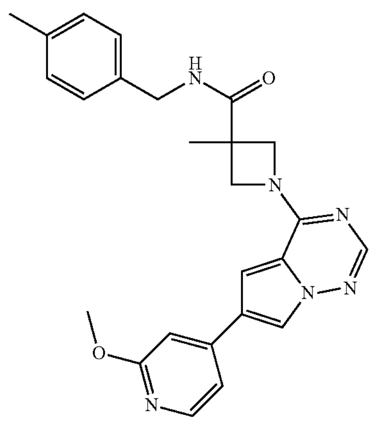 [SMILES: COc1cc(-c2cc3c(N4CC(C)(C(=O)NCc5ccc(C)cc5)C4)ncnn3c2)ccn1] | B | C |
| 83 | 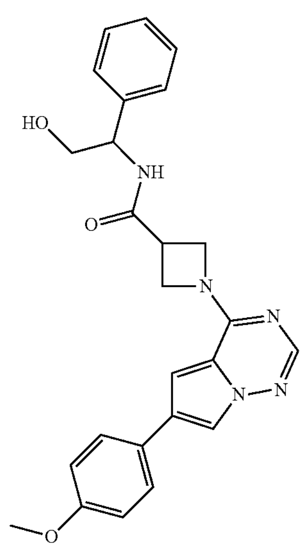 [SMILES: COc1ccc(-c2cc3c(N4CC(C(=O)NC(CO)c5ccccc5)C4)ncnn3c2)cc1] | B | D |

-continued
| Compound Number | Structure | D816V IC50 (nM) | WT IC50 (nM) |
|---|---|---|---|
| 84 | 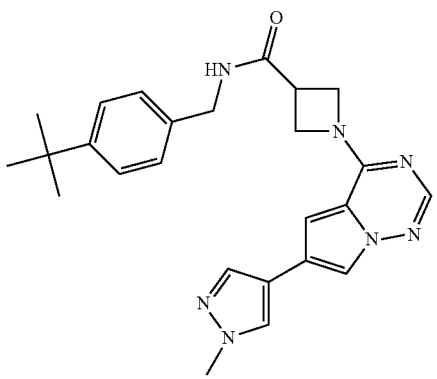 [SMILES: Cn1cc(-c2cc3c(N4CC(C(=O)NCc5ccc(C(C)(C)C)cc5)C4)ncnn3c2)cn1] | C | B |
| 85 | 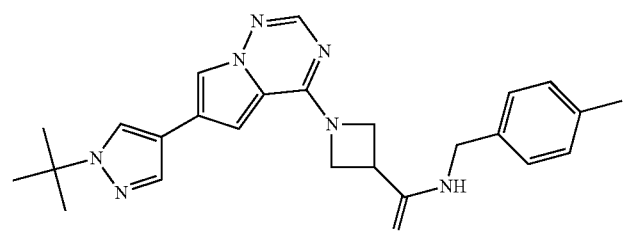 | A | C |
| 86 | 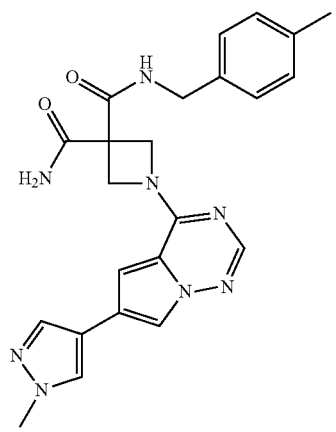 [SMILES: Cc1ccc(CNC(=O)C2(C(N)=O)CN(c3ncnn4cc(-c5cnn(C)c5)cc34)C2)cc1] | B | C |
| 87 | 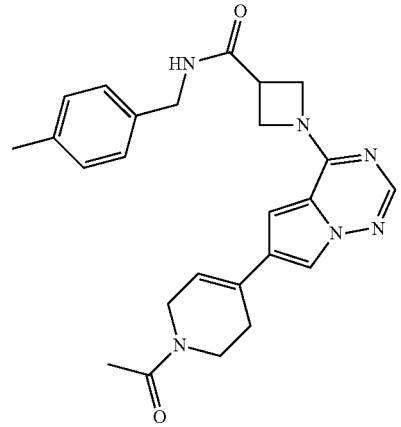 [SMILES: CC(=O)N1CC=C(c2cc3c(N4CC(C(=O)NCc5ccc(C)cc5)C4)ncnn3c2)CC1] | B | C |

| Compound Number | Structure | D816V IC$_{50}$ (nM) | WT IC$_{50}$ (nM) |
|---|---|---|---|
| 88 | 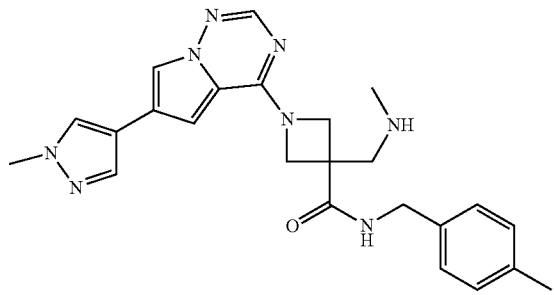 | B | C |
| 89 | 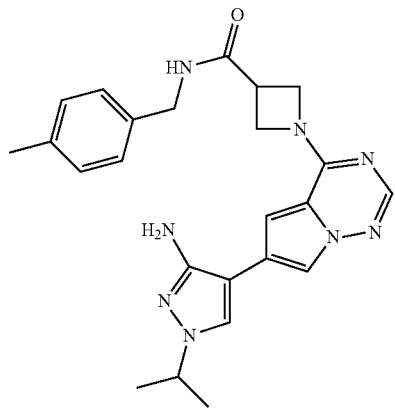 [SMILES: Cc1ccc(CNC(=O)C2CN(c3ncnn4cc(-c5cn(C(C)C)nc5N)cc34)C2)cc1] | A | C |
| 90 | 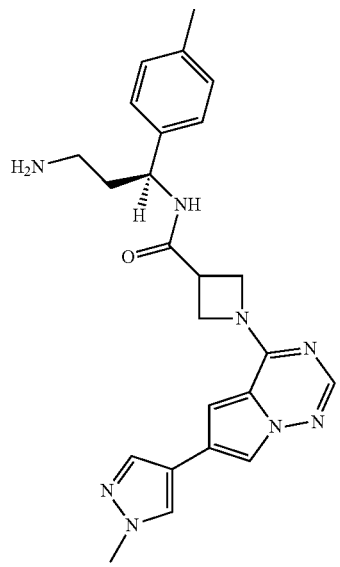 [SMILES: Cc1ccc([C@H](CCN)NC(=O)C2CN(c3ncnn4cc(-c5cnn(C)c5)cc34)C2)cc1] | A | C |

| Compound Number | Structure | D816V IC$_{50}$ (nM) | WT IC$_{50}$ (nM) |
|---|---|---|---|
| 91 | 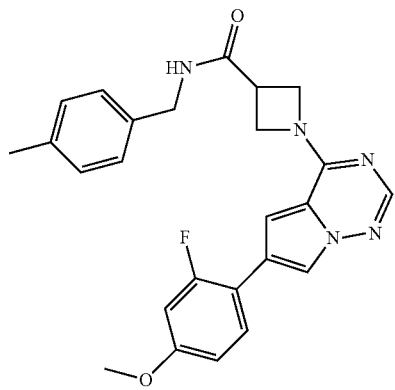 [SMILES: COc1ccc(-c2cc3c(N4CC(C(=O)NCc5ccc(C)cc5)C4)ncnn3c2)c(F)c1] | B | C |
| 92 | 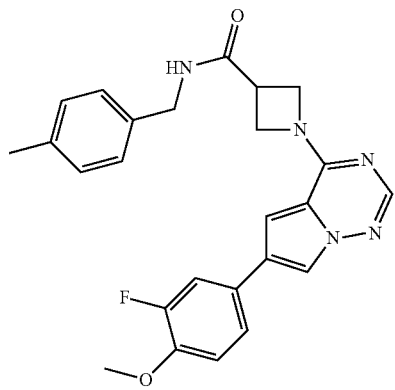 [SMILES: COc1ccc(-c2cc3c(N4CC(C(=O)NCc5ccc(C)cc5)C4)ncnn3c2)cc1F] | A | C |
| 93 | 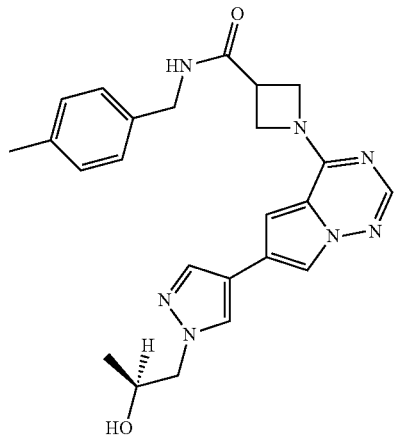 [SMILES: Cc1ccc(CNC(=O)C2CN(c3ncnn4cc(-c5cnn(C[C@H](C)O)c5)cc34)C2)cc1] | A | C |

| Compound Number | Structure | D816V IC$_{50}$ (nM) | WT IC$_{50}$ (nM) |
|---|---|---|---|
| 94 | 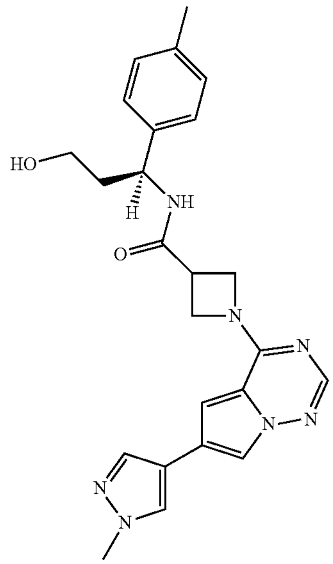 [SMILES: Cc1ccc([C@H](CCO)NC(=O)C2CN(c3ncnn4cc(-c5cnn(C)c5)cc34)C2)cc1] | A | C |
| 95 | 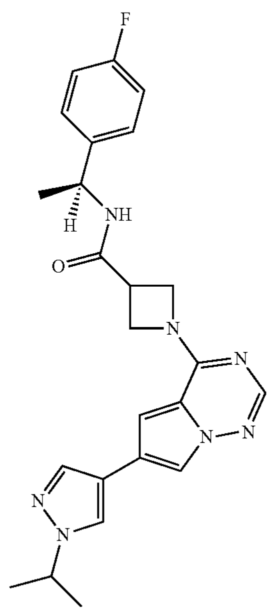 [SMILES: CC(C)n1cc(-c2cc3c(N4CC(C(=O)N[C@@H](C)c5ccc(F)cc5)C4)ncnn3c2)cn1] | B | C |
| 96 | 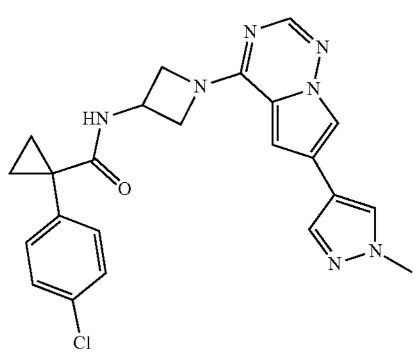 [SMILES: Cn1cc(-c2cc3c(N4CC(NC(=O)C5(c6ccc(Cl)cc6)CC5)C4)ncnn3c2)cn1] | B | C |

-continued

| Compound Number | Structure | D816V IC$_{50}$ (nM) | WT IC$_{50}$ (nM) |
| --- | --- | --- | --- |
| 97 | 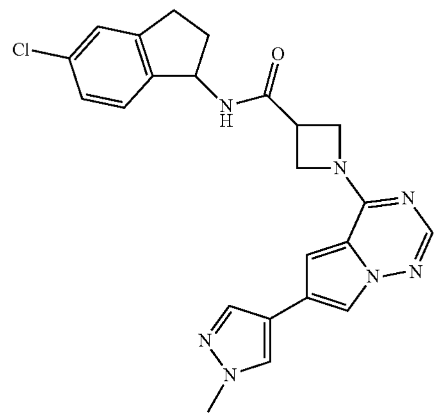 [SMILES: Cn1cc(-c2cc3c(N4CC(C(=O)NC5CCc6cc(Cl)ccc65)C4)ncnn3c2)cn1] | B | C |
| 98 | 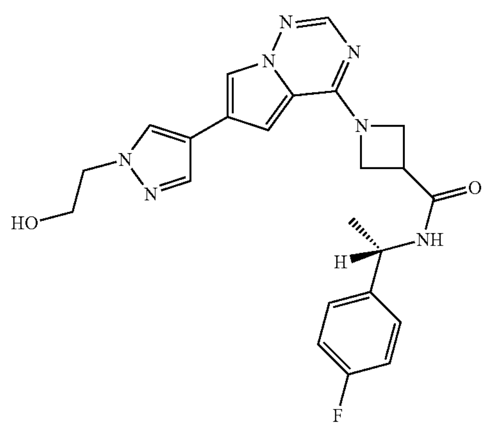 [SMILES: C[C@H](NC(=O)C1CN(c2ncnn3cc(-c4cnn(CCO)c4)cc23)C1)c1ccc(F)cc1] | B | C |
| 99 | 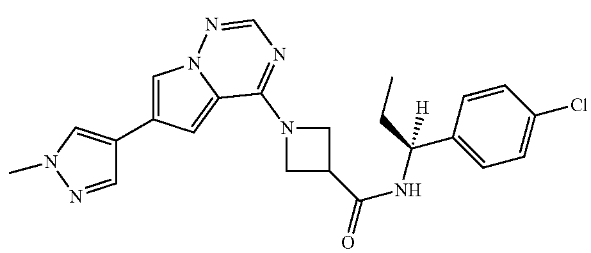 [SMILES: CC[C@H](NC(=O)C1CN(c2ncnn3cc(-c4cnn(C)c4)cc23)C1)c1ccc(Cl)cc1] | B | C |
| 100 | 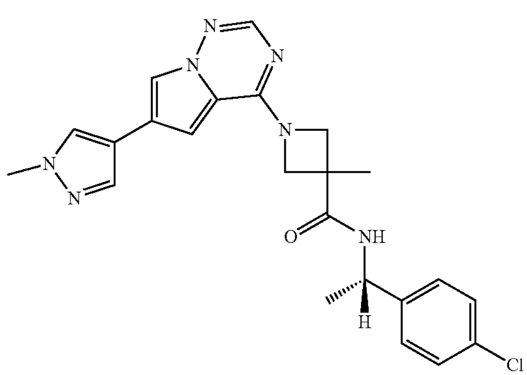 [SMILES: C[C@H](NC(=O)C1(C)CN(c2ncnn3cc(-c4cnn(C)c4)cc23)C1)c1ccc(Cl)cc1] | B | C |

| Compound Number | Structure | D816V IC$_{50}$ (nM) | WT IC$_{50}$ (nM) |
|---|---|---|---|
| 101 | 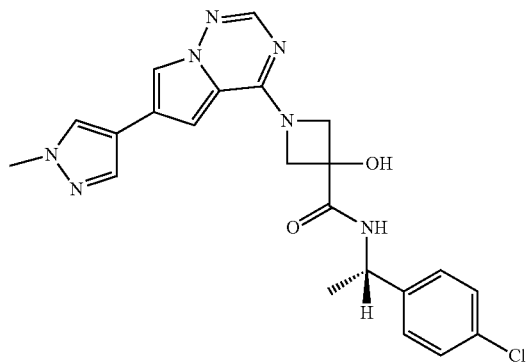 [SMILES: C[C@H](NC(=O)C1(O)CN(c2ncnn3cc(-c4cnn(C)c4)cc23)C1)c1ccc(Cl)cc1] | B | C |
| 102 | 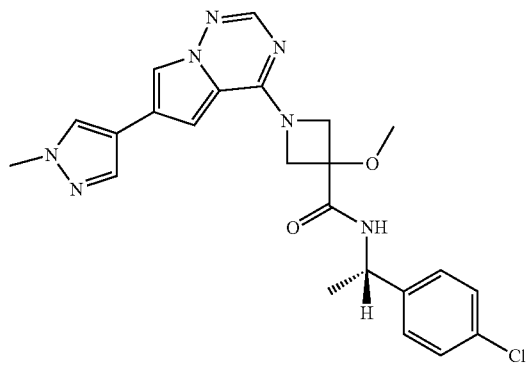 [SMILES: COC1(C(=O)N[C@@H](C)c2ccc(Cl)cc2)CN(c2ncnn3cc(-c4cnn(C)c4)cc23)C1] | B | C |
| 103 | 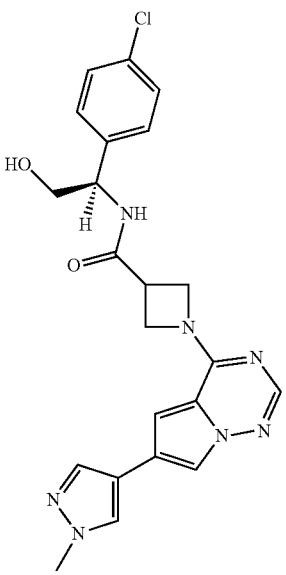 [SMILES: Cn1cc(-c2cc3c(N4CC(C(=O)N[C@@H](CO)c5ccc(Cl)cc5)C4)ncnn3c2)cn1] | A | C |

| Compound Number | Structure | D816V IC$_{50}$ (nM) | WT IC$_{50}$ (nM) |
|---|---|---|---|
| 104 | 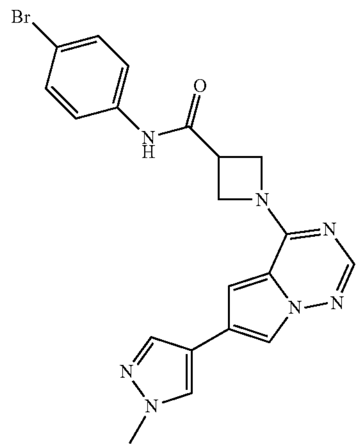 | B | B |
| 105 | 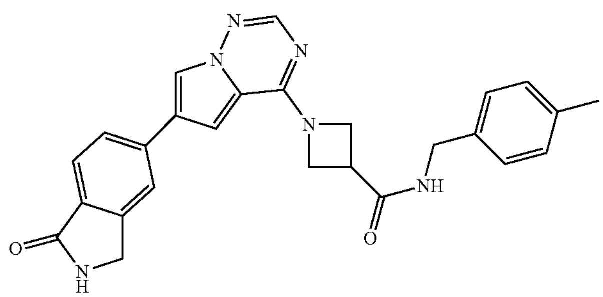 [SMILES: Cc1ccc(CNC(=O)C2CN(c3ncnn4cc(-c5ccc6c(c5)CNC6=O)cc34)C2)cc1] | A | C |
| 106 | 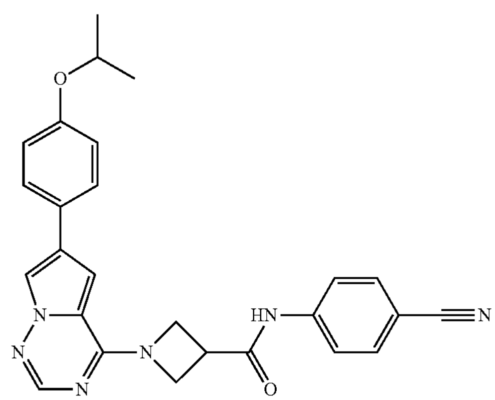 [SMILES: CC(C)Oc1ccc(-c2cc3c(N4CC(C(=O)Nc5ccc(C#N)cc5)C4)ncnn3c2)cc1] | B | C |
| 107 | 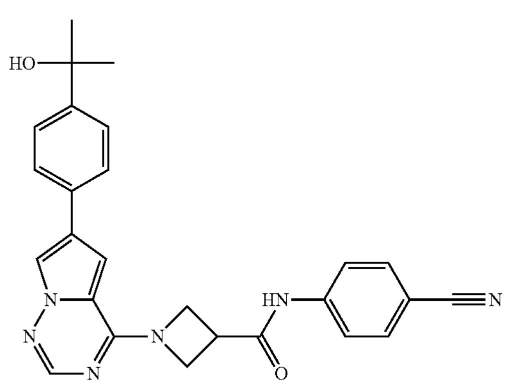 [SMILES: CC(C)(O)c1ccc(-c2cc3c(N4CC(C(=O)Nc5ccc(C#N)cc5)C4)ncnn3c2)cc1] | A | B |

-continued
| Compound Number | Structure | D816V IC$_{50}$ (nM) | WT IC$_{50}$ (nM) |
|---|---|---|---|
| 108 | 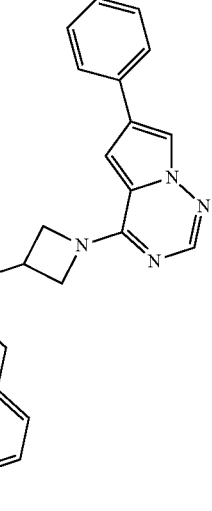 | A | C |
| 109 | 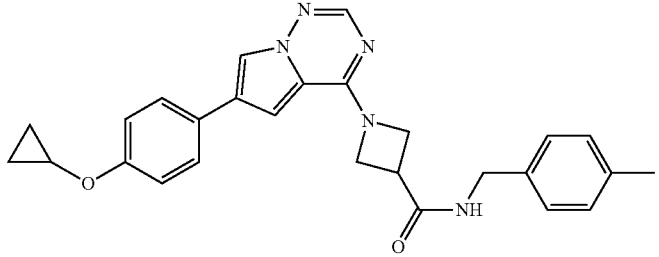 [SMILES: Cc1ccc(CNC(=O)C2CN(c3ncnn4cc(-c5ccc(OC6CC6)cc5)cc34)C2)cc1] | A | C |
| 110 | 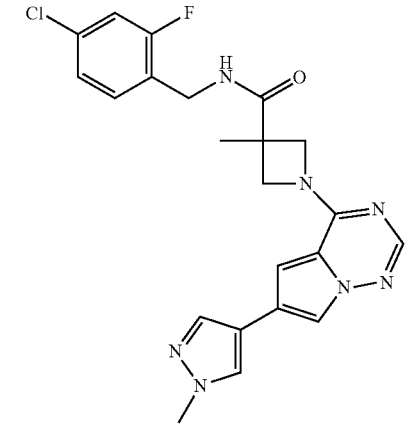 [SMILES: Cn1cc(-c2cc3c(N4CC(C)(C(=O)NCc5ccc(Cl)cc5F)C4)ncnn3c2)cn1] | B | C |
| 111 | 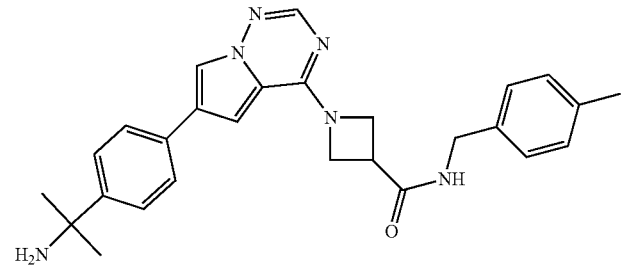 [SMILES: Cc1ccc(CNC(=O)C2CN(c3ncnn4cc(-c5ccc(C(C)(C)N)cc5)cc34)C2)cc1] | A | B |

-continued
| Compound Number | Structure | D816V IC$_{50}$ (nM) | WT IC$_{50}$ (nM) |
|---|---|---|---|
| 112 | 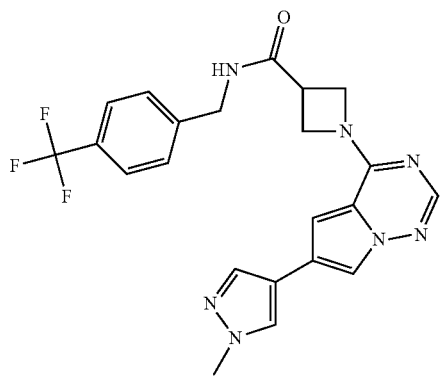 [SMILES: Cn1cc(-c2cc3c(N4CC(C(=O)NCc5ccc(C(F)(F)F)cc5)C4)ncnn3c2)cn1] | B | C |
| 113 | 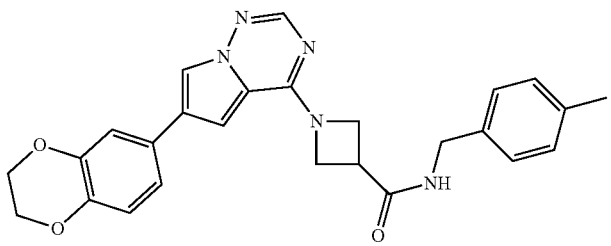 [SMILES: Cc1ccc(CNC(=O)C2CN(c3ncnn4cc(-c5ccc6c(c5)OCCO6)cc34)C2)cc1] | B | C |
| 114 | 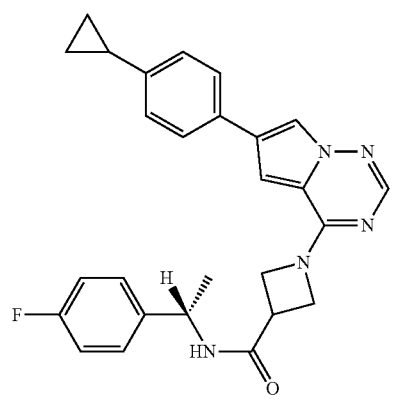 [SMILES: C[C@H](NC(=O)C1CN(c2ncnn3cc(-c4ccc(C5CC5)cc4)cc23)C1)c1ccc(F)cc1] | C | C |
| 115 | 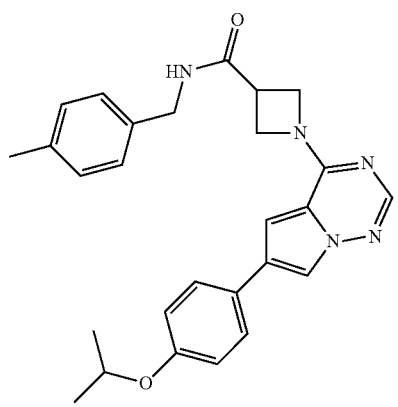 [SMILES: Cc1ccc(CNC(=O)C2CN(c3ncnn4cc(-c5ccc(OC(C)C)cc5)cc34)C2)cc1] | B | D |

-continued

| Compound Number | Structure | D816V IC$_{50}$ (nM) | WT IC$_{50}$ (nM) |
|---|---|---|---|
| 116 | 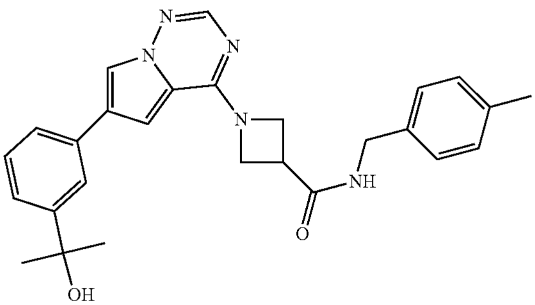 [SMILES: Cc1ccc(CNC(=O)C2CN(c3ncnn4cc(-c5cccc(C(C)(C)O)c5)cc34)C2)cc1] | A | C |
| 117 | 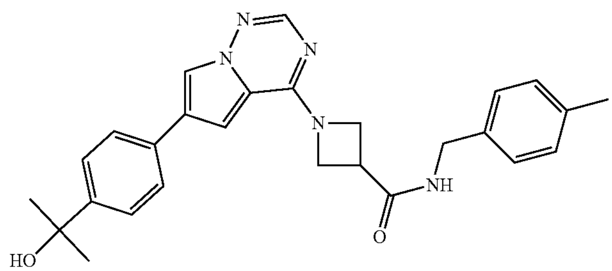 [SMILES: Cc1ccc(CNC(=O)C2CN(c3ncnn4cc(-c5ccc(C(C)(C)O)cc5)cc34)C2)cc1] | A | C |
| 118 | 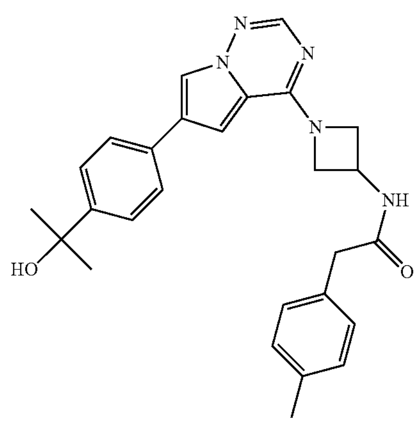 [SMILES: Cc1ccc(CC(=O)NC2CN(c3ncnn4cc(-c5ccc(C(C)(C)O)cc5)cc34)C2)cc1] | B | C |
| 119 | 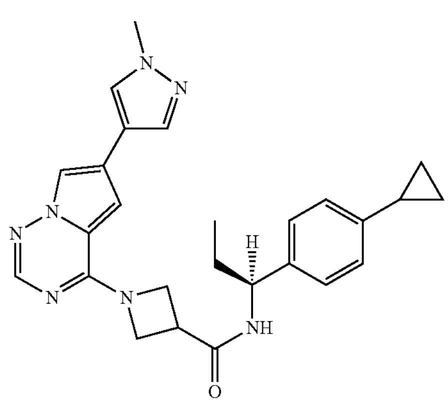 [SMILES: CC[C@H](NC(=O)C1CN(c2ncnn3cc(-c4cnn(C)c4)cc23)C1)c1ccc(C2CC2)cc1] | A | C |

-continued

| Compound Number | Structure | D816V IC$_{50}$ (nM) | WT IC$_{50}$ (nM) |
|---|---|---|---|
| 120 | 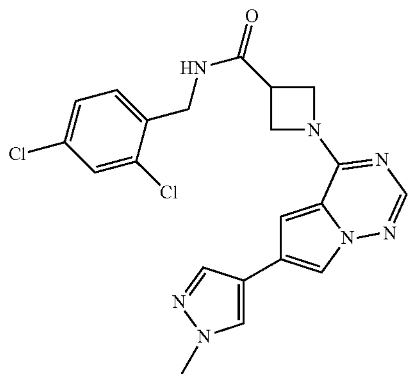 [SMILES: Cn1cc(-c2cc3c(N4CC(C(=O)NCc5ccc(Cl)cc5Cl)C4)ncnn3c2)cn1] | A | B |
| 121 | 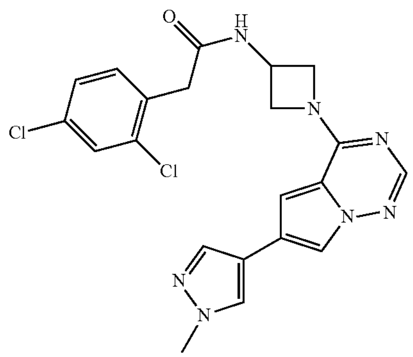 [SMILES: Cn1cc(-c2cc3c(N4CC(NC(=O)Cc5ccc(Cl)cc5Cl)C4)ncnn3c2)cn1] | A | D |
| 122 | 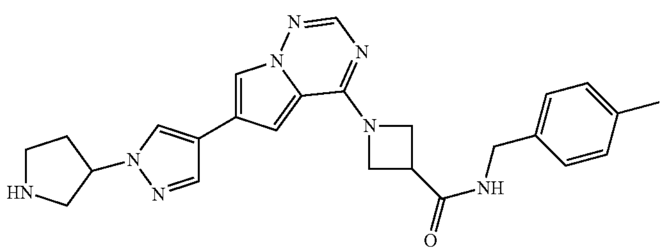 [SMILES: Cc1ccc(CNC(=O)C2CN(c3ncnn4cc(-c5cnn(C6CCNC6)c5)cc34)C2)cc1] | A | C |
| 123 | 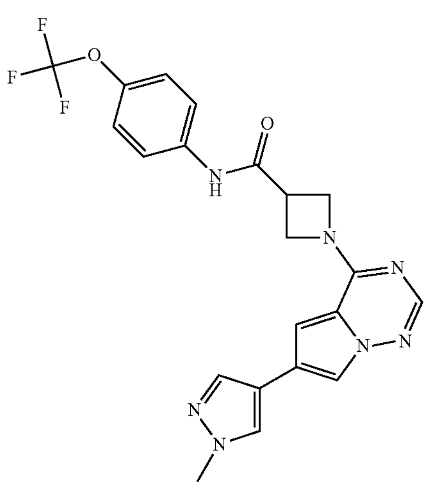 [SMILES: Cn1cc(-c2cc3c(N4CC(C(=O)Nc5ccc(OC(F)(F)F)cc5)C4)ncnn3c2)cn1] | B | B |

-continued

| Compound Number | Structure | D816V IC$_{50}$ (nM) | WT IC$_{50}$ (nM) |
|---|---|---|---|
| 124 | 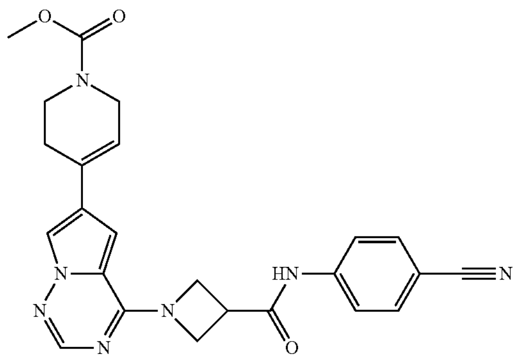 [SMILES: COC(=O)N1CC=C(c2cc3c(N4CC(C(=O)Nc5ccc(C#N)cc5)C4)ncnn3c2)CC1] | A | B |
| 125 | 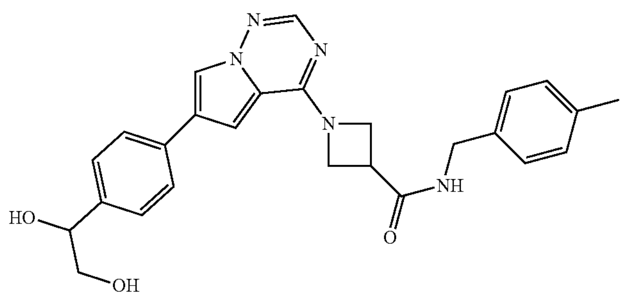 [SMILES: Cc1ccc(CNC(=O)C2CN(c3ncnn4cc(-c5ccc(C(O)CO)cc5)cc34)C2)cc1] | A | C |
| 126 | 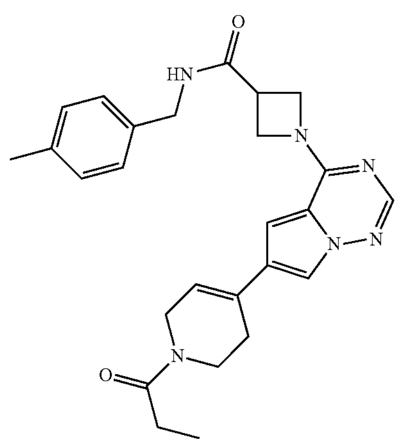 [SMILES: CCC(=O)N1CC=C(c2cc3c(N4CC(C(=O)NCc5ccc(C)cc5)C4)ncnn3c2)CC1] | A | C |
| 127 | 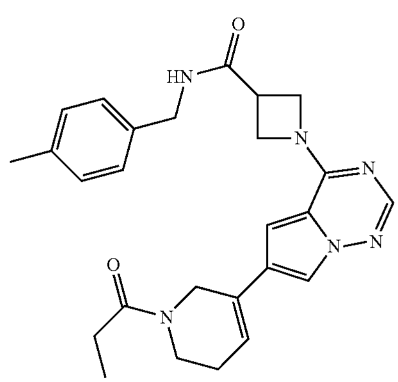 [SMILES: CCC(=O)N1CCC=C(c2cc3c(N4CC(C(=O)NCc5ccc(C)cc5)C4)ncnn3c2)C1] | A | C |

| Compound Number | Structure | D816V IC$_{50}$ (nM) | WT IC$_{50}$ (nM) |
|---|---|---|---|
| 128 | 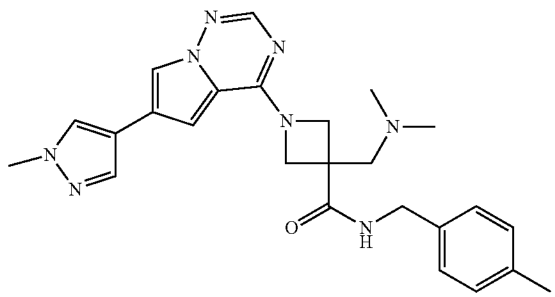 | B | C |
| 129 | 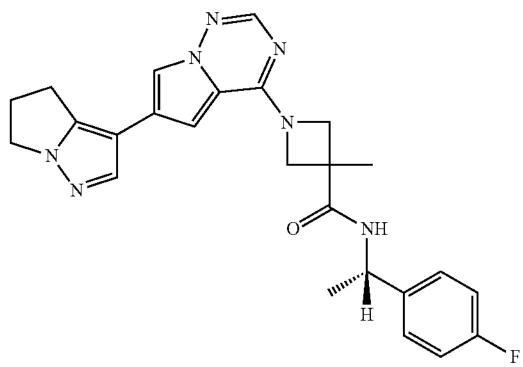 [SMILES: C[C@H](NC(=O)C1(C)CN(c2ncnn3cc(-c4cnn5c4CCC5)cc23)C1)c1ccc(F)cc1] | B | C |
| 130 | 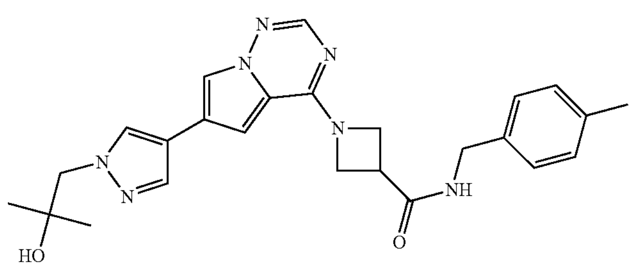 [SMILES: Cc1ccc(CNC(=O)C2CN(c3ncnn4cc(-c5cnn(CC(C)(C)O)c5)cc34)C2)cc1] | A | C |
| 131 | 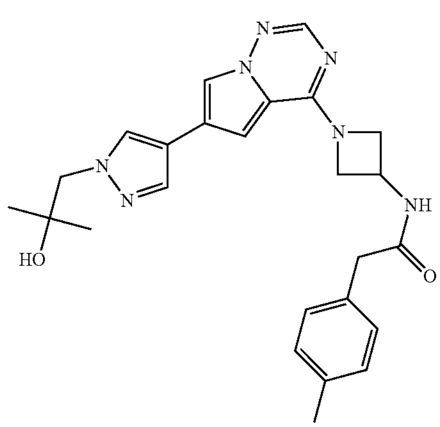 [SMILES: Cc1ccc(CC(=O)NC2CN(c3ncnn4cc(-c5cnn(CC(C)(C)O)c5)cc34)C2)cc1] | B | C |

-continued
| Compound Number | Structure | D816V IC$_{50}$ (nM) | WT IC$_{50}$ (nM) |
|---|---|---|---|
| 132 | 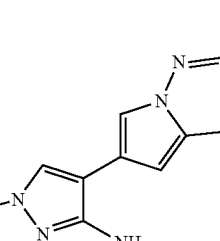 | A | C |
| 133 | 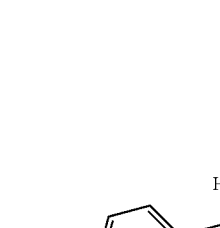 | A | C |
| 134 | 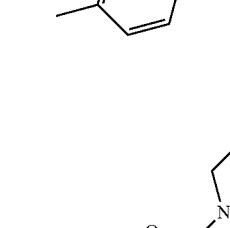 | A | C |
| 135 | 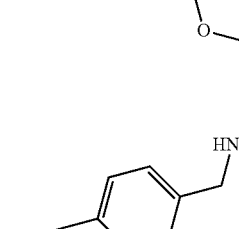 | B | C |

-continued

| Compound Number | Structure | D816V IC$_{50}$ (nM) | WT IC$_{50}$ (nM) |
|---|---|---|---|
| 136 | 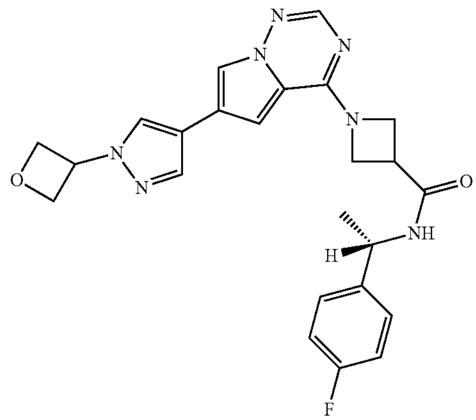 [SMILES: C[C@H](NC(=O)C1CN(c2ncnn3cc(-c4cnn(C5COC5)c4)cc23)C1)c1ccc(F)cc1] | B | C |
| 137 | 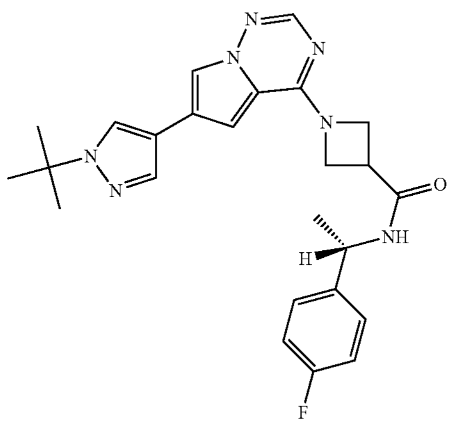 [SMILES: C[C@H](NC(=O)C1CN(c2ncnn3cc(-c4cnn(C(C)(C)C)c4)cc23)C1)c1ccc(F)cc1] | B | C |
| 138 | 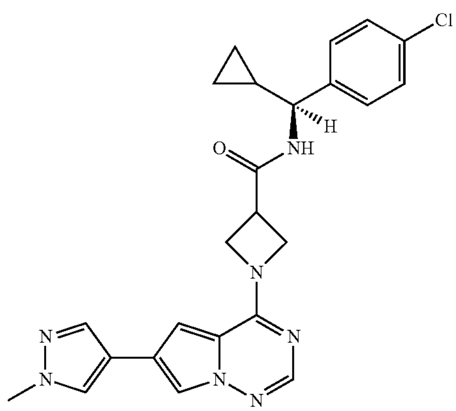 [SMILES: Cn1cc(-c2cc3c(N4CC(C(=O)N[C@H](c5ccc(Cl)cc5)C5CC5)C4)ncnn3c2)cn1] | A | C |
| 139 | 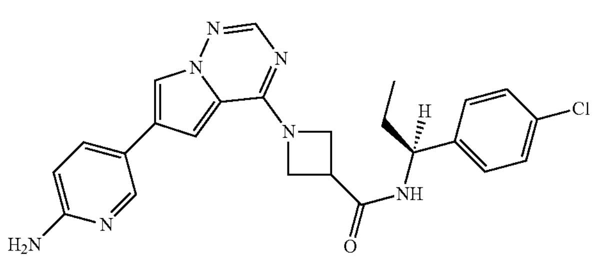 [SMILES: CC[C@H](NC(=O)C1CN(c2ncnn3cc(-c4ccc(N)nc4)cc23)C1)c1ccc(Cl)cc1] | B | C |

-continued
| Compound Number | Structure | D816V IC$_{50}$ (nM) | WT IC$_{50}$ (nM) |
|---|---|---|---|
| 140 | 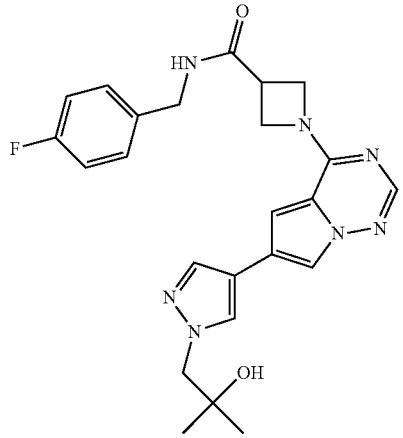 [SMILES: CC(C)(O)Cn1cc(-c2cc3c(N4CC(C(=O)NCc5ccc(F)cc5)C4)ncnn3c2)cn1] | B | C |
| 141 | 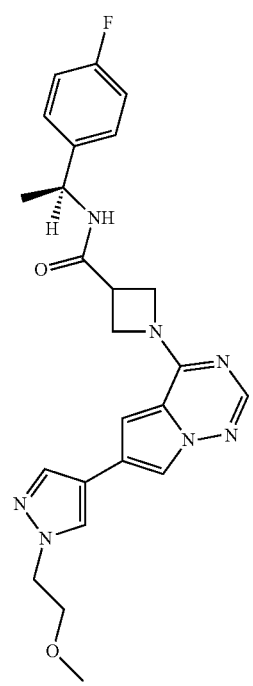 [SMILES: COCCn1cc(-c2cc3c(N4CC(C(=O)N[C@@H](C)c5ccc(F)cc5)C4)ncnn3c2)cn1] | B | C |

-continued
| Compound Number | Structure | D816V IC$_{50}$ (nM) | WT IC$_{50}$ (nM) |
|---|---|---|---|
| 142 | 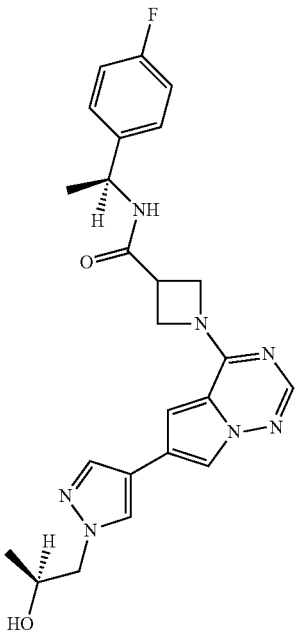 [SMILES: C[C@H](O)Cn1cc(-c2cc3c(N4CC(C(=O)N[C@@H](C)c5ccc(F)cc5)C4)ncnn3c2)cn1] | B | C |
| 143 | 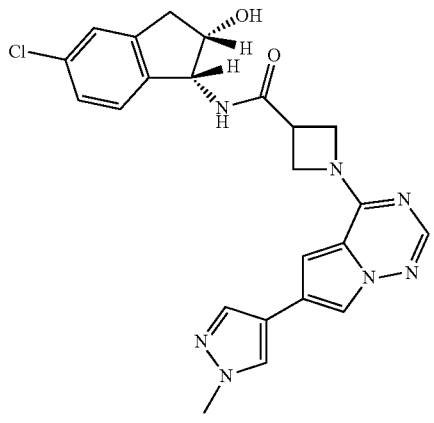 [SMILES: Cn1cc(-c2cc3c(N4CC(C(=O)N[C@@H]5c6ccc(Cl)cc6C[C@@H]5O)C4)ncnn3c2)cn1] | A | B |
| 144 | 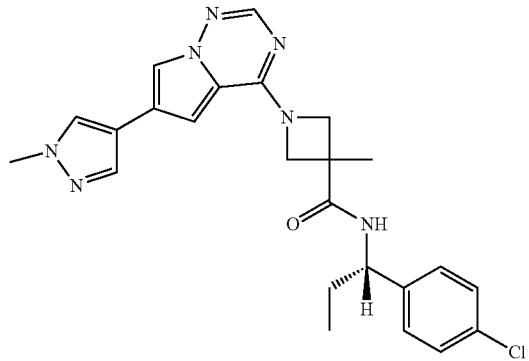 [SMILES: CC[C@H](NC(=O)C1(C)CN(c2ncnn3cc(-c4cnn(C)c4)cc23)C1)c1ccc(Cl)cc1] | B | C |

-continued

| Compound Number | Structure | D816V IC$_{50}$ (nM) | WT IC$_{50}$ (nM) |
|---|---|---|---|
| 145 | 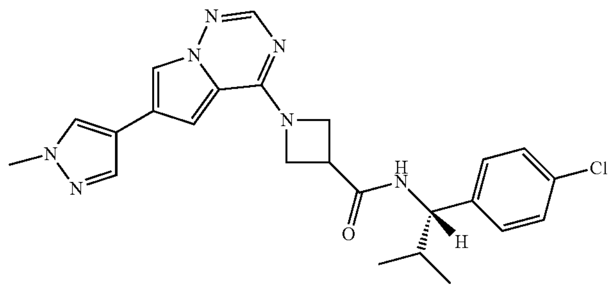 [SMILES: CC(C)[C@H](NC(=O)C1CN(c2ncnn3cc(-c4cnn(C)c4)cc23)C1)c1ccc(Cl)cc1] | B | C |
| 146 | 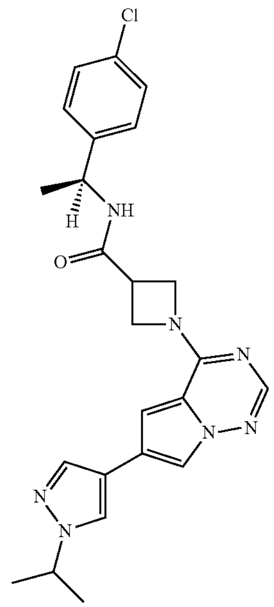 [SMILES: CC(C)n1cc(-c2cc3c(N4CC(C(=O)N[C@@H](C)c5ccc(Cl)cc5)C4)ncnn3c2)cn1] | A | C |
| 147 | 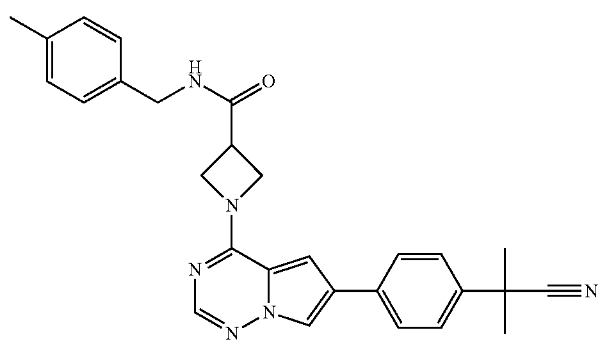 [SMILES: Cc1ccc(CNC(=O)C2CN(c3ncnn4cc(-c5ccc(C(C)(C)C#N)cc5)cc34)C2)cc1] | A | C |
| 148 | 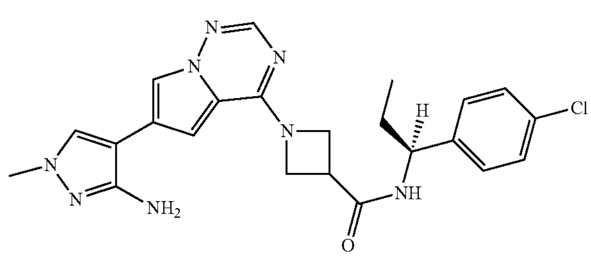 [SMILES: CC[C@H](NC(=O)C1CN(c2ncnn3cc(-c4cn(C)nc4N)cc23)C1)c1ccc(Cl)cc1] | B | C |

| Compound Number | Structure | D816V IC$_{50}$ (nM) | WT IC$_{50}$ (nM) |
|---|---|---|---|
| 149 | 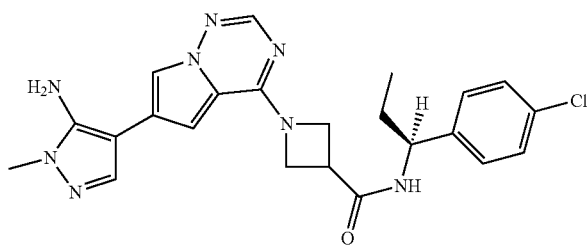 [SMILES: CC[C@H](NC(=O)C1CN(c2ncnn3cc(-c4cnn(C)c4N)cc23)C1)c1ccc(Cl)cc1] | B | C |
| 150 | 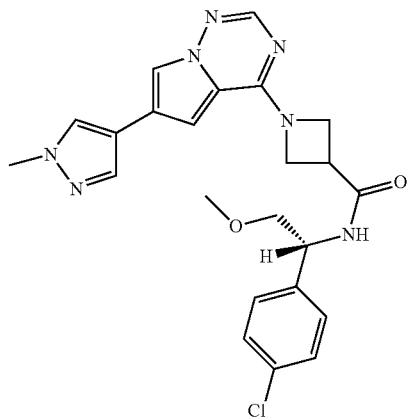 [SMILES: COC[C@H](NC(=O)C1CN(c2ncnn3cc(-c4cnn(C)c4)cc23)C1)c1ccc(Cl)cc1] | B | C |
| 151 | 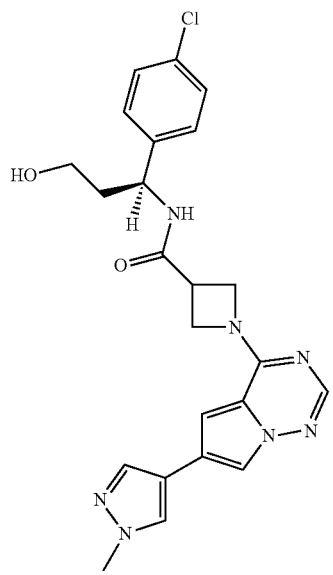 [SMILES: Cn1cc(-c2cc3c(N4CC(C(=O)N[C@@H](CCO)c5ccc(Cl)cc5)C4)ncnn3c2)cn1] | A | C |

-continued

| Compound Number | Structure | D816V IC$_{50}$ (nM) | WT IC$_{50}$ (nM) |
| --- | --- | --- | --- |
| 152 | 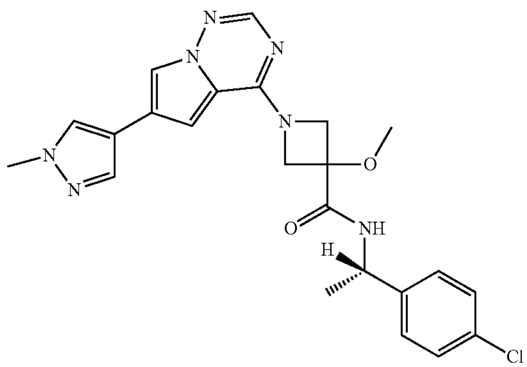 [SMILES: COC1(C(=O)N[C@@H](C)c2ccc(Cl)cc2)CN(c2ncnn3cc(-c4cnn(C)c4)cc23)C1] | B | C |
| 153 | 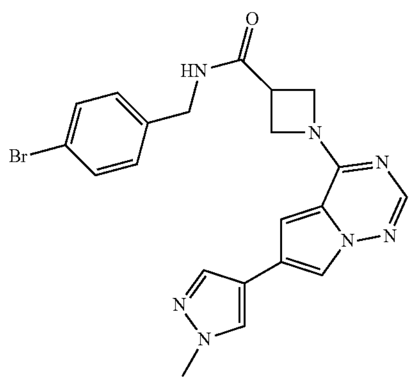 | A | B |
| 154 | 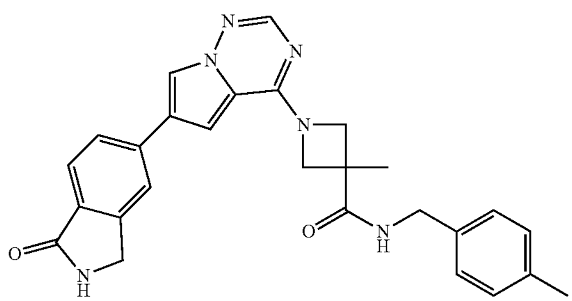 [SMILES: Cc1ccc(CNC(=O)C2(C)CN(c3ncnn4cc(-c5ccc6c(c5)CNC6=O)cc34)C2)cc1] | A | C |
| 155 | 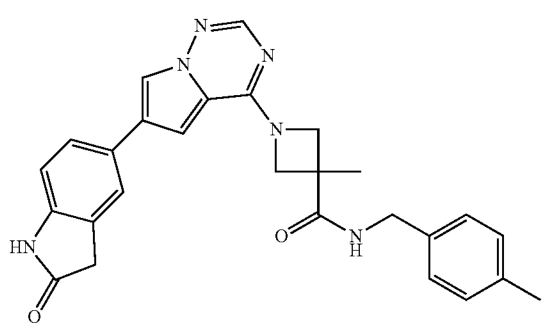 [SMILES: Cc1ccc(CNC(=O)C2(C)CN(c3ncnn4cc(-c5ccc6c(c5)CC(=O)N6)cc34)C2)cc1] | A | C |

-continued
| Compound Number | Structure | D816V IC$_{50}$ (nM) | WT IC$_{50}$ (nM) |
|---|---|---|---|
| 156 | 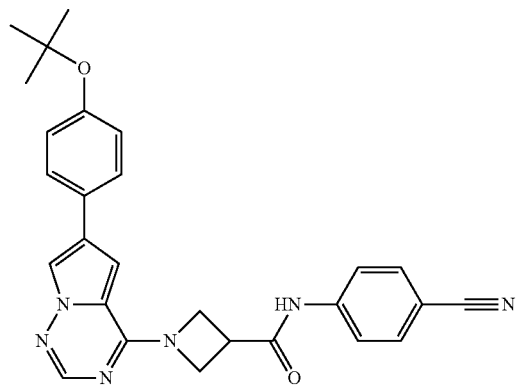 [SMILES: CC(C)(C)Oc1ccc(-c2cc3c(N4CC(C(=O)Nc5ccc(C#N)cc5)C4)ncnn3c2)cc1] | B | C |
| 157 | 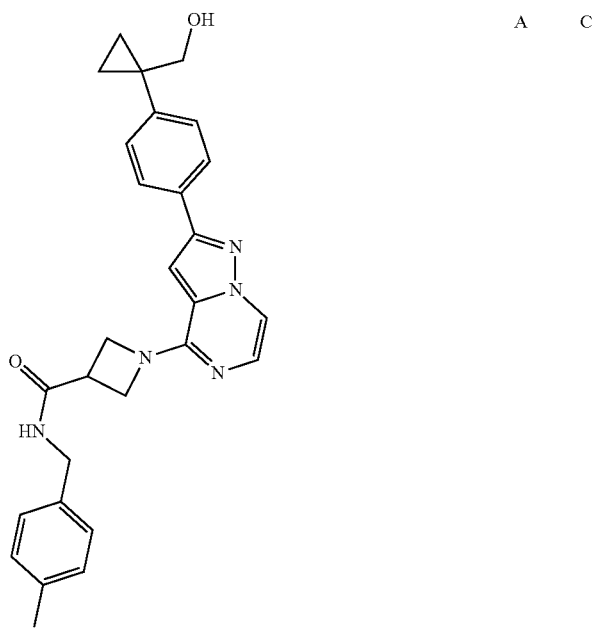 | A | C |
| 158 | 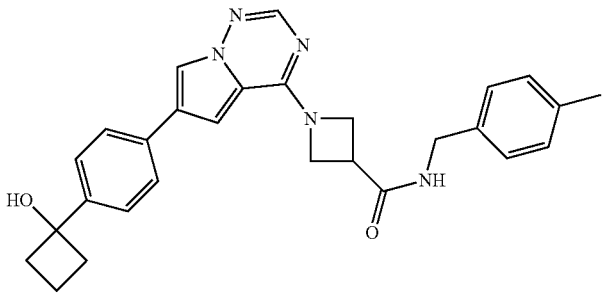 [SMILES: Cc1ccc(CNC(=O)C2CN(c3ncnn4cc(-c5ccc(C6(O)CCC6)cc5)cc34)C2)cc1] | A | C |

-continued

| Compound Number | Structure | D816V IC$_{50}$ (nM) | WT IC$_{50}$ (nM) |
|---|---|---|---|
| 159 | 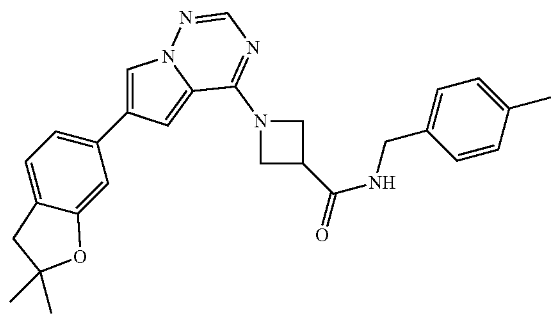 | B | C |
| 160 | 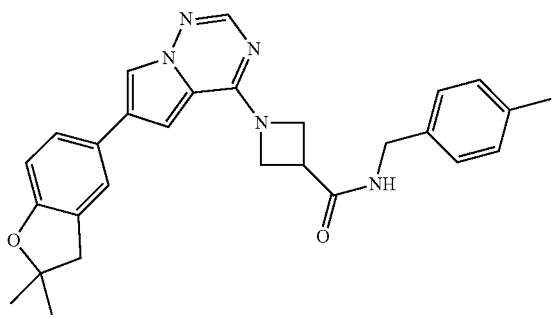 | B | C |
| 161 | 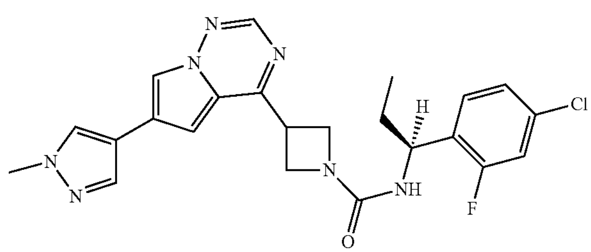 [SMILES: CC[C@H](NC(=O)N1CC(c2ncnn3cc(-c4cnn(C)c4)cc23)C1)c1ccc(Cl)cc1F] | B | C |
| 162 | 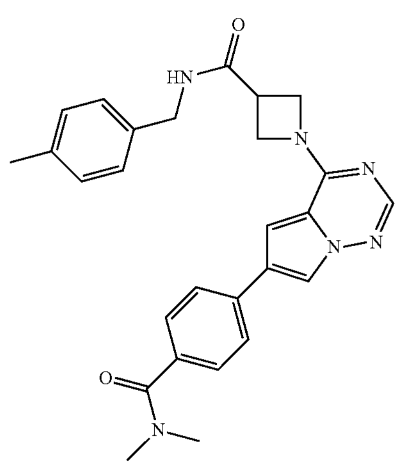 [SMILES: Cc1ccc(CNC(=O)C2CN(c3ncnn4cc(-c5ccc(C(=O)N(C)C)cc5)cc34)C2)cc1] | A | C |

-continued

| Compound Number | Structure | D816V IC$_{50}$ (nM) | WT IC$_{50}$ (nM) |
|---|---|---|---|
| 163 | 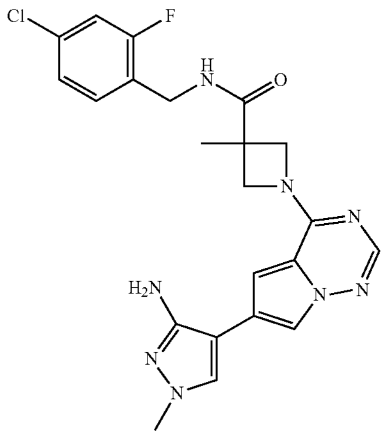 [SMILES: Cn1cc(-c2cc3c(N4CC(C)(C(=O)NCc5ccc(Cl)cc5F)C4)ncnn3c2)c(N)n1] | B | C |
| 164 | 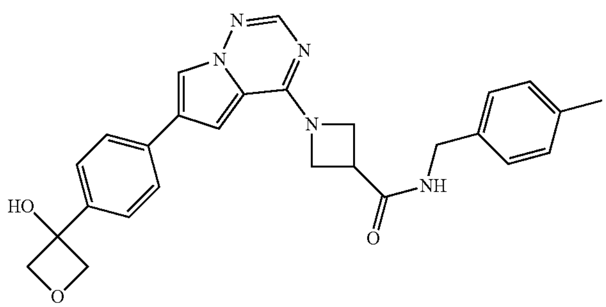 [SMILES: Cc1ccc(CNC(=O)C2CN(c3ncnn4cc(-c5ccc(C6(O)COC6)cc5)cc34)C2)cc1] | A | C |
| 165 | 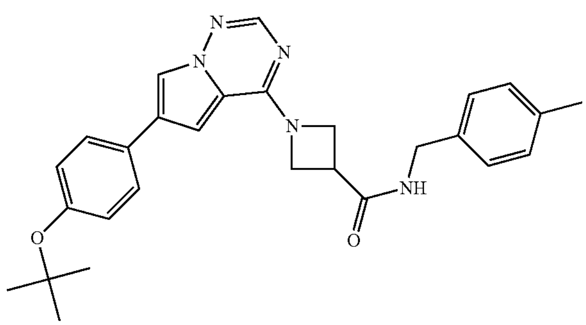 [SMILES: Cc1ccc(CNC(=O)C2CN(c3ncnn4cc(-c5ccc(OC(C)(C)C)cc5)cc34)C2)cc1] | B | D |
| 166 | 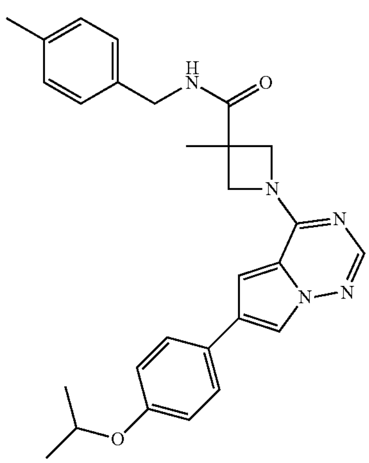 [SMILES: Cc1ccc(CNC(=O)C2(C)CN(c3ncnn4cc(-c5ccc(OC(C)C)cc5)cc34)C2)cc1] | B | C |

-continued

| Compound Number | Structure | D816V IC$_{50}$ (nM) | WT IC$_{50}$ (nM) |
|---|---|---|---|
| 167 | 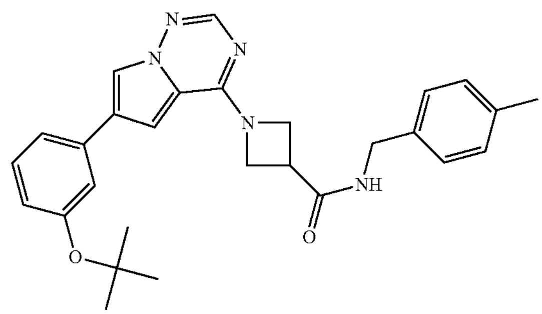 [SMILES: Cc1ccc(CNC(=O)C2CN(c3ncnn4cc(-c5cccc(OC(C)(C)C)c5)cc34)C2)cc1] | B | C |
| 168 | 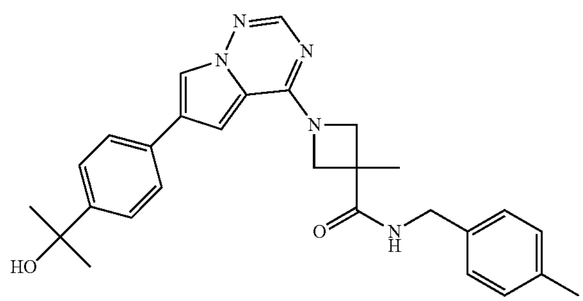 [SMILES: Cc1ccc(CNC(=O)C2(C)CN(c3ncnn4cc(-c5ccc(C(C)(C)O)cc5)cc34)C2)cc1] | A | C |
| 169 | 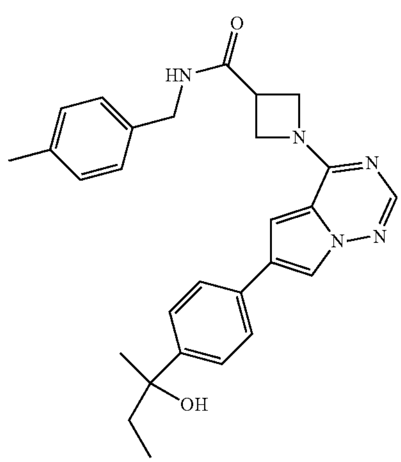 [SMILES: CCC(C)(O)c1ccc(-c2cc3c(N4CC(C(=O)NCc5ccc(C)cc5)C4)ncnn3c2)cc1] | A | C |
| 170 | 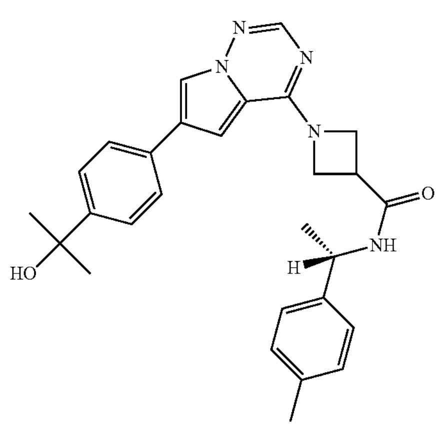 [SMILES: Cc1ccc([C@H](C)NC(=O)C2CN(c3ncnn4cc(-c5ccc(C(C)(C)O)cc5)cc34)C2)cc1] | A | C |

-continued

| Compound Number | Structure | D816V IC$_{50}$ (nM) | WT IC$_{50}$ (nM) |
|---|---|---|---|
| 171 | 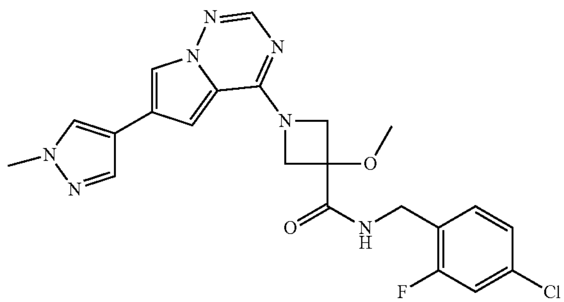 [SMILES: COC1(C(=O)NCc2ccc(Cl)cc2F)CN(c2ncnn3cc(-c4cnn(C)c4)cc23)C1] | B | C |
| 172 | 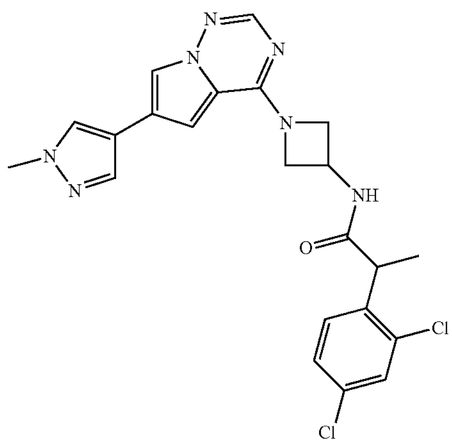 [SMILES: CC(C(=O)NC1CN(c2ncnn3cc(-c4cnn(C)c4)cc23)C1)c1ccc(Cl)cc1Cl] | B | C |
| 173 | 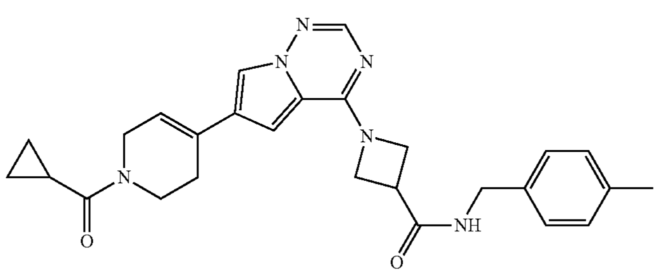 [SMILES: Cc1ccc(CNC(=O)C2CN(c3ncnn4cc(C5=CCN(C(=O)C6CC6)CC5)cc34)C2)cc1] | A | C |
| 174 | 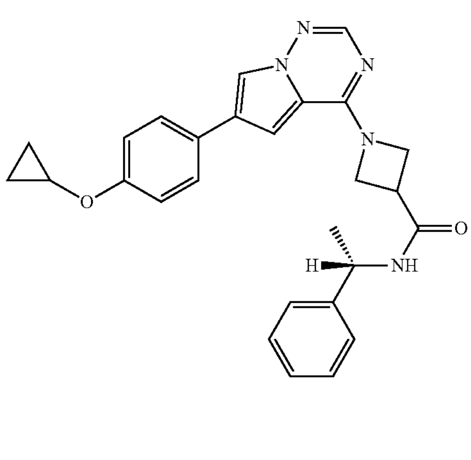 [SMILES: C[C@H](NC(=O)C1CN(c2ncnn3cc(-c4ccc(OC5CC5)cc4)cc23)C1)c1ccccc1] | B | D |

-continued

| Compound Number | Structure | D816V IC$_{50}$ (nM) | WT IC$_{50}$ (nM) |
|---|---|---|---|
| 175 | 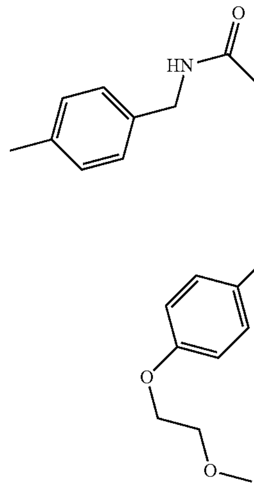 | A | C |
| 176 | 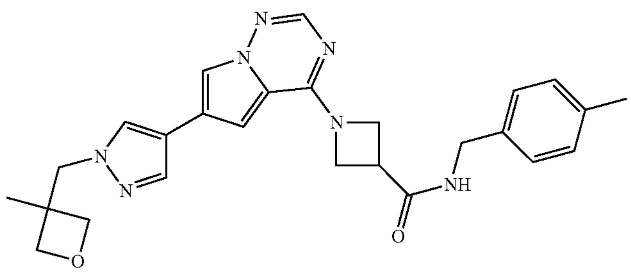 | A | C |
| 177 | 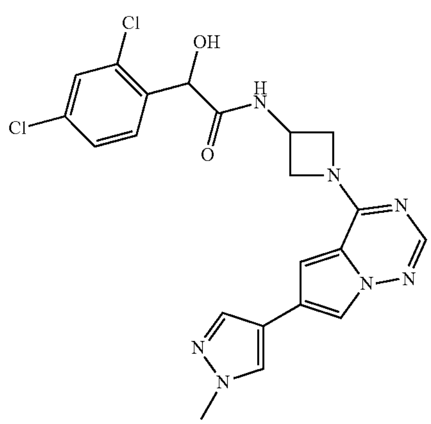 [SMILES: Cn1cc(-c2cc3c(N4CC(NC(=O)C(O)c5ccc(Cl)cc5Cl)C4)ncnn3c2)cn1] | B | C |
| 178 | 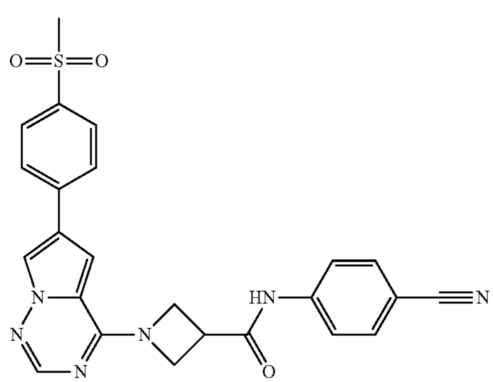 [SMILES: CS(=O)(=O)c1ccc(-c2cc3c(N4CC(C(=O)Nc5ccc(C#N)cc5)C4)ncnn3c2)cc1] | A | B |

-continued

| Compound Number | Structure | D816V IC$_{50}$ (nM) | WT IC$_{50}$ (nM) |
|---|---|---|---|
| 179 | 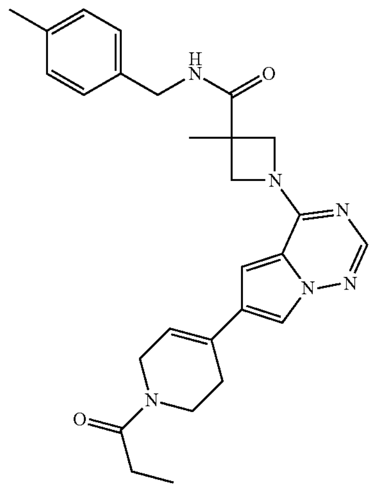 [SMILES: CCC(=O)N1CC=C(c2cc3c(N4CC(C)(C(=O)NCc5ccc(C)cc5)C4)ncnn3c2)CC1] | A | C |
| 180 | 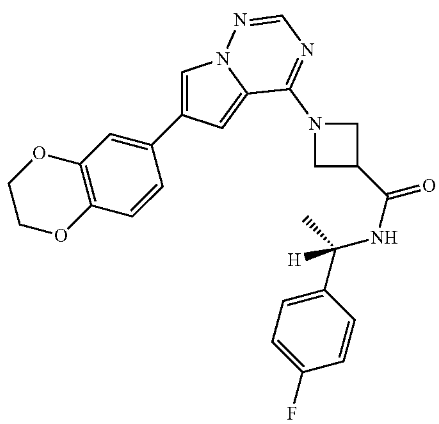 [SMILES: C[C@H](NC(=O)C1CN(c2ncnn3cc(-c4ccc5c(c4)OCCO5)cc23)C1)c1ccc(F)cc1] | B | C |
| 181 | 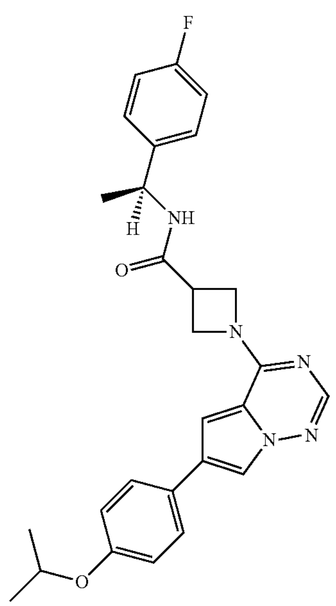 [SMILES: CC(C)Oc1ccc(-c2cc3c(N4CC(C(=O)N[C@@H](C)c5ccc(F)cc5)C4)ncnn3c2)cc1] | B | C |

| Compound Number | Structure | D816V IC$_{50}$ (nM) | WT IC$_{50}$ (nM) |
| --- | --- | --- | --- |
| 182 | 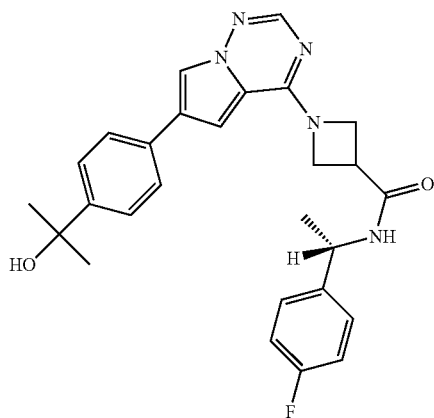 [SMILES: C[C@H](NC(=O)C1CN(c2ncnn3cc(-c4ccc(C(C)(C)O)cc4)cc23)C1)c1ccc(F)cc1] | B | C |
| 183 | 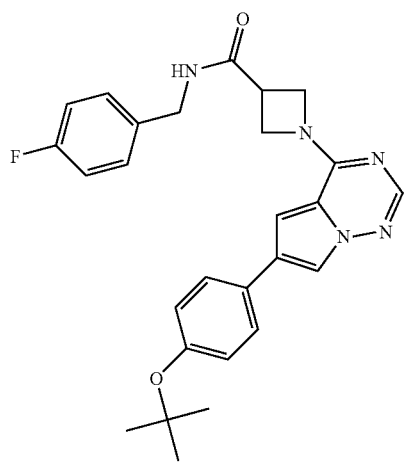 [SMILES: CC(C)(C)Oc1ccc(-c2cc3c(N4CC(C(=O)NCc5ccc(F)cc5)C4)ncnn3c2)cc1] | B | C |
| 184 | 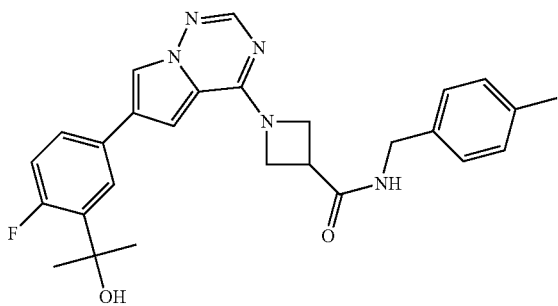 [SMILES: Cc1ccc(CNC(=O)C2CN(c3ncnn4cc(-c5ccc(F)c(C(C)(C)O)c5)cc34)C2)cc1] | B | C |

-continued

| Compound Number | Structure | D816V IC$_{50}$ (nM) | WT IC$_{50}$ (nM) |
|---|---|---|---|
| 185 | 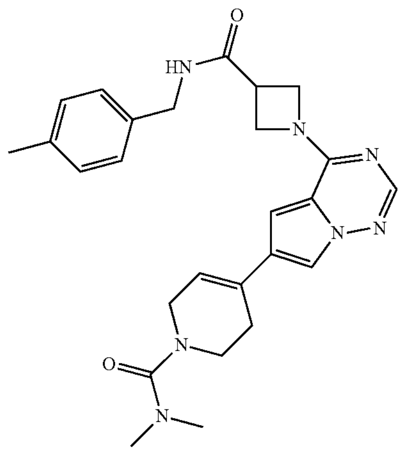 [SMILES: Cc1ccc(CNC(=O)C2CN(c3ncnn4cc(C5=CCN(C(=O)N(C)C)CC5)cc34)C2)cc1] | A | C |
| 186 | 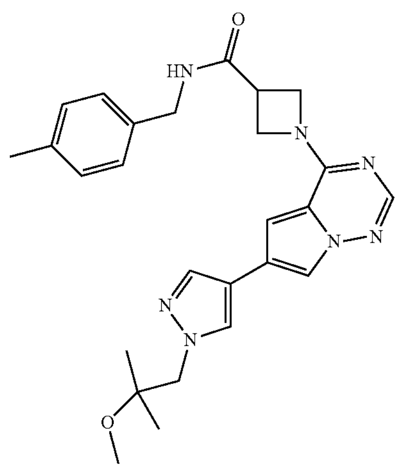 [SMILES: COC(C)(C)Cn1cc(-c2cc3c(N4CC(C(=O)NCc5ccc(C)cc5)C4)ncnn3c2)cn1] | A | C |
| 187 | 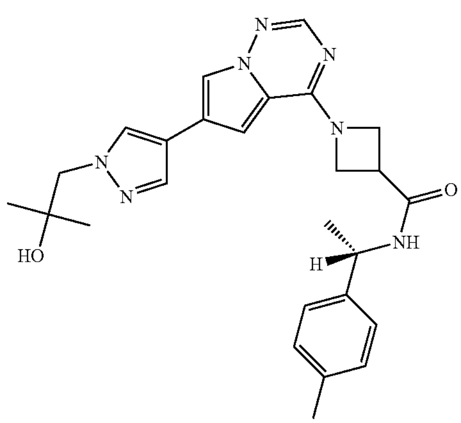 [SMILES: Cc1ccc([C@H](C)NC(=O)C2CN(c3ncnn4cc(-c5cnn(CC(C)(C)O)c5)cc34)C2)cc1] | A | C |

-continued

| Compound Number | Structure | D816V IC$_{50}$ (nM) | WT IC$_{50}$ (nM) |
|---|---|---|---|
| 188 | 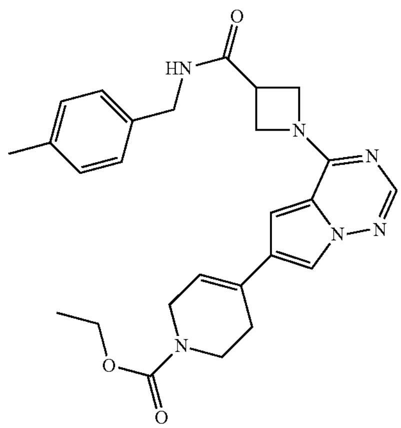 [SMILES: CCOC(=O)N1CC=C(c2cc3c(N4CC(C(=O)NCc5ccc(C)cc5)C4)ncnn3c2)CC1] | A | C |
| 189 | 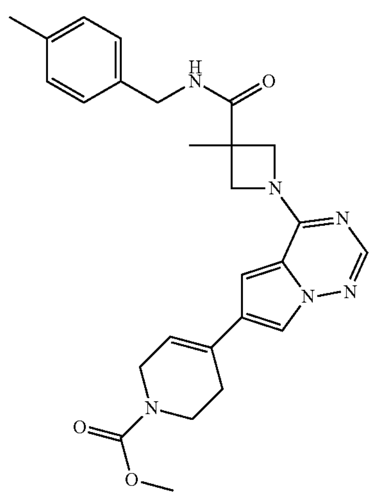 [SMILES: COC(=O)N1CC=C(c2cc3c(N4CC(C)(C(=O)NCc5ccc(C)cc5)C4)ncnn3c2)CC1] | B | C |
| 190 | 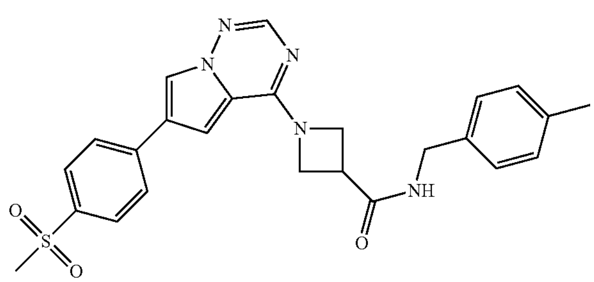 | A | C |
| 191 | 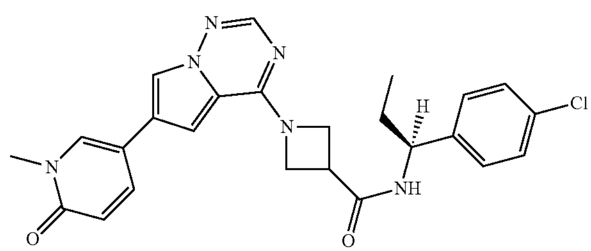 [SMILES: CC[C@H](NC(=O)C1CN(c2ncnn3cc(-c4ccc(=O)n(C)c4)cc23)C1)c1ccc(Cl)cc1] | B | C |

-continued
| Compound Number | Structure | D816V IC$_{50}$ (nM) | WT IC$_{50}$ (nM) |
|---|---|---|---|
| 192 | 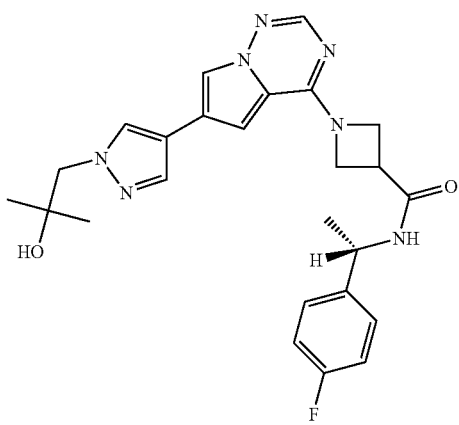 [SMILES: C[C@H](NC(=O)C1CN(c2ncnn3cc(-c4cnn(CC(C)(C)O)c4)cc23)C1)c1ccc(F)cc1] | A | C |
| 193 | 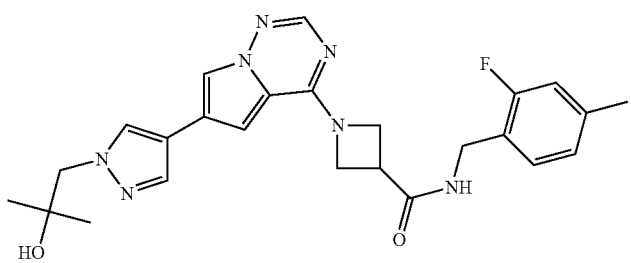 [SMILES: Cc1ccc(CNC(=O)C2CN(c3ncnn4cc(-c5cnn(CC(C)(C)O)c5)cc34)C2)c(F)c1] | A | C |
| 194 | 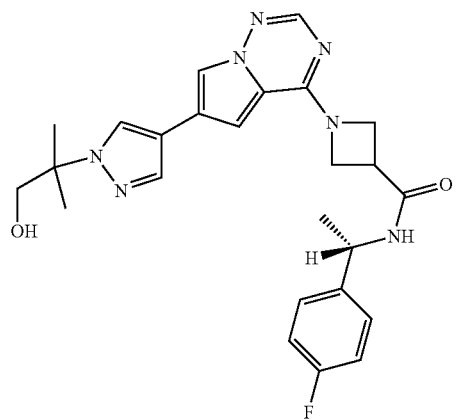 [SMILES: C[C@H](NC(=O)C1CN(c2ncnn3cc(-c4cnn(C(C)(C)CO)c4)cc23)C1)c1ccc(F)cc1] | B | C |

-continued
| Compound Number | Structure | D816V IC$_{50}$ (nM) | WT IC$_{50}$ (nM) |
|---|---|---|---|
| 195 | 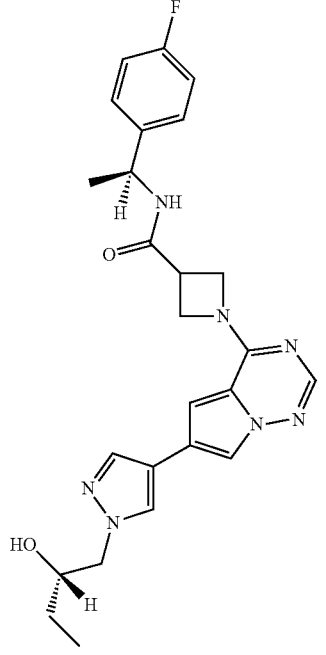 [SMILES: CC[C@H](O)Cn1cc(-c2cc3c(N4CC(C(=O)N[C@@H](C)c5ccc(F)cc5)C4)ncnn3c2)cn1] | A | C |
| 196 | 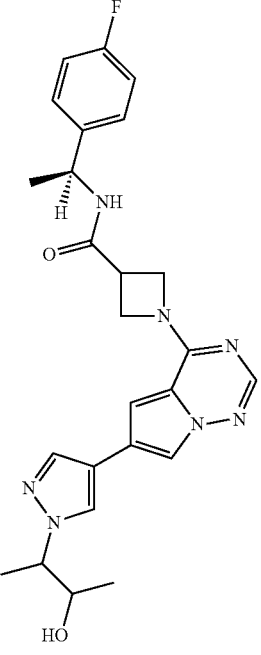 [SMILES: CC(O)C(C)n1cc(-c2cc3c(N4CC(C(=O)N[C@@H](C)c5ccc(F)cc5)C4)ncnn3c2)cn1] | B | C |
| 197 | 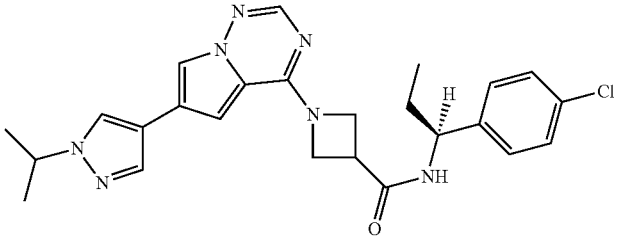 [SMILES: CC[C@H](NC(=O)C1CN(c2ncnn3cc(-c4cnn(C(C)C)c4)cc23)C1)c1ccc(Cl)cc1] | B | C |

-continued
| Compound Number | Structure | D816V IC$_{50}$ (nM) | WT IC$_{50}$ (nM) |
|---|---|---|---|
| 198 | 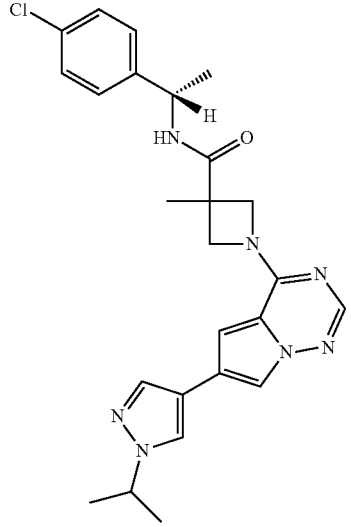 [SMILES: CC(C)n1cc(-c2cc3c(N4CC(C)(C(=O)N[C@@H](C)c5ccc(Cl)cc5)C4)ncnn3c2)cn1] | B | C |
| 199 | 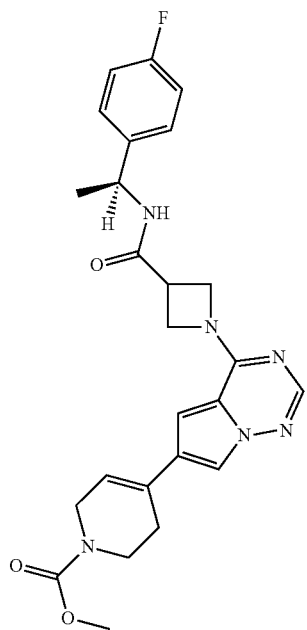 [SMILES: COC(=O)N1CC=C(c2cc3c(N4CC(C(=O)N[C@@H](C)c5ccc(F)cc5)C4)ncnn3c2)CC1] | A | C |

-continued

| Compound Number | Structure | D816V IC$_{50}$ (nM) | WT IC$_{50}$ (nM) |
|---|---|---|---|
| 200 | 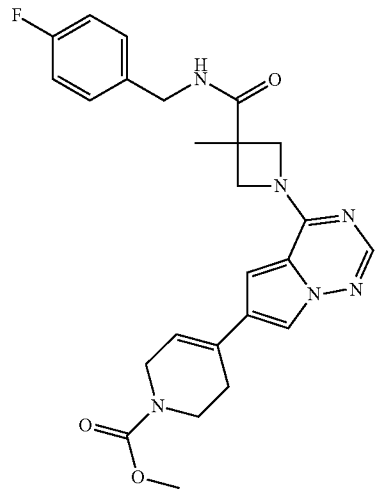 [SMILES: COC(=O)N1CC=C(c2cc3c(N4CC(C)(C(=O)NCc5ccc(F)cc5)C4)ncnn3c2)CC1] | B | C |
| 201 | 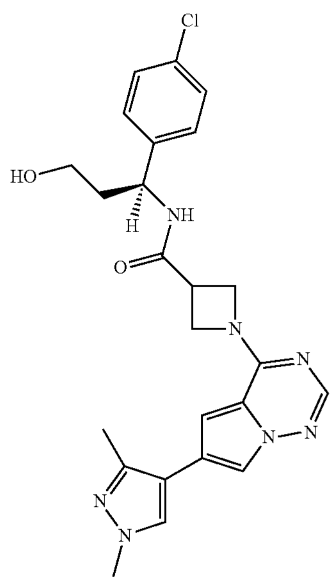 [SMILES: Cc1nn(C)cc1-c1cc2c(N3CC(C(=O)N[C@@H](CCO)c4ccc(Cl)cc4)C3)ncnn2c1] | B | C |
| 202 | 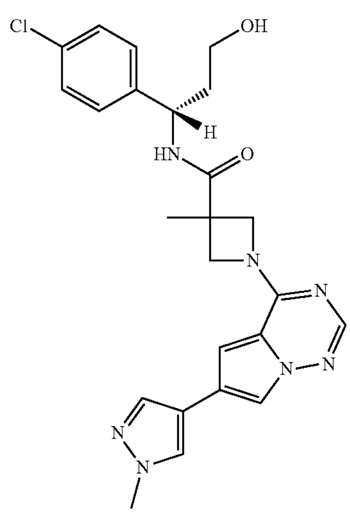 [SMILES: Cn1cc(-c2cc3c(N4CC(C)(C(=O)N[C@@H](CCO)c5ccc(Cl)cc5)C4)ncnn3c2)cn1] | A | C |

-continued

| Compound Number | Structure | D816V IC$_{50}$ (nM) | WT IC$_{50}$ (nM) |
|---|---|---|---|
| 203 | 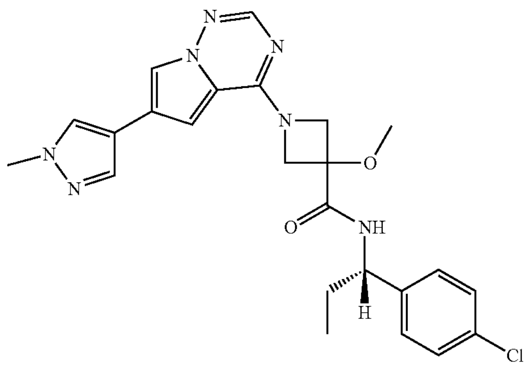 [SMILES: CC[C@H](NC(=O)C1(OC)CN(c2ncnn3cc(-c4cnn(C)c4)cc23)C1)c1ccc(Cl)cc1] | B | C |
| 204 | 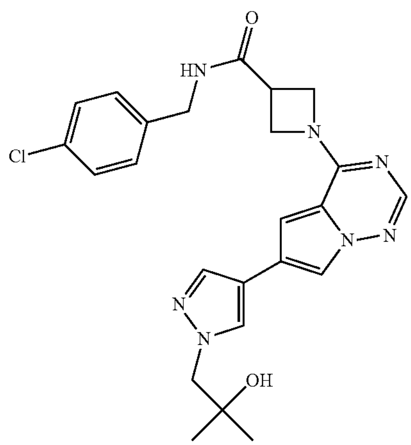 [SMILES: CC(C)(O)Cn1cc(-c2cc3c(N4CC(C(=O)NCc5ccc(Cl)cc5)C4)ncnn3c2)cn1] | A | C |
| 205 | 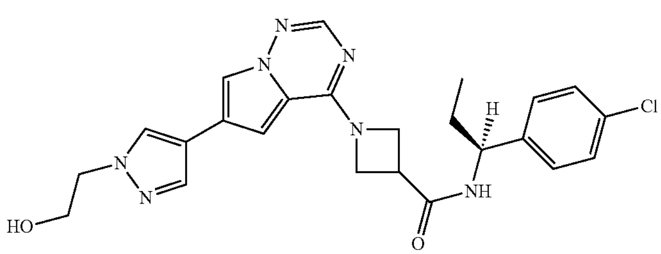 [SMILES: CC[C@H](NC(=O)C1CN(c2ncnn3cc(-c4cnn(CCO)c4)cc23)C1)c1ccc(Cl)cc1] | B | C |
| 206 | 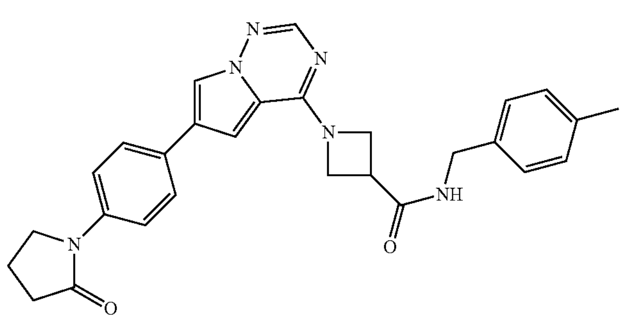 [SMILES: Cc1ccc(CNC(=O)C2CN(c3ncnn4cc(-c5ccc(N6CCCC6=O)cc5)cc34)C2)cc1] | A | C |

| Compound Number | Structure | D816V IC$_{50}$ (nM) | WT IC$_{50}$ (nM) |
| --- | --- | --- | --- |
| 207 | 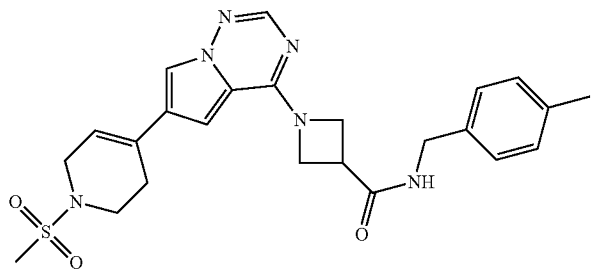 | A | C |
| 208 | 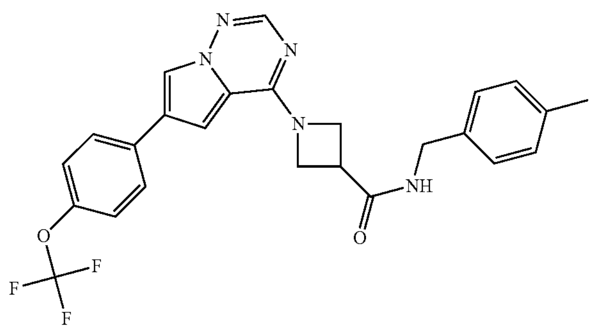 [SMILES: Cc1ccc(CNC(=O)C2CN(c3ncnn4cc(-c5ccc(OC(F)(F)F)cc5)cc34)C2)cc1] | B | C |
| 209 | 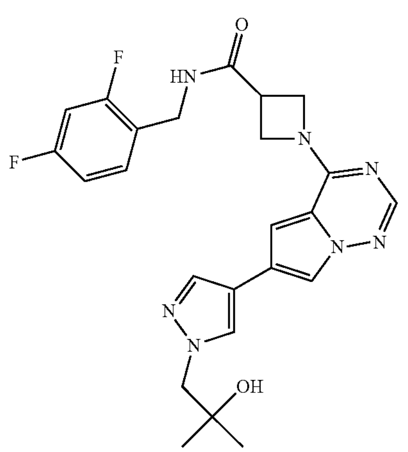 [SMILES: CC(C)(O)Cn1cc(-c2cc3c(N4CC(C(=O)NCc5ccc(F)cc5F)C4)ncnn3c2)cn1] | B | C |

-continued
| Compound Number | Structure | D816V IC$_{50}$ (nM) | WT IC$_{50}$ (nM) |
|---|---|---|---|
| 210 | 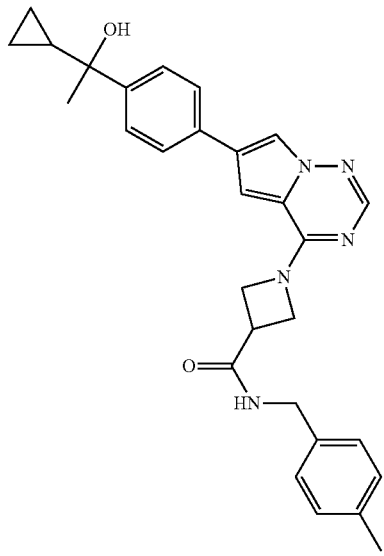 [SMILES: Cc1ccc(CNC(=O)C2CN(c3ncnn4cc(-c5ccc(C(C)(O)C6CC6)cc5)cc34)C2)cc1] | A | C |
| 211 | 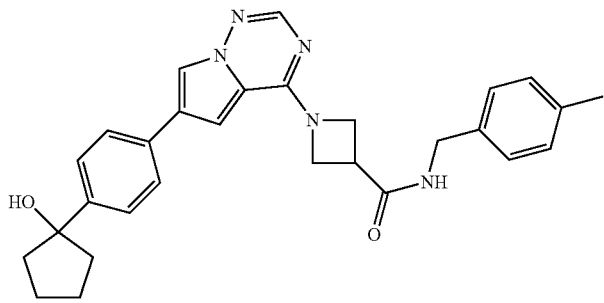 [SMILES: Cc1ccc(CNC(=O)C2CN(c3ncnn4cc(-c5ccc(C6(O)CCCC6)cc5)cc34)C2)cc1] | B | C |
| 212 | 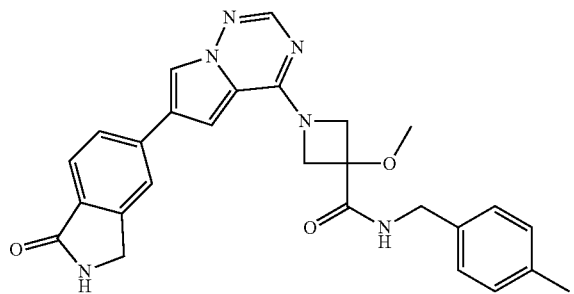 [SMILES: COC1(C(=O)NCc2ccc(C)cc2)CN(c2ncnn3cc(-c4ccc5c(c4)CNC5=O)cc23)C1] | B | C |
| 213 | 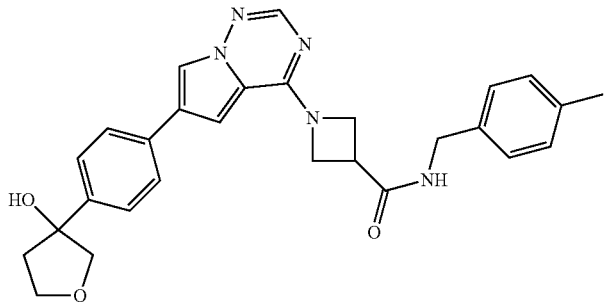 [SMILES: Cc1ccc(CNC(=O)C2CN(c3ncnn4cc(-c5ccc(C6(O)CCOC6)cc5)cc34)C2)cc1] | A | C |

-continued

| Compound Number | Structure | D816V IC$_{50}$ (nM) | WT IC$_{50}$ (nM) |
|---|---|---|---|
| 214 | 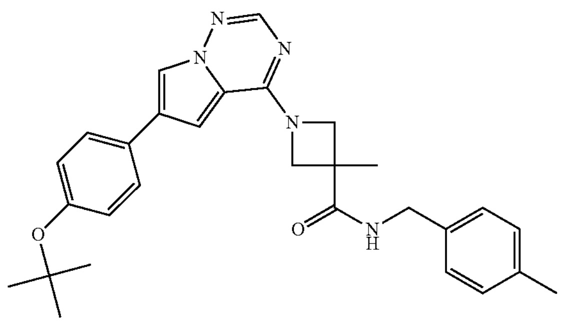 [SMILES: Cc1ccc(CNC(=O)C2(C)CN(c3ncnn4cc(-c5ccc(OC(C)(C)C)cc5)cc34)C2)cc1] | B | C |
| 215 | 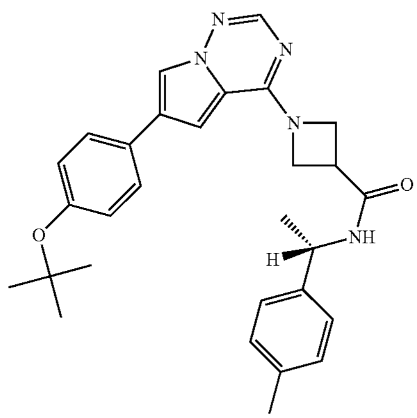 [SMILES: Cc1ccc([C@H](C)NC(=O)C2CN(c3ncnn4cc(-c5ccc(OC(C)(C)C)cc5)cc34)C2)cc1] | B | C |
| 216 | 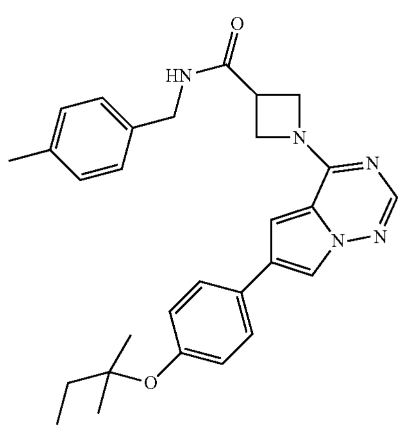 [SMILES: CCC(C)(C)Oc1ccc(-c2cc3c(N4CC(C(=O)NCc5ccc(C)cc5)C4)ncnn3c2)cc1] | B | C |
| 217 | 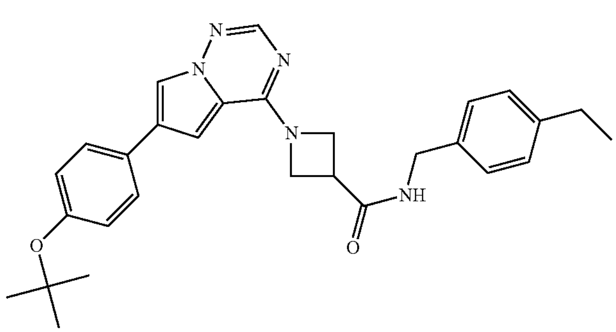 [SMILES: CCc1ccc(CNC(=O)C2CN(c3ncnn4cc(-c5ccc(OC(C)(C)C)cc5)cc34)C2)cc1] | B | C |

| Compound Number | Structure | D816V IC$_{50}$ (nM) | WT IC$_{50}$ (nM) |
|---|---|---|---|
| 218 | 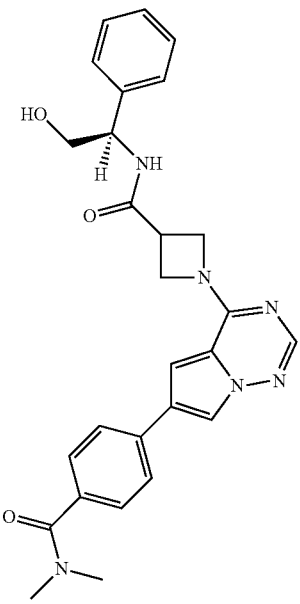 [SMILES: CN(C)C(=O)c1ccc(-c2cc3c(N4CC(C(=O)N[C@@H](CO)c5ccccc5)C4)ncnn3c2)cc1] | A | C |
| 219 | 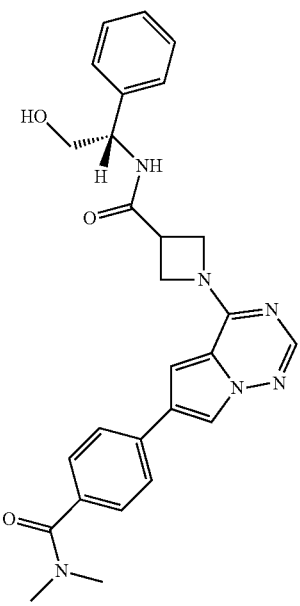 [SMILES: CN(C)C(=O)c1ccc(-c2cc3c(N4CC(C(=O)N[C@H](CO)c5ccccc5)C4)ncnn3c2)cc1] | A | D |

-continued
| Compound Number | Structure | D816V IC$_{50}$ (nM) | WT IC$_{50}$ (nM) |
|---|---|---|---|
| 220 | 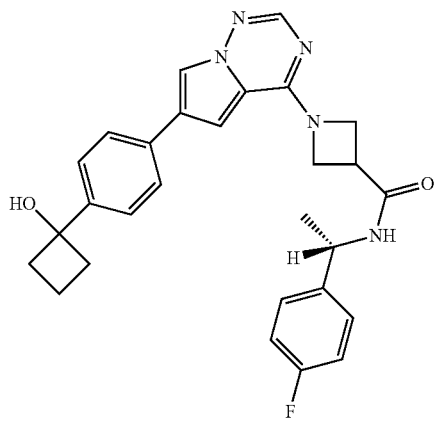 [SMILES: C[C@H](NC(=O)C1CN(c2ncnn3cc(-c4ccc(C5(O)CCC5)cc4)cc23)C1)c1ccc(F)cc1] | A | C |
| 221 | 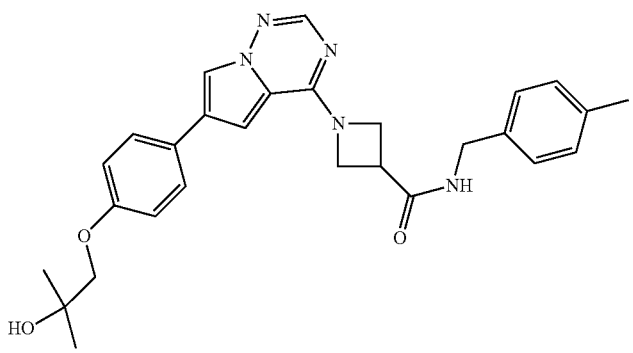 [SMILES: Cc1ccc(CNC(=O)C2CN(c3ncnn4cc(-c5ccc(OCC(C)(C)O)cc5)cc34)C2)cc1] | B | C |
| 222 | 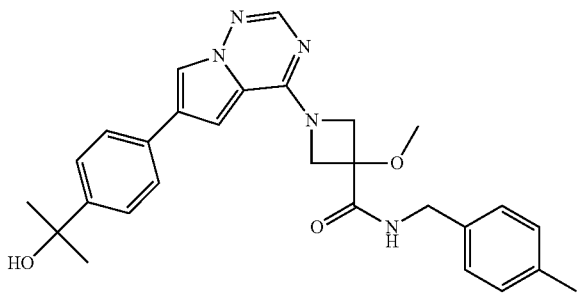 [SMILES: COC1(C(=O)NCc2ccc(C)cc2)CN(c2ncnn3cc(-c4ccc(C(C)(C)O)cc4)cc23)C1] | A | C |
| 223 | 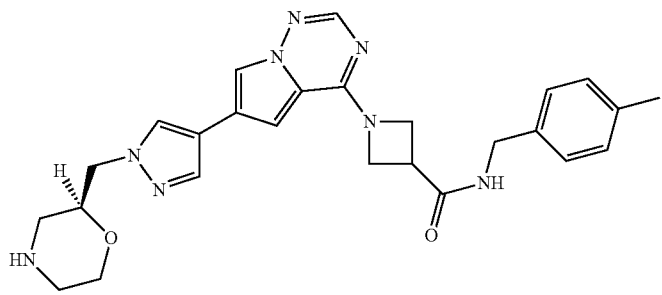 [SMILES: Cc1ccc(CNC(=O)C2CN(c3ncnn4cc(-c5cnn(C[C@@H]6CNCCO6)c5)cc34)C2)cc1] | A | C |

-continued
| Compound Number | Structure | D816V IC50 (nM) | WT IC50 (nM) |
|---|---|---|---|
| 224 | 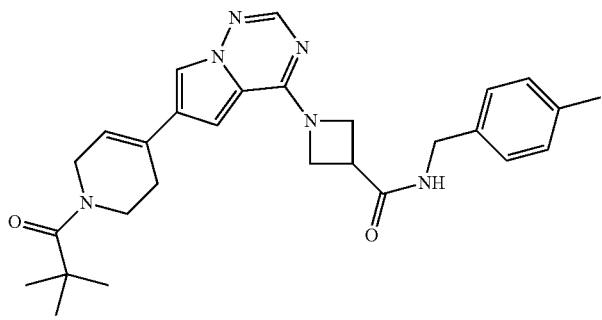 [SMILES: Cc1ccc(CNC(=O)C2CN(c3ncnn4cc(C5=CCN(C(=O)C(C)(C)C)CC5)cc34)C2)cc1] | A | C |
| 225 | 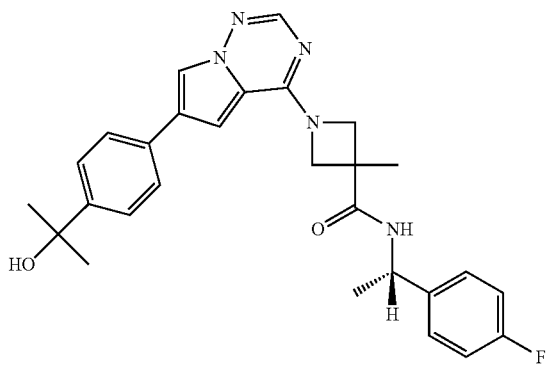 [SMILES: C[C@H](NC(=O)C1(C)CN(c2ncnn3cc(-c4ccc(C(C)(C)O)cc4)cc23)C1)c1ccc(F)cc1] | B | C |
| 226 | 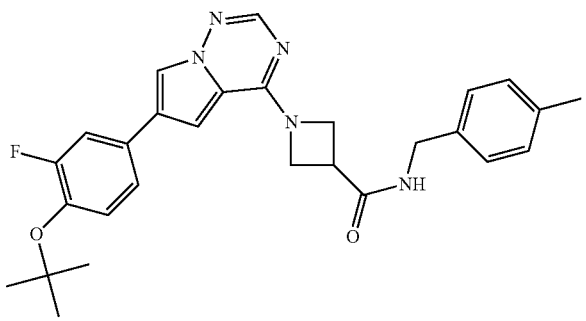 [SMILES: Cc1ccc(CNC(=O)C2CN(c3ncnn4cc(-c5ccc(OC(C)(C)C)c(F)c5)cc34)C2)cc1] | B | C |
| 227 | 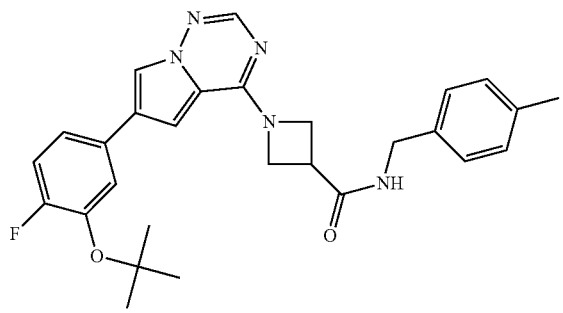 [SMILES: Cc1ccc(CNC(=O)C2CN(c3ncnn4cc(-c5ccc(F)c(OC(C)(C)C)c5)cc34)C2)cc1] | B | C |

-continued
| Compound Number | Structure | D816V IC$_{50}$ (nM) | WT IC$_{50}$ (nM) |
|---|---|---|---|
| 228 | 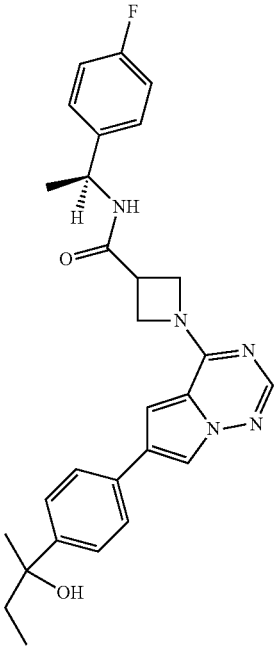 [SMILES: CCC(C)(O)c1ccc(-c2cc3c(N4CC(C(=O)N[C@@H](C)c5ccc(F)cc5)C4)ncnn3c2)cc1] | B | C |
| 229 | 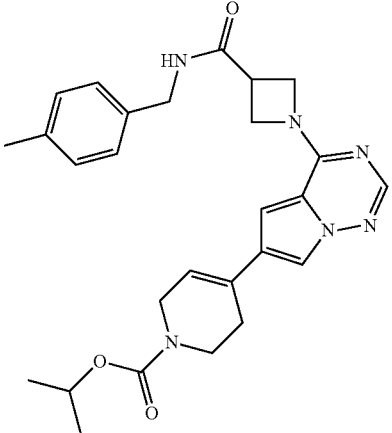 [SMILES: Cc1ccc(CNC(=O)C2CN(c3ncnn4cc(C5=CCN(C(=O)OC(C)C)CC5)cc34)C2)cc1] | A | C |
| 230 | 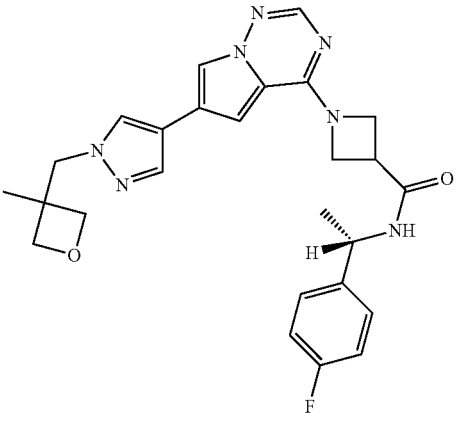 [SMILES: C[C@H](NC(=O)C1CN(c2ncnn3cc(-c4cnn(CC5(C)COC5)c4)cc23)C1)c1ccc(F)cc1] | A | C |

| Compound Number | Structure | D816V IC$_{50}$ (nM) | WT IC$_{50}$ (nM) |
| --- | --- | --- | --- |
| 231 | 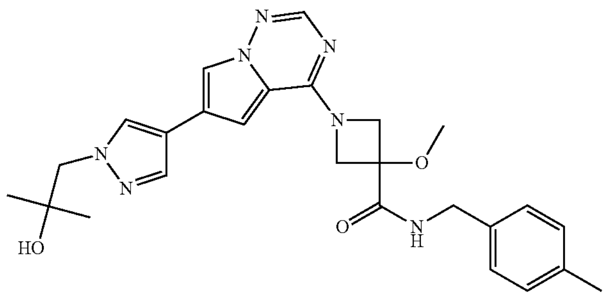 [SMILES: COC1(C(=O)NCc2ccc(C)cc2)CN(c2ncnn3cc(-c4cnn(CC(C)(C)O)c4)cc23)C1] | B | C |
| 232 | 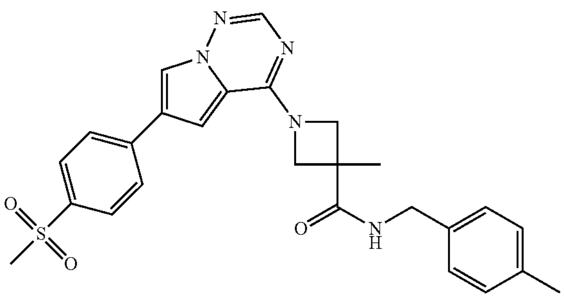 | A | C |
| 233 | 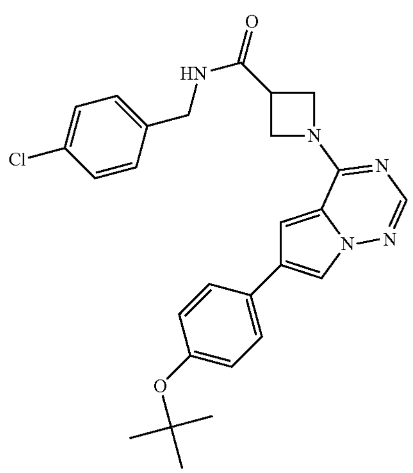 [SMILES: CC(C)(C)Oc1ccc(-c2cc3c(N4CC(C(=O)NCc5ccc(Cl)cc5)C4)ncnn3c2)cc1] | B | C |
| 234 | 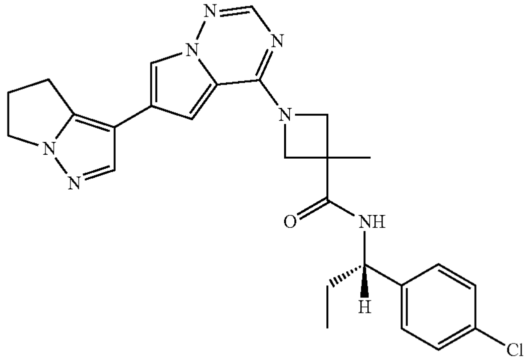 [SMILES: CC[C@H](NC(=O)C1(C)CN(c2ncnn3cc(-c4cnn5c4CCC5)cc23)C1)c1ccc(Cl)cc1] | B | C |

-continued

| Compound Number | Structure | D816V IC$_{50}$ (nM) | WT IC$_{50}$ (nM) |
|---|---|---|---|
| 235 | 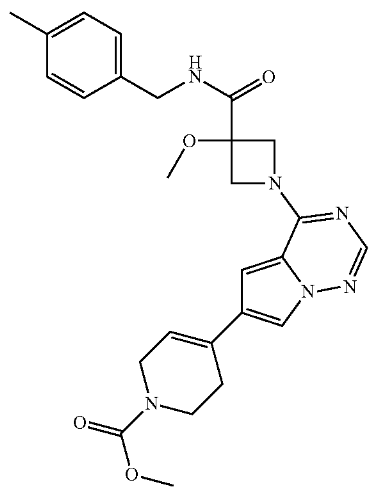 [SMILES: COC(=O)N1CC=C(c2cc3c(N4CC(OC)(C(=O)NCc5ccc(C)cc5)C4)ncnn3c2)CC1] | A | C |
| 236 | 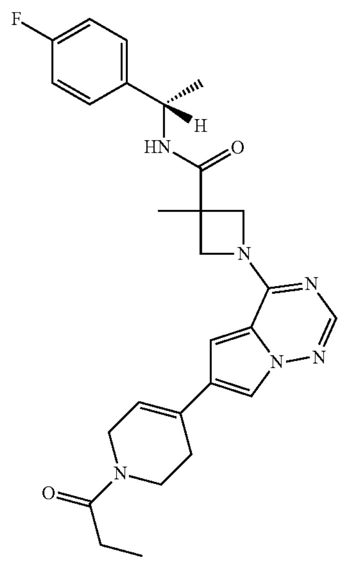 [SMILES: CCC(=O)N1CC=C(c2cc3c(N4CC(C)(C(=O)N[C@@H](C)c5ccc(F)cc5)C4)ncnn3c2)CC1] | B | C |
| 237 | 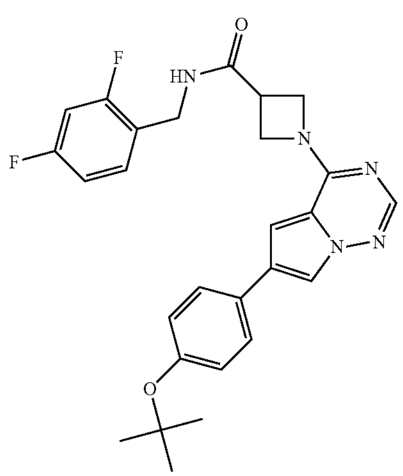 [SMILES: CC(C)(C)Oc1ccc(-c2cc3c(N4CC(C(=O)NCc5ccc(F)cc5F)C4)ncnn3c2)cc1] | B | C |

-continued

| Compound Number | Structure | D816V IC$_{50}$ (nM) | WT IC$_{50}$ (nM) |
|---|---|---|---|
| 238 | 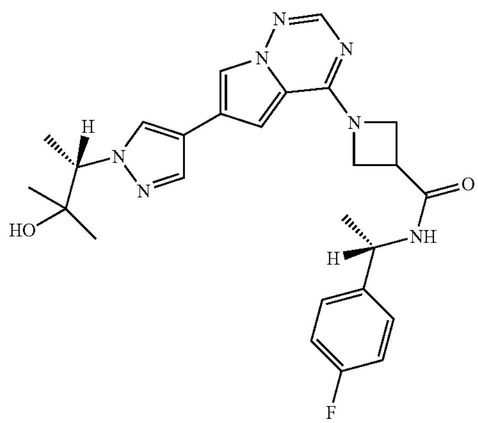 [SMILES: C[C@H](NC(=O)C1CN(c2ncnn3cc(-c4cnn([C@@H](C)C(C)(C)O)c4)cc23)C1)c1ccc(F)cc1] | A | C |
| 239 | 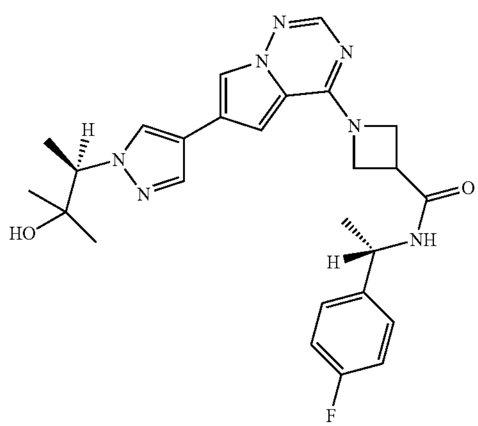 [SMILES: C[C@H](NC(=O)C1CN(c2ncnn3cc(-c4cnn([C@H](C)C(C)(C)O)c4)cc23)C1)c1ccc(F)cc1] | A | C |
| 240 | 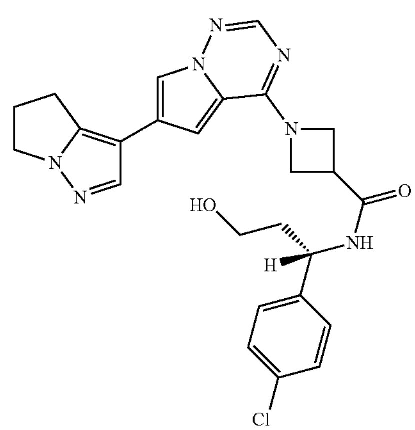 [SMILES: O=C(N[C@@H](CCO)c1ccc(Cl)cc1)C1CN(c2ncnn3cc(-c4cnn5c4CCC5)cc23)C1] | A | C |
| 241 | 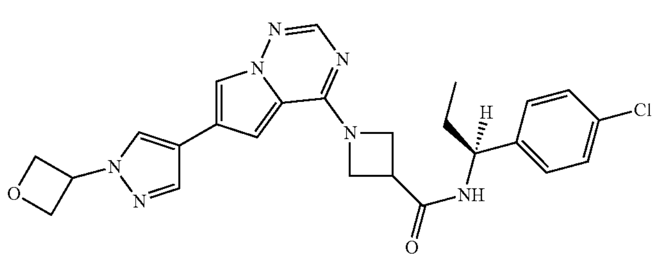 [SMILES: CC[C@H](NC(=O)C1CN(c2ncnn3cc(-c4cnn(C5COC5)c4)cc23)C1)c1ccc(Cl)cc1] | B | C |

| Compound Number | Structure | D816V IC$_{50}$ (nM) | WT IC$_{50}$ (nM) |
|---|---|---|---|
| 242 | 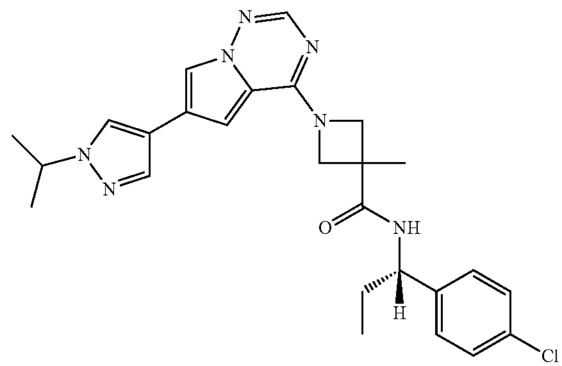 [SMILES: CC[C@H](NC(=O)C1(C)CN(c2ncnn3cc(-c4cnn(C(C)C)c4)cc23)C1)c1ccc(Cl)cc1] | B | C |
| 243 | 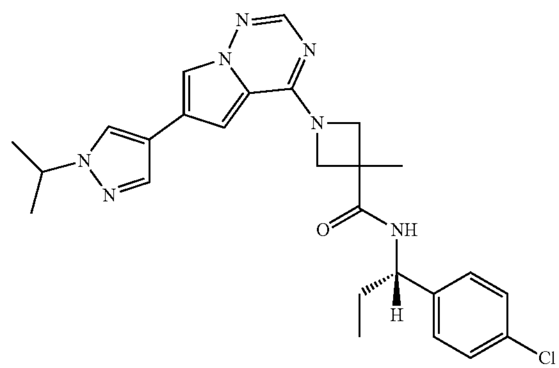 [SMILES: CC[C@H](NC(=O)C1(C)CN(c2ncnn3cc(-c4cnn(C(C)C)c4)cc23)C1)c1ccc(Cl)cc1] | B | C |
| 244 | 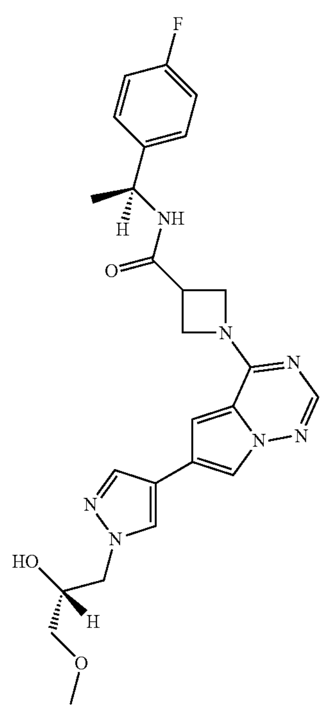 [SMILES: COC[C@H](O)Cn1cc(-c2cc3c(N4CC(C(=O)N[C@@H](C)c5ccc(F)cc5)C4)ncnn3c2)cn1] | B | C |

-continued
| Compound Number | Structure | D816V IC$_{50}$ (nM) | WT IC$_{50}$ (nM) |
|---|---|---|---|
| 245 | 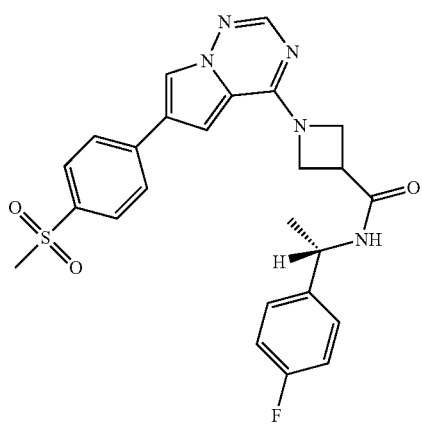 [SMILES: C[C@H](NC(=O)C1CN(c2ncnn3cc(-c4ccc(S(C)(=O)=O)cc4)cc23)C1)c1ccc(F)cc1] | B | C |
| 246 | 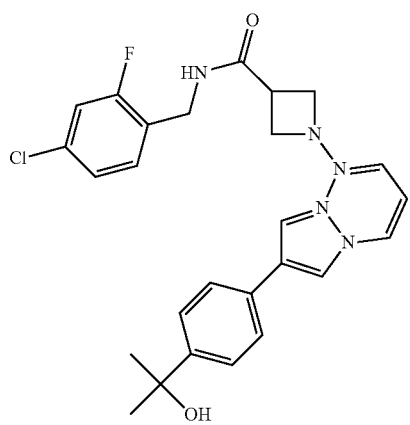 | A | C |
| 247 | 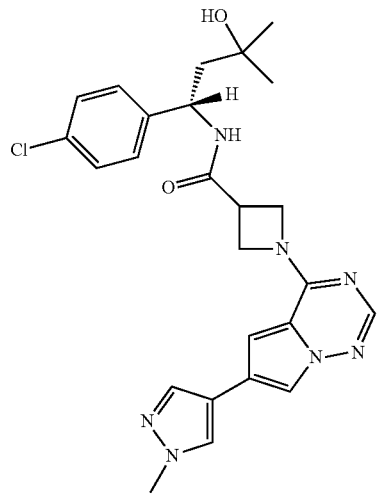 [SMILES: Cn1cc(-c2cc3c(N4CC(C(=O)N[C@@H](CC(C)(C)O)c5ccc(Cl)cc5)C4)ncnn3c2)cn1] | B | C |

-continued

| Compound Number | Structure | D816V IC$_{50}$ (nM) | WT IC$_{50}$ (nM) |
|---|---|---|---|
| 248 | 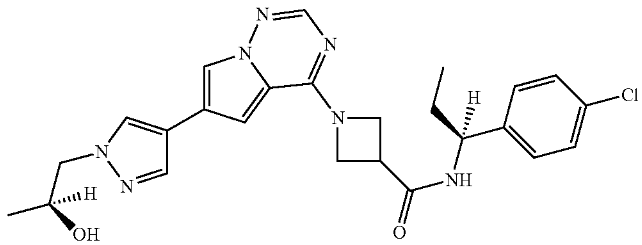 [SMILES: CC[C@H](NC(=O)C1CN(c2ncnn3cc(-c4cnn(C[C@H](C)O)c4)cc23)C1)c1ccc(Cl)cc1] | B | C |
| 249 | 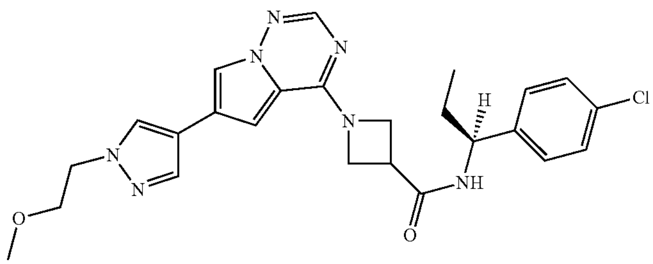 [SMILES: CC[C@H](NC(=O)C1CN(c2ncnn3cc(-c4cnn(CCOC)c4)cc23)C1)c1ccc(Cl)cc1] | B | C |
| 250 | 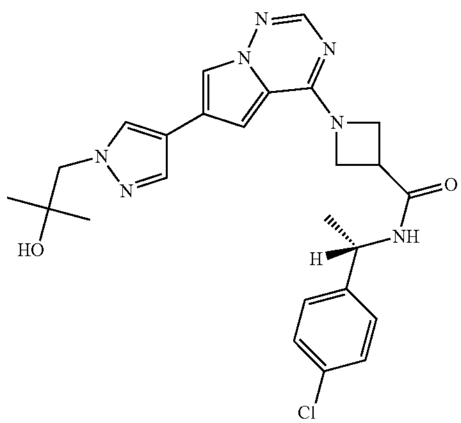 | A | C |
| 251 | 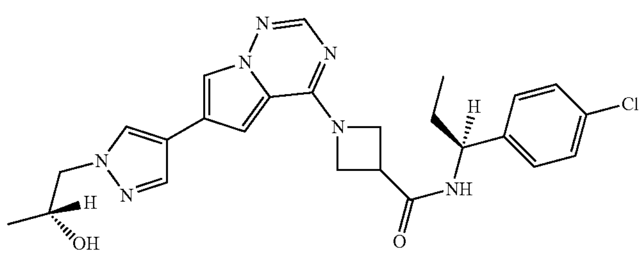 [SMILES: CC[C@H](NC(=O)C1CN(c2ncnn3cc(-c4cnn(C[C@@H](C)O)c4)cc23)C1)c1ccc(Cl)cc1] | A | C |
| 252 | 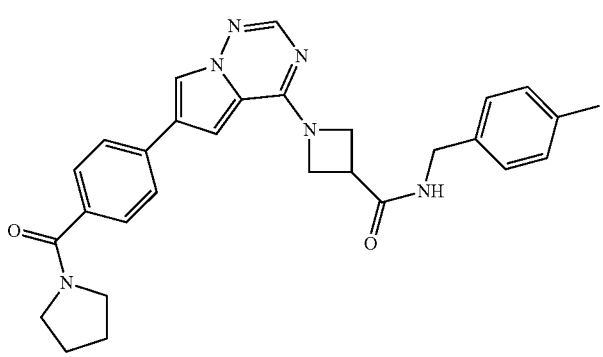 [SMILES: Cc1ccc(CNC(=O)C2CN(c3ncnn4cc(-c5ccc(C(=O)N6CCCC6)cc5)cc34)C2)cc1] | A | C |

-continued

| Compound Number | Structure | D816V IC$_{50}$ (nM) | WT IC$_{50}$ (nM) |
|---|---|---|---|
| 253 | 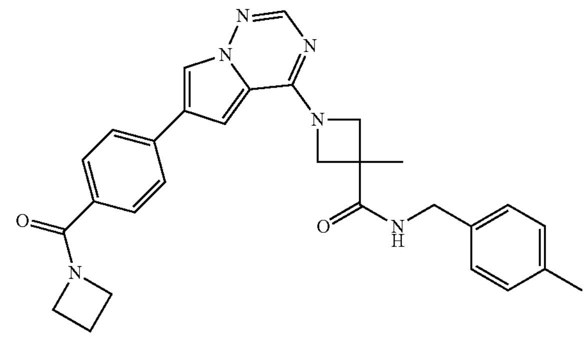 [SMILES: Cc1ccc(CNC(=O)C2(C)CN(c3ncnn4cc(-c5ccc(C(=O)N6CCC6)cc5)cc34)C2)cc1] | A | C |
| 254 | 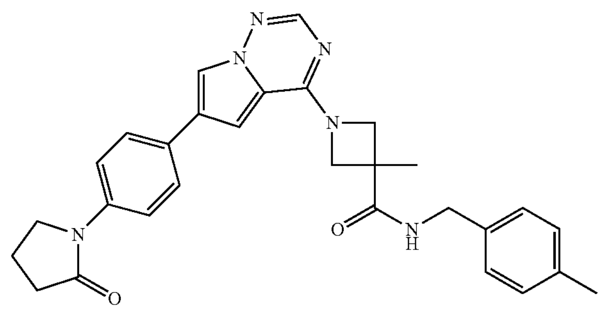 [SMILES: Cc1ccc(CNC(=O)C2(C)CN(c3ncnn4cc(-c5ccc(N6CCCC6=O)cc5)cc34)C2)cc1] | A | C |
| 255 | 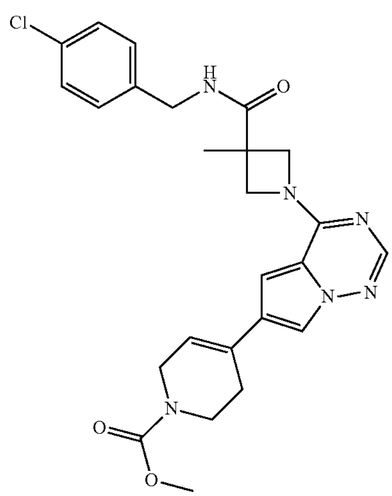 [SMILES: COC(=O)N1CC=C(c2cc3c(N4CC(C)(C(=O)NCc5ccc(Cl)cc5)C4)ncnn3c2)CC1] | A | C |
| 256 | 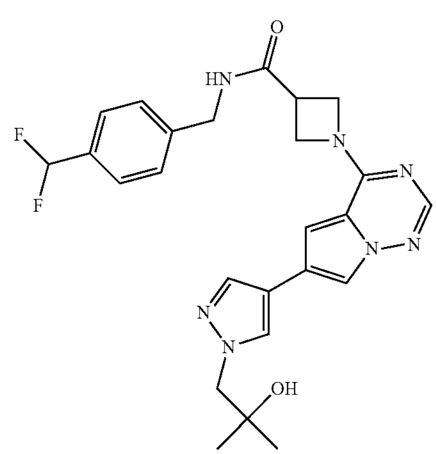 [SMILES: CC(C)(O)Cn1cc(-c2cc3c(N4CC(C(=O)NCc5ccc(C(F)F)cc5)C4)ncnn3c2)cn1] | B | C |

| Compound Number | Structure | D816V IC$_{50}$ (nM) | WT IC$_{50}$ (nM) |
|---|---|---|---|
| 257 | 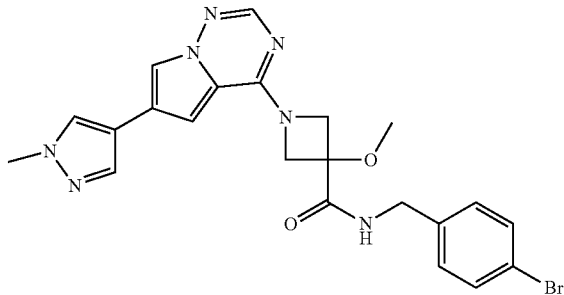 [SMILES: COC1(C(=O)NCc2ccc(Br)cc2)CN(c2ncnn3cc(-c4cnn(C)c4)cc23)C1] | B | C |
| 258 | 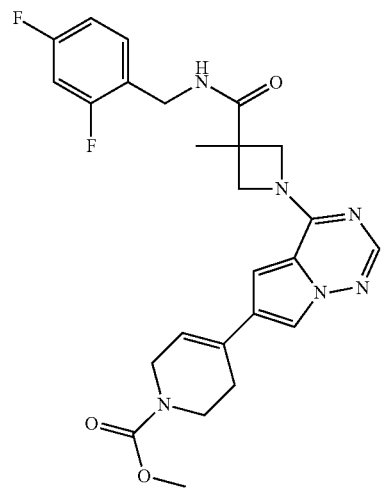 [SMILES: COC(=O)N1CC=C(c2cc3c(N4CC(C)(C(=O)NCc5ccc(F)cc5F)C4)ncnn3c2)CC1] | B | C |
| 259 | 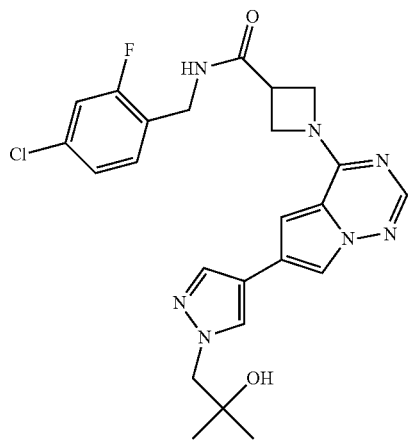 [SMILES: CC(C)(O)Cn1cc(-c2cc3c(N4CC(C(=O)NCc5ccc(Cl)cc5F)C4)ncnn3c2)cn1] | A | C |

-continued

| Compound Number | Structure | D816V IC$_{50}$ (nM) | WT IC$_{50}$ (nM) |
|---|---|---|---|
| 260 | 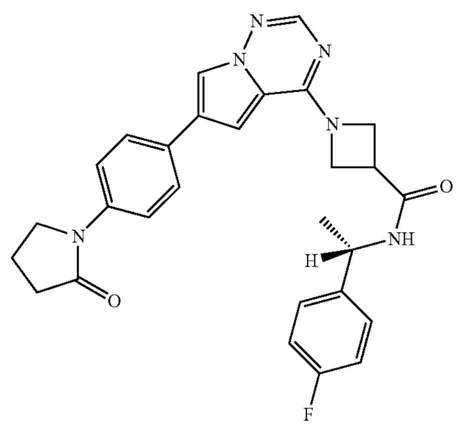 [SMILES: C[C@H](NC(=O)C1CN(c2ncnn3cc(-c4ccc(N5CCCC5=O)cc4)cc23)C1)c1ccc(F)cc1] | B | C |
| 261 | 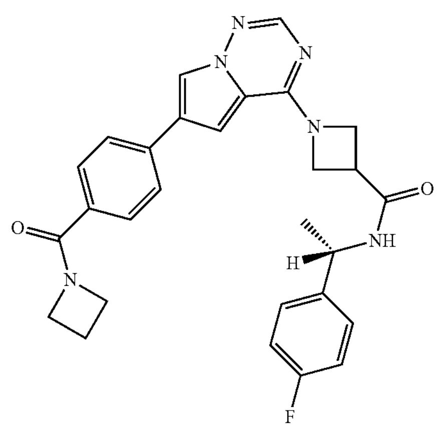 [SMILES: C[C@H](NC(=O)C1CN(c2ncnn3cc(-c4ccc(C(=O)N5CCC5)cc4)cc23)C1)c1ccc(F)cc1] | B | C |
| 262 | 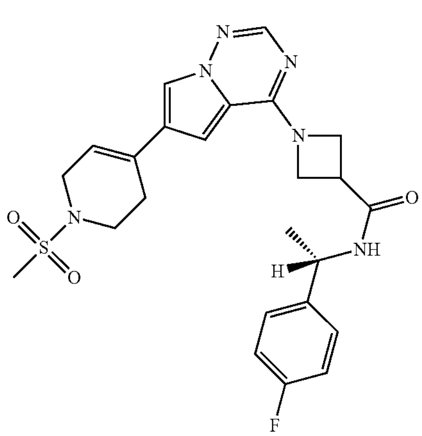 [SMILES: C[C@H](NC(=O)C1CN(c2ncnn3cc(C4=CCN(S(C)(=O)=O)CC4)cc23)C1)c1ccc(F)cc1] | B | C |

-continued
| Compound Number | Structure | D816V IC$_{50}$ (nM) | WT IC$_{50}$ (nM) |
|---|---|---|---|
| 263 | 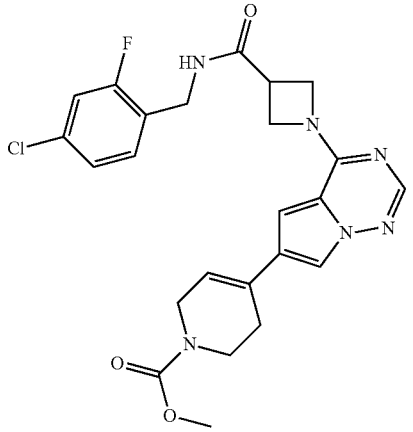 [SMILES: COC(=O)N1CC=C(c2cc3c(N4CC(C(=O)NCc5ccc(Cl)cc5F)C4)ncnn3c2)CC1] | A | C |
| 264 | 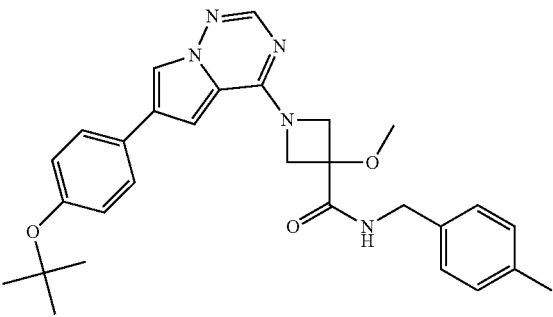 [SMILES: COC1(C(=O)NCc2ccc(C)cc2)CN(c2ncnn3cc(-c4ccc(OC(C)(C)C)cc4)cc23)C1] | B | C |
| 265 | 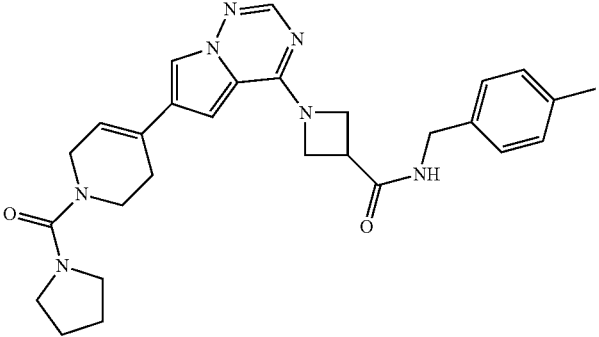 [SMILES: Cc1ccc(CNC(=O)C2CN(c3ncnn4cc(C5=CCN(C(=O)N6CCCC6)CC5)cc34)C2)cc1] | A | C |
| 266 | 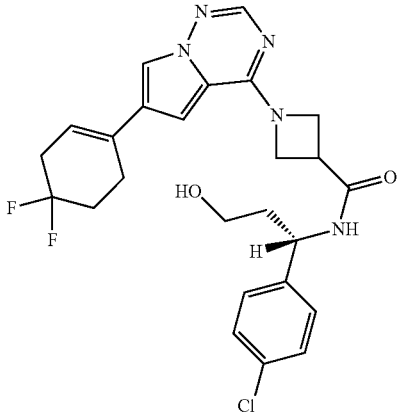 [SMILES: O=C(N[C@@H](CCO)c1ccc(Cl)cc1)C1CN(c2ncnn3cc(C4=CCC(F)(F)CC4)cc23)C1] | B | C |

-continued
| Compound Number | Structure | D816V IC$_{50}$ (nM) | WT IC$_{50}$ (nM) |
|---|---|---|---|
| 267 | 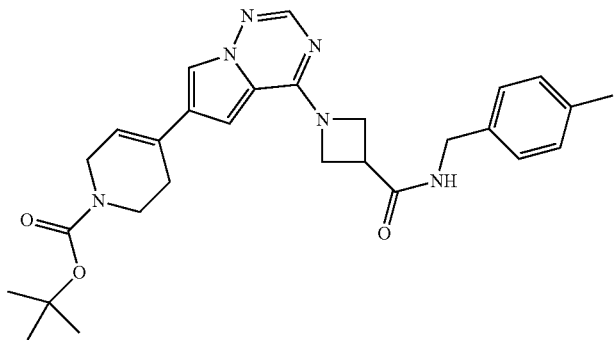 [SMILES: Cc1ccc(CNC(=O)C2CN(c3ncnn4cc(C5=CCN(C(=O)OC(C)(C)C)CC5)cc34)C2)cc1] | A | C |
| 268 | 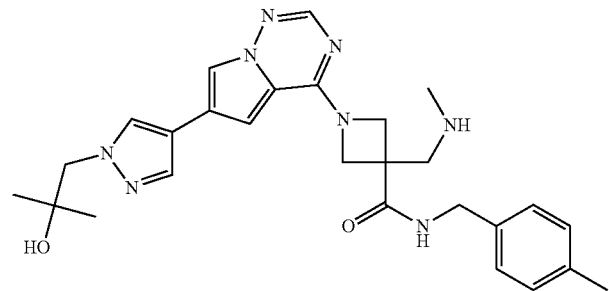 [SMILES: CNCC1(C(=O)NCc2ccc(C)cc2)CN(c2ncnn3cc(-c4cnn(CC(C)(C)O)c4)cc23)C1] | B | C |
| 269 | 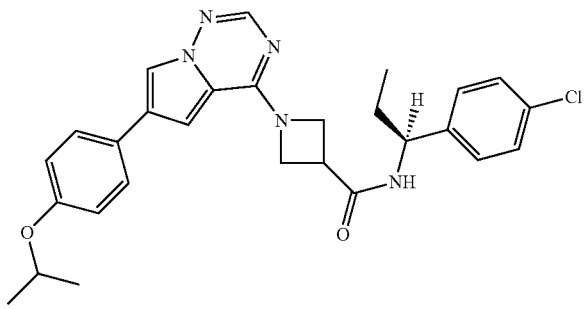 [SMILES: CC[C@H](NC(=O)C1CN(c2ncnn3cc(-c4ccc(OC(C)C)cc4)cc23)C1)c1ccc(Cl)cc1] | C | C |
| 270 | 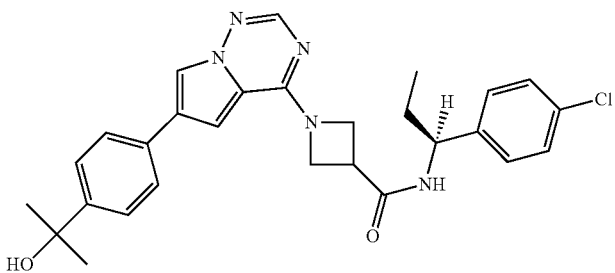 [SMILES: CC[C@H](NC(=O)C1CN(c2ncnn3cc(-c4ccc(C(C)(C)O)cc4)cc23)C1)c1ccc(Cl)cc1] | B | C |

| Compound Number | Structure | D816V IC$_{50}$ (nM) | WT IC$_{50}$ (nM) |
|---|---|---|---|
| 271 | 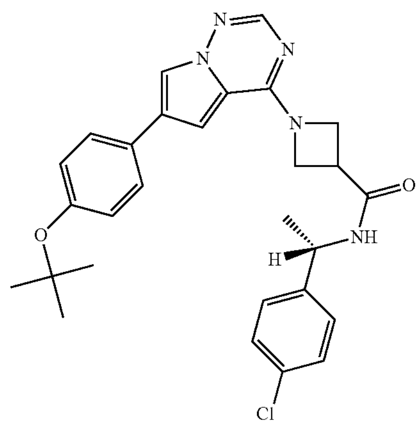 [SMILES: C[C@H](NC(=O)C1CN(c2ncnn3cc(-c4ccc(OC(C)(C)C)cc4)cc23)C1)c1ccc(Cl)cc1] | B | C |
| 272 | 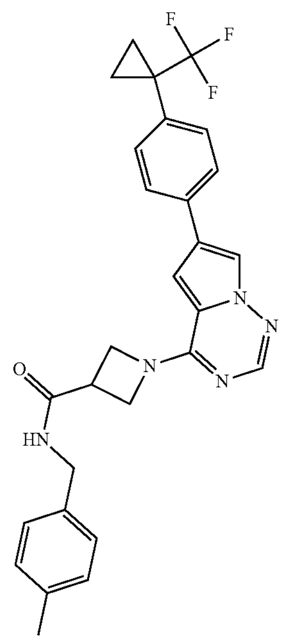 [SMILES: Cc1ccc(CNC(=O)C2CN(c3ncnn4cc(-c5ccc(C6(C(F)(F)F)CC6)cc5)cc34)C2)cc1] | B | C |
| 273 | 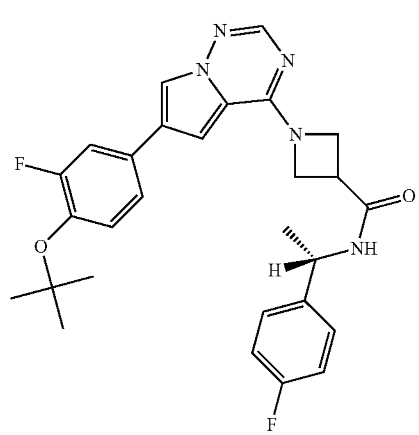 [SMILES: C[C@H](NC(=O)C1CN(c2ncnn3cc(-c4ccc(OC(C)(C)C)c(F)c4)cc23)C1)c1ccc(F)cc1] | B | C |

-continued

| Compound Number | Structure | D816V IC$_{50}$ (nM) | WT IC$_{50}$ (nM) |
|---|---|---|---|
| 274 | 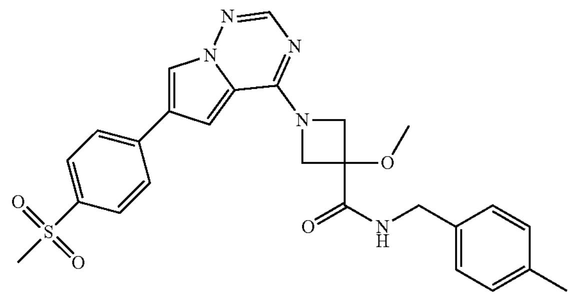 | B | C |
| 275 | 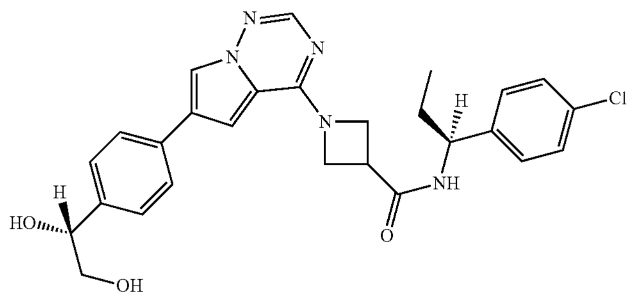 [SMILES: CC[C@H](NC(=O)C1CN(c2ncnn3cc(-c4ccc([C@@H](O)CO)cc4)cc23)C1)c1ccc(Cl)cc1] | A | C |
| 276 | 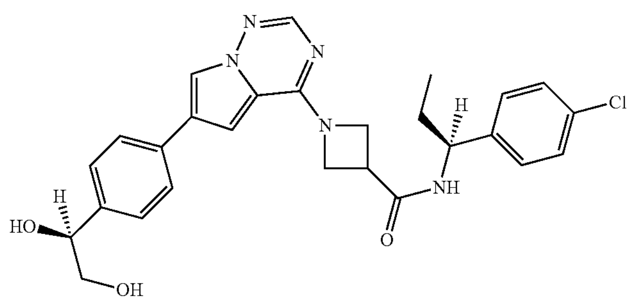 [SMILES: CC[C@H](NC(=O)C1CN(c2ncnn3cc(-c4ccc([C@H](O)CO)cc4)cc23)C1)c1ccc(Cl)cc1] | B | C |
| 277 | 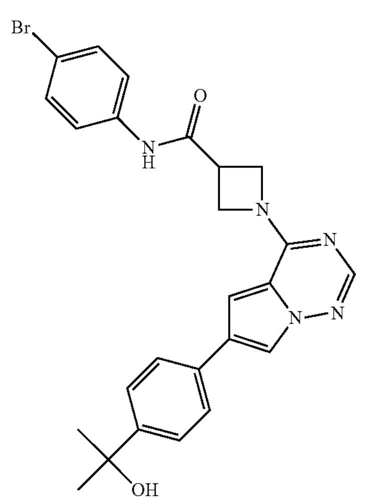 [SMILES: CC(C)(O)c1ccc(-c2cc3c(N4CC(C(=O)Nc5ccc(Br)cc5)C4)ncnn3c2)cc1] | B | C |

-continued

| Compound Number | Structure | D816V IC$_{50}$ (nM) | WT IC$_{50}$ (nM) |
|---|---|---|---|
| 278 | 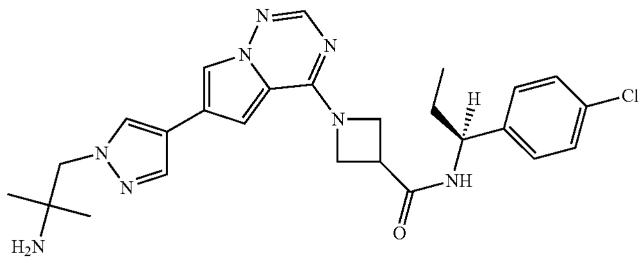 [SMILES: CC[C@H](NC(=O)C1CN(c2ncnn3cc(-c4cnn(CC(C)(C)N)c4)cc23)C1)c1ccc(Cl)cc1] | A | C |
| 279 | 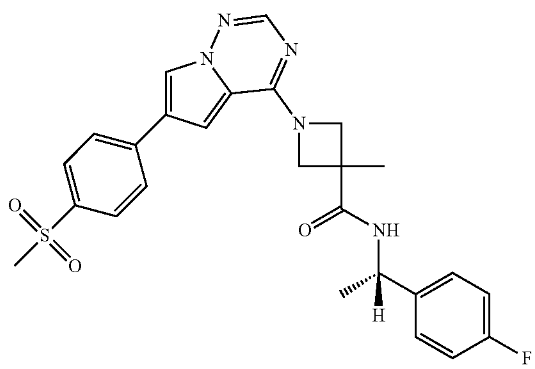 [SMILES: C[C@H](NC(=O)C1(C)CN(c2ncnn3cc(-c4ccc(S(C)(=O)=O)cc4)cc23)C1)c1ccc(F)cc1] | B | C |
| 280 | 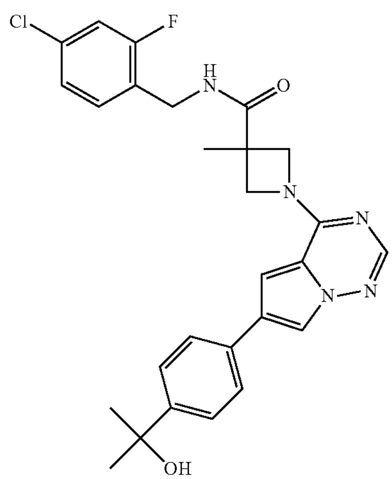 [SMILES: CC1(C(=O)NCc2ccc(Cl)cc2F)CN(c2ncnn3cc(-c4ccc(C(C)(C)O)cc4)cc23)C1] | A | C |
| 281 | 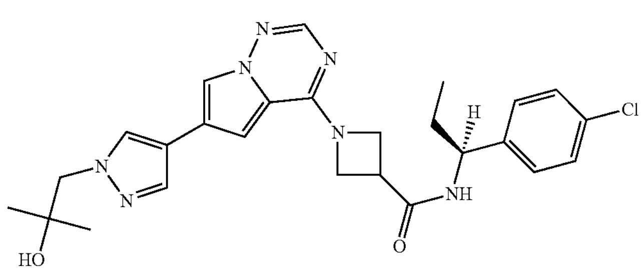 [SMILES: CC[C@H](NC(=O)C1CN(c2ncnn3cc(-c4cnn(CC(C)(C)O)c4)cc23)C1)c1ccc(Cl)cc1] | B | C |

-continued

| Compound Number | Structure | D816V IC$_{50}$ (nM) | WT IC$_{50}$ (nM) |
|---|---|---|---|
| 282 | 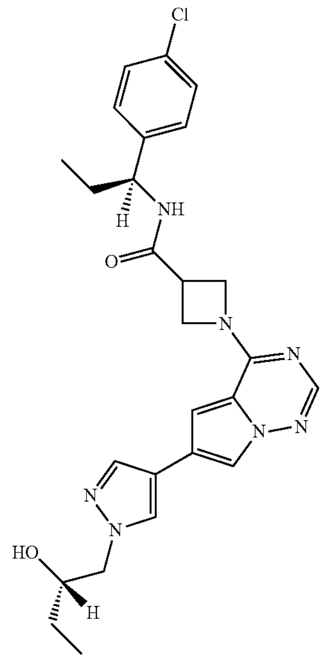 [SMILES: CC[C@H](O)Cn1cc(-c2cc3c(N4CC(C(=O)N[C@@H](CC)c5ccc(Cl)cc5)C4)ncnn3c2)cn1] | A | C |
| 283 | 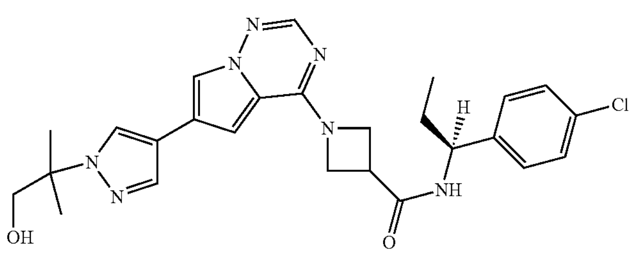 [SMILES: CC[C@H](NC(=O)C1CN(c2ncnn3cc(-c4cnn(C(C)(C)CO)c4)cc23)C1)c1ccc(Cl)cc1] | B | C |
| 284 | 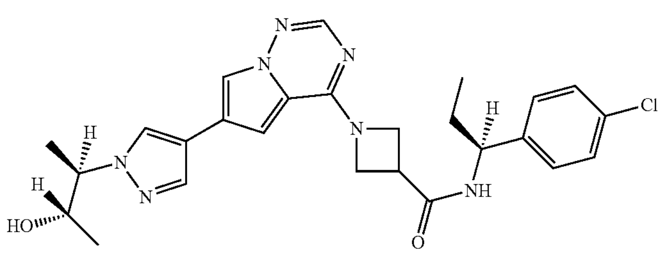 [SMILES: CC[C@H](NC(=O)C1CN(c2ncnn3cc(-c4cnn([C@H](C)[C@H](C)O)c4)cc23)C1)c1ccc(Cl)cc1] | A | C |
| 285 | 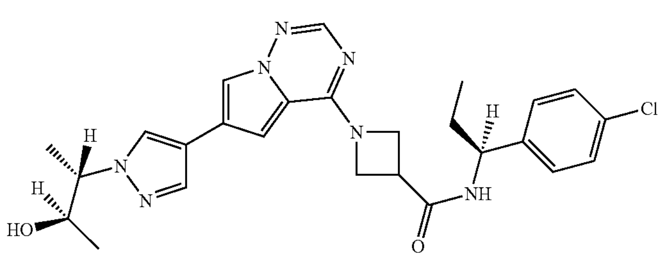 [SMILES: CC[C@H](NC(=O)C1CN(c2ncnn3cc(-c4cnn([C@@H](C)[C@@H](C)O)c4)cc23)C1)c1ccc(Cl)cc1] | A | C |

-continued

| Compound Number | Structure | D816V IC$_{50}$ (nM) | WT IC$_{50}$ (nM) |
|---|---|---|---|
| 286 | 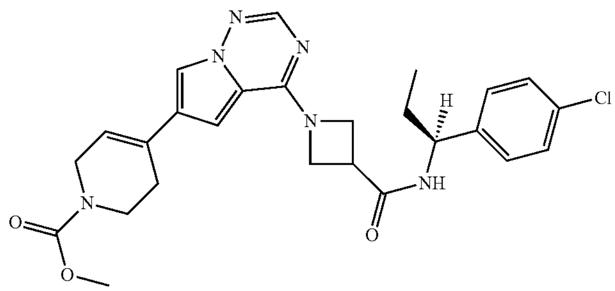 [SMILES: CC[C@H](NC(=O)C1CN(c2ncnn3cc(C4=CCN(C(=O)OC)CC4)cc23)C1)c1ccc(Cl)cc1] | A | C |
| 287 | 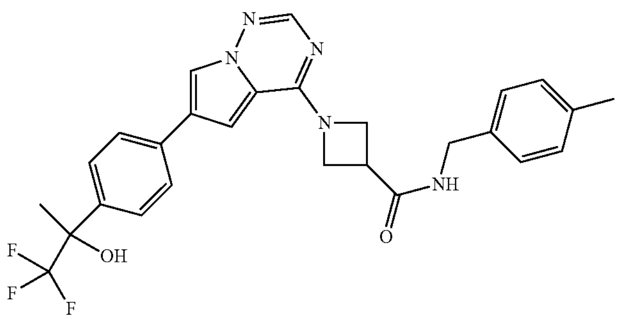 [SMILES: Cc1ccc(CNC(=O)C2CN(c3ncnn4cc(-c5ccc(C(C)(O)C(F)(F)F)cc5)cc34)C2)cc1] | A | C |
| 288 | 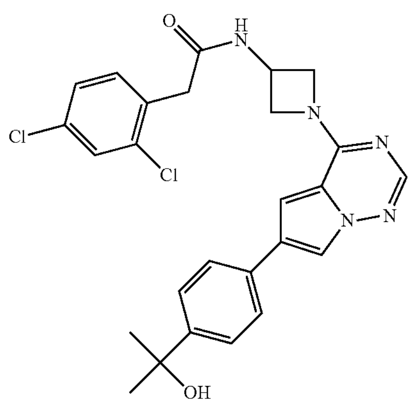 [SMILES: CC(C)(O)c1ccc(-c2cc3c(N4CC(NC(=O)Cc5ccc(Cl)cc5Cl)C4)ncnn3c2)cc1] | A | C |
| 289 | 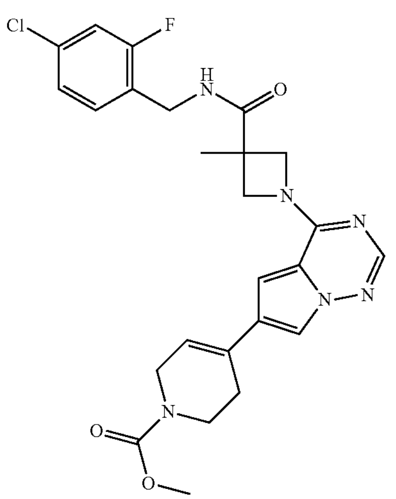 [SMILES: COC(=O)N1CC=C(c2cc3c(N4CC(C)(C(=O)NCc5ccc(Cl)cc5F)C4)ncnn3c2)CC1] | B | C |

-continued
| Compound Number | Structure | D816V IC$_{50}$ (nM) | WT IC$_{50}$ (nM) |
|---|---|---|---|
| 290 | 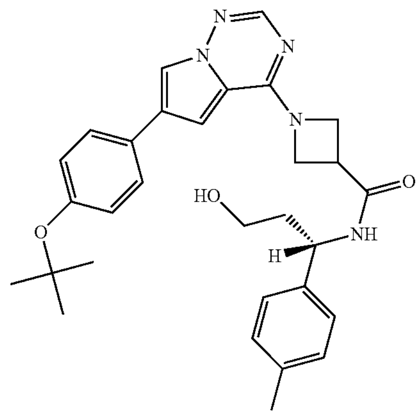 [SMILES: Cc1ccc([C@H](CCO)NC(=O)C2CN(c3ncnn4cc(-c5ccc(OC(C)(C)C)cc5)cc34)C2)cc1] | A | C |
| 291 | 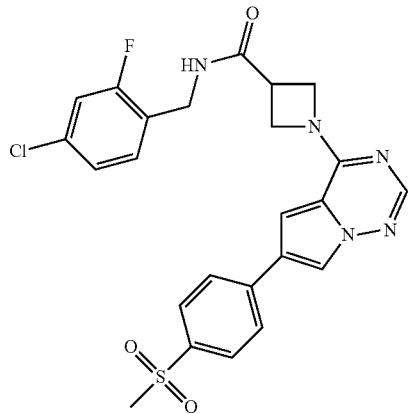 [SMILES: CS(=O)(=O)c1ccc(-c2cc3c(N4CC(C(=O)NCc5ccc(Cl)cc5F)C4)ncnn3c2)cc1] | A | C |
| 292 | 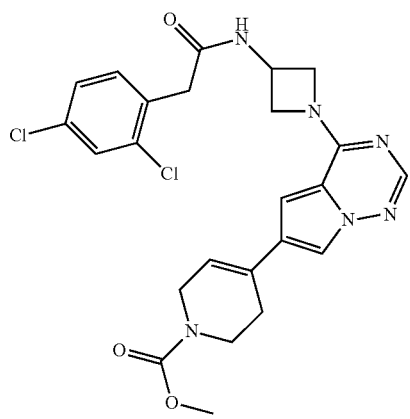 [SMILES: COC(=O)N1CC=C(c2cc3c(N4CC(NC(=O)Cc5ccc(Cl)cc5Cl)C4)ncnn3c2)CC1] | A | C |
| 293 | 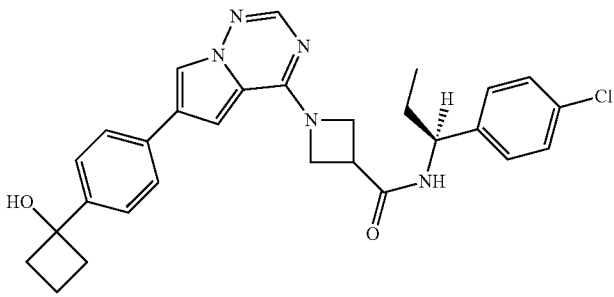 [SMILES: CC[C@H](NC(=O)C1CN(c2ncnn3cc(-c4ccc(C5(O)CCC5)cc4)cc23)C1)c1ccc(Cl)cc1] | B | C |

-continued

| Compound Number | Structure | D816V IC$_{50}$ (nM) | WT IC$_{50}$ (nM) |
|---|---|---|---|
| 294 | 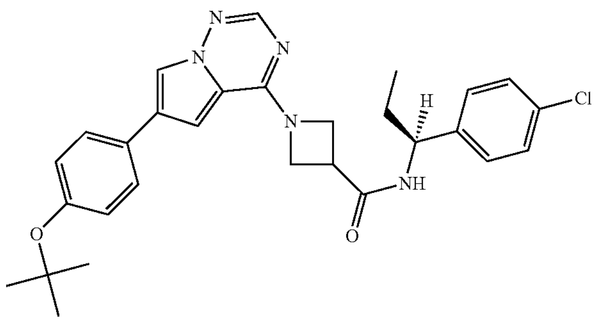 [SMILES: CC[C@H](NC(=O)C1CN(c2ncnn3cc(-c4ccc(OC(C)(C)C)cc4)cc23)C1)c1ccc(Cl)cc1] | B | C |
| 295 | 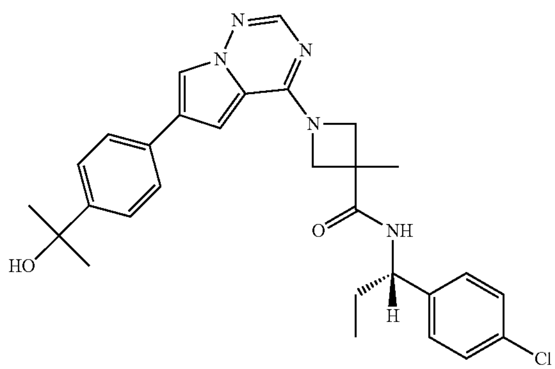 [SMILES: CC[C@H](NC(=O)C1(C)CN(c2ncnn3cc(-c4ccc(C(C)(C)O)cc4)cc23)C1)c1ccc(Cl)cc1] | B | C |
| 296 | 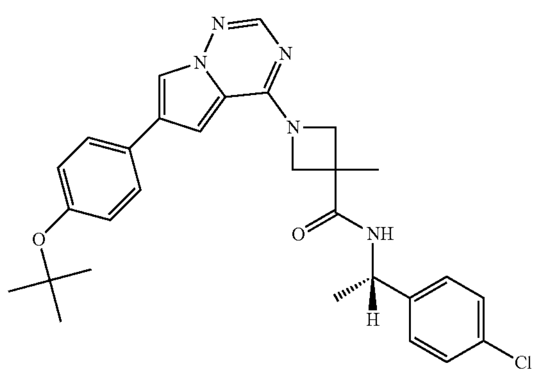 [SMILES: C[C@H](NC(=O)C1(C)CN(c2ncnn3cc(-c4ccc(OC(C)(C)C)cc4)cc23)C1)c1ccc(Cl)cc1] | C | C |
| 297 | 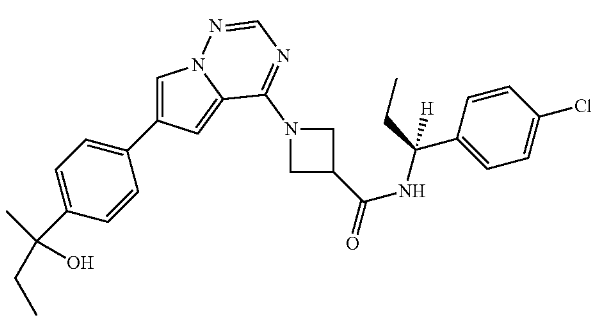 [SMILES: CC[C@H](NC(=O)C1CN(c2ncnn3cc(-c4ccc(C(C)(O)CC)cc4)cc23)C1)c1ccc(Cl)cc1] | B | C |

-continued

| Compound Number | Structure | D816V IC$_{50}$ (nM) | WT IC$_{50}$ (nM) |
| --- | --- | --- | --- |
| 298 | 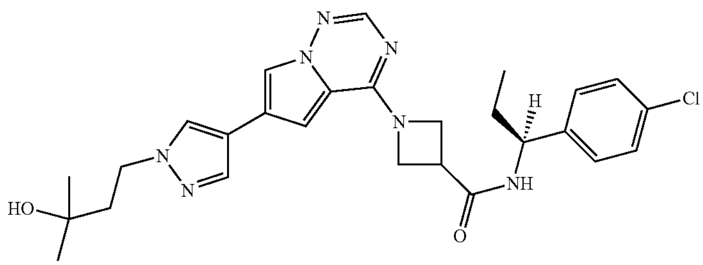 [SMILES: CC[C@H](NC(=O)C1CN(c2ncnn3cc(-c4cnn(CCC(C)(C)O)c4)cc23)C1)c1ccc(Cl)cc1] | B | C |
| 299 | 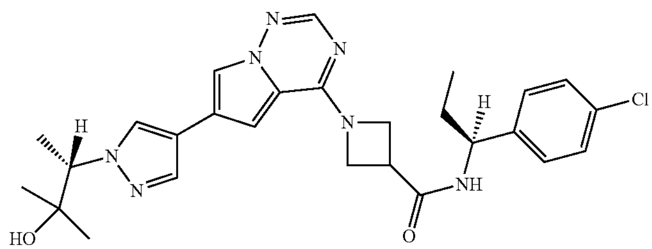 [SMILES: CC[C@H](NC(=O)C1CN(c2ncnn3cc(-c4cnn([C@@H](C)C(C)(C)O)c4)cc23)C1)c1ccc(Cl)cc1] | A | C |
| 300 | 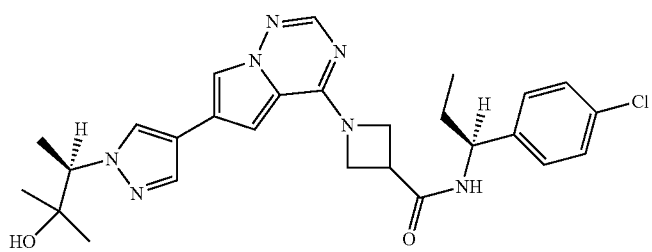 [SMILES: CC[C@H](NC(=O)C1CN(c2ncnn3cc(-c4cnn([C@H](C)C(C)(C)O)c4)cc23)C1)c1ccc(Cl)cc1] | A | C |
| 301 | 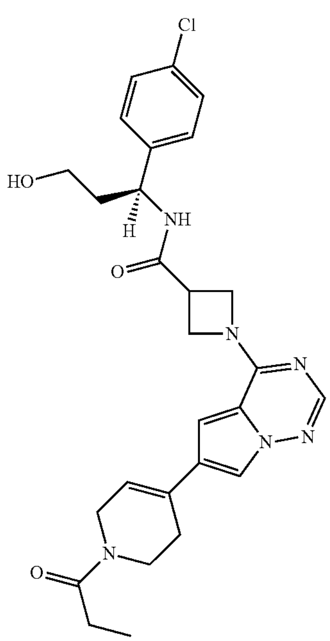 [SMILES: CCC(=O)N1CC=C(c2cc3c(N4CC(C(=O)N[C@@H](CCO)c5ccc(Cl)cc5)C4)ncnn3c2)CC1] | A | C |

-continued
| Compound Number | Structure | D816V IC$_{50}$ (nM) | WT IC$_{50}$ (nM) |
|---|---|---|---|
| 302 | 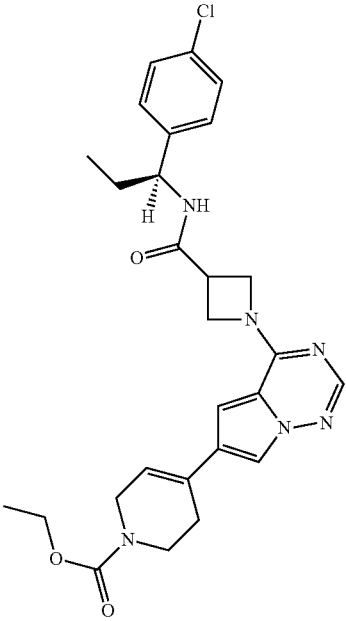 [SMILES: CCOC(=O)N1CC=C(c2cc3c(N4CC(C(=O)N[C@@H](CC)c5ccc(Cl)cc5)C4)ncnn3c2)CC1] | A | C |
| 303 | 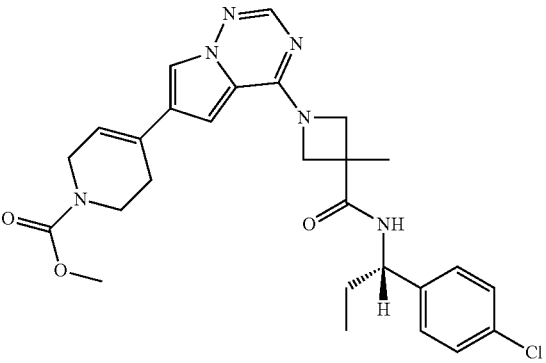 [SMILES: CC[C@H](NC(=O)C1(C)CN(c2ncnn3cc(C4=CCN(C(=O)OC)CC4)cc23)C1)c1ccc(Cl)cc1] | B | C |
| 304 | 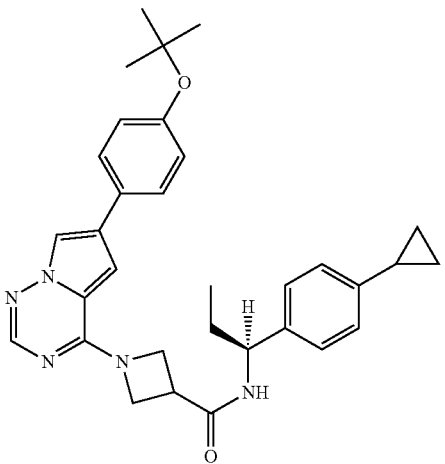 [SMILES: CC[C@H](NC(=O)C1CN(c2ncnn3cc(-c4ccc(OC(C)(C)C)cc4)cc23)C1)c1ccc(C2CC2)cc1] | B | C |

-continued

| Compound Number | Structure | D816V IC$_{50}$ (nM) | WT IC$_{50}$ (nM) |
|---|---|---|---|
| 305 | 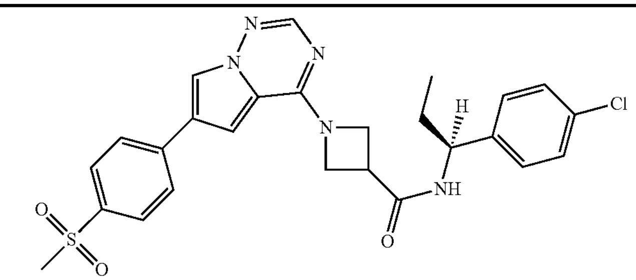 | A | C |
| 306 | 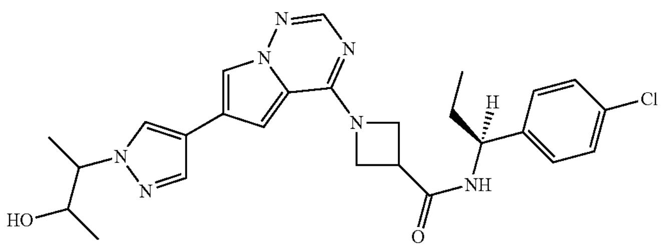 [SMILES: CC[C@H](NC(=O)C1CN(c2ncnn3cc(-c4cnn(C(C)C(C)O)c4)cc23)C1)c1ccc(Cl)cc1] | B | C |
| 307 | 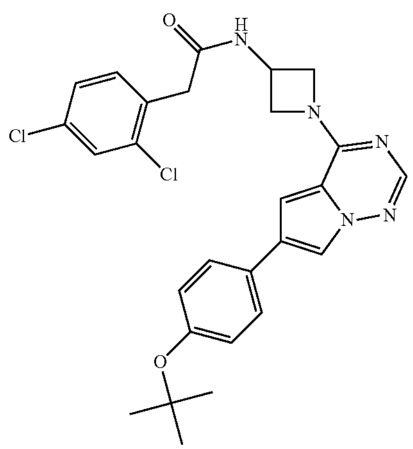 [SMILES: CC(C)(C)Oc1ccc(-c2cc3c(N4CC(NC(=O)Cc5ccc(Cl)cc5Cl)C4)ncnn3c2)cc1] | B | C |
| 308 | 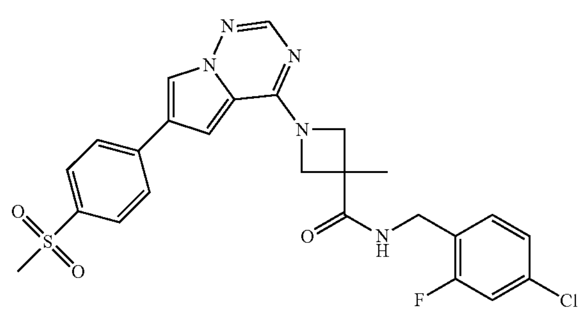 [SMILES: CC1(C(=O)NCc2ccc(Cl)cc2F)CN(c2ncnn3cc(-c4ccc(S(C)(=O)=O)cc4)cc23)C1] | A | C |
| 309 | 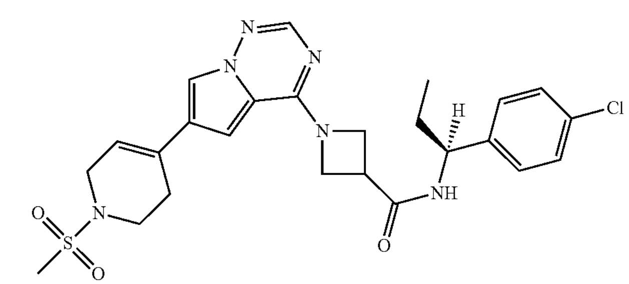 [SMILES: CC[C@H](NC(=O)C1CN(c2ncnn3cc(C4=CCN(S(C)(=O)=O)CC4)cc23)C1)c1ccc(Cl)cc1] | A | C |

-continued

| Compound Number | Structure | D816V IC$_{50}$ (nM) | WT IC$_{50}$ (nM) |
|---|---|---|---|
| 310 | 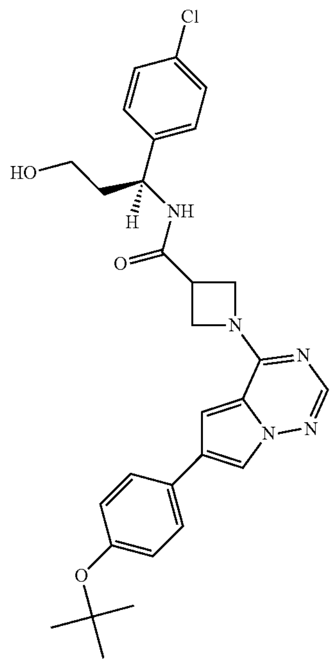 [SMILES: CC(C)(C)Oc1ccc(-c2cc3c(N4CC(C(=O)N[C@@H](CCO)c5ccc(Cl)cc5)C4)ncnn3c2)cc1] | B | C |
| 311 | 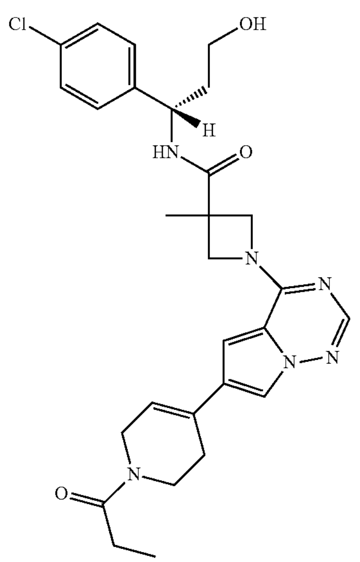 [SMILES: CCC(=O)N1CC=C(c2cc3c(N4CC(C)(C(=O)N[C@@H](CCO)c5ccc(Cl)cc5)C4)ncnn3c2)CC1] | A | C |
| 312 | 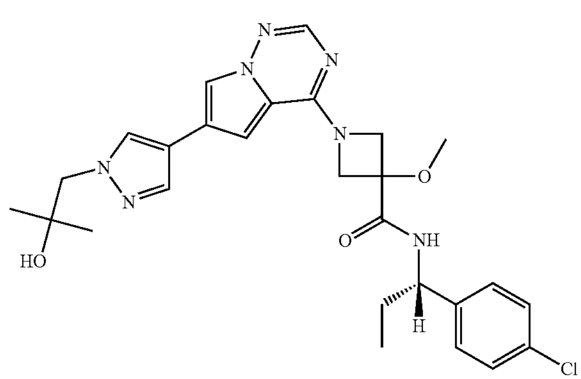 [SMILES: CC[C@H](NC(=O)C1(OC)CN(c2ncnn3cc(-c4cnn(CC(C)(C)O)c4)cc23)C1)c1ccc(Cl)cc1] | B | C |

-continued
| Compound Number | Structure | D816V IC$_{50}$ (nM) | WT IC$_{50}$ (nM) |
|---|---|---|---|
| 313 | 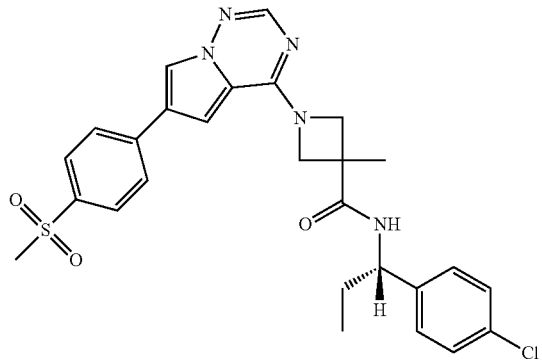 [SMILES: CC[C@H](NC(=O)C1(C)CN(c2ncnn3cc(-c4ccc(S(C)(=O)=O)cc4)cc23)C1)c1ccc(Cl)cc1] | B | C |
| 314 | 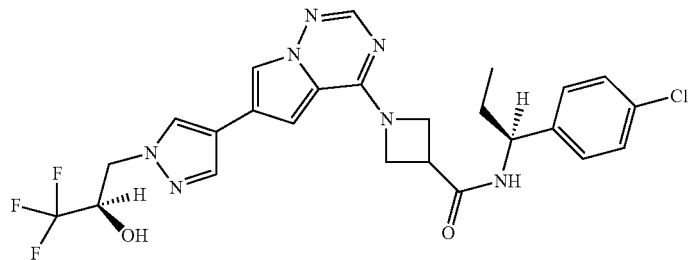 [SMILES: CC[C@H](NC(=O)C1CN(c2ncnn3cc(-c4cnn(C[C@@H](O)C(F)(F)F)c4)cc23)C1)c1ccc(Cl)cc1] | B | C |
| 315 | 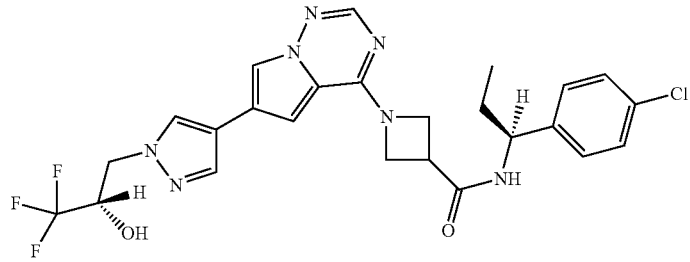 [SMILES: CC[C@H](NC(=O)C1CN(c2ncnn3cc(-c4cnn(C[C@H](O)C(F)(F)F)c4)cc23)C1)c1ccc(Cl)cc1] | B | C |

-continued

| Compound Number | Structure | D816V IC$_{50}$ (nM) | WT IC$_{50}$ (nM) |
|---|---|---|---|
| 316 | 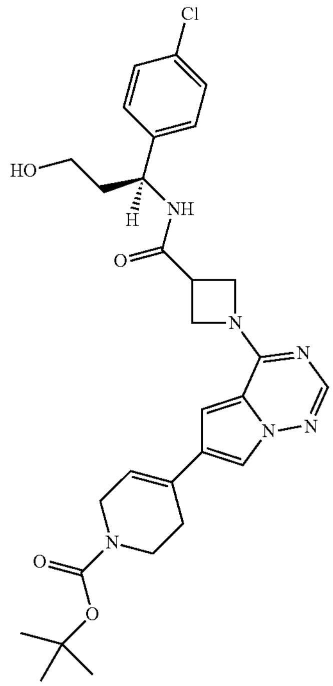 [SMILES: CC(C)(C)OC(=O)N1CC=C(c2cc3c(N4CC(C(=O)N[C@@H](CCO)c5ccc(Cl)cc5)C4)ncnn3c2)CC1] | B | C |
| 317 | 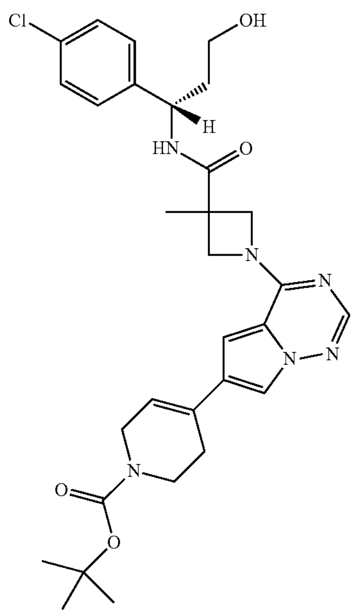 [SMILES: CC(C)(C)OC(=O)N1CC=C(c2cc3c(N4CC(C)(C(=O)N[C@@H](CCO)c5ccc(Cl)cc5)C4)ncnn3c2)CC1] | B | C |

Compounds 16, 20, 101, 104, and 123 were at least 10 times, but less than 25 times, more potent against the D816V mutant than against the wild-type Kit.

Compounds 17, 18, 19, 81, 156, 243, 277, and 296 were at least 25 times, but less than 50 times, more potent against the D816V mutant than against the wild-type Kit.

Compounds 5, 37, 41, 43, 57, 78, 107, 114, 120, 182, 225, 227, and 269 were at least 50 times, but less than 100 times, more potent against the D816V mutant than against the wild-type Kit.

Compounds 1, 2, 3, 4, 6, 7, 8, 9, 10, 11, 13, 14, 15, 24, 26, 28, 30, 32, 35, 36, 38, 40, 42, 44, 48, 51, 55, 58, 59, 62, 64, 66, 68, 69, 70, 71, 72, 73, 75, 76, 79, 82, 84, 86, 88, 90, 91, 93, 94, 97, 98, 99, 100, 102, 106, 108, 110, 111, 112, 118, 119, 124, 128, 129, 139, 141, 145, 148, 149, 150, 152, 153, 159, 161, 166, 167, 168, 171, 172, 174, 177, 178, 180, 181, 186, 187, 194, 197, 200, 203, 205, 208, 214, 215, 216, 221, 228, 231, 233, 236, 241, 242, 244, 247, 248, 249, 250, 251, 256, 257, 258, 243, 259, 262, 264, 268, 270, 271, 272, 273, 275, 276, 279, 280, 281, 282, 283, 293, 294, 295, 297, 298, 304, 306, 307, 308, 310, 312, 313, 314, 315, and 317 were at least 100 times, but less than 500 times, more potent against the D816V mutant than against the wild-type Kit.

Compounds 27, 31, 34, 39, 49, 50, 53, 54, 60, 63, 65, 67, 87, 95, 96, 113, 117, 122, 130, 131, 135, 136, 137, 138, 140, 142, 143, 144, 147, 160, 163, 170, 183, 189, 191, 196, 198, 201, 204, 209, 211, 212, 217, 222, 226, 232, 234, 237, 245, 253, 254, 255, 260, 261, 266, 274, 278, 284, 285, 289, 299, 300, 303, and 316 were at least 500 times, but less than 1000 times, more potent against the D816V mutant than against the wild-type Kit.

Compounds 12, 21, 22, 23, 25, 29, 33, 45, 47, 52, 56, 61, 74, 77, 80, 83, 85, 89, 92, 103, 105, 109, 115, 116, 121, 125, 126, 127, 132, 133, 134, 146, 151, 154, 155, 157, 158, 162, 164, 165, 169, 173, 175, 176, 179, 184, 185, 188, 190, 192, 193, 195, 199, 202, 206, 207, 210, 213, 218, 219, 220, 223, 224, 229, 230, 235, 238, 239, 240, 246, 252, 263, 265, 267, 286, 287, 288, 290, 291, 292, 301, 302, 305, 309, and 311 were greater than 1000 times more potent against the D816V mutant than against the wild-type Kit.

Cellular Activity

HMC1.2 Autophosphorylation Assay:

10,000 HMC1.2 cells were incubated in 22 ul culture media (phenol-red free IMDM, no serum) in each well of a 384-well plate and serum starved overnight in a tissue culture incubator (5% $CO_2$, 37° C.). A 10-point dose concentration series of compound (25 uM-95.4 pM) were then added to the cells in a volume of 3.1 ul to each well (0.25% DMSO final concentration). After 90 minutes, 6 ul of 5× AlphaLISA Lysis Buffer (Perkin Elmer) supplemented with a protease and phosphatase inhibitor cocktail (Cell Signaling Technologies) was added to each well and shaken at 450 rpm for 15 minutes at 4° C. 10 ul of phospho-Y719 c-Kit and total c-Kit antibodies (15 nM final concentration, Cell Signaling Technologies) and 50 ug/ml AlphaLISA rabbit acceptor beads (Perkin Elmer) were added to each well and shaken at 300 rpm at room temperature for 2 hours. 10 ul of 100 ug/ml streptavidin donor beads (Perkin Elmer) were added to each well, blocked from light with aluminum adhesive and shaken at 300 rpm at room temperature for 2 hours. Fluorescence signal was obtained on Envision (Perkin Elmer) by AlphaScreen 384 well HTS protocol. Data was normalized to 0% and 100% inhibition controls and the IC50 was calculated using Four Parameter Logistic IC50 curve fitting.

The Table below shows the activity of compounds in a Mast cell leukemia cell line, HMC 1.2. This cell line contains Kit mutated at positions V560G and D816V resulting in constitutive activation of the kinase. The following compounds were tested in an assay to measure direct inhibition of Kit D816V kinase activity by assaying Kit autophosphorylation at tyrosine 719 on the Kit protein.

In the Table below, the following designations are used: <10 nM=A; 10.01-100 nM=B; 100.01-1000 nM=C; 1000-10000 nM=D, >10000.01 nM=E; and ND=not determined.

| Compound Number | Inhibition of Phosphorylation $IC_{50}$ (nM) |
|---|---|
| 1 | C |
| 2 | B |
| 3 | B |
| 4 | C |
| 5 | B |
| 6 | B |
| 7 | C |
| 8 | C |
| 9 | C |
| 10 | A |
| 11 | B |
| 12 | B |
| 13 | C |
| 14 | B |
| 15 | B |
| 16 | C |
| 17 | B |
| 18 | B |
| 19 | C |
| 20 | C |
| 21 | B |
| 22 | B |
| 23 | B |
| 24 | B |
| 25 | B |
| 26 | B |
| 27 | C |
| 28 | B |
| 29 | B |
| 30 | C |
| 31 | C |
| 32 | C |
| 33 | B |
| 34 | B |
| 35 | B |
| 36 | B |
| 37 | C |
| 38 | B |
| 39 | B |
| 40 | C |
| 41 | C |
| 42 | C |
| 43 | B |
| 44 | C |
| 45 | B |
| 46 | B |
| 47 | A |
| 48 | B |
| 49 | A |
| 50 | B |
| 51 | C |
| 52 | C |
| 53 | C |
| 54 | A |
| 55 | C |
| 56 | B |
| 57 | B |
| 58 | C |
| 59 | C |
| 60 | B |
| 61 | B |
| 62 | C |
| 63 | B |
| 64 | C |
| 65 | C |
| 66 | C |
| 67 | B |
| 68 | C |
| 69 | B |
| 70 | C |
| 71 | C |
| 72 | C |
| 73 | B |
| 74 | B |
| 75 | C |
| 76 | B |
| 77 | B |
| 78 | C |
| 79 | A |
| 80 | B |
| 81 | C |
| 82 | C |

| Compound Number | Inhibition of Phosphorylation IC$_{50}$ (nM) |
|---|---|
| 83 | C |
| 84 | B |
| 85 | A |
| 86 | C |
| 87 | B |
| 88 | B |
| 89 | B |
| 90 | B |
| 91 | C |
| 92 | B |
| 93 | A |
| 94 | B |
| 95 | B |
| 96 | C |
| 97 | C |
| 98 | C |
| 99 | B |
| 100 | C |
| 101 | C |
| 102 | C |
| 103 | C |
| 104 | C |
| 105 | B |
| 106 | B |
| 107 | A |
| 108 | A |
| 109 | B |
| 110 | C |
| 111 | A |
| 112 | C |
| 113 | B |
| 114 | C |
| 115 | B |
| 116 | B |
| 117 | A |
| 118 | B |
| 119 | B |
| 120 | B |
| 121 | B |
| 122 | ND |
| 123 | C |
| 124 | B |
| 125 | A |
| 126 | A |
| 127 | B |
| 128 | B |
| 129 | C |
| 130 | B |
| 131 | B |
| 132 | B |
| 133 | B |
| 134 | A |
| 135 | B |
| 136 | B |
| 137 | B |
| 138 | B |
| 139 | C |
| 140 | C |
| 141 | C |
| 142 | C |
| 143 | B |
| 144 | B |
| 145 | B |
| 146 | B |
| 147 | B |
| 148 | C |
| 149 | C |
| 150 | C |
| 151 | B |
| 152 | C |
| 153 | B |
| 154 | B |
| 155 | B |
| 156 | B |
| 157 | B |
| 158 | A |
| 159 | B |
| 160 | B |
| 161 | B |
| 162 | A |
| 163 | C |
| 164 | B |
| 165 | B |
| 166 | B |
| 167 | C |
| 168 | B |
| 169 | A |
| 170 | A |
| 171 | B |
| 172 | C |
| 173 | A |
| 174 | C |
| 175 | B |
| 176 | A |
| 177 | C |
| 178 | B |
| 179 | B |
| 180 | C |
| 181 | C |
| 182 | C |
| 183 | B |
| 184 | B |
| 185 | A |
| 186 | B |
| 187 | B |
| 188 | A |
| 189 | B |
| 190 | A |
| 191 | C |
| 192 | C |
| 193 | B |
| 194 | B |
| 195 | B |
| 196 | B |
| 197 | B |
| 198 | B |
| 199 | B |
| 200 | C |
| 201 | C |
| 202 | C |
| 203 | B |
| 204 | B |
| 205 | B |
| 206 | B |
| 207 | A |
| 208 | C |
| 209 | C |
| 210 | A |
| 211 | A |
| 212 | B |
| 213 | A |
| 214 | B |
| 215 | B |
| 216 | B |
| 217 | B |
| 218 | C |
| 219 | C |
| 220 | B |
| 221 | B |
| 222 | B |
| 223 | A |
| 224 | A |
| 225 | C |
| 226 | B |
| 227 | C |
| 228 | B |
| 229 | A |
| 230 | B |
| 231 | B |
| 232 | B |

-continued

| Compound Number | Inhibition of Phosphorylation IC$_{50}$ (nM) |
|---|---|
| 233 | C |
| 234 | C |
| 235 | B |
| 236 | B |
| 237 | B |
| 238 | B |
| 239 | B |
| 240 | B |
| 241 | B |
| 242 | B |
| 243 | C |
| 244 | C |
| 245 | B |
| 246 | B |
| 247 | C |
| 248 | B |
| 249 | B |
| 250 | B |
| 251 | B |
| 252 | A |
| 253 | B |
| 254 | B |
| 255 | B |
| 256 | B |
| 257 | C |
| 258 | C |
| 259 | B |
| 260 | C |
| 261 | B |
| 262 | C |
| 263 | B |
| 264 | B |
| 265 | A |
| 266 | B |
| 267 | A |
| 268 | B |
| 269 | C |
| 270 | B |
| 271 | B |
| 272 | C |
| 273 | C |
| 274 | B |
| 275 | B |
| 276 | B |
| 277 | B |
| 278 | B |
| 279 | C |
| 280 | B |
| 281 | B |
| 282 | B |
| 283 | B |
| 284 | B |
| 285 | A |
| 286 | B |
| 287 | A |
| 288 | A |
| 289 | B |
| 290 | A |
| 291 | B |
| 292 | B |
| 293 | B |
| 294 | C |
| 295 | B |
| 296 | C |
| 297 | B |
| 298 | B |
| 299 | B |
| 300 | B |
| 301 | B |
| 302 | B |
| 303 | B |
| 304 | C |
| 305 | B |
| 306 | B |
| 307 | C |
| 308 | B |
| 309 | B |
| 310 | B |
| 311 | B |
| 312 | B |
| 313 | B |
| 314 | B |
| 315 | B |
| 316 | B |
| 317 | B |

INCORPORATION BY REFERENCE

All publications and patents mentioned herein are hereby incorporated by reference in their entirety as if each individual publication or patent was specifically and individually indicated to be incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

I claim:
1. A compound of Formula I:

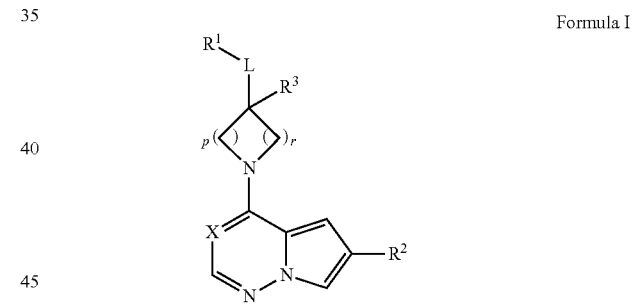

or a pharmaceutically acceptable salt thereof, wherein:
X is selected from CH or N;
L is a bond, —(CR$^c$R$^c$)$_n$—, —(CR$^c$R$^c$)$_n$NR$^b$—, —NR$^b$(CR$^c$R$^c$)$_n$—, —S(O)$_2$—, —S(O)—, —C(O)—, —OC(O)—, —C(O)O—, —(CR$^c$R$^c$)$_n$—OC(O)—, —OC(O)—(CR$^c$R$^c$)$_n$—, —(CR$^c$R$^c$)$_n$—C(O)—, —C(O)—(CR$^c$R$^c$)$_n$—, —NR$^b$C(O)(CR$^c$R$^c$), —C(O)NR$^b$—(CR$^c$R$^c$), where the two R$^c$'s, together with the carbon to which they are attached, can form a carbocycle, —C(O)NR$^b$—(CR$^c$R$^b$), —(CR$^c$R$^c$)$_n$NR$^b$—(CR$^c$R$^c$), —NR$^b$C(S)—, —C(S)NR$^b$—, —NR$^b$C(O)—, —C(O)NR$^b$—, —NR$^b$S(O)$_2$, -or —S(O)$_2$NR$^b$—;
R$^1$ is alkyl, carbocyclyl, carbocyclylalkyl, aryl, aralkyl, heteroaryl, heteroaralkyl, heterocyclyl, or heterocyclylalkyl each of which is substituted with 0-5 occurrences of R$^d$;
R$^2$ is H, halo, aryl, alkenyl, heteroaryl, carbocyclyl, or heterocyclyl, wherein each of aryl, alkenyl, heteroaryl, carbocyclyl, and heterocyclyl is substituted with 0-5 occurrences of R$^d$;

R³ is H, alkyl, heteroalkyl, haloalkyl, haloalkoxyl, —OR^c, —C(O)OR^c, —C(O)NR^aR^b, —(CR^cR^c)_nNR^b—(CR^cR^c)—H, —NR^aR^b, or cyano, wherein each of alkyl, heteroalkyl, haloalkyl, and haloalkoxyl is substituted with 0-5 occurrences of R^d;

R^a and R^b are each independently H, alkyl, heteroalkyl, aryl, aralkyl, heteroaryl, heterocyclyl, or heterocyclylalkyl, wherein each of alkyl, heteroalkyl, aryl, aralkyl, heterocyclyl, and heterocyclylalkyl is substituted with 0-5 occurrences of R^d; or R^a and R^b together with the nitrogen atom to which they are attached form a heterocyclyl substituted with 0-5 occurrences of R^d;

R^c is H or alkyl;

each R^d is independently halo, heteroalkyl, haloalkyl, haloalkoxyl, alkyl, alkynyl, hydroxyalkyl, carbocyclyl, carbocyclylalkyl, aryl, aralkyl, heteroaryl, heterocyclyl, heterocyclylalkyl, nitro, cyano, hydroxyl, —C(O)R^a1, —OC(O)R^a1, —C(O)OR^a1, —SR^a1, —S(O)_2R^a1, —NR^a1R^b1, —C(O)NR^a1R^b1, —NR^a1S(O)_2R^a1, or —OR^a1; wherein each of heteroalkyl, haloalkyl, haloalkoxyl, alkyl, alkynyl, hydroxyalkyl, carbocyclyl, carbocyclylalkyl, aryl, aralkyl, heteroaryl, heterocyclyl, and heterocyclylalkyl is substituted with 0-5 occurrences of R^c1; or two R^d together with the atoms to which they are attached form a carbocyclyl or heterocyclyl, each optionally substituted with halo or alkyl;

R^a1 and R^b1 are each independently H, alkyl, aralkyl, carbocyclyl, heteroaryl, or heterocyclyl; or R^a1 and R^b1 together with the nitrogen atom to which they are attached form a heterocyclyl optionally substituted with halo or alkyl;

each R^c1 is independently halo, —OR^c2, —NR^a1R^b1, alkyl, cyano, heteroalkyl, haloalkyl, haloalkoxyl, carbocyclyl, carbocyclylalkyl, heterocyclyl, heterocyclylalkyl, heteroaryl, heteroaralkyl, aryl, or aralkyl;

R^c2 is H or alkyl;

p and r are each independently 1 or 2; and n is 1, 2, 3 or 4.

2. The compound of claim 1, wherein L is a bond, —(CR^cR^c)_n—, —(CR^cR^c)_nNR^b—, —NR^b(CR^cR^c)_n—, —(CR^cR^c)_n—C(O)—, —C(O)—(CR^cR^c)_n—, —C(O)NR^b—(CR^cR^c), where the two Rc's, together with the C to which they are attached, can form a carbocycle, —C(O)NR^b—(CR^cR^b), —(CR^cR^c)_nNR^b—(CR^cR^c), —NR^bC(O)—, —C(O)NR^b—, -or —S(O)_2NR^b—.

3. The compound of claim 1, wherein L is —(CR^cR^c)_nNR^b—, —NR^b(CR^cR^c)_n—, —NR^bC(O)—, or —C(O)NR^b—.

4. The compound of claim 1, wherein R¹ is aryl, carbocyclyl, carbocyclylalkyl, heterocyclyl, or heterocyclylalkyl, each of which is substituted with 0-5 occurrences of R^d.

5. The compound of claim 1, wherein R² is alkenyl, aryl, carbocyclyl, heteroaryl, or heterocyclyl, each of which is substituted with 0-5 occurrences of R^d.

6. The compound of claim 1, wherein R² is a 5- or 6-membered heterocyclyl substituted with 0-5 occurrences of R^d.

7. The compound of claim 1, wherein R² is a 5- or 6-membered heteroaryl substituted with 0-5 occurrences of R^d.

8. The compound of claim 1, wherein R² is selected from pyrrolyl, imidazolyl, pyrazolyl, pyridinyl, pyrimidinyl, thiophenyl, isoxazolyl, phenyl, dihydropyranyl, and tetrahydropyridinyl, each optionally substituted with 0-5 occurrences of R^d.

9. The compound of claim 1, wherein R³ is H, alkyl, —OR^c, or —NR^aR^b.

10. The compound of claim 1, wherein each R^d is independently selected from halo, alkyl, carbocyclyl, carbocyclylalkyl, heterocyclyl, heterocyclylalkyl, nitro, cyano, hydroxyl, —C(O)R^a1, —C(O)OR^a1, —S(O)_2R^a1, —NR^a1R^b1, —C(O) NR^a1R^b1, and —OR^a1; wherein each of alkyl, carbocyclyl, carbocyclylalkyl, heterocyclyl, heterocyclylalkyl is substituted with 0-5 occurrences of R^c1; or two R^d together with the atoms to which they are attached form a carbocyclyl or heterocyclyl, each optionally substituted with halo or alkyl.

11. The compound of claim 1, wherein p is 1 and r is 1.

12. The compound of claim 1, wherein the compound is a compound of Formula II:

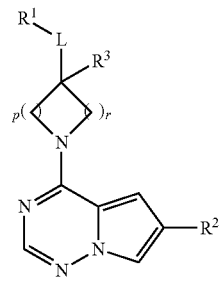

or a pharmaceutically acceptable salt thereof.

13. The compound of claim 1, wherein the compound is a compound of Formula III:

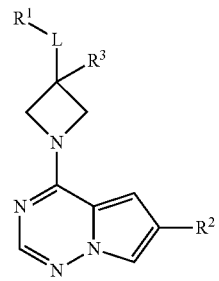

or a pharmaceutically acceptable salt thereof.

14. The compound of claim 1, wherein the compound is a compound of Formula IV:

IV

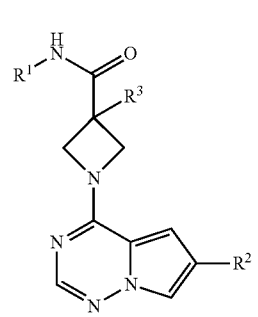

or a pharmaceutically acceptable salt thereof.

15. A pharmaceutical composition comprising a compound of claim 1 or a pharmaceutically acceptable salt thereof and a pharmaceutically acceptable carrier.

16. A method of treating mastocytosis, the method comprising administering to a patient in need thereof a therapeutically effective amount of a compound of claim 1.

17. A method of treating gastrointestinal stromal tumor, the method comprising administering to a patient in need thereof a therapeutically effective amount of a compound of claim 1.

18. A method of treating acute myeloid leukemia, the method comprising administering to a patient in need thereof a therapeutically effective amount of a compound of claim 1.

19. The method of claim 16, wherein the mastocytosis is selected from cutaneous mastocytosis (CM) and systemic mastocytosis (SM).

20. The method of claim 19, wherein the systemic mastocytosis is selected from indolent systemic mastocytosis (ISM), smoldering systemic mastocytosis (SSM), aggressive systemic mastocytosis (ASM), SM with associated hematologic non-mast cell lineage disease (SM-AHNMD), and mast cell leukemia (MCL).

21. The compound of claim 1 selected from any one of the compounds below, or a pharmaceutically acceptable salt thereof:

| # | Structure |
|---|---|
| 1 | 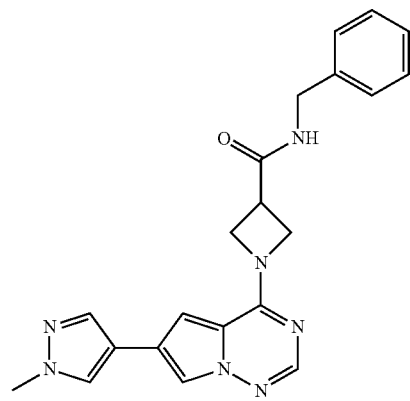 [SMILES: Cn1cc(-c2cc3c(N4CC(C(=O)NCc5ccccc5)C4)ncnn3c2)cn1] |
| 2 | 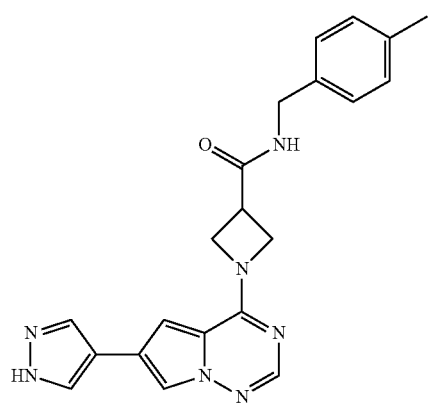 [SMILES: Cc1ccc(CNC(=O)C2CN(c3ncnn4cc(-c5cn[nH]c5)cc34)C2)cc1] |

-continued

| # | Structure |
|---|---|
| 3 | 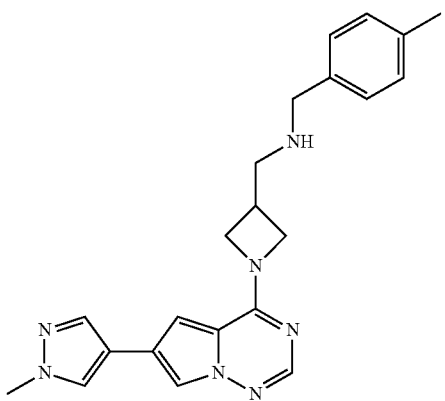 |
| 4 | 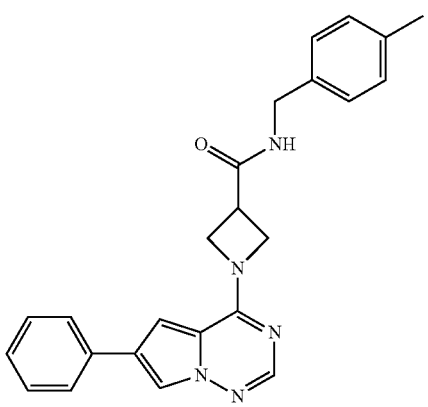 [SMILES: Cc1ccc(CNC(=O)C2CN(c3ncnn4cc(-c5ccccc5)cc34)C2)cc1] |
| 5 | 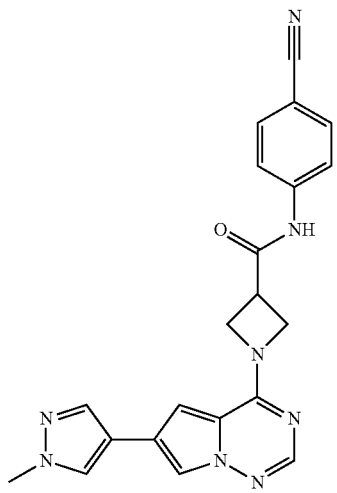 [SMILES: Cn1cc(-c2cc3c(N4CC(C(=O)Nc5ccc(C#N)cc5)C4)ncnn3c2)cn1] |

285
-continued
| # | Structure |
|---|---|
| 6 | 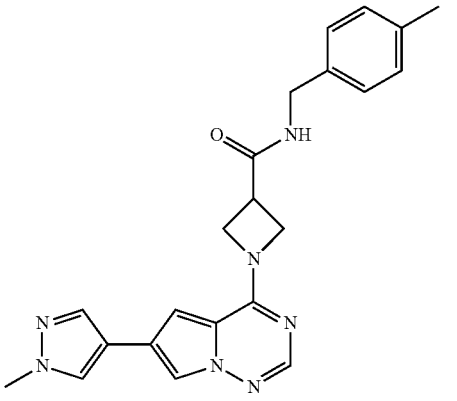 |
| 7 | 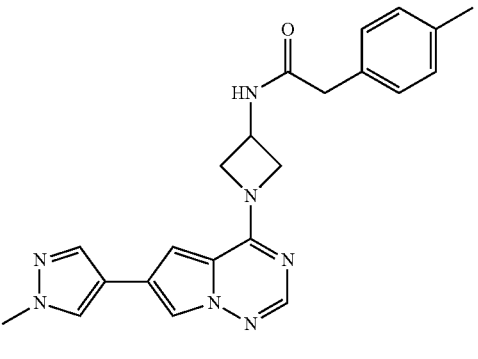 |
| 8 | 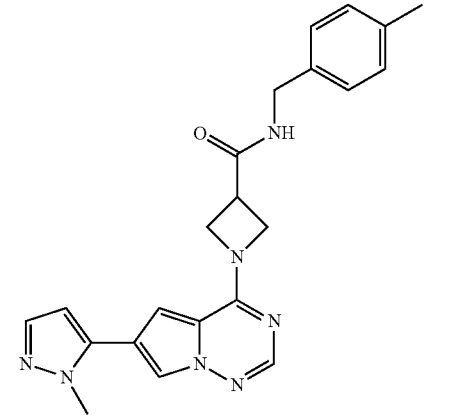 [SMILES: Cc1ccc(CNC(=O)C2CN(c3ncnn4cc(-c5ccnn5C)cc34)C2)cc1] |
| 9 | 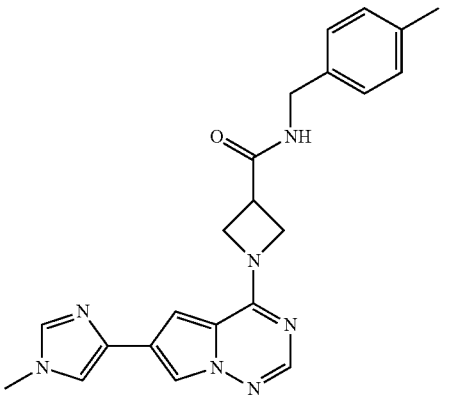 |
286
-continued
| # | Structure |
|---|---|
| 10 | 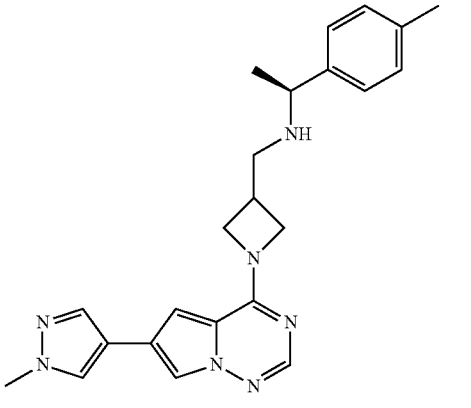 |
| 11 | 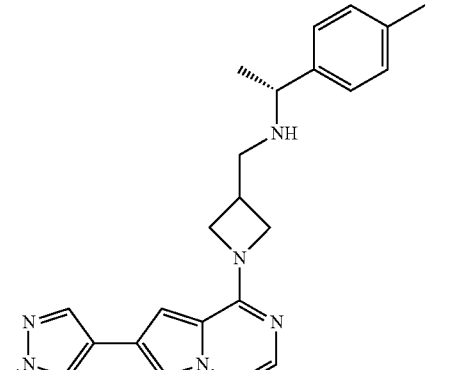 |
| 12 | 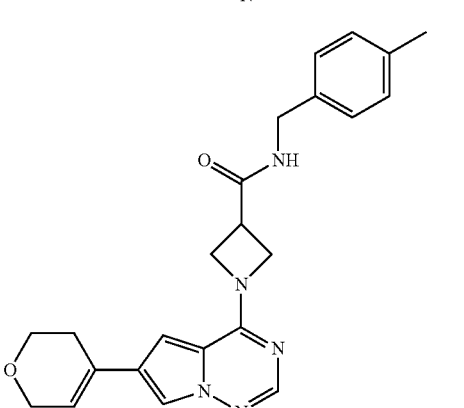 |
| 13 | 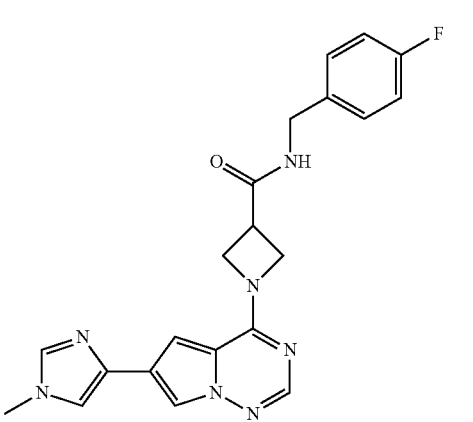 [SMILES: Cn1cnc(-c2cc3c(N4CC(C(=O)NCc5ccc(F)cc5)C4)ncnn3c2)c1] |

| # | Structure |
|---|---|
| 14 | 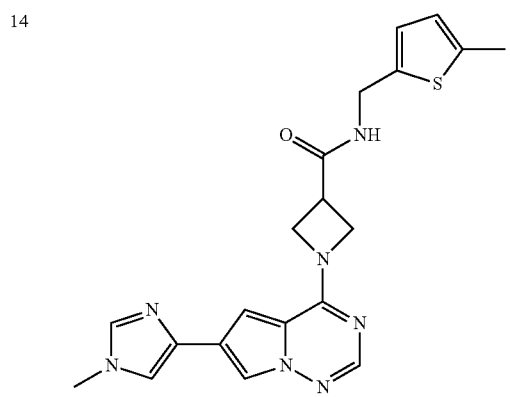 |
| 15 | 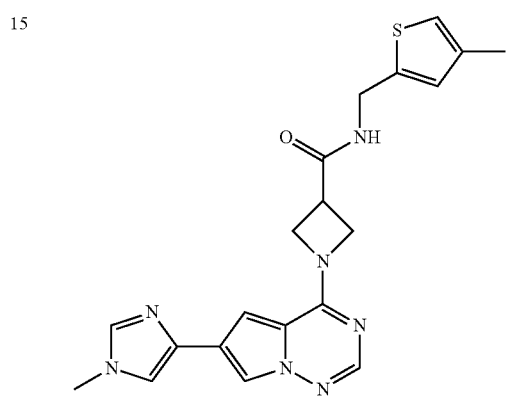 |
| 16 | 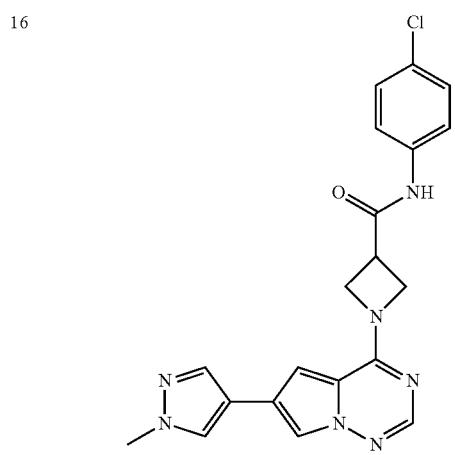 |
| # | Structure |
|---|---|
| 17 | 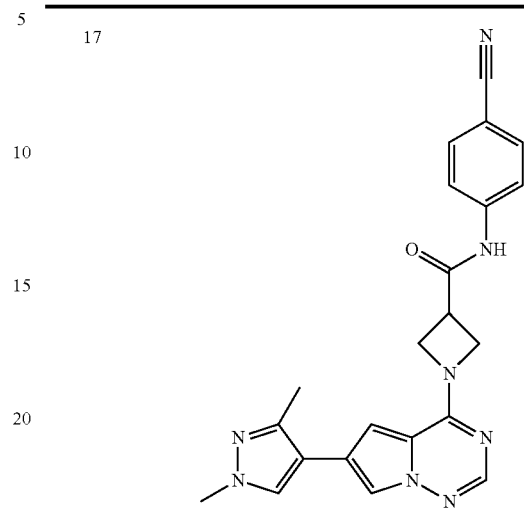 |
| 18 | 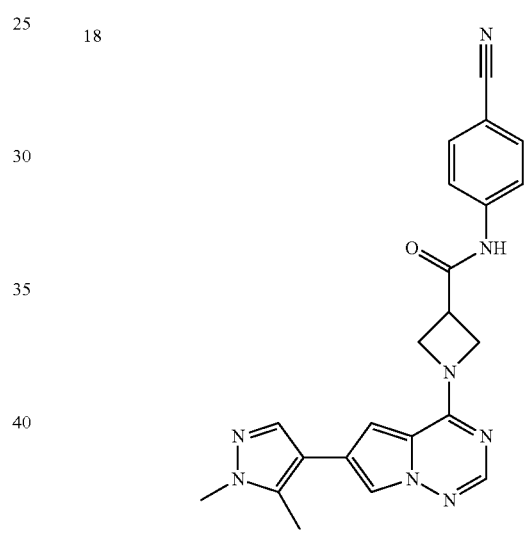 |
| 19 |  |

-continued
| # | Structure |
|---|---|
| 20 | 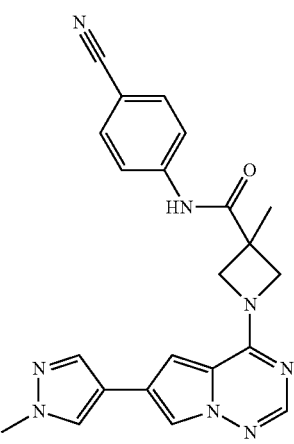 [SMILES: Cn1cc(-c2cc3c(N4CC(C)(C(=O)Nc5ccc(C#N)cc5)C4)ncnn3c2)cn1] |
| 21 | 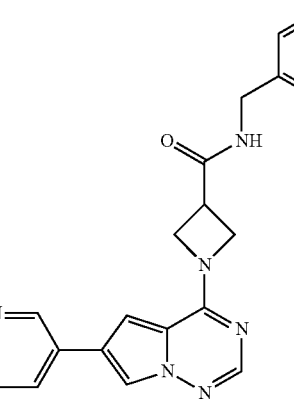 |
| 22 | 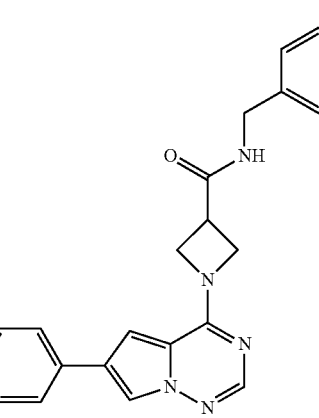 |
-continued
| # | Structure |
|---|---|
| 23 | 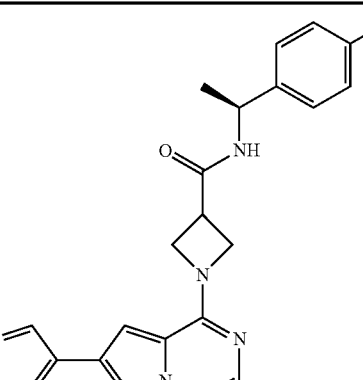 |
| 24 | 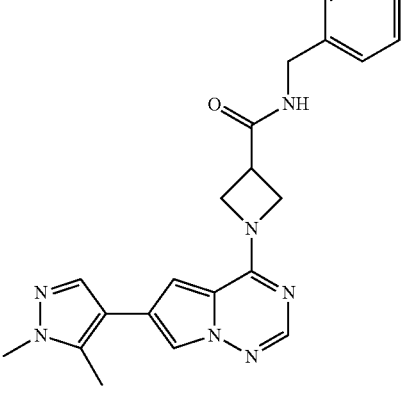 |
| 25 | 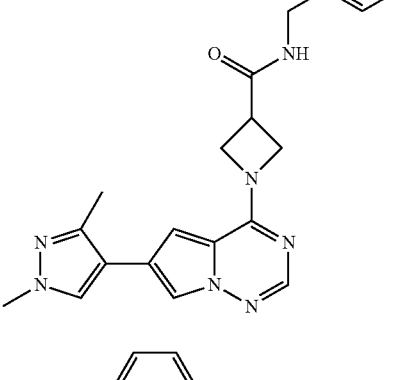 |
| 26 | 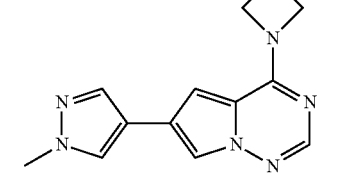 |

| # | Structure |
|---|---|
| 27 | 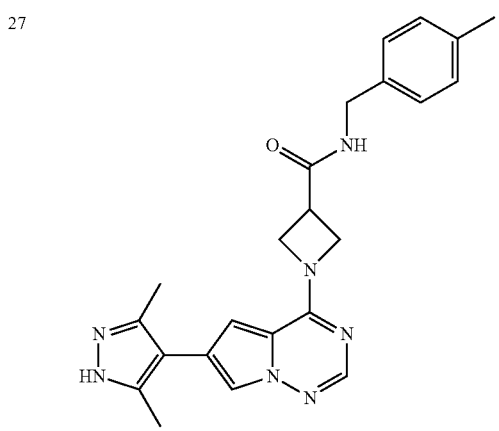 |
| 28 | 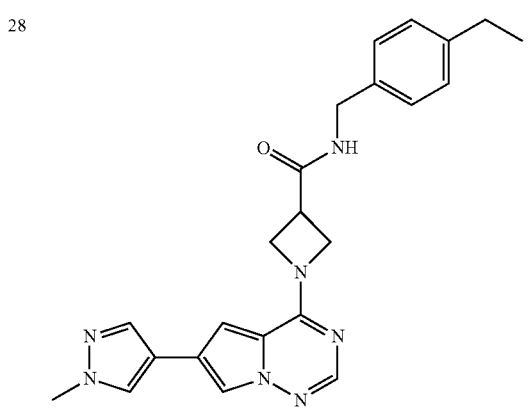 |
| 29 | 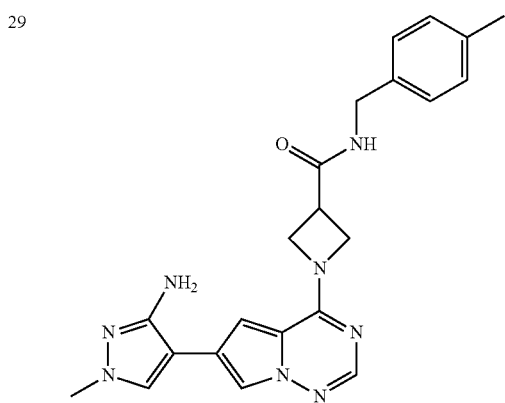 |
| # | Structure |
|---|---|
| 30 | 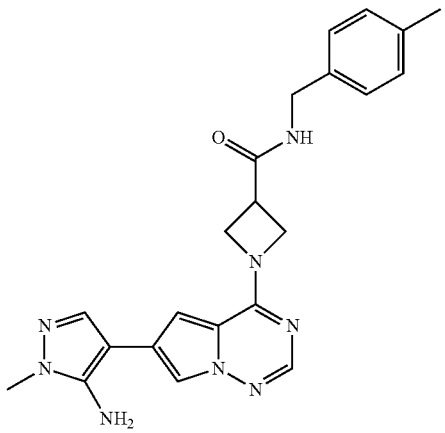 |
| 31 | 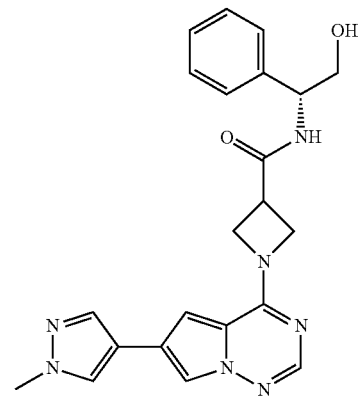 [SMILES: Cn1cc(-c2cc3c(N4CC(C(=O)N[C@@H](CO)c5ccccc5)C4)ncnn3c2)cn1] |
| 32 | |

-continued
| # | Structure |
|---|---|
| 33 | 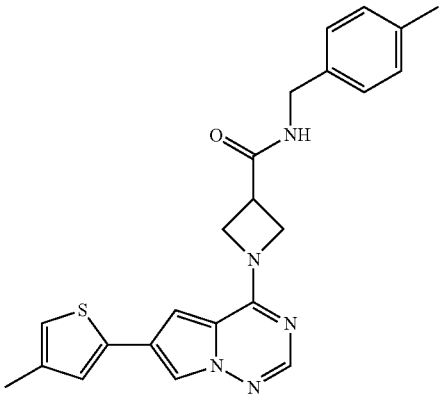 |
| 34 | 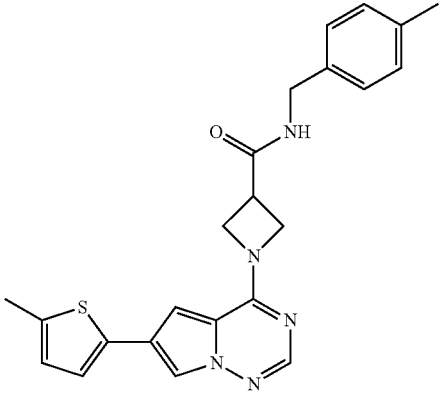 |
| 35 | 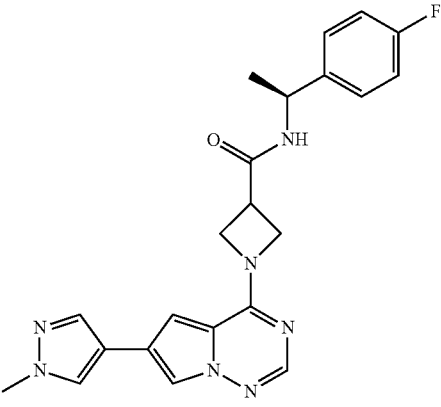 [SMILES: C[C@H](NC(=O)C1CN(c2ncnn3cc(-c4cnn(C)c4)cc23)C1)c1ccc(F)cc1] |
-continued
| # | Structure |
|---|---|
| 36 | 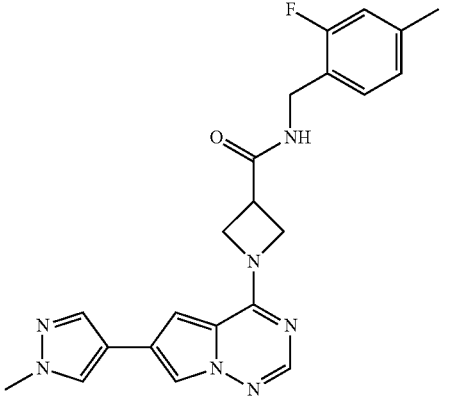 |
| 37 | 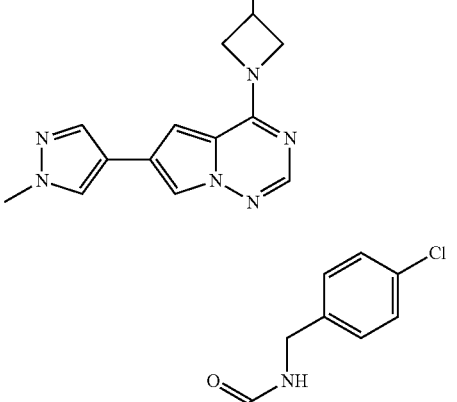 |
| 38 | 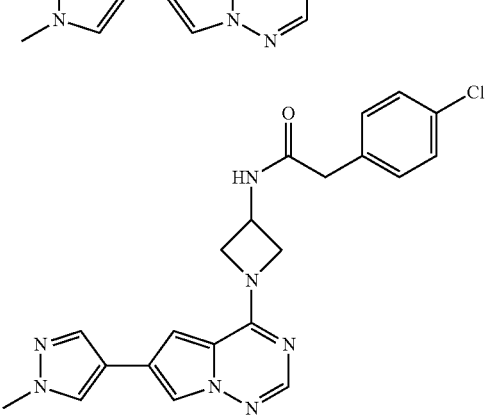 |
| 39 | 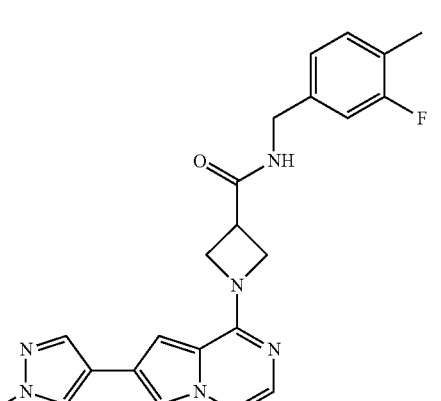 |

| # | Structure |
|---|---|
| 40 | 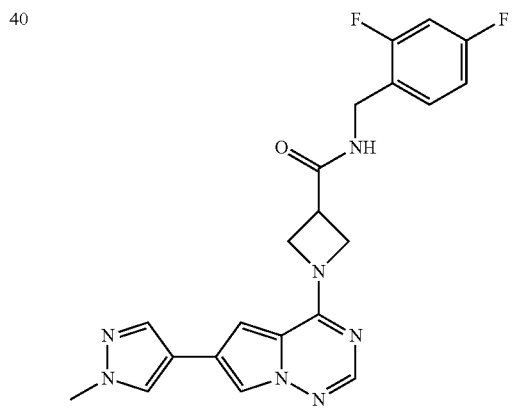 |
| 41 | 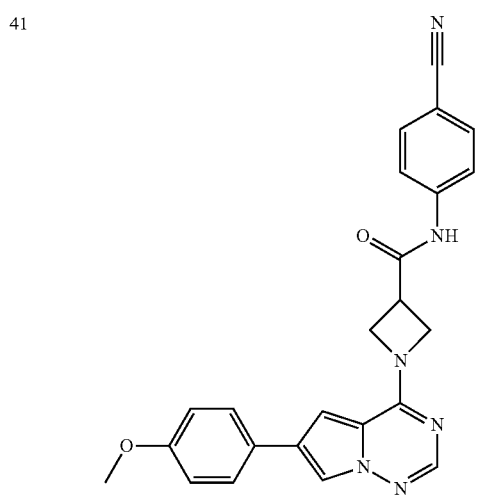 |
| 42 | 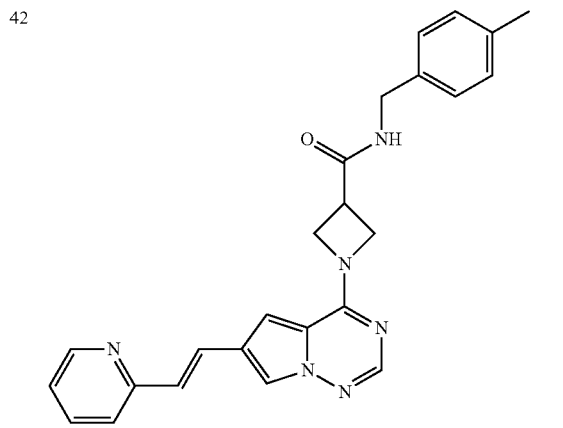 |
| # | Structure |
|---|---|
| 43 | 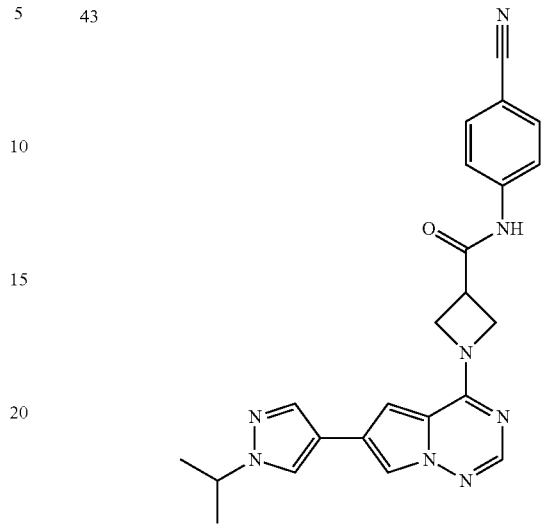 |
| 44 | 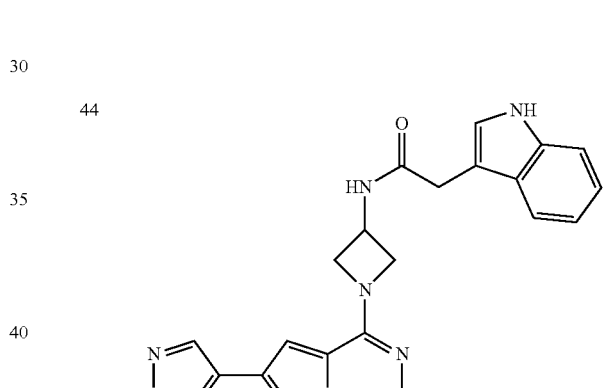 |
| 45 | 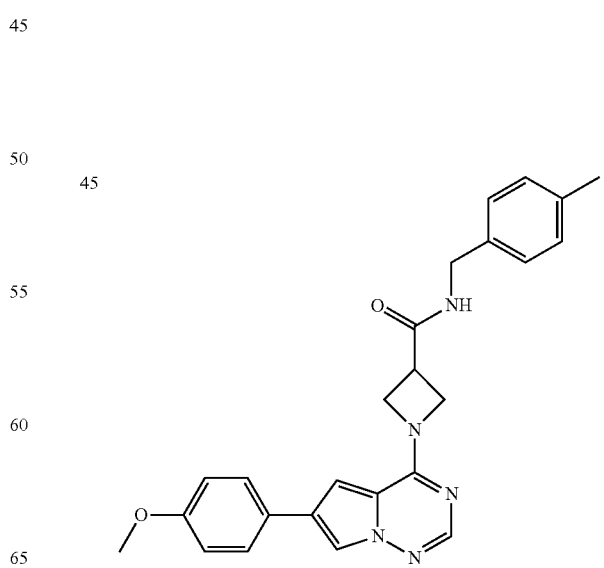 |

| # | Structure |
|---|---|
| 46 | 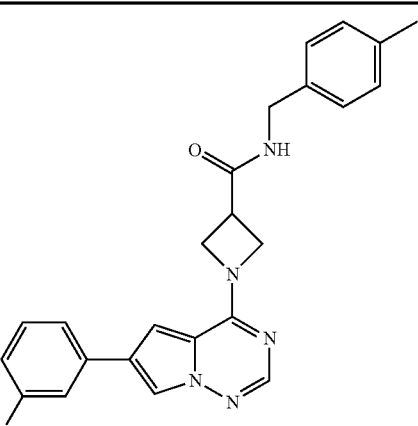 |
| 47 | |
| 48 | |
| # | Structure |
|---|---|
| 49 | 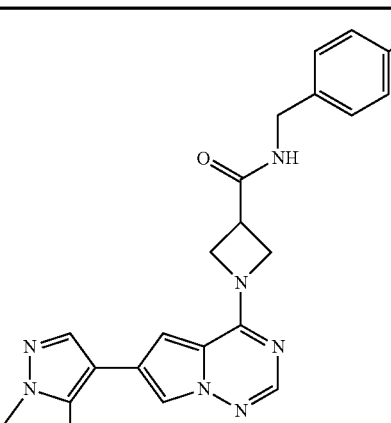 |
| 50 | |
| 51 | |

| # | Structure |
|---|---|
| 52 | 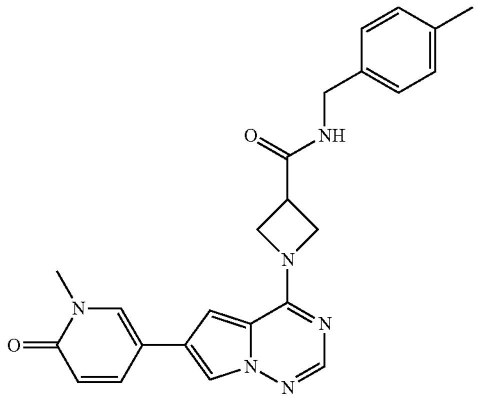 [SMILES: Cc1ccc(CNC(=O)C2CN(c3ncnn4cc(-c5ccc(=O)n(C)c5)cc34)C2)cc1] |
| 53 | 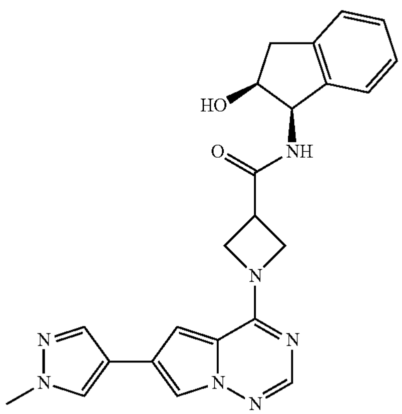 [SMILES: Cn1cc(-c2cc3c(N4CC(C(=O)N[C@@H]5c6ccccc6C[C@@H]5O)C4)ncnn3c2)cn1] |
| 54 | 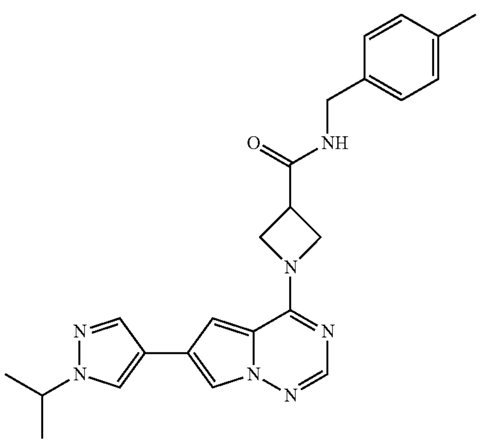 [SMILES: Cc1ccc(CNC(=O)C2CN(c3ncnn4cc(-c5cnn(C(C)C)c5)cc34)C2)cc1] |
| 55 | 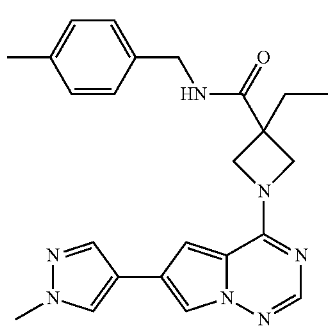 [SMILES: CCC1(C(=O)NCc2ccc(C)cc2)CN(c2ncnn3cc(-c4cnn(C)c4)cc23)C1] |
| 56 | |
| 57 | |
| 58 | |
| 59 | |

301
-continued
| # | Structure |
|---|---|
| 60 | 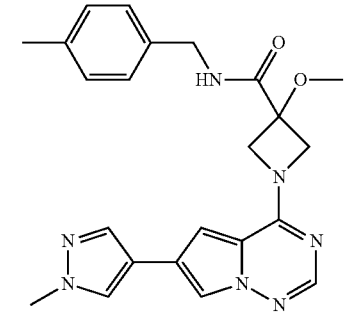 |
| 61 | 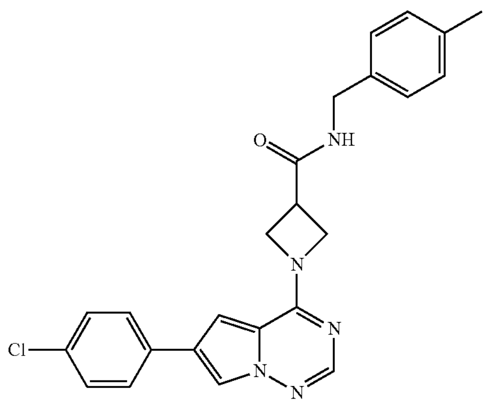 [SMILES: Cc1ccc(CNC(=O)C2CN(c3ncnn4cc(-c5ccc(Cl)cc5)cc34)C2)cc1] |
| 62 | 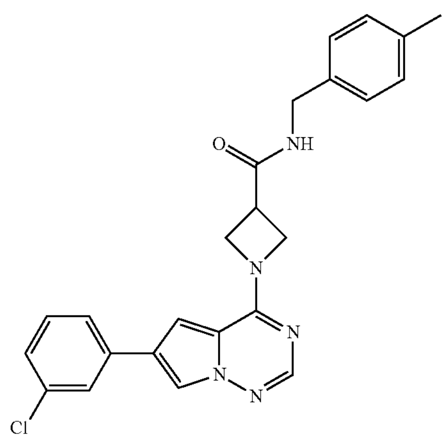 [SMILES: Cc1ccc(CNC(=O)C2CN(c3ncnn4cc(-c5cccc(Cl)c5)cc34)C2)cc1] |
| 63 | 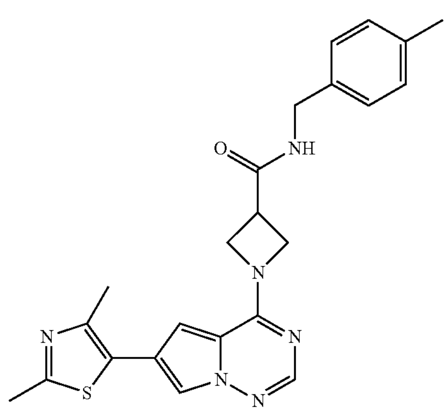 |
302
-continued
| # | Structure |
|---|---|
| 64 | 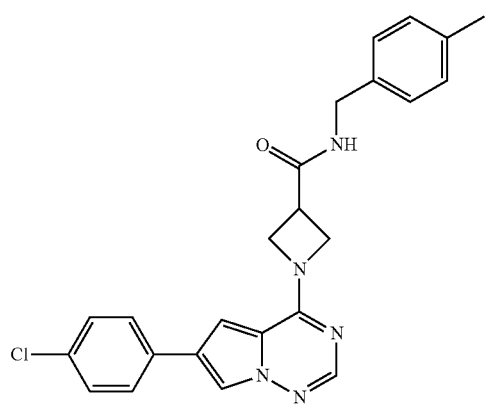 |
| 65 | 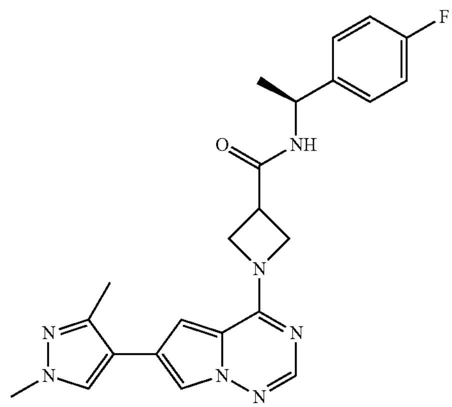 [SMILES: Cc1nn(C)cc1-c1cc2c(N3CC(C(=O)N[C@@H](C)c4ccc(F)cc4)C3)ncnn2c1] |
| 66 | 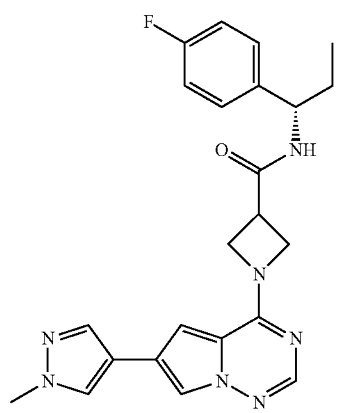 [SMILES: CC[C@H](NC(=O)C1CN(c2ncnn3cc(-c4cnn(C)c4)cc23)C1)c1ccc(F)cc1] |
| 67 | 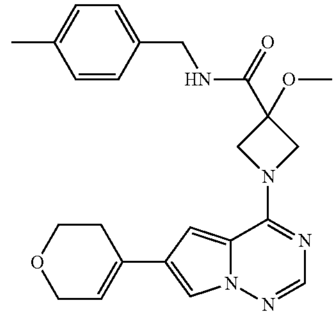 |

-continued

| # | Structure |
|---|---|
| 68 | 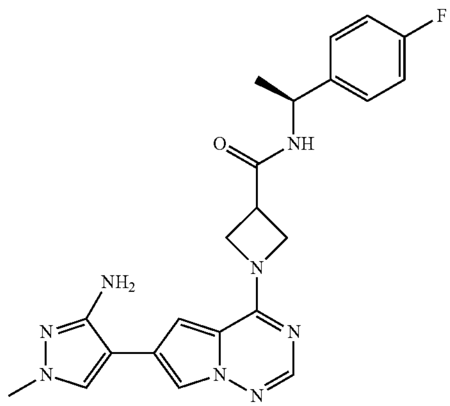 [SMILES: C[C@H](NC(=O)C1CN(c2ncnn3cc(-c4cn(C)nc4N)cc23)C1)c1ccc(F)cc1] |
| 69 | 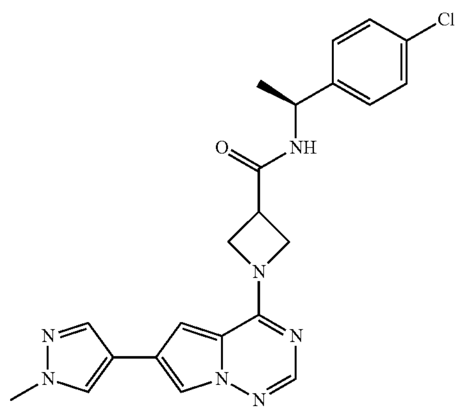 [SMILES: C[C@H](NC(=O)C1CN(c2ncnn3cc(-c4cnn(C)c4)cc23)C1)c1ccc(Cl)cc1] |
| 70 | 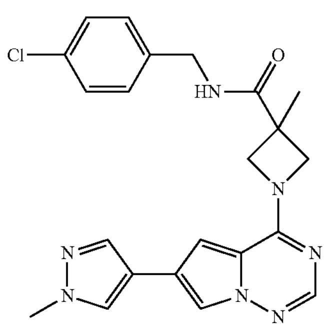 [SMILES: Cn1cc(-c2cc3c(N4CC(C)(C(=O)NCc5ccc(Cl)cc5)C4)ncnn3c2)cn1] |
| 71 | 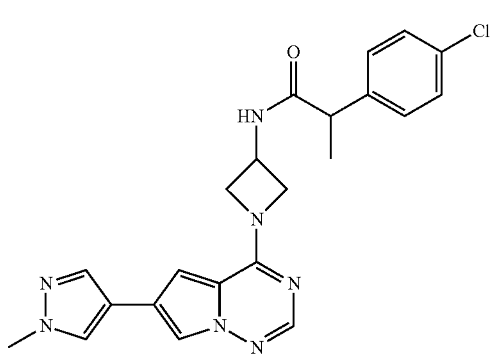 [SMILES: CC(C(=O)NC1CN(c2ncnn3cc(-c4cnn(C)c4)cc23)C1)c1ccc(Cl)cc1] |

-continued

| # | Structure |
|---|---|
| 72 | 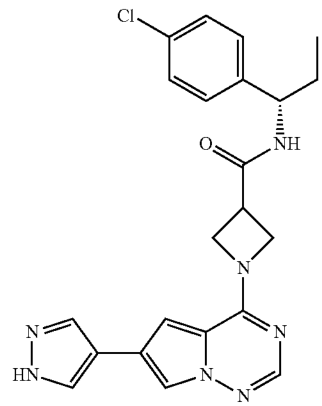 [SMILES: CC[C@H](NC(=O)C1CN(c2ncnn3cc(-c4cn[nH]c4)cc23)C1)c1ccc(Cl)cc1] |
| 73 | 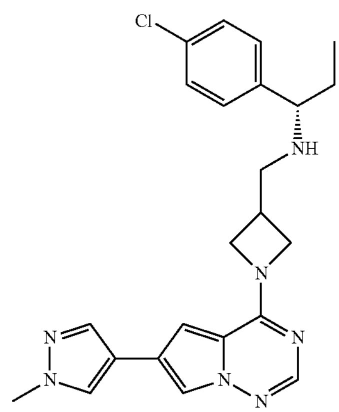 [SMILES: CC[C@H](NCC1CN(c2ncnn3cc(-c4cnn(C)c4)cc23)C1)c1ccc(Cl)cc1] |
| 74 | 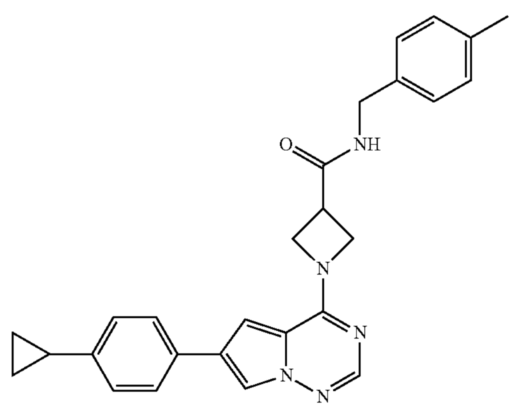 [SMILES: Cc1ccc(CNC(=O)C2CN(c3ncnn4cc(-c5ccc(C6CC6)cc5)cc34)C2)cc1] |
| 75 | 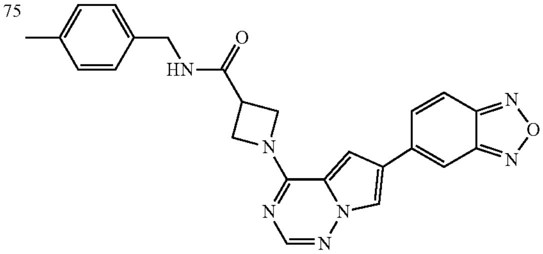 |

305
-continued
| # | Structure |
|---|---|
| 76 | 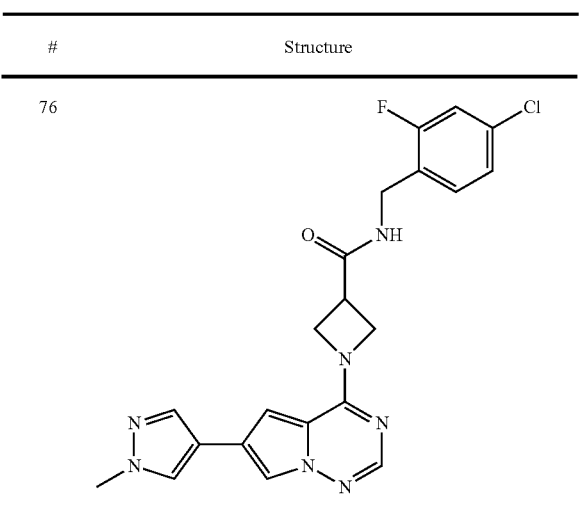 |
| 77 | 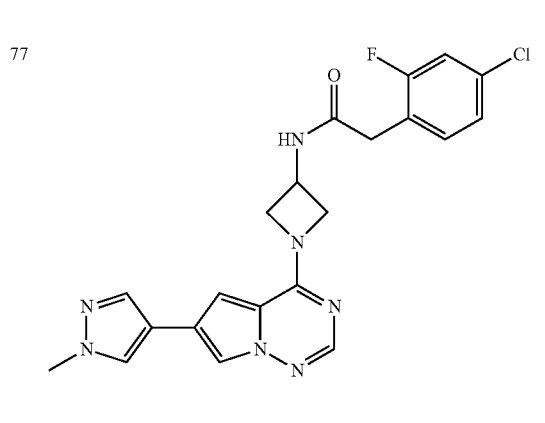 |
| 78 | 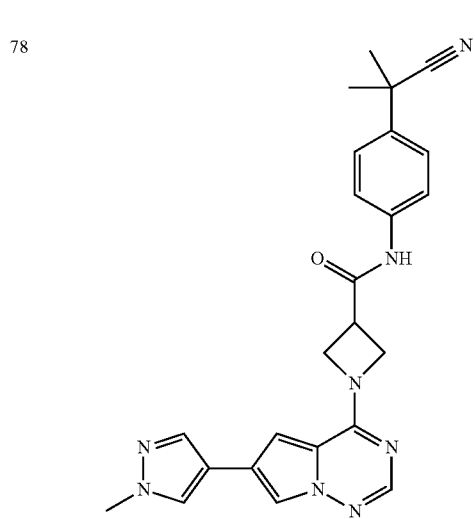 |
306
-continued
| # | Structure |
|---|---|
| 79 | 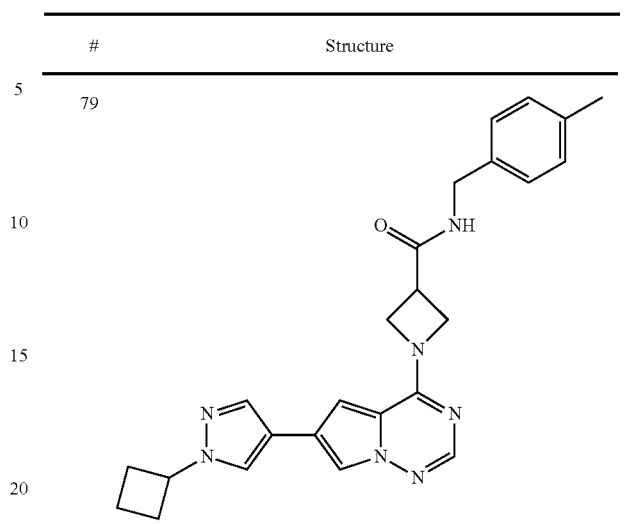 |
| 80 | 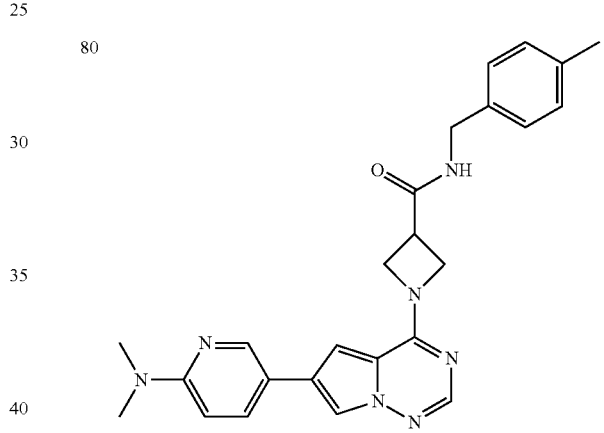 |
| 81 | 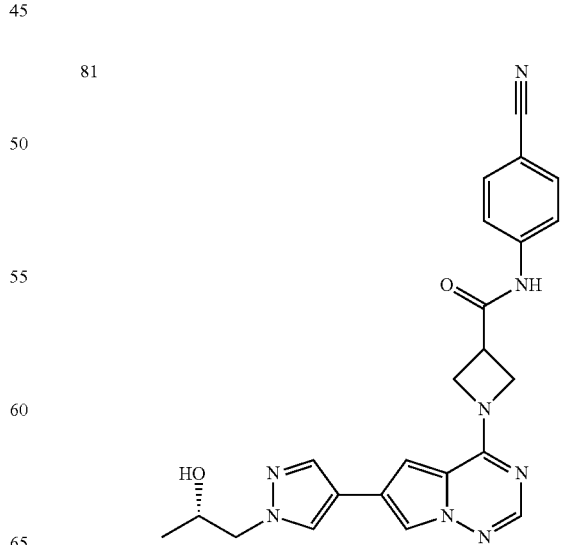 |

| # | Structure |
|---|---|
| 82 | 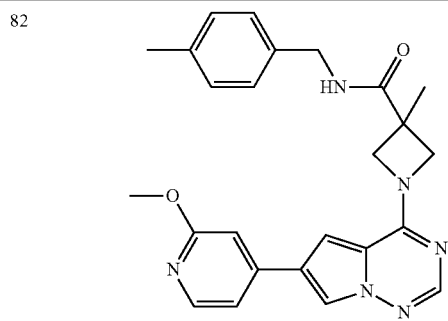 |
| 83 | 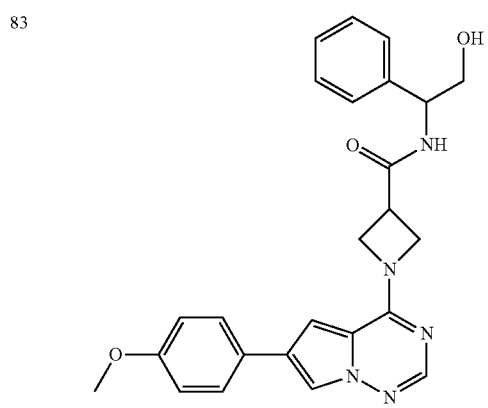 |
| 84 | 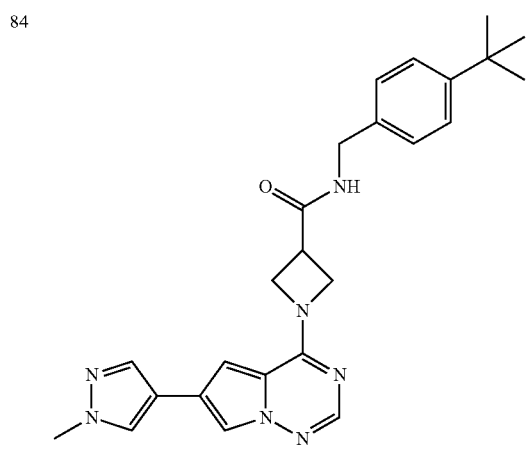 |
| 85 | 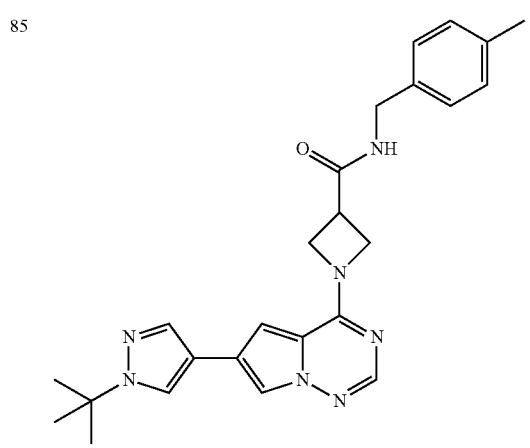 |
| # | Structure |
|---|---|
| 86 | 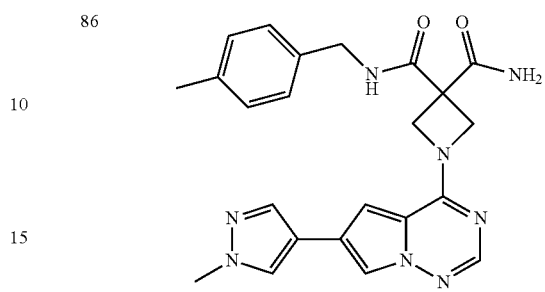 |
| 87 | 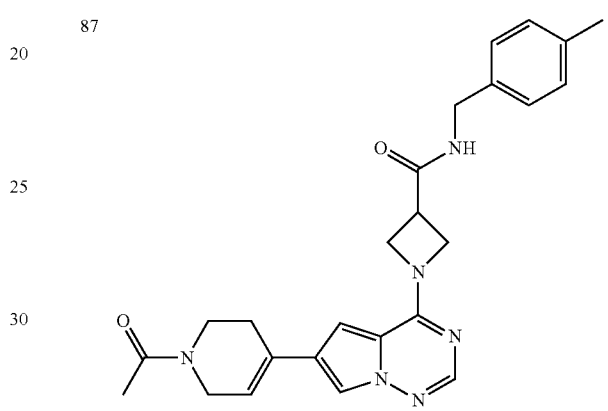 |
| 88 | 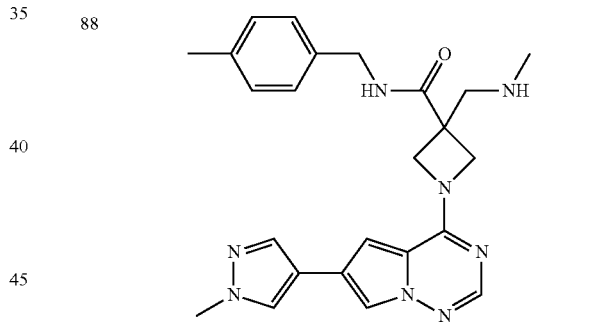 |
| 89 | 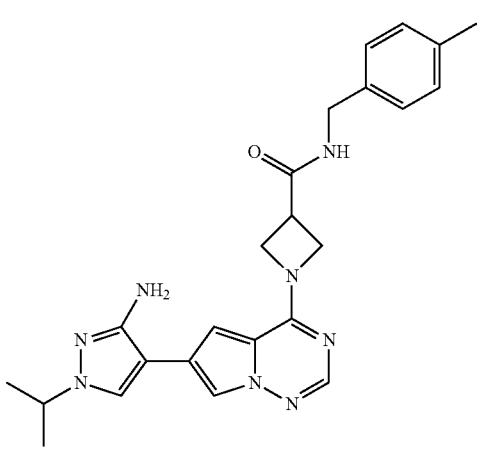 [SMILES: Cc1ccc(CNC(=O)C2CN(c3ncnn4cc(-c5cn(C(C)C)nc5N)cc34)C2)cc1] |

| # | Structure |
|---|---|
| 90 | 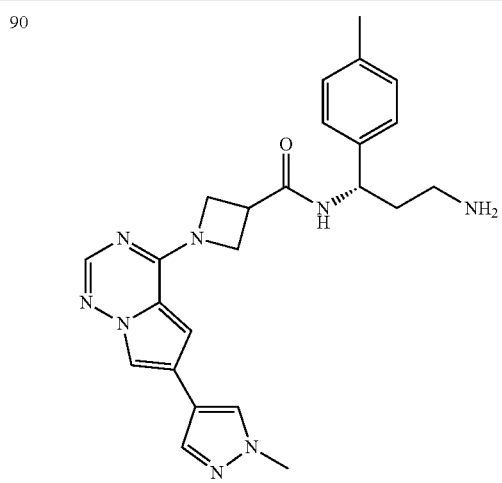 |
| 91 | 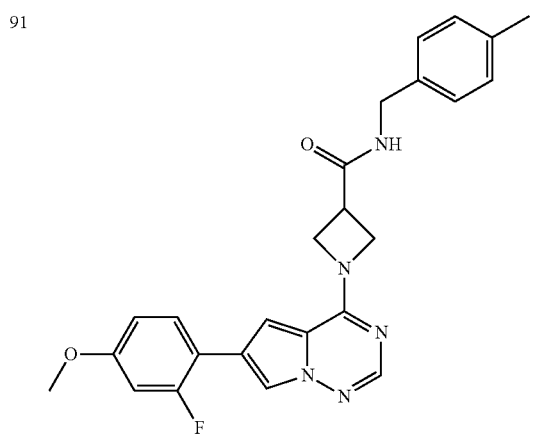 |
| 92 | 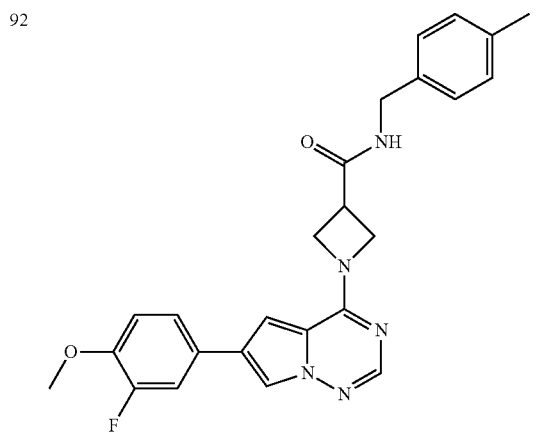 |
| # | Structure |
|---|---|
| 93 | 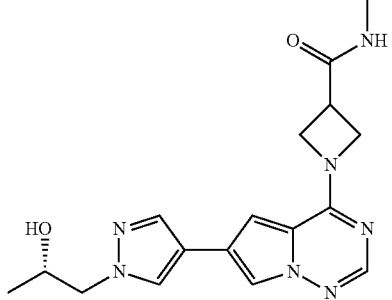 |
| 94 | 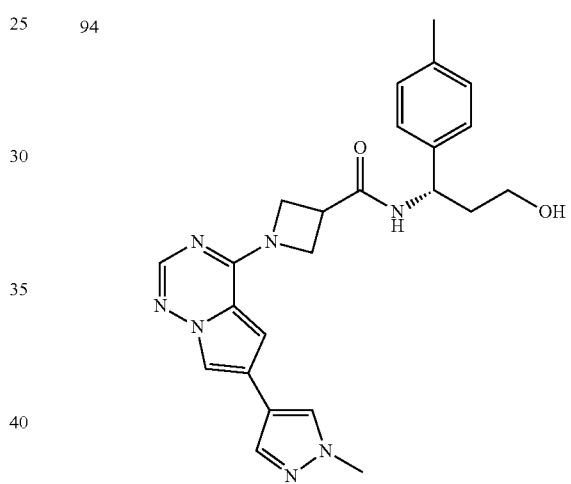 |
| 95 | 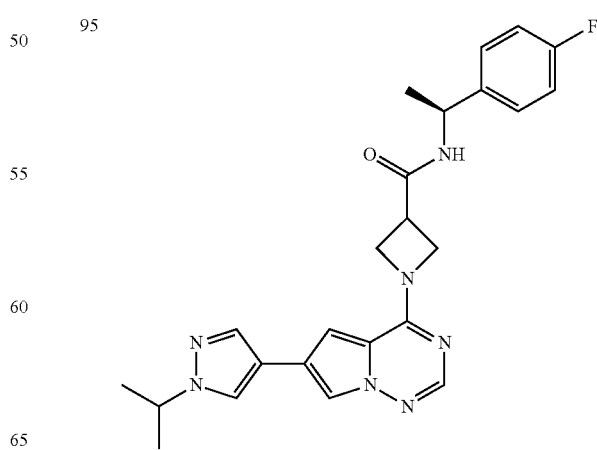 |

-continued

| # | Structure |
|---|-----------|
| 96 | 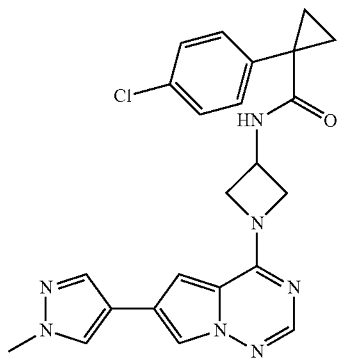 [SMILES: Cn1cc(-c2cc3c(N4CC(NC(=O)C5(c6ccc(Cl)cc6)CC5)C4)ncnn3c2)cn1] |
| 97 | 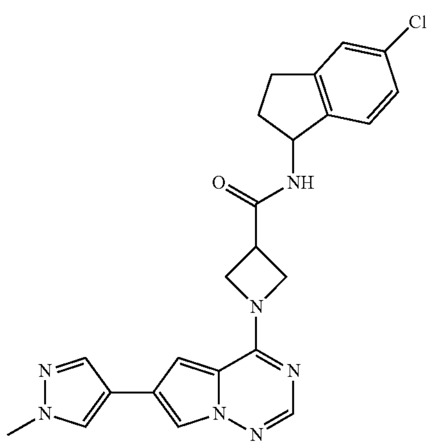 [SMILES: Cn1cc(-c2cc3c(N4CC(C(=O)NC5CCc6cc(Cl)ccc65)C4)ncnn3c2)cn1] |
| 98 | 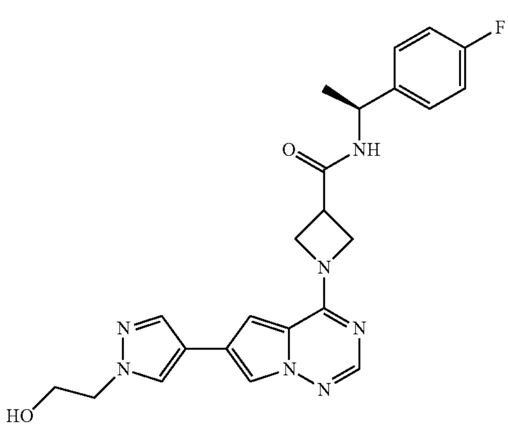 [SMILES: C[C@H](NC(=O)C1CN(c2ncnn3cc(-c4cnn(CCO)c4)cc23)C1)c1ccc(F)cc1] |

-continued

| # | Structure |
|---|-----------|
| 99 | 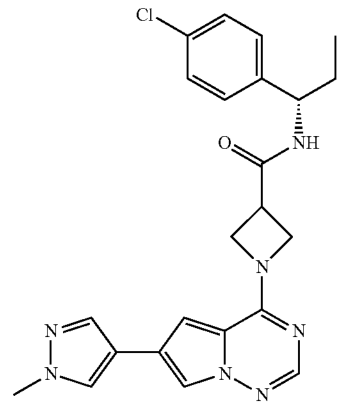 [SMILES: CC[C@H](NC(=O)C1CN(c2ncnn3cc(-c4cnn(C)c4)cc23)C1)c1ccc(Cl)cc1] |
| 100 | 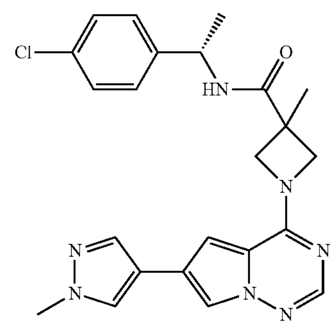 [SMILES: C[C@H](NC(=O)C1(C)CN(c2ncnn3cc(-c4cnn(C)c4)cc23)C1)c1ccc(Cl)cc1] |
| 101 | 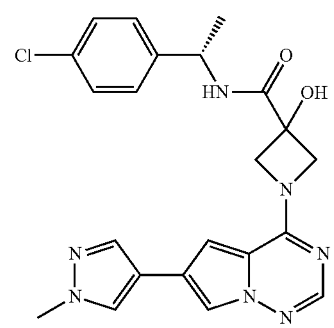 [SMILES: C[C@H](NC(=O)C1(O)CN(c2ncnn3cc(-c4cnn(C)c4)cc23)C1)c1ccc(Cl)cc1] |
| 102 | 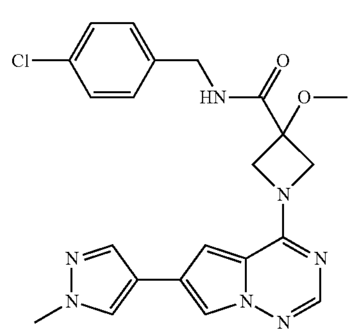 |

| # | Structure |
|---|---|
| 103 | 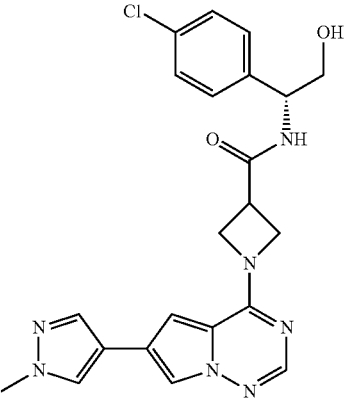 [SMILES: Cn1cc(-c2cc3c(N4CC(C(=O)N[C@@H](CO)c5ccc(Cl)cc5)C4)ncnn3c2)cn1] |
| 104 | 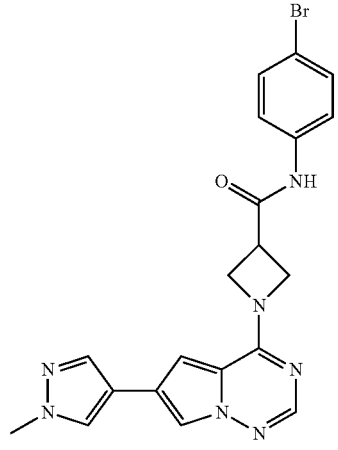 |
| 105 | 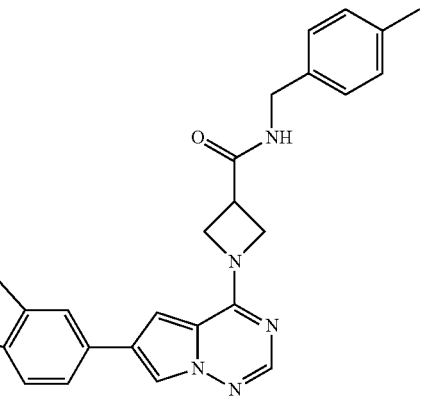 |
| # | Structure |
|---|---|
| 106 | 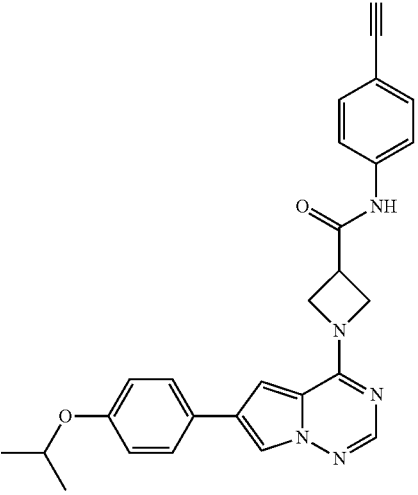 |
| 107 | 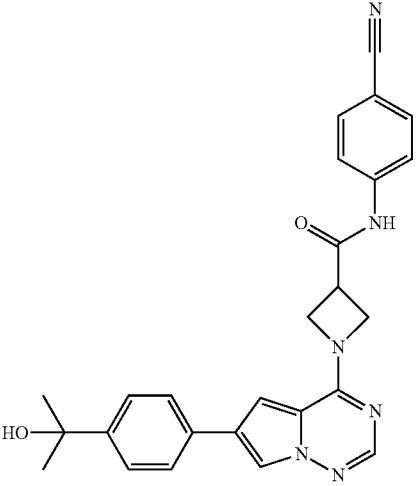 [SMILES: CC(C)(O)c1ccc(-c2cc3c(N4CC(C(=O)Nc5ccc(C#N)cc5)C4)ncnn3c2)cc1] |
| 108 | 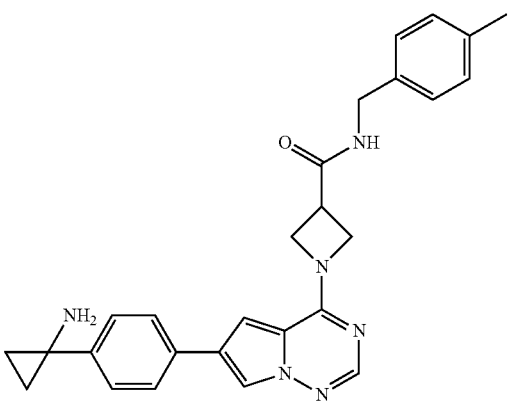 [SMILES: Cc1ccc(CNC(=O)C2CN(c3ncnn4cc(-c5ccc(C6(N)CC6)cc5)cc34)C2)cc1] |

-continued
| # | Structure |
|---|---|
| 109 | 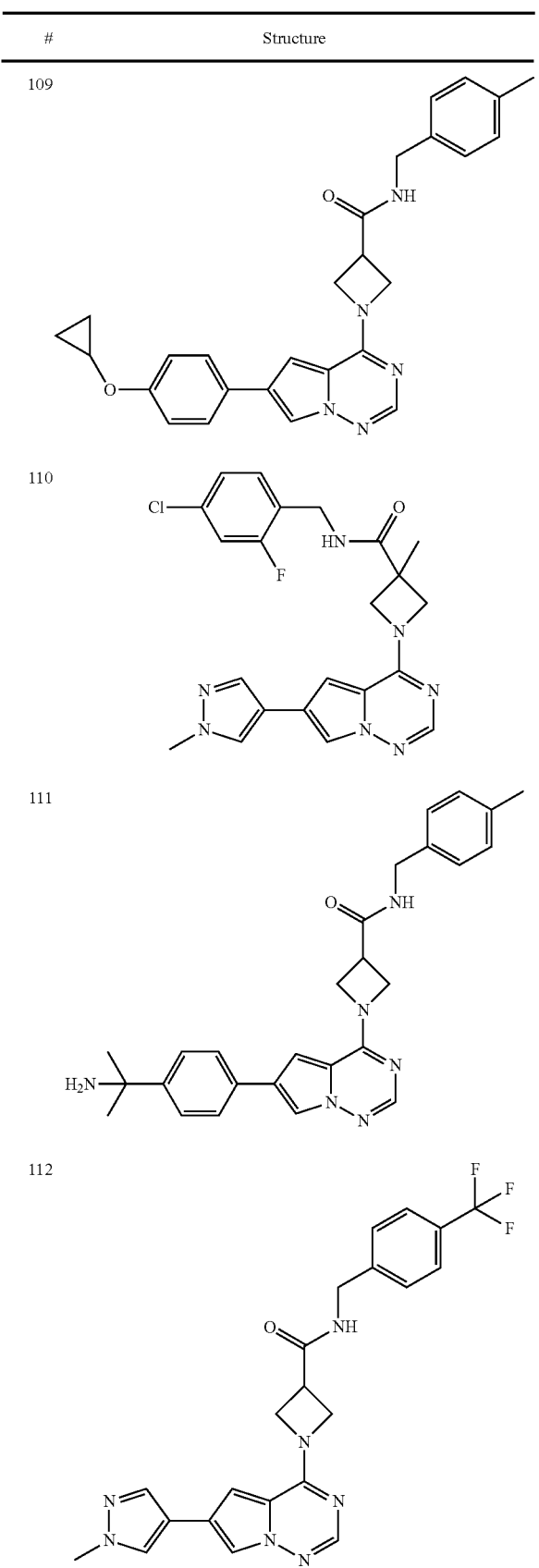 |
| 110 | 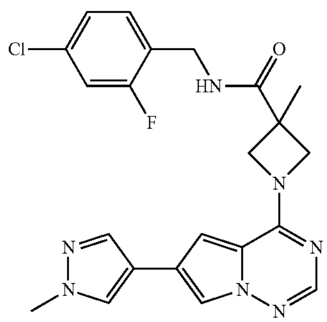 [SMILES: Cn1cc(-c2cc3c(N4CC(C)(C(=O)NCc5ccc(Cl)cc5F)C4)ncnn3c2)cn1] |
| 111 | 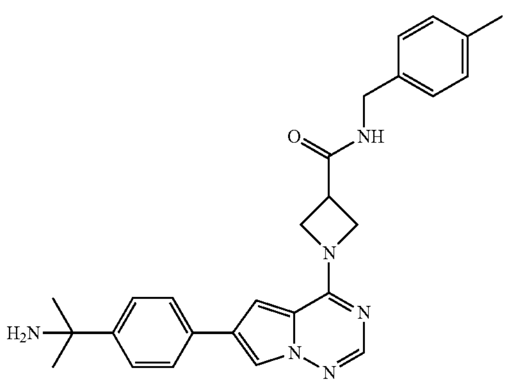 [SMILES: Cc1ccc(CNC(=O)C2CN(c3ncnn4cc(-c5ccc(C(C)(C)N)cc5)cc34)C2)cc1] |
| 112 | 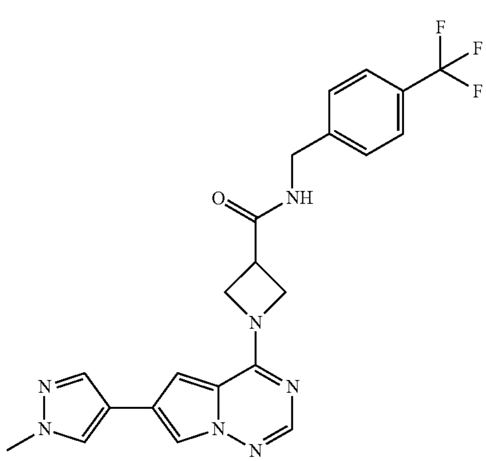 [SMILES: Cn1cc(-c2cc3c(N4CC(C(=O)NCc5ccc(C(F)(F)F)cc5)C4)ncnn3c2)cn1] |
-continued
| # | Structure |
|---|---|
| 113 | 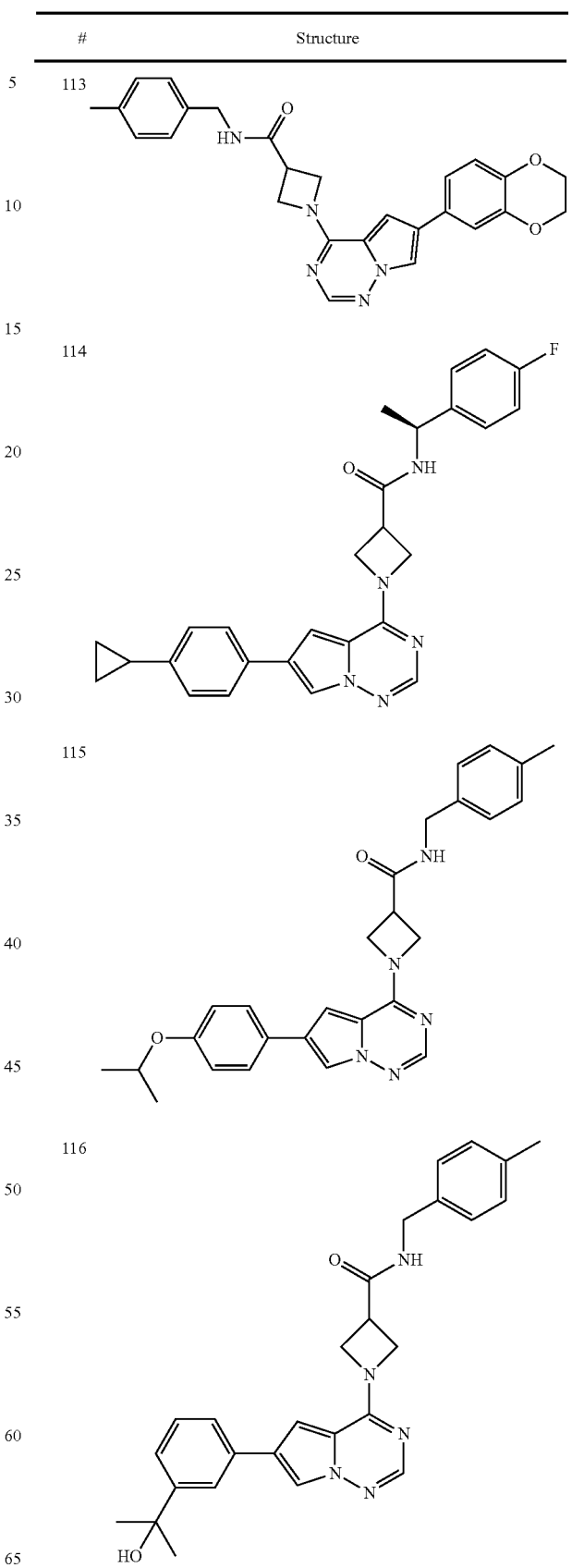 |
| 114 | 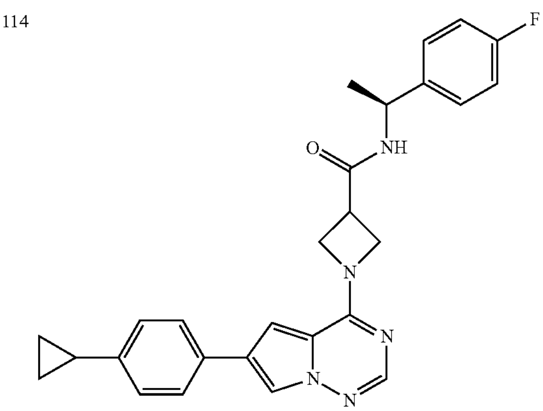 |
| 115 | 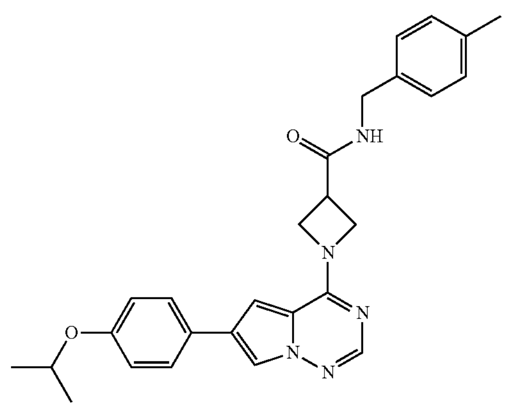 [SMILES: Cc1ccc(CNC(=O)C2CN(c3ncnn4cc(-c5ccc(OC(C)C)cc5)cc34)C2)cc1] |
| 116 | 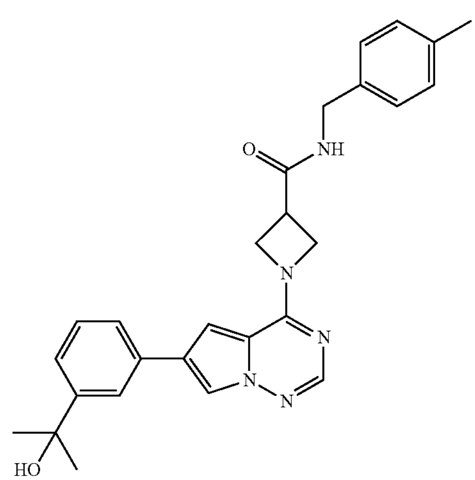 [SMILES: Cc1ccc(CNC(=O)C2CN(c3ncnn4cc(-c5cccc(C(C)(C)O)c5)cc34)C2)cc1] |

-continued

| # | Structure |
|---|---|
| 117 | 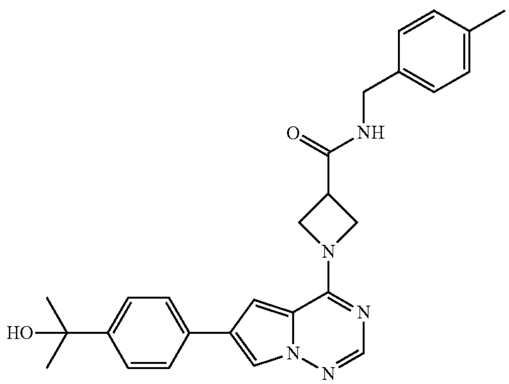 [SMILES: Cc1ccc(CNC(=O)C2CN(c3ncnn4cc(-c5ccc(C(C)(C)O)cc5)cc34)C2)cc1] |
| 118 | 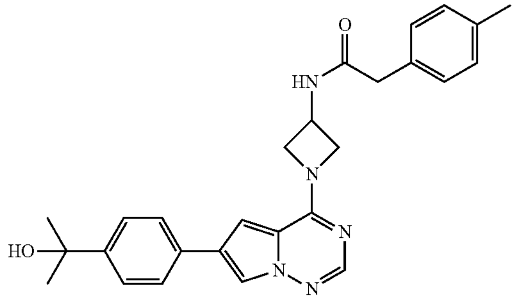 [SMILES: Cc1ccc(CC(=O)NC2CN(c3ncnn4cc(-c5ccc(C(C)(C)O)cc5)cc34)C2)cc1] |
| 119 | 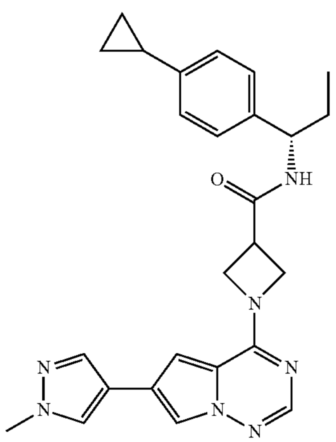 [SMILES: CC[C@H](NC(=O)C1CN(c2ncnn3cc(-c4cnn(C)c4)cc23)C1)c1ccc(C2CC2)cc1] |
| 120 | 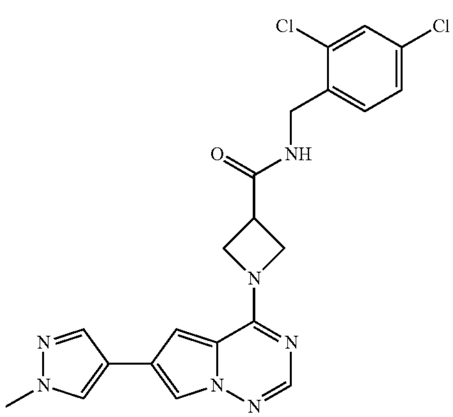 [SMILES: Cn1cc(-c2cc3c(N4CC(C(=O)NCc5ccc(Cl)cc5Cl)C4)ncnn3c2)cn1] |

-continued

| # | Structure |
|---|---|
| 121 | 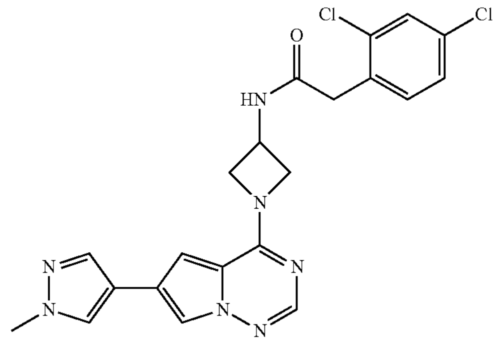 |
| 122 | 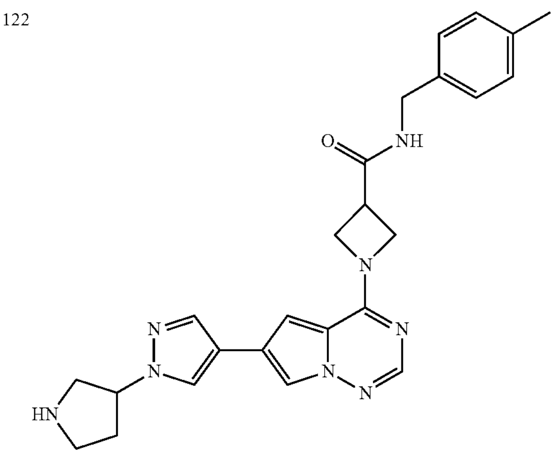 |
| 123 | 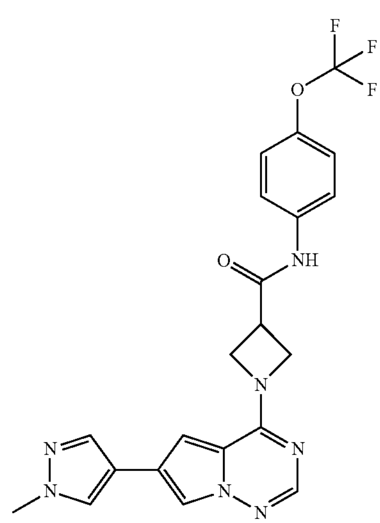 [SMILES: Cn1cc(-c2cc3c(N4CC(C(=O)Nc5ccc(OC(F)(F)F)cc5)C4)ncnn3c2)cn1] |

| # | Structure |
|---|---|
| 124 | 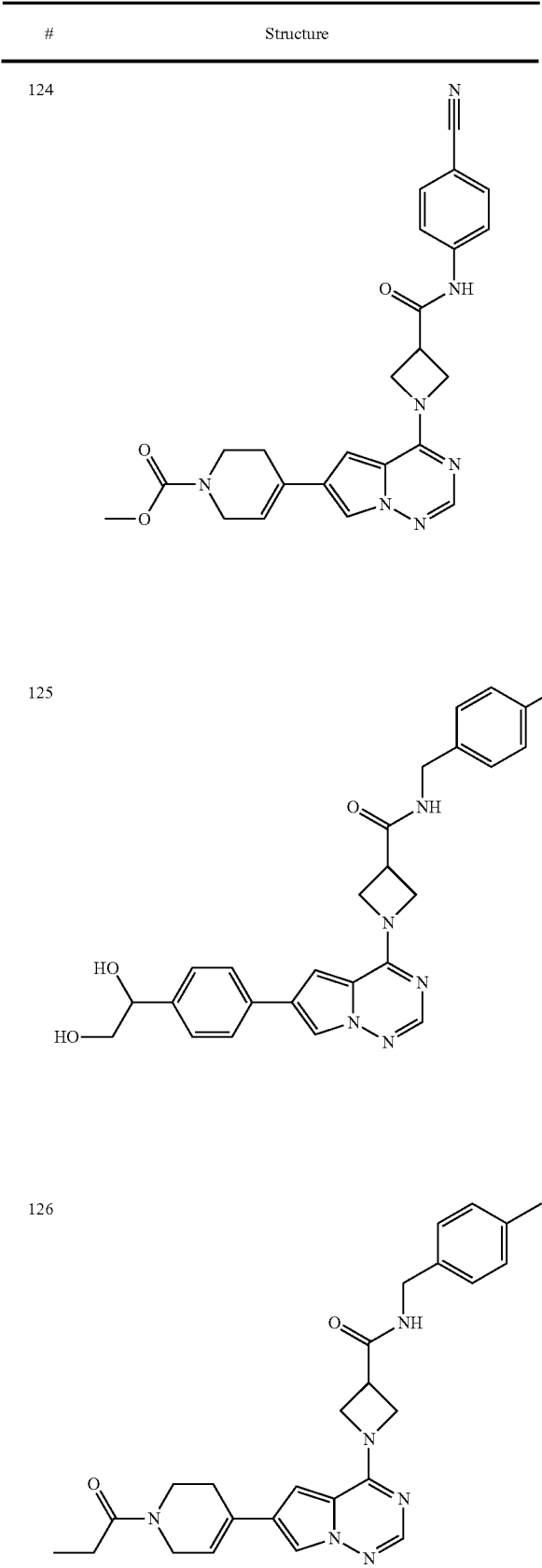 |
| 125 | |
| 126 | |
| # | Structure |
|---|---|
| 127 | 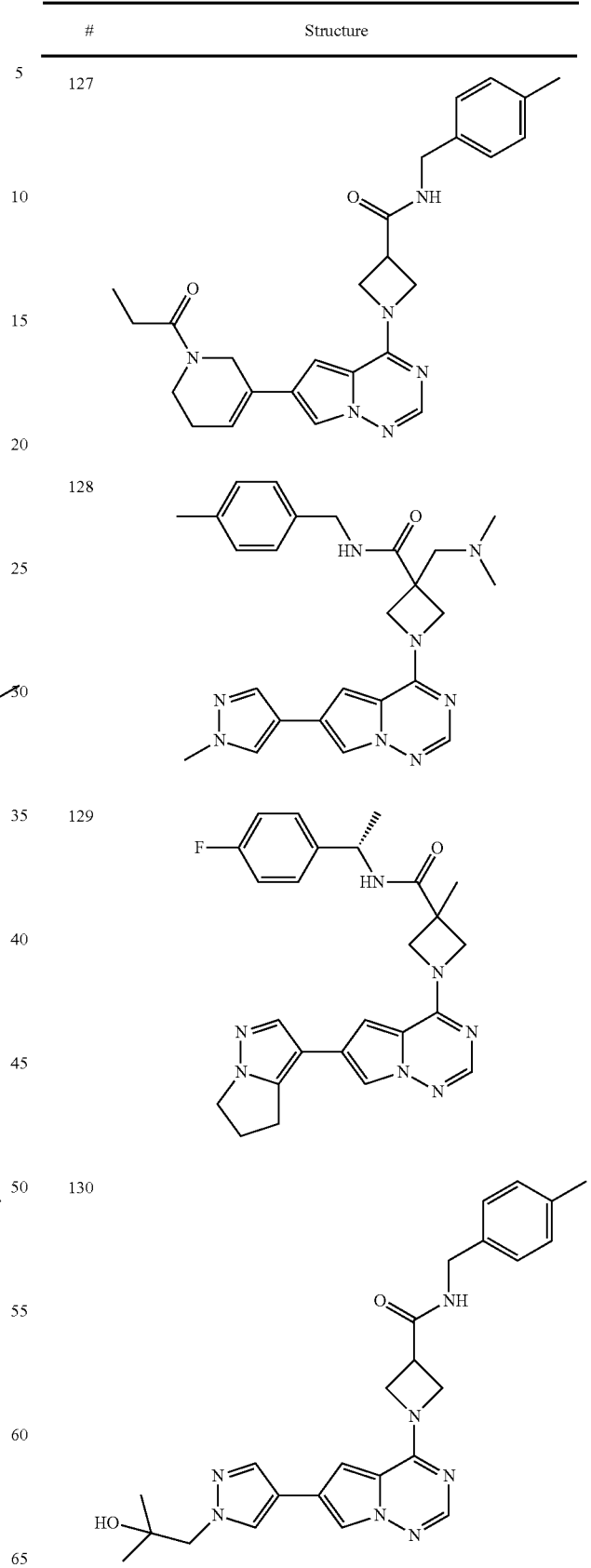 |
| 128 | |
| 129 | |
| 130 | |

US 9,688,680 B2
321
-continued
| # | Structure |
|---|---|
| 131 | 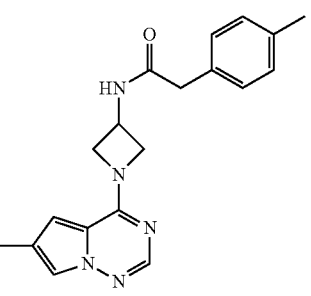 |
| 132 | 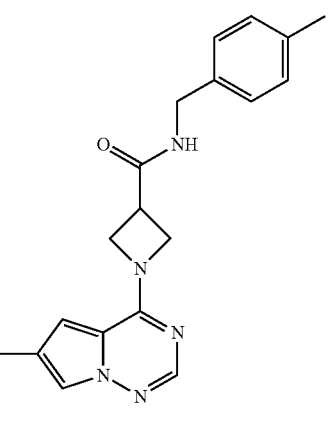 |
| 133 | 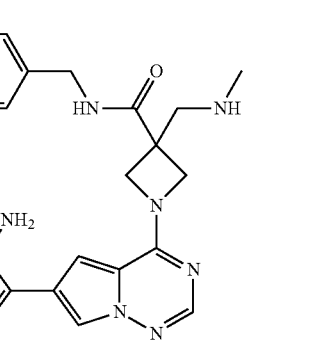 |
| 134 | 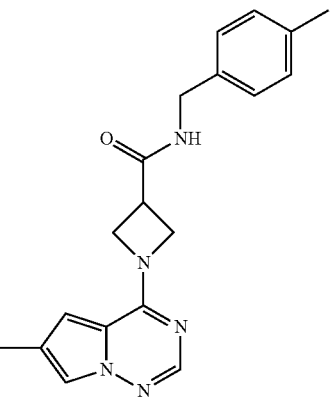 |
322
-continued
| # | Structure |
|---|---|
| 135 | 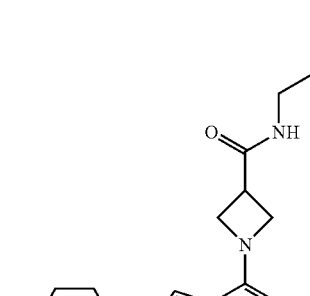 |
| 136 | 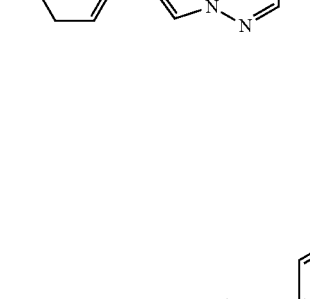 |
| 137 | 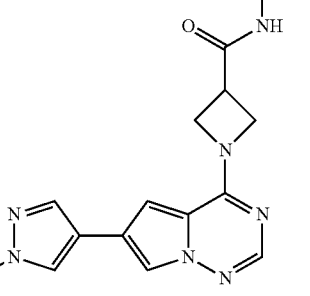 |

| # | Structure |
|---|---|
| 138 | 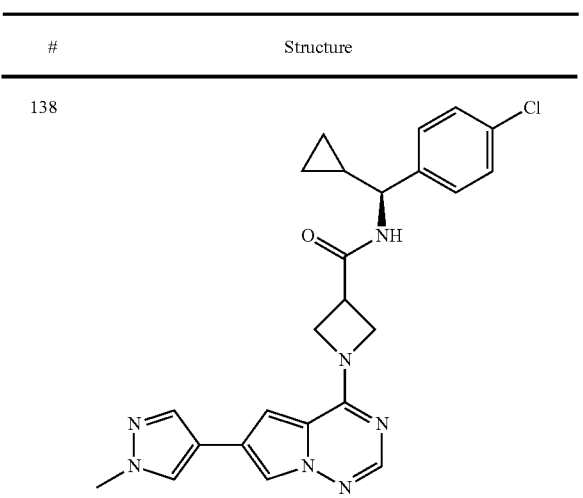 |
| 139 | 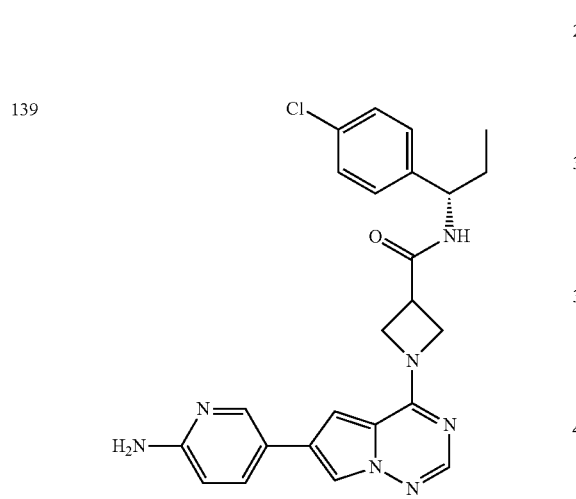 |
| 140 | 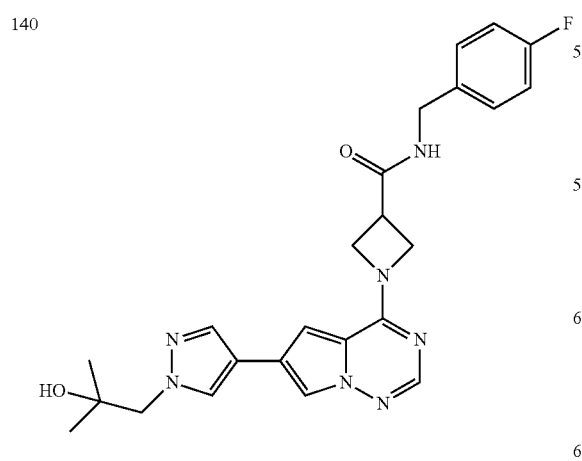 |
| # | Structure |
|---|---|
| 141 | 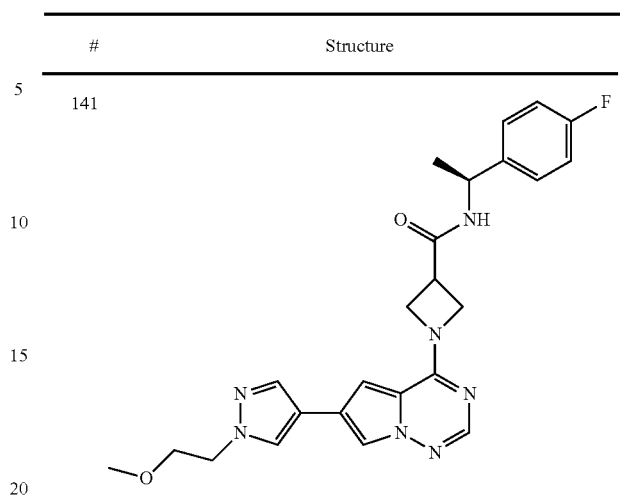 |
| 142 | 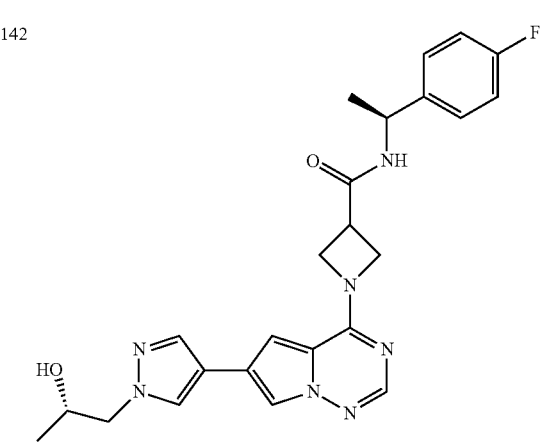 |
| 143 | 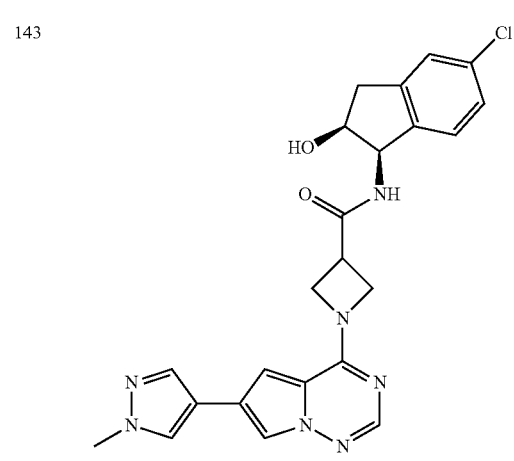 |

| # | Structure |
|---|---|
| 144 | 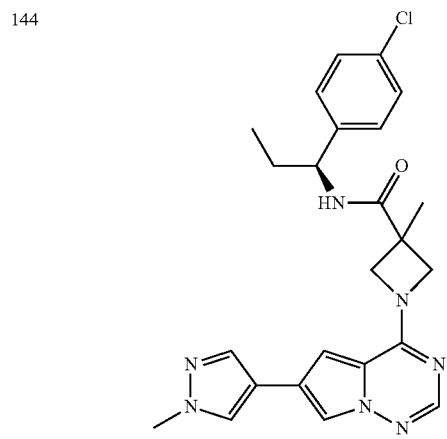 |
| 145 | 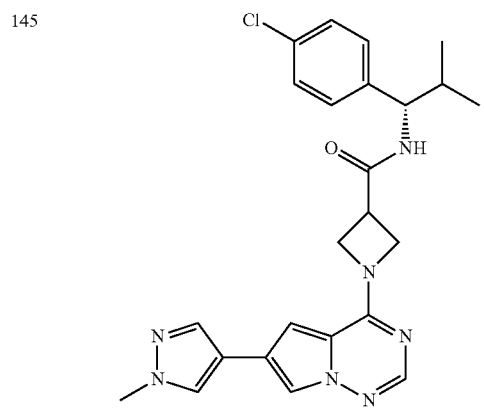 |
| 146 | 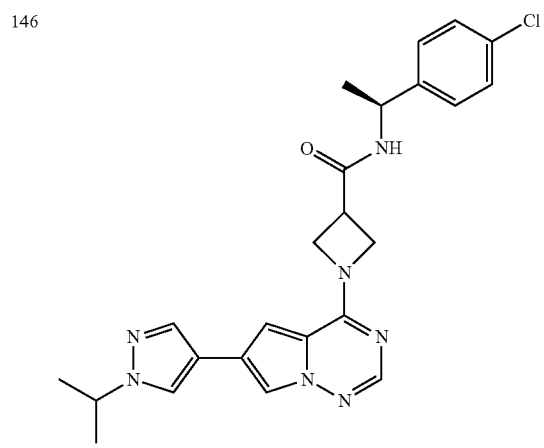 |
| # | Structure |
|---|---|
| 147 | 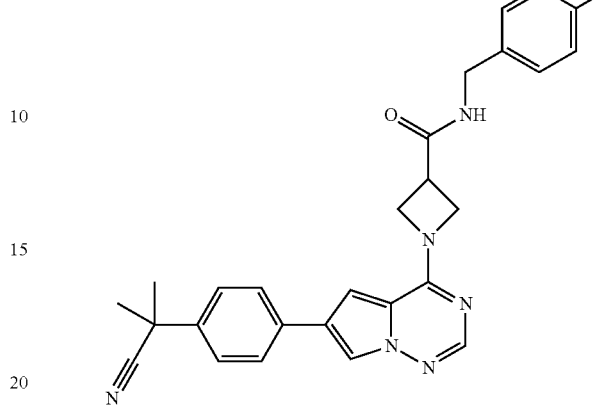 |
| 148 | 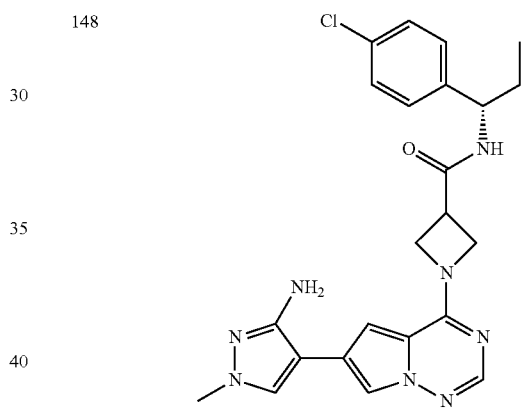 |
| 149 | 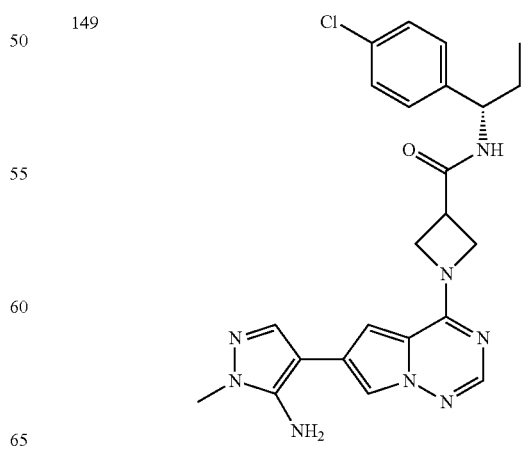 |

| # | Structure |
|---|---|
| 150 | |
| 151 | |
| 152 | |
| 153 | 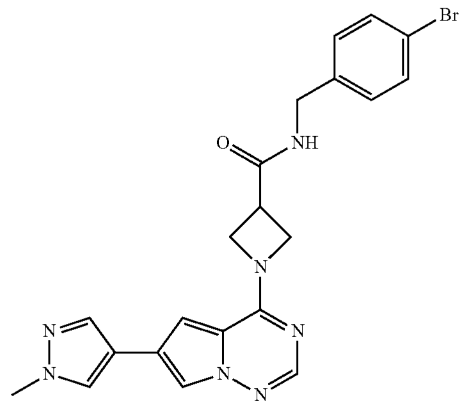 [SMILES: Cn1cc(-c2cc3c(N4CC(C(=O)NCc5ccc(Br)cc5)C4)ncnn3c2)cn1] |
| 154 | 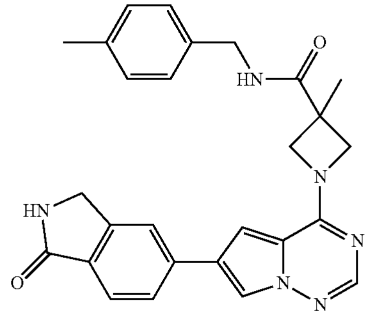 [SMILES: Cc1ccc(CNC(=O)C2(C)CN(c3ncnn4cc(-c5ccc6c(c5)CNC6=O)cc34)C2)cc1] |
| 155 | 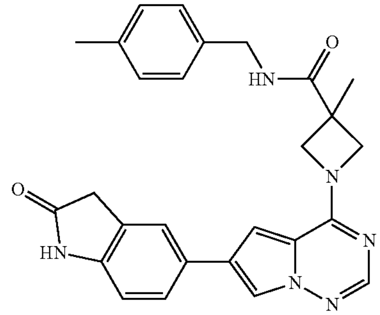 [SMILES: Cc1ccc(CNC(=O)C2(C)CN(c3ncnn4cc(-c5ccc6c(c5)CC(=O)N6)cc34)C2)cc1] |
| 156 | 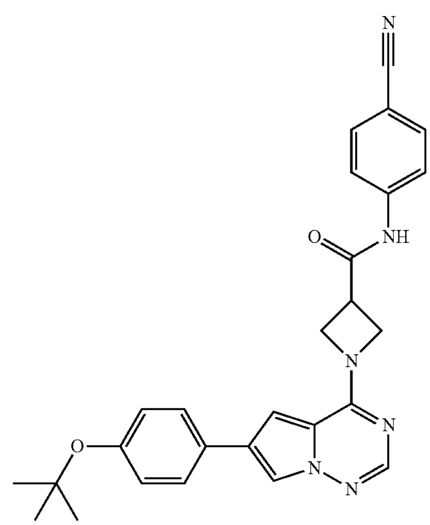 [SMILES: CC(C)(C)Oc1ccc(-c2cc3c(N4CC(C(=O)Nc5ccc(C#N)cc5)C4)ncnn3c2)cc1] |

329
-continued
| # | Structure |
|---|---|
| 157 | 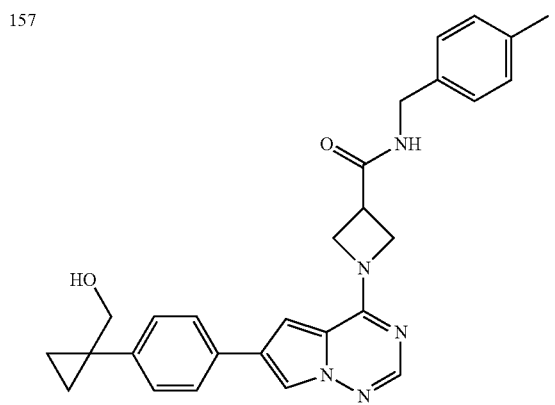 |
| 158 | 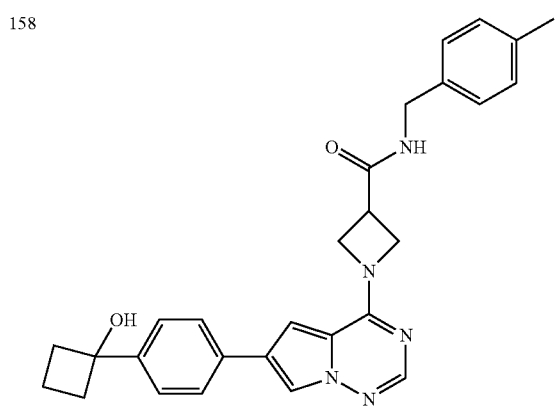 |
| 159 | 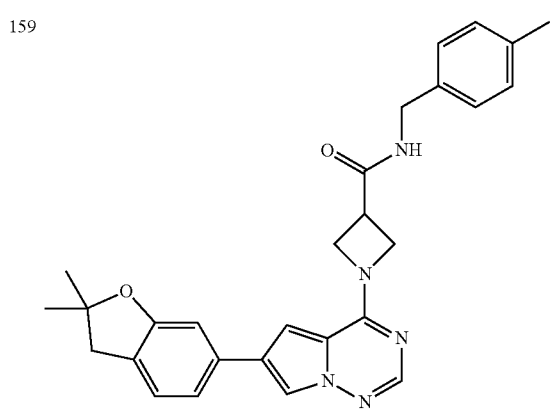 |
330
-continued
| # | Structure |
|---|---|
| 160 | 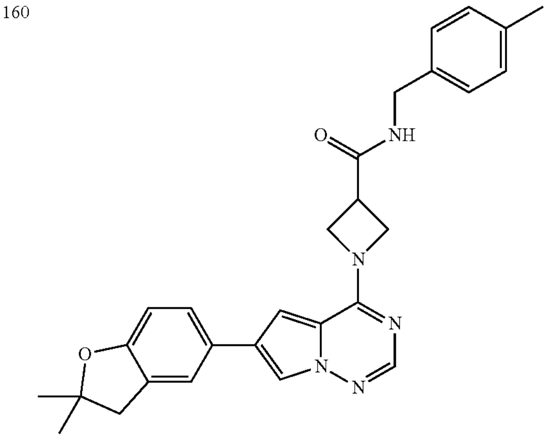 |
| 161 | 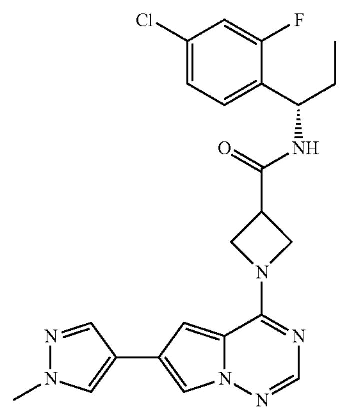 [SMILES: CC[C@H](NC(=O)C1CN(c2ncnn3cc(-c4cnn(C)c4)cc23)C1)c1ccc(Cl)cc1F] |
| 162 | 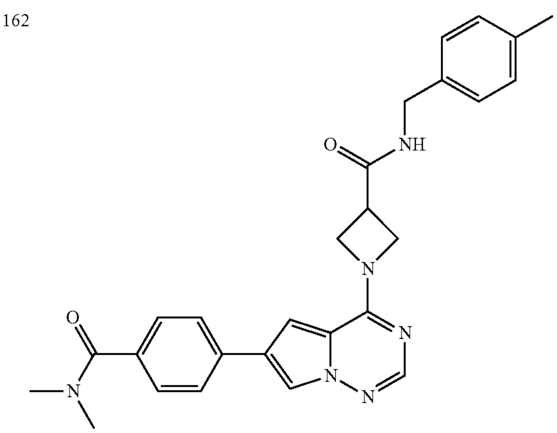 |
| 163 | 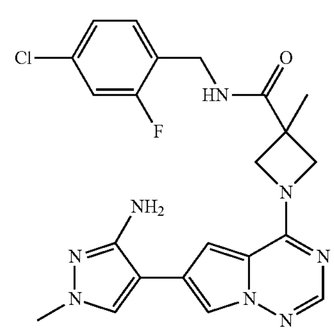 [SMILES: Cn1cc(-c2cc3c(N4CC(C)(C(=O)NCc5ccc(Cl)cc5F)C4)ncnn3c2)c(N)n1] |
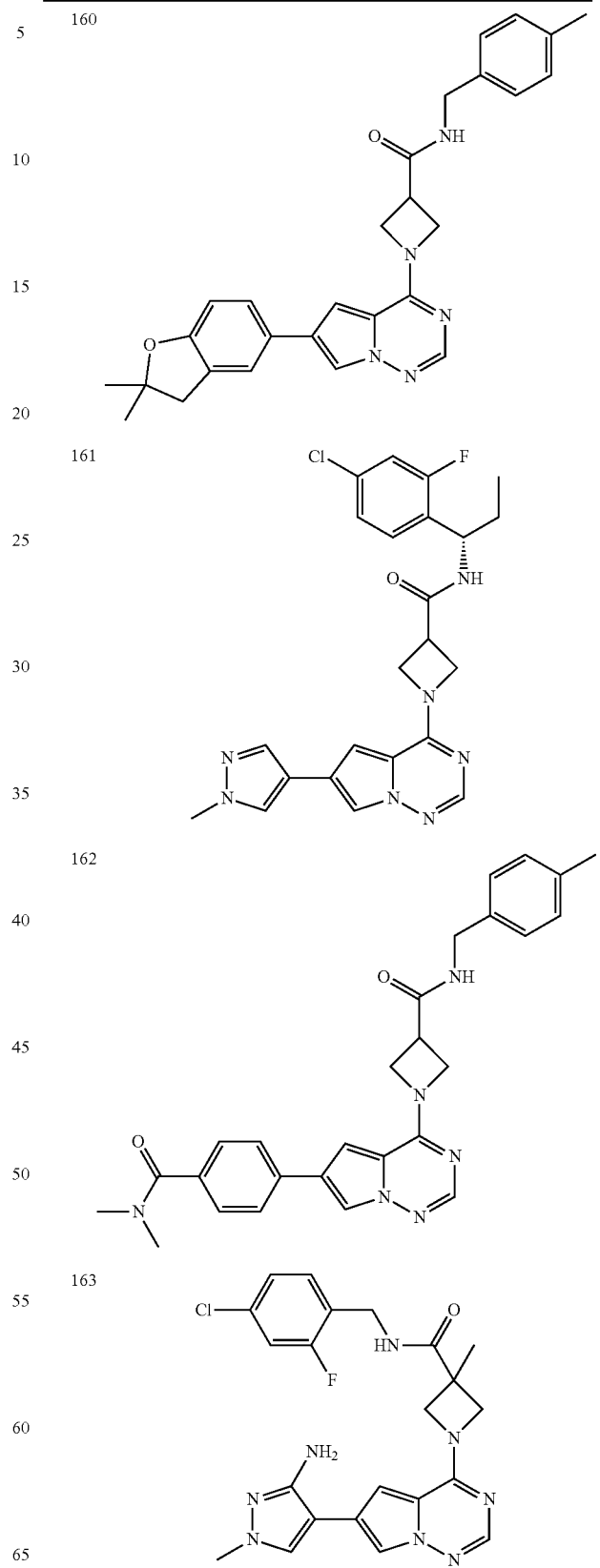

331
-continued

| # | Structure |
|---|---|
| 164 | 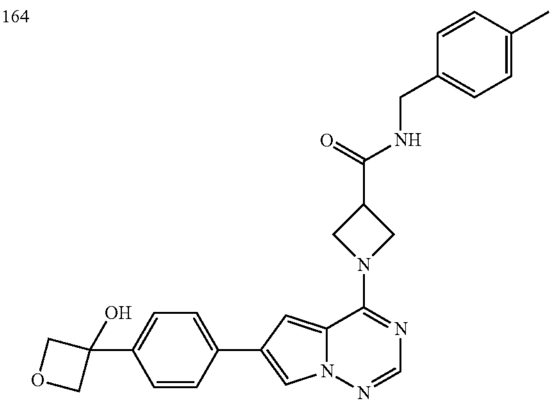 |
| 165 | 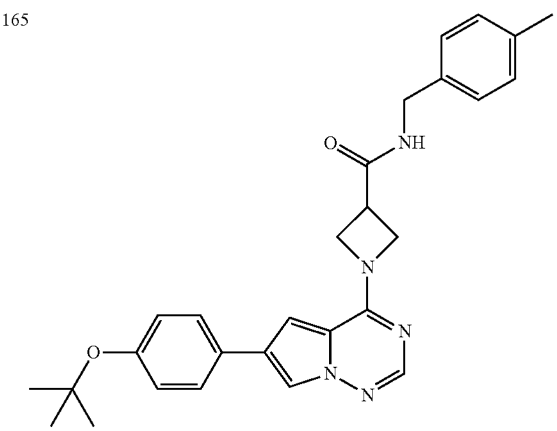 |
| 166 | 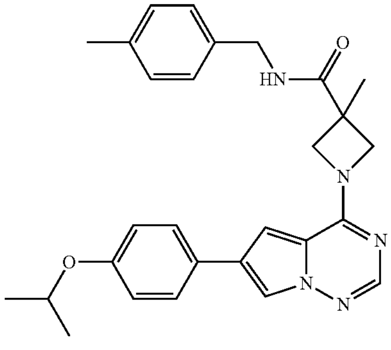 [SMILES: Cc1ccc(CNC(=O)C2(C)CN(c3ncnn4cc(-c5ccc(OC(C)C)cc5)cc34)C2)cc1] |

332
-continued

| # | Structure |
|---|---|
| 167 | 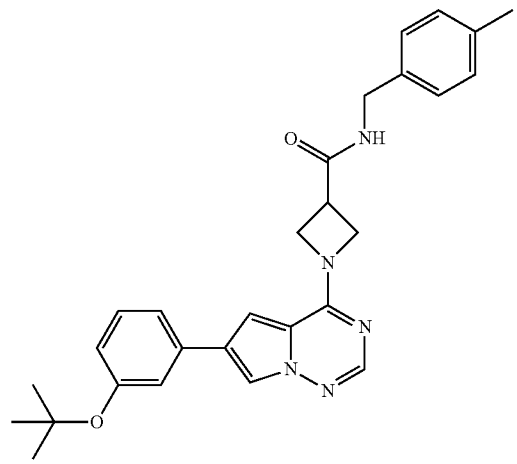 [SMILES: Cc1ccc(CNC(=O)C2CN(c3ncnn4cc(-c5cccc(OC(C)(C)C)c5)cc34)C2)cc1] |
| 168 | 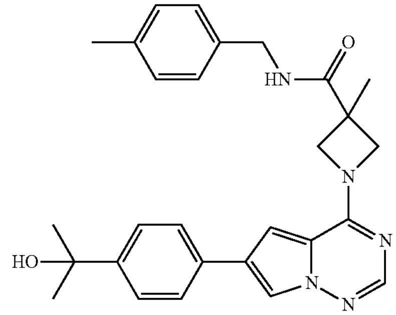 [SMILES: Cc1ccc(CNC(=O)C2(C)CN(c3ncnn4cc(-c5ccc(C(C)(C)O)cc5)cc34)C2)cc1] |
| 169 | 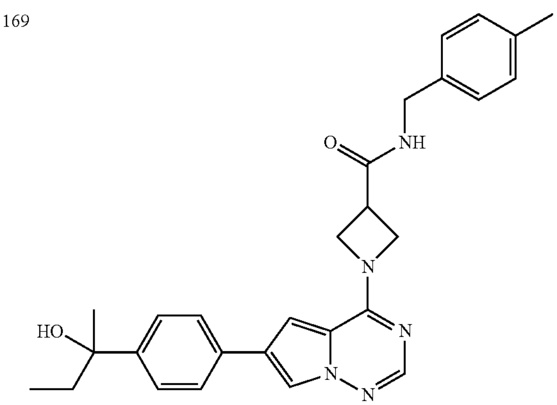 |
| 170 | 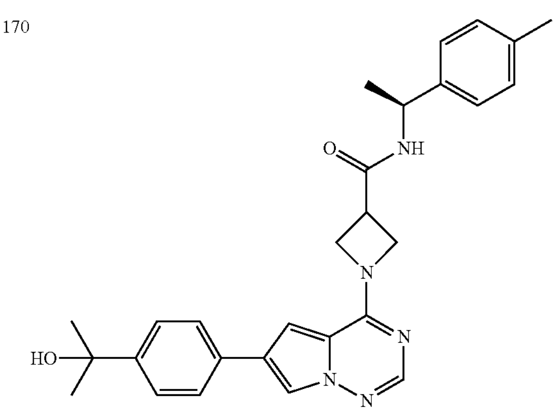 |

333
-continued
| # | Structure |
|---|---|
| 171 | 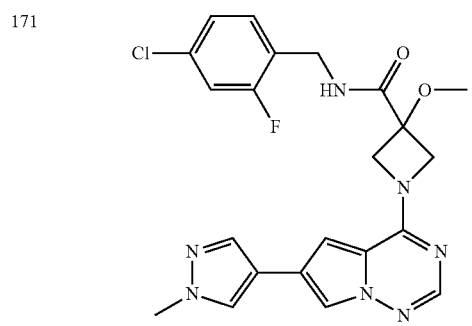 |
| 172 | 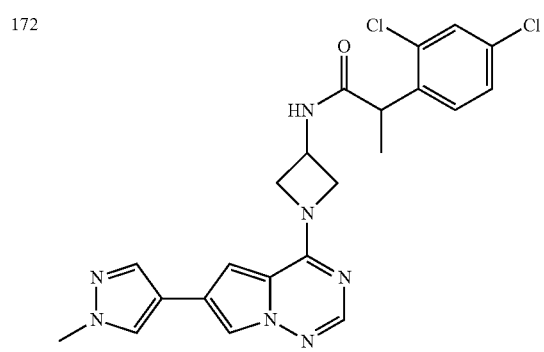 |
| 173 | 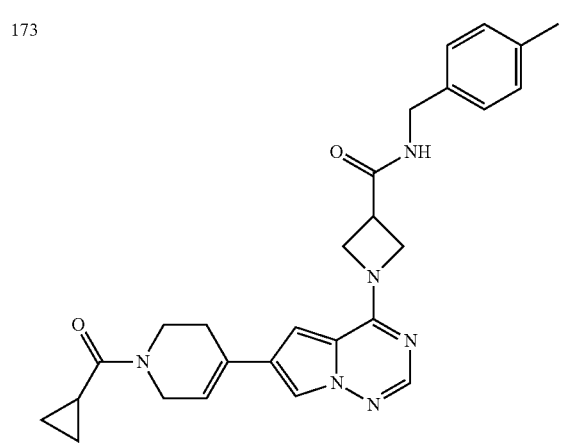 |
| 174 | 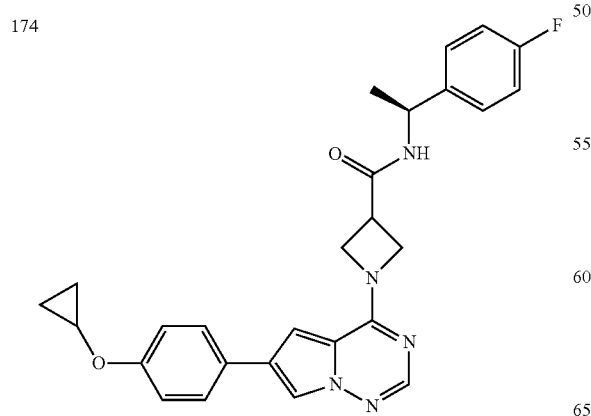 |
334
-continued
| # | Structure |
|---|---|
| 175 | 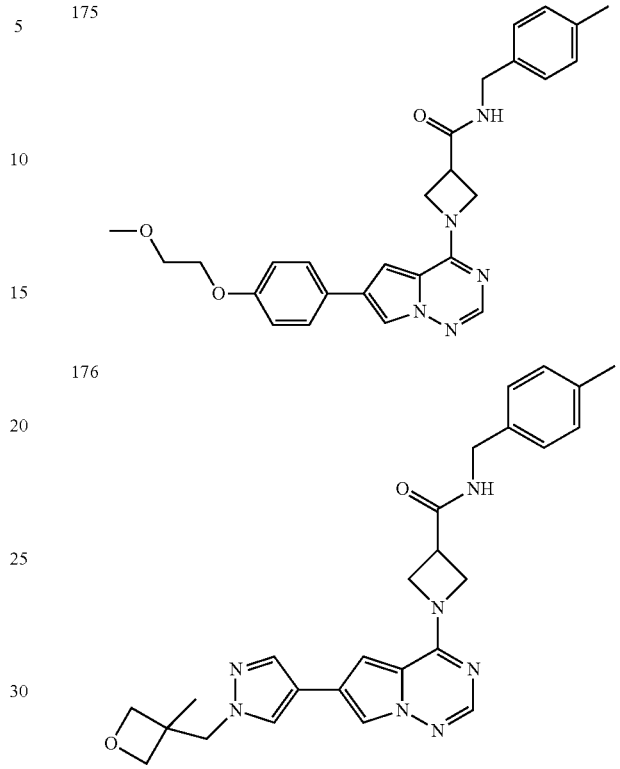 |
| 176 | 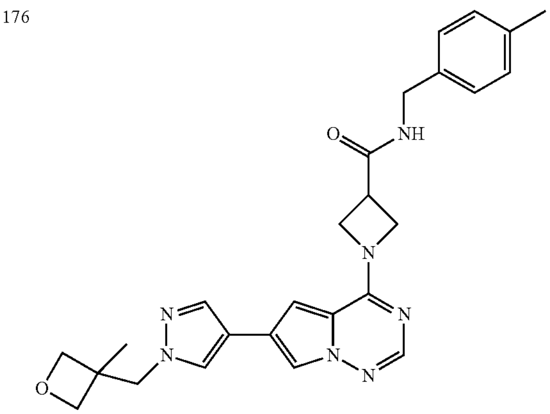 |
| 177 | 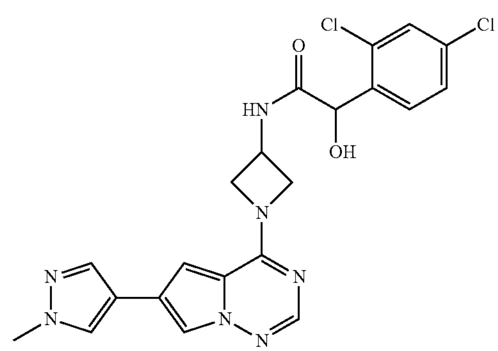 [SMILES: Cn1cc(-c2cc3c(N4CC(NC(=O)C(O)c5ccc(Cl)cc5Cl)C4)ncnn3c2)cn1] |
| 178 | 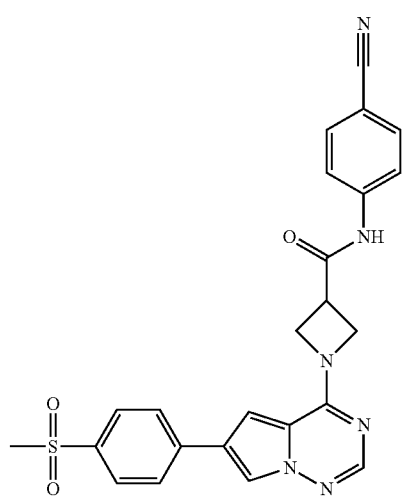 [SMILES: CS(=O)(=O)c1ccc(-c2cc3c(N4CC(C(=O)Nc5ccc(C#N)cc5)C4)ncnn3c2)cc1] |

| # | Structure |
|---|---|
| 179 | 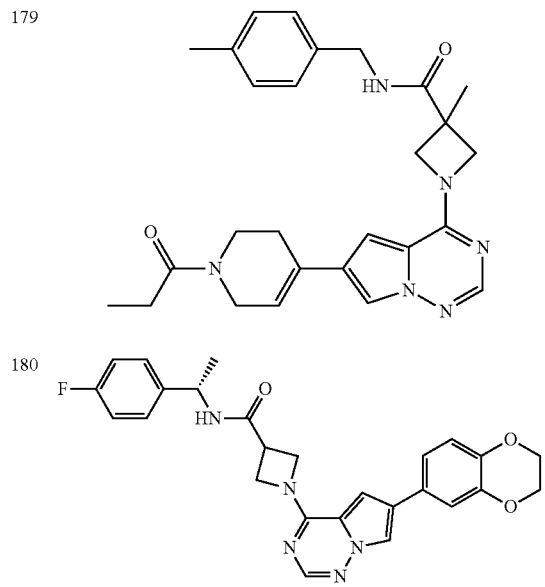 |
| 180 | |
| 181 | 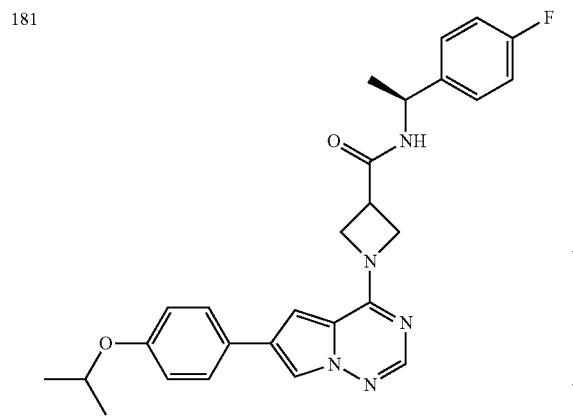 |
| 182 | 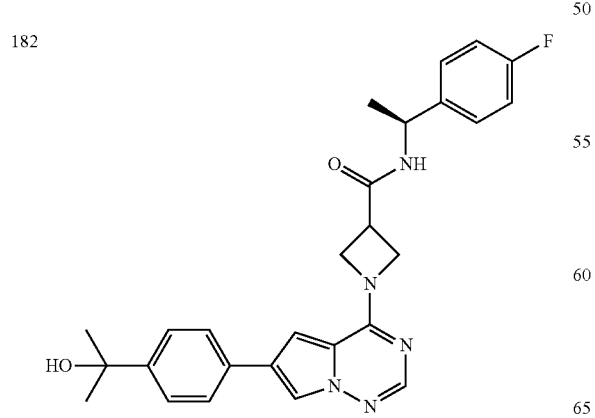 |
| # | Structure |
|---|---|
| 183 | 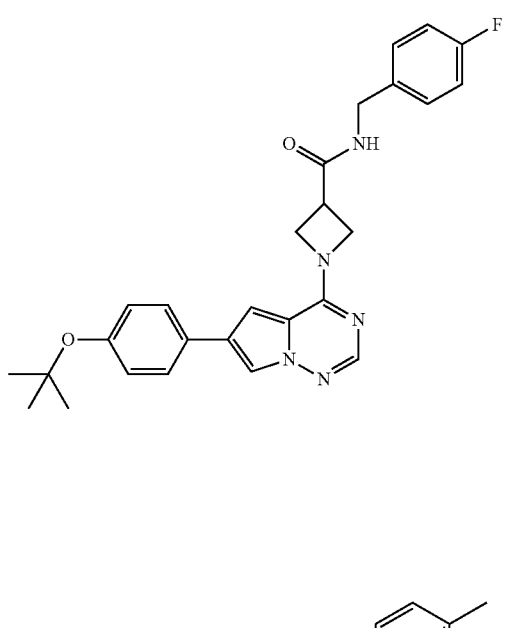 |
| 184 | |
| 185 | 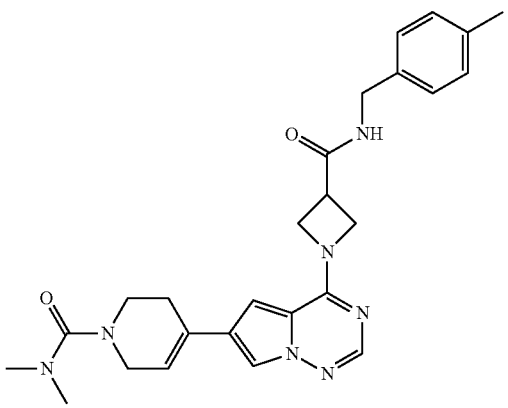 |

-continued
| # | Structure |
|---|---|
| 186 | 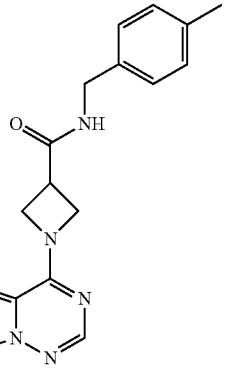 |
| 187 | 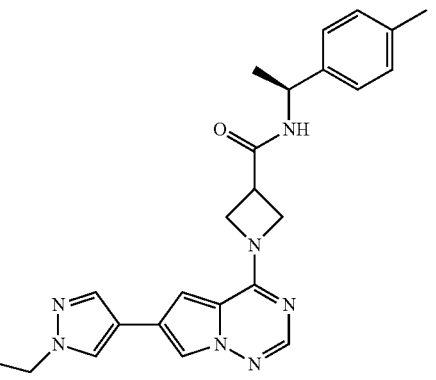 |
| 188 | 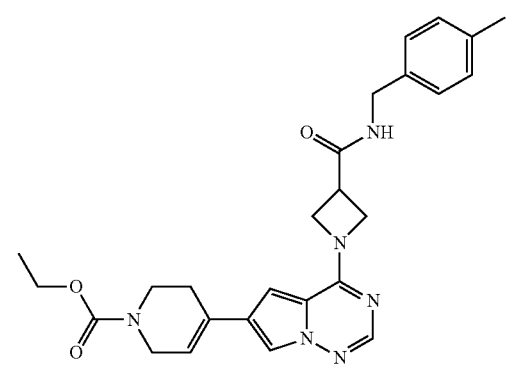 [SMILES: CCOC(=O)N1CC=C(c2cc3c(N4CC(C(=O)NCc5ccc(C)cc5)C4)ncnn3c2)CC1] |
| 189 | 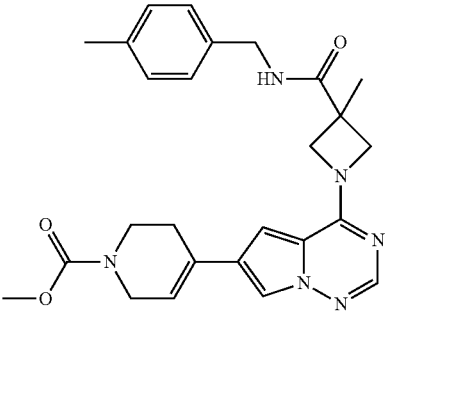 [SMILES: COC(=O)N1CC=C(c2cc3c(N4CC(C)(C(=O)NCc5ccc(C)cc5)C4)ncnn3c2)CC1] |
-continued
| # | Structure |
|---|---|
| 190 | 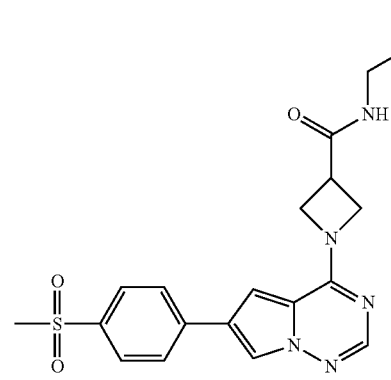 |
| 191 | 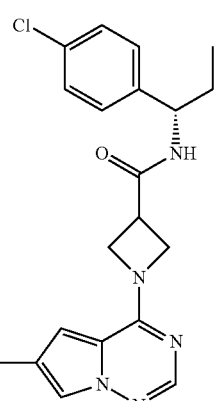 |
| 192 | 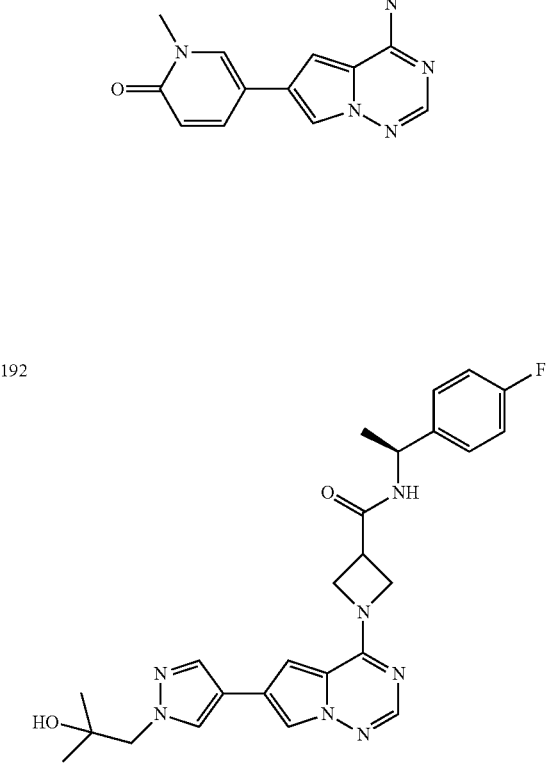 |

| # | Structure |
|---|---|
| 193 | 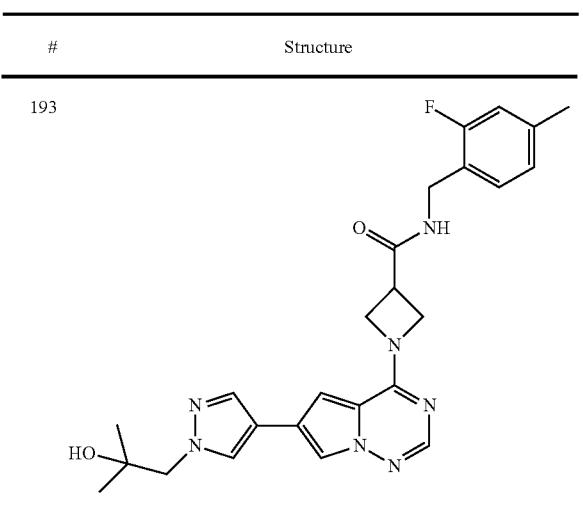 |
| 194 | 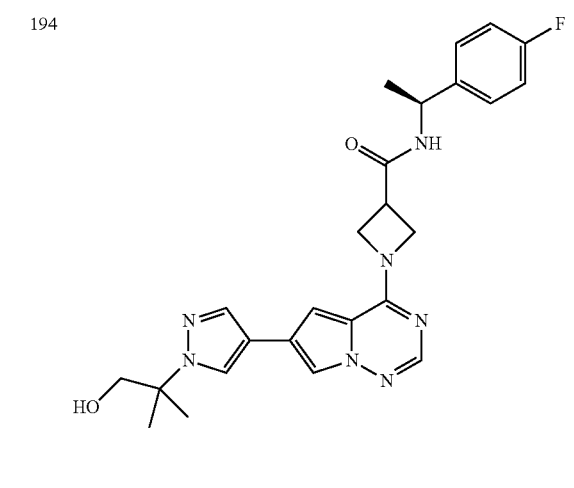 |
| 195 | 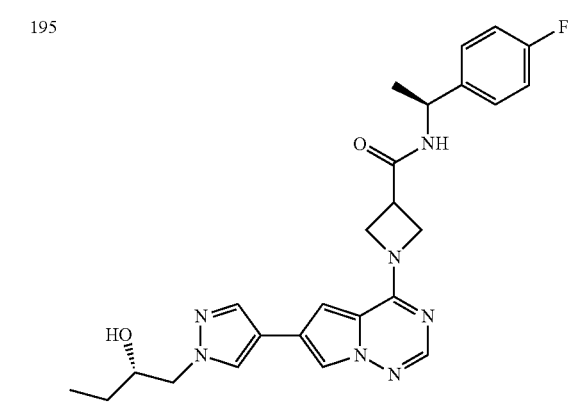 |
| # | Structure |
|---|---|
| 196 | 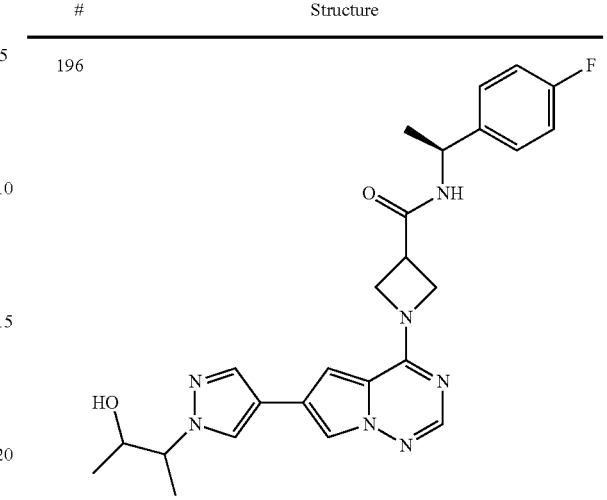 |
| 197 | 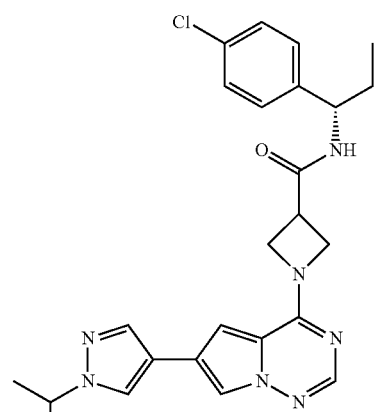 |
| 198 | 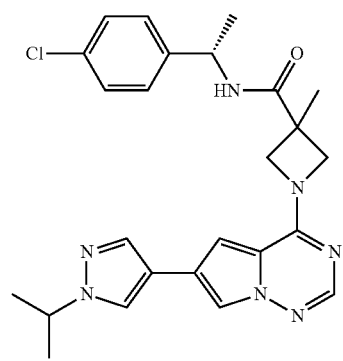 [SMILES: CC(C)n1cc(-c2cc3c(N4CC(C)(C(=O)N[C@@H](C)c5ccc(Cl)cc5)C4)ncnn3c2)cn1] |

-continued

| # | Structure |
|---|---|
| 199 | 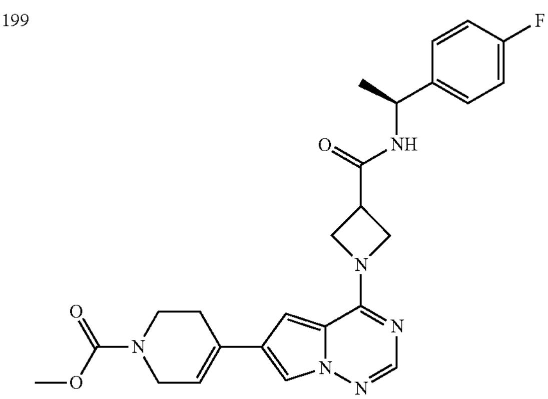 |
| 200 | 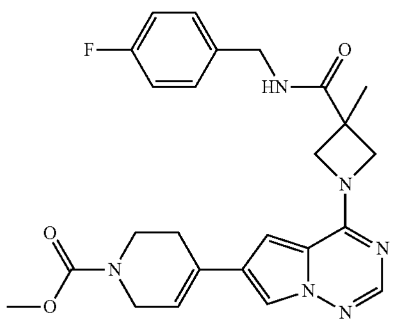 |
| 201 | 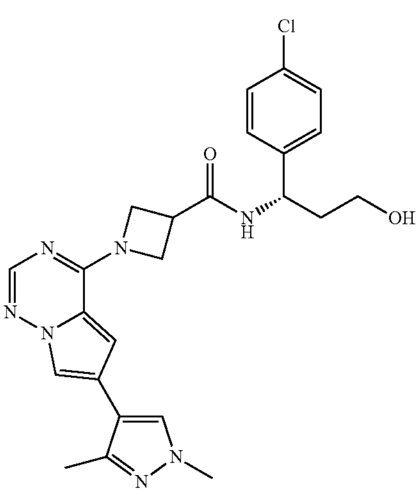 [SMILES: Cc1nn(C)cc1-c1cc2c(N3CC(C(=O)N[C@@H](CCO)c4ccc(Cl)cc4)C3)ncnn2c1] |

-continued

| # | Structure |
|---|---|
| 202 | 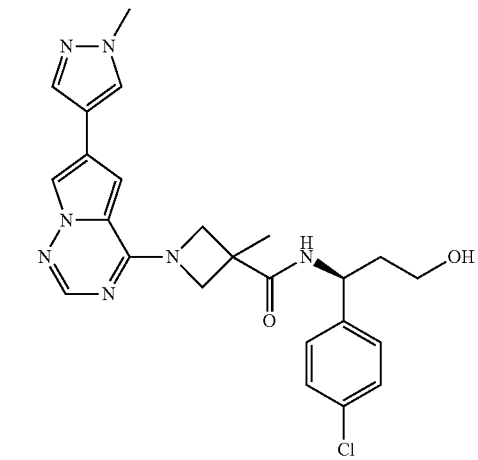 [SMILES: Cn1cc(-c2cc3c(N4CC(C)(C(=O)N[C@@H](CCO)c5ccc(Cl)cc5)C4)ncnn3c2)cn1] |
| 203 | 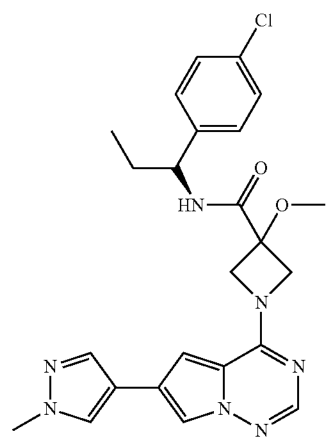 |
| 204 | 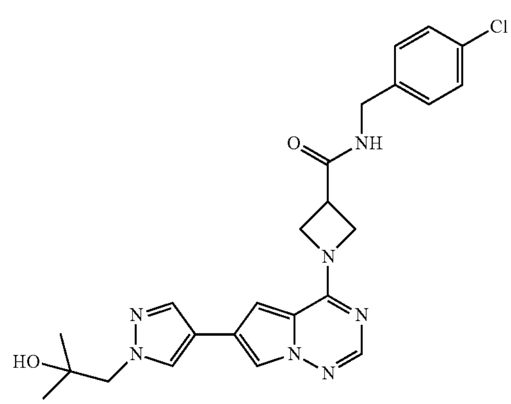 [SMILES: CC(C)(O)Cn1cc(-c2cc3c(N4CC(C(=O)NCc5ccc(Cl)cc5)C4)ncnn3c2)cn1] |

| # | Structure |
|---|---|
| 205 | 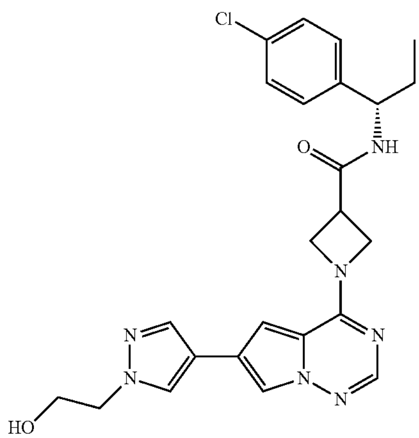 [SMILES: CC[C@H](NC(=O)C1CN(c2ncnn3cc(-c4cnn(CCO)c4)cc23)C1)c1ccc(Cl)cc1] |
| 206 | 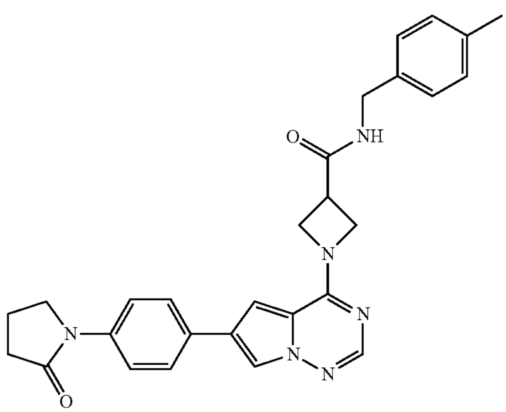 [SMILES: Cc1ccc(CNC(=O)C2CN(c3ncnn4cc(-c5ccc(N6CCCC6=O)cc5)cc34)C2)cc1] |
| 207 | 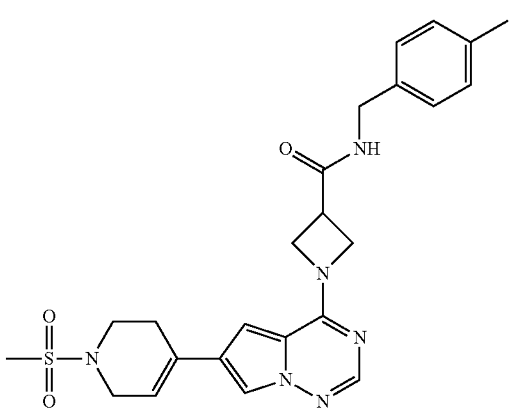 |
| 208 | |
| 209 | |
| 210 | |

-continued

| # | Structure |
|---|---|
| 211 | 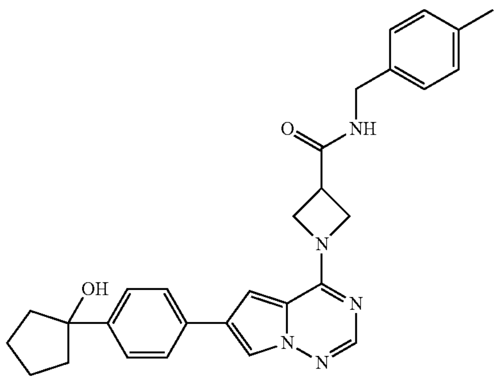 [SMILES: Cc1ccc(CNC(=O)C2CN(c3ncnn4cc(-c5ccc(C6(O)CCCC6)cc5)cc34)C2)cc1] |
| 212 | 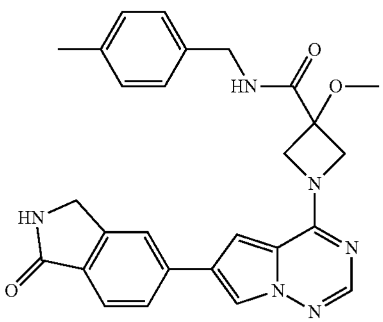 [SMILES: COC1(C(=O)NCc2ccc(C)cc2)CN(c2ncnn3cc(-c4ccc5c(c4)CNC5=O)cc23)C1] |
| 213 | 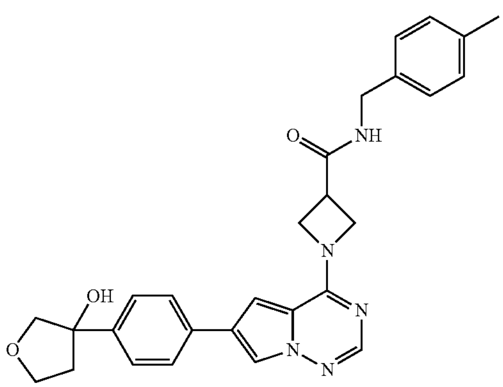 [SMILES: Cc1ccc(CNC(=O)C2CN(c3ncnn4cc(-c5ccc(C6(O)CCOC6)cc5)cc34)C2)cc1] |
| 214 | 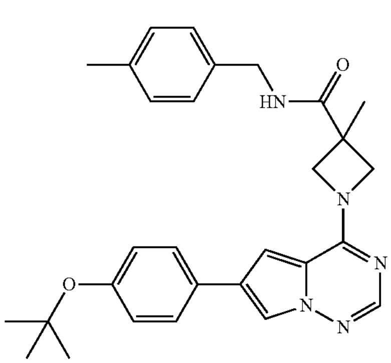 |

-continued

| # | Structure |
|---|---|
| 215 | 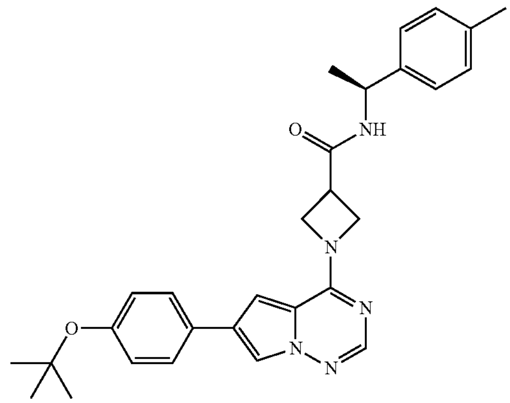 [SMILES: Cc1ccc([C@H](C)NC(=O)C2CN(c3ncnn4cc(-c5ccc(OC(C)(C)C)cc5)cc34)C2)cc1] |
| 216 | 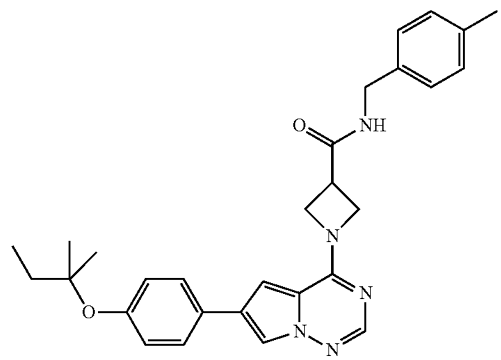 [SMILES: CCC(C)(C)Oc1ccc(-c2cc3c(N4CC(C(=O)NCc5ccc(C)cc5)C4)ncnn3c2)cc1] |
| 217 | 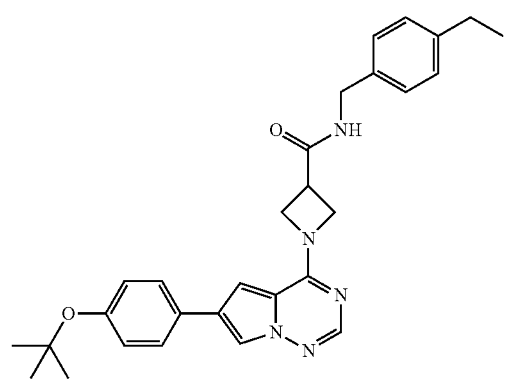 [SMILES: CCc1ccc(CNC(=O)C2CN(c3ncnn4cc(-c5ccc(OC(C)(C)C)cc5)cc34)C2)cc1] |
| 218 | 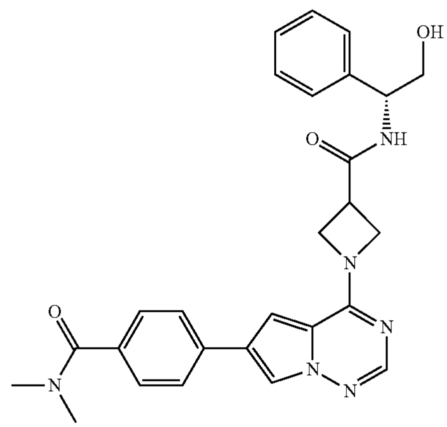 [SMILES: CN(C)C(=O)c1ccc(-c2cc3c(N4CC(C(=O)N[C@@H](CO)c5ccccc5)C4)ncnn3c2)cc1] |

-continued

| # | Structure |
|---|---|
| 219 | 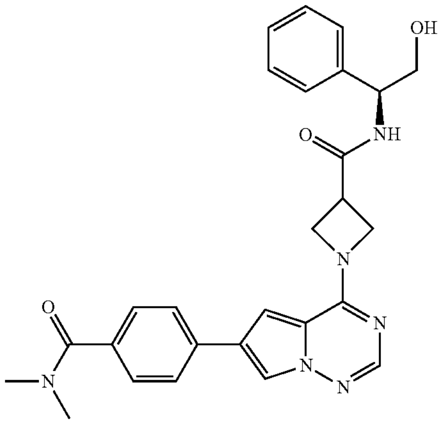 [SMILES: CN(C)C(=O)c1ccc(-c2cc3c(N4CC(C(=O)N[C@H](CO)c5ccccc5)C4)ncnn3c2)cc1] |
| 220 | 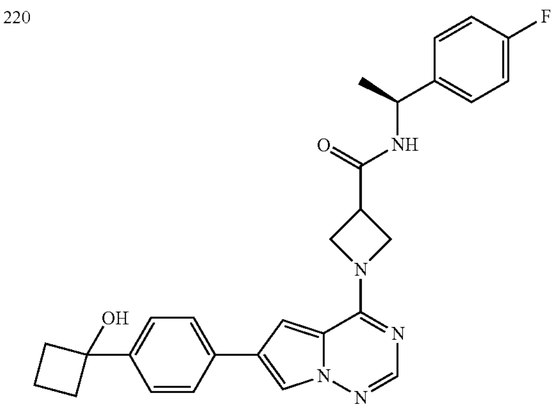 |
| 221 | 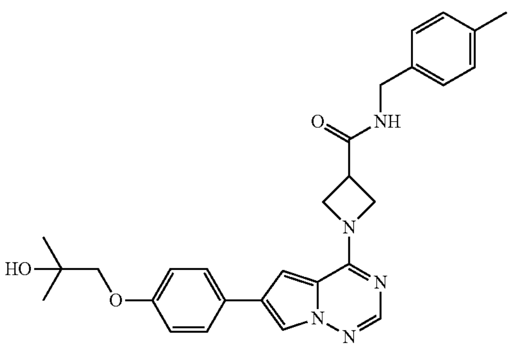 [SMILES: Cc1ccc(CNC(=O)C2CN(c3ncnn4cc(-c5ccc(OCC(C)(C)O)cc5)cc34)C2)cc1] |
| 222 | 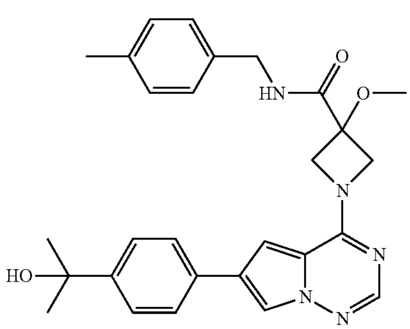 [SMILES: COC1(C(=O)NCc2ccc(C)cc2)CN(c2ncnn3cc(-c4ccc(C(C)(C)O)cc4)cc23)C1] |

-continued

| # | Structure |
|---|---|
| 223 | 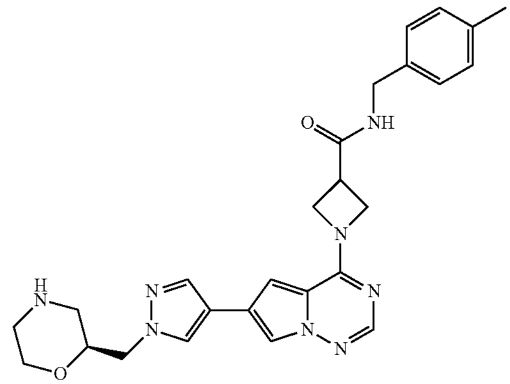 [SMILES: Cc1ccc(CNC(=O)C2CN(c3ncnn4cc(-c5cnn(C[C@@H]6CNCCO6)c5)cc34)C2)cc1] |
| 224 | 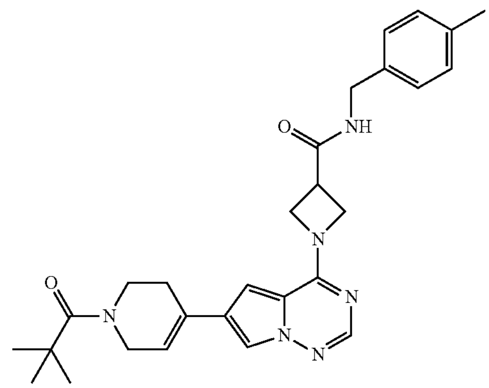 [SMILES: Cc1ccc(CNC(=O)C2CN(c3ncnn4cc(C5=CCN(C(=O)C(C)(C)C)CC5)cc34)C2)cc1] |
| 225 | 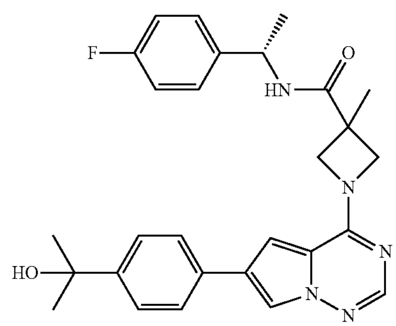 [SMILES: C[C@H](NC(=O)C1(C)CN(c2ncnn3cc(-c4ccc(C(C)(C)O)cc4)cc23)C1)c1ccc(F)cc1] |
| 226 | 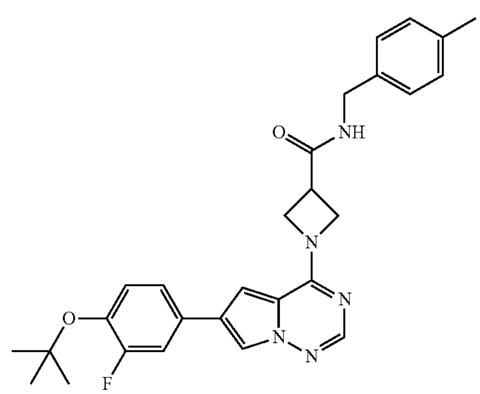 [SMILES: Cc1ccc(CNC(=O)C2CN(c3ncnn4cc(-c5ccc(OC(C)(C)C)c(F)c5)cc34)C2)cc1] |

-continued
| # | Structure |
|---|---|
| 227 | 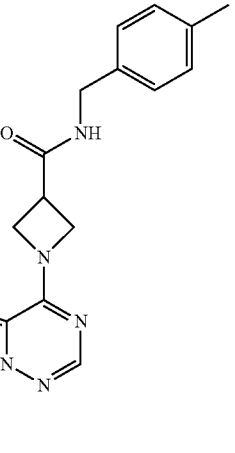 |
| 228 | 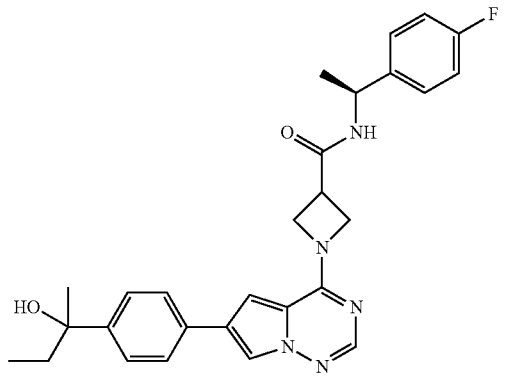 [SMILES: CCC(C)(O)c1ccc(-c2cc3c(N4CC(C(=O)N[C@@H](C)c5ccc(F)cc5)C4)ncnn3c2)cc1] |
| 229 | 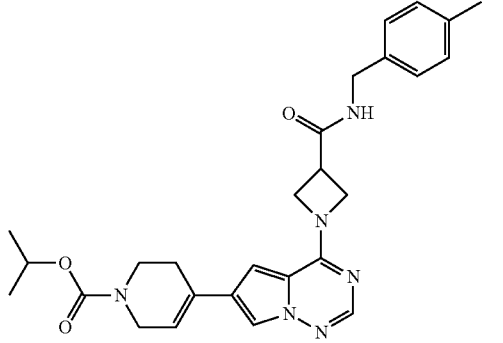 |
| 230 | 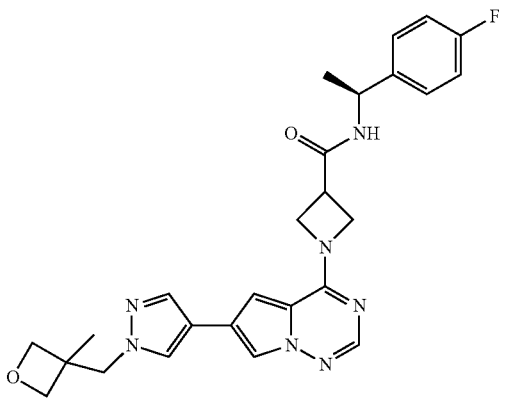 [SMILES: C[C@H](NC(=O)C1CN(c2ncnn3cc(-c4cnn(CC5(C)COC5)c4)cc23)C1)c1ccc(F)cc1] |
-continued
| # | Structure |
|---|---|
| 231 | 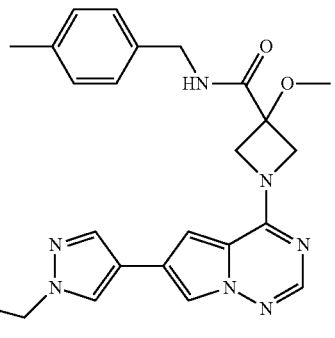 |
| 232 | 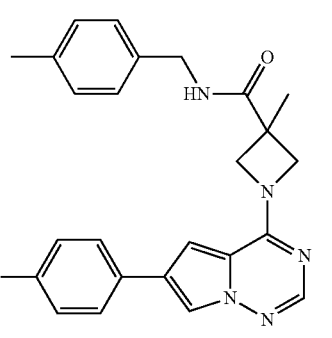 |
| 233 | 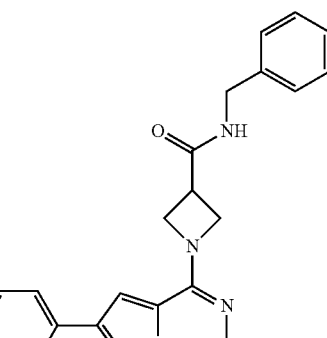 |
| 234 | 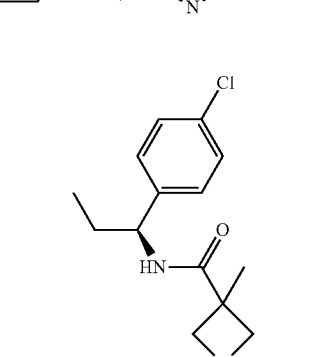 |

| # | Structure |
|---|---|
| 235 | 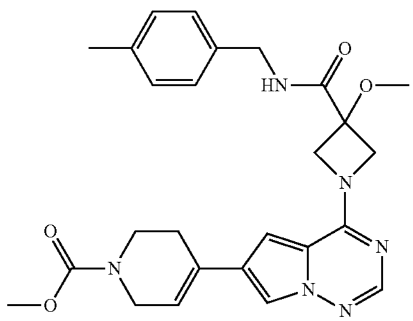 |
| 236 | 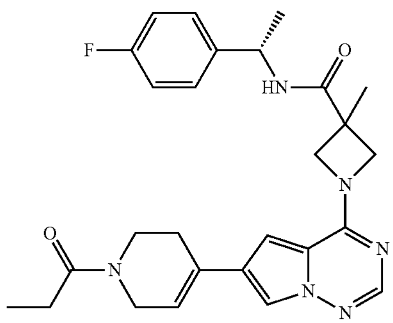 [SMILES: CCC(=O)N1CC=C(c2cc3c(N4CC(C)(C(=O)N[C@@H](C)c5ccc(F)cc5)C4)ncnn3c2)CC1] |
| 237 | 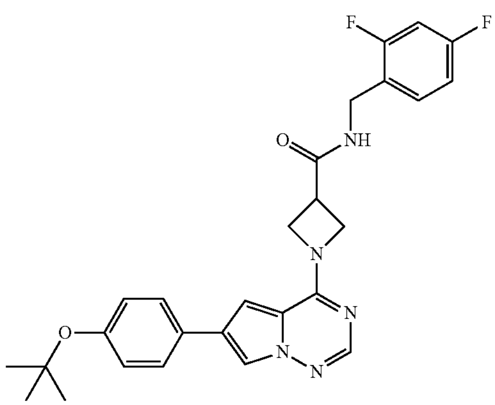 [SMILES: CC(C)(C)Oc1ccc(-c2cc3c(N4CC(C(=O)NCc5ccc(F)cc5F)C4)ncnn3c2)cc1] |
| 238 | 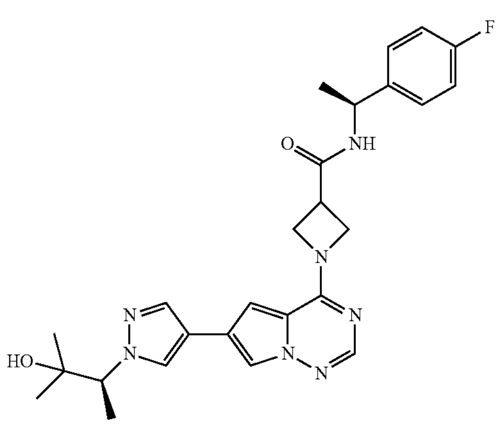 [SMILES: C[C@H](NC(=O)C1CN(c2ncnn3cc(-c4cnn([C@@H](C)C(C)(C)O)c4)cc23)C1)c1ccc(F)cc1] |
| 239 | |
| 240 | |
| 241 | |

353
-continued
| # | Structure |
|---|---|
| 242 | 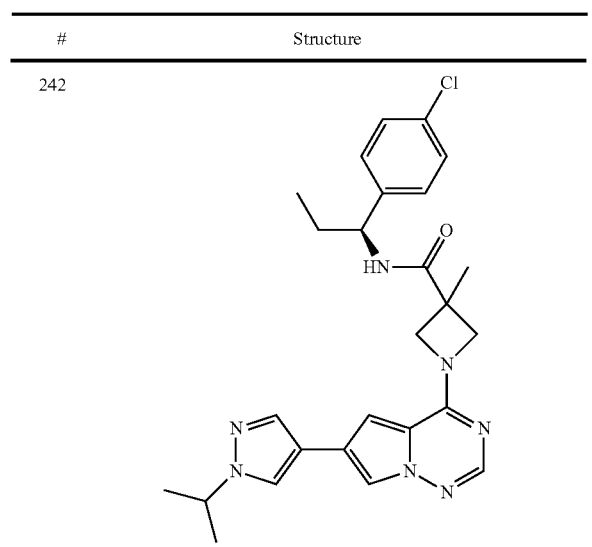 |
| 243 | 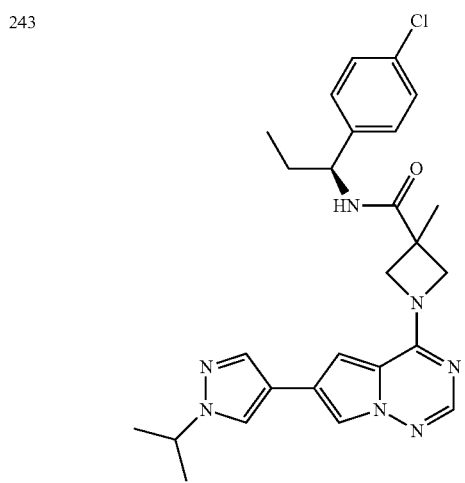 |
| 244 | 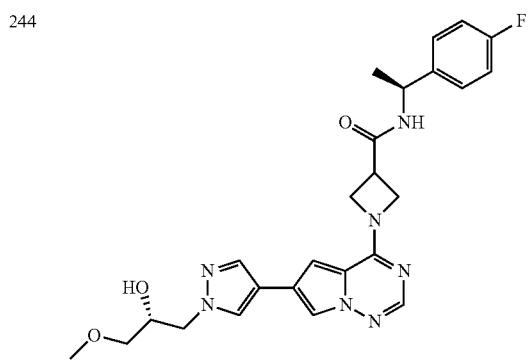 |
354
-continued
| # | Structure |
|---|---|
| 245 | 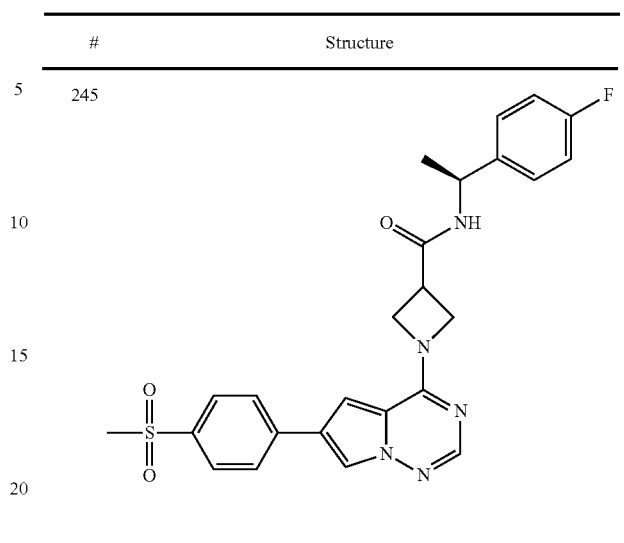 |
| 246 | 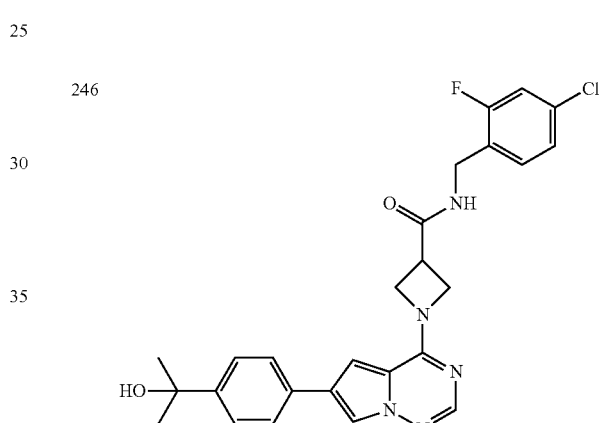 |
| 247 | 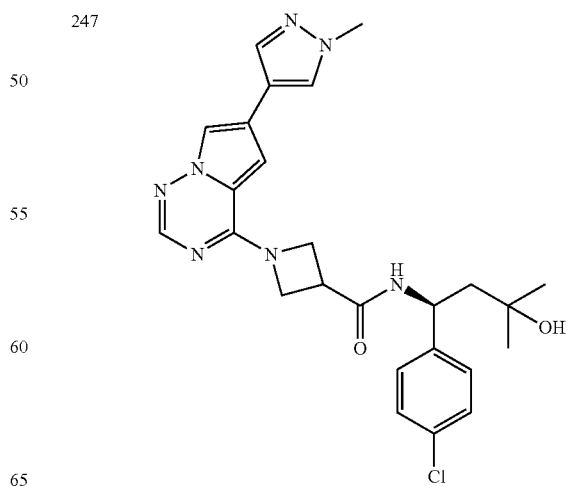 |

355
-continued
| # | Structure |
|---|---|
| 248 | 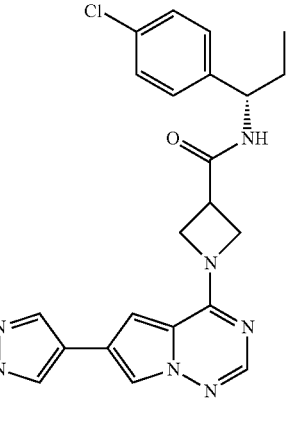 |
| 249 | 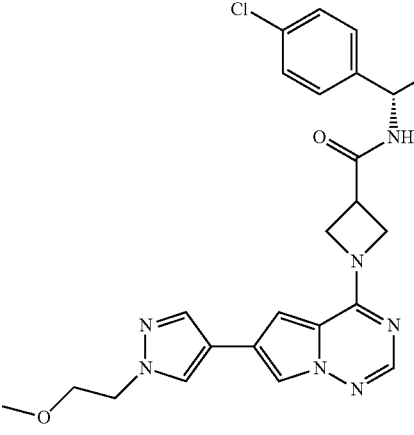 |
| 250 | 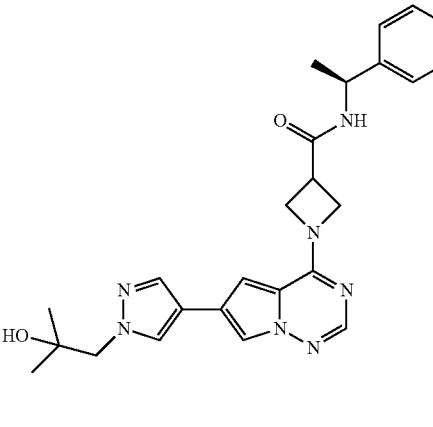 |
356
-continued
| # | Structure |
|---|---|
| 251 | 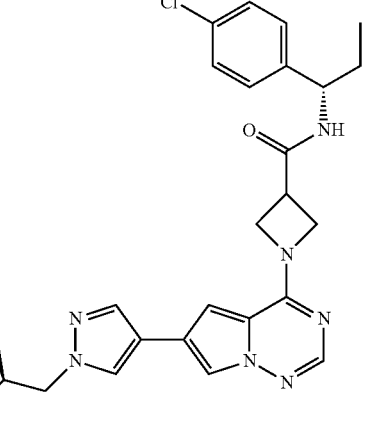 |
| 252 | 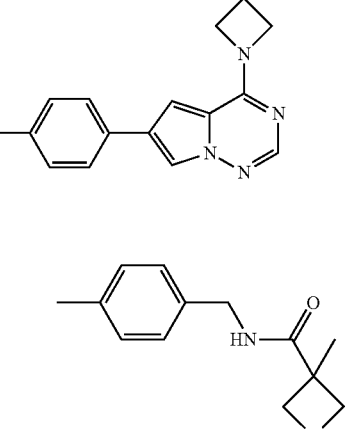 |
| 253 | 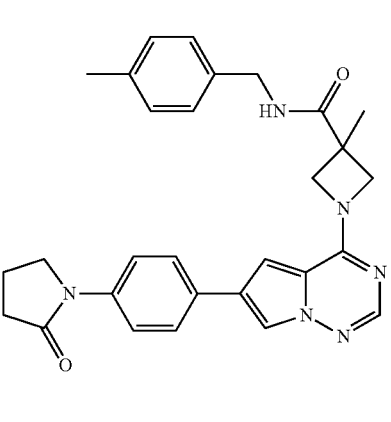 [SMILES: Cc1ccc(CNC(=O)C2(C)CN(c3ncnn4cc(-c5ccc(N6CCCC6=O)cc5)cc34)C2)cc1] |
| 254 | 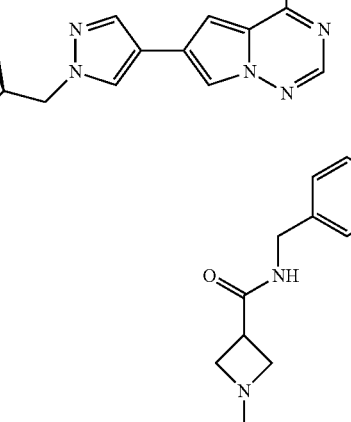 |

| # | Structure |
|---|---|
| 255 | 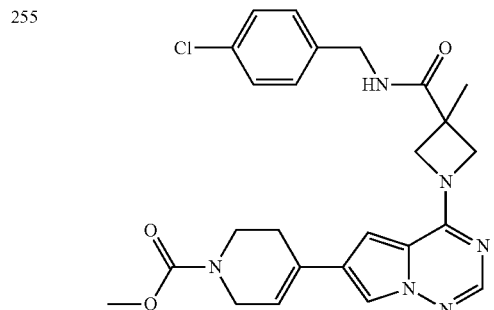 |
| 256 | 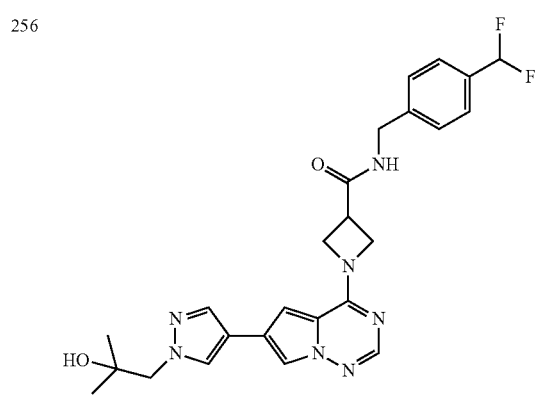 |
| 257 | 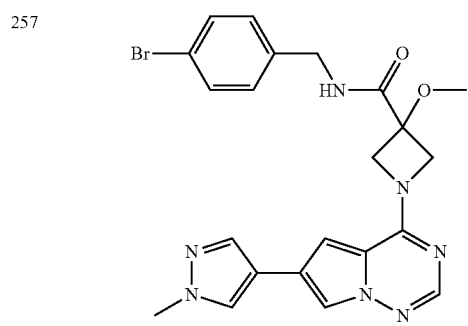 |
| 258 | 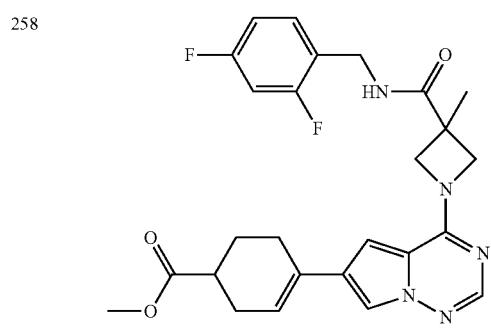 |
| # | Structure |
|---|---|
| 259 | 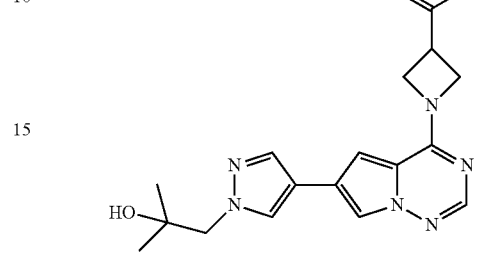 |
| 260 | 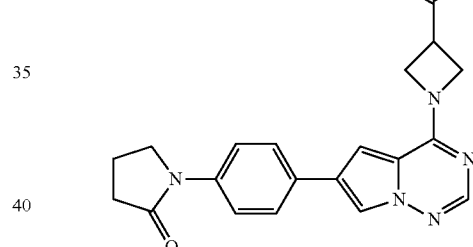 |
| 261 | 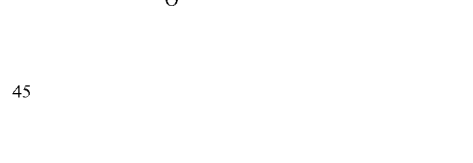 |

359
-continued
| # | Structure |
|---|---|
| 262 | 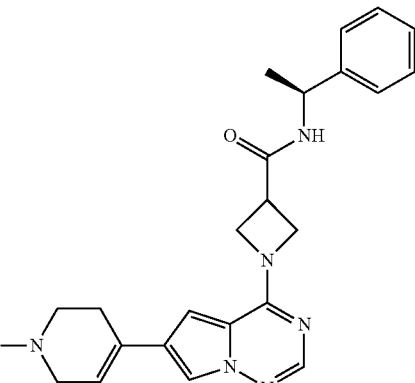 |
| 263 | 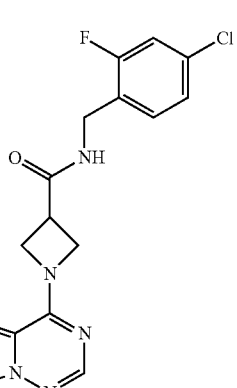 |
| 264 | 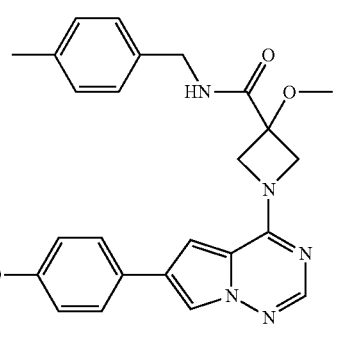 |
| 265 | 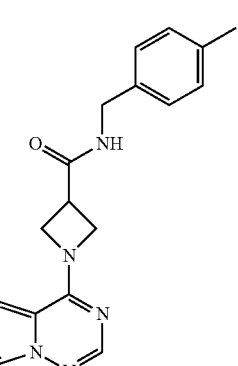 |
360
-continued
| # | Structure |
|---|---|
| 266 | 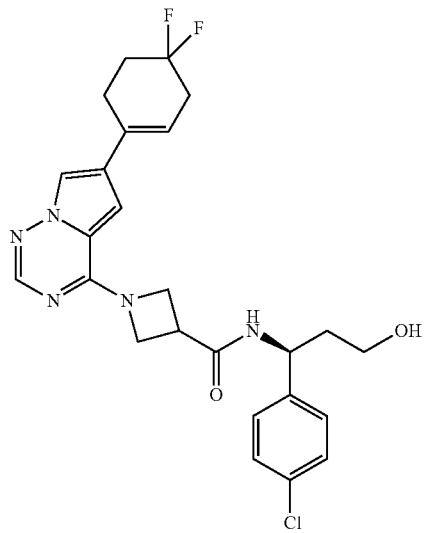 [SMILES: O=C(N[C@@H](CCO)c1ccc(Cl)cc1)C1CN(c2ncnn3cc(C4=CCC(F)(F)CC4)cc23)C1] |
| 267 | 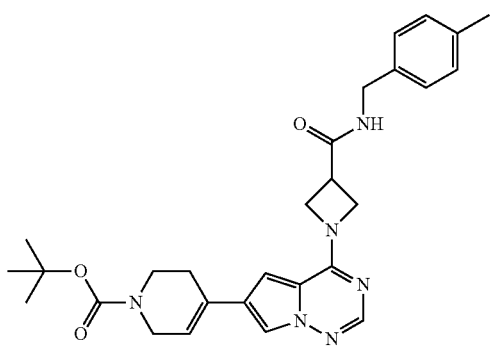 [SMILES: Cc1ccc(CNC(=O)C2CN(c3ncnn4cc(C5=CCN(C(=O)OC(C)(C)C)CC5)cc34)C2)cc1] |
| 268 | 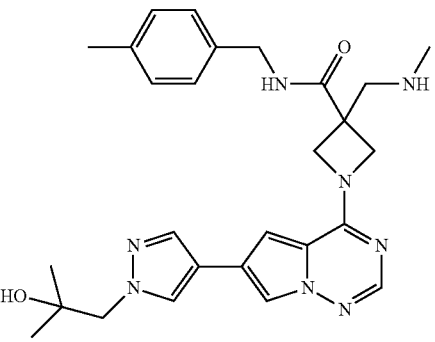 [SMILES: CNCC1(C(=O)NCc2ccc(C)cc2)CN(c2ncnn3cc(-c4cnn(CC(C)(C)O)c4)cc23)C1] |

| # | Structure |
|---|---|
| 269 | |
| 270 | |
| 271 | |
| 272 | 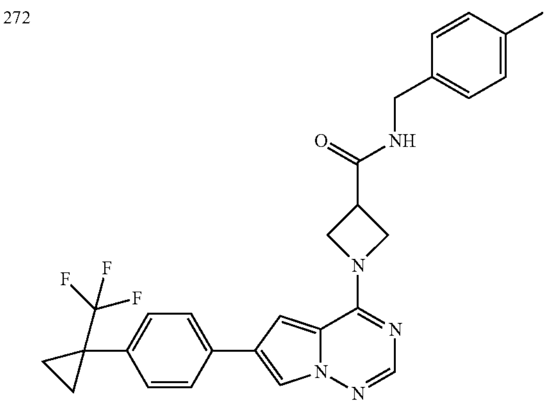 |
| 273 | 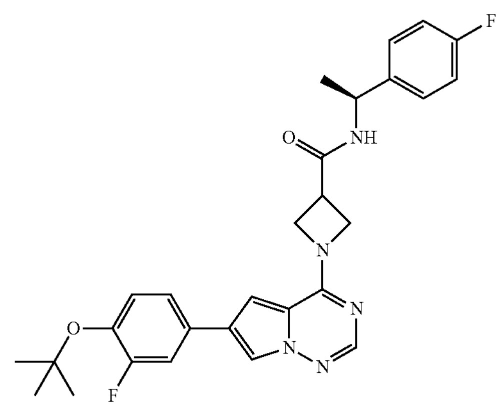 [SMILES: C[C@H](NC(=O)C1CN(c2ncnn3cc(-c4ccc(OC(C)(C)C)c(F)c4)cc23)C1)c1ccc(F)cc1] |
| 274 | 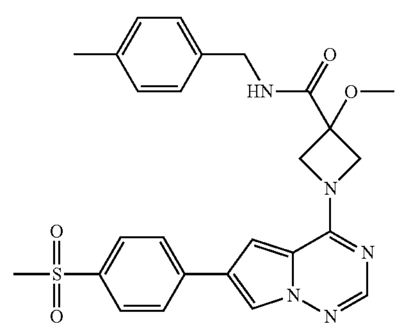 |
| 275 | 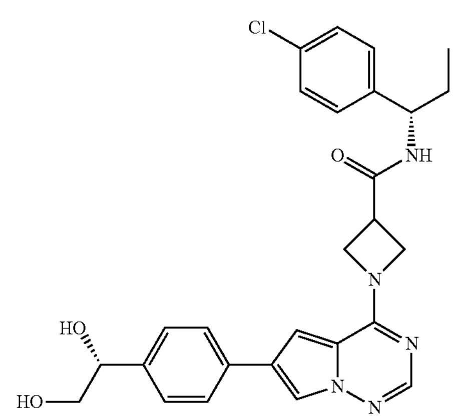 [SMILES: CC[C@H](NC(=O)C1CN(c2ncnn3cc(-c4ccc([C@@H](O)CO)cc4)cc23)C1)c1ccc(Cl)cc1] |

| # | Structure |
|---|---|
| 276 | 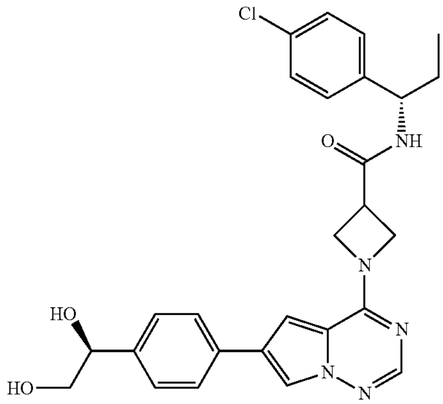 [SMILES: CC[C@H](NC(=O)C1CN(c2ncnn3cc(-c4ccc([C@H](O)CO)cc4)cc23)C1)c1ccc(Cl)cc1] |
| 278 | |
| 278 | |
| 279 | 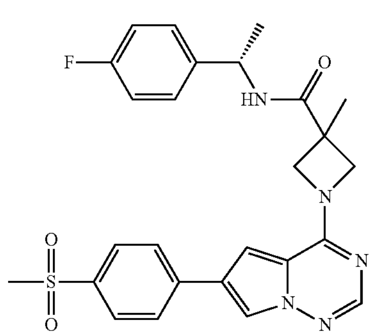 [SMILES: C[C@H](NC(=O)C1(C)CN(c2ncnn3cc(-c4ccc(S(C)(=O)=O)cc4)cc23)C1)c1ccc(F)cc1] |

| # | Structure |
|---|---|
| 280 | 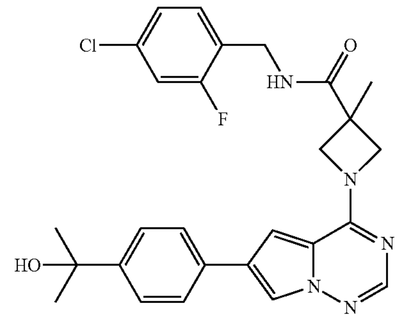 [SMILES: CC1(C(=O)NCc2ccc(Cl)cc2F)CN(c2ncnn3cc(-c4ccc(C(C)(C)O)cc4)cc23)C1] |
| 281 | 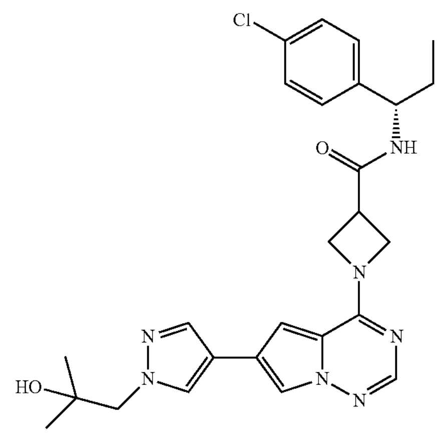 [SMILES: CC[C@H](NC(=O)C1CN(c2ncnn3cc(-c4cnn(CC(C)(C)O)c4)cc23)C1)c1ccc(Cl)cc1] |
| 282 | 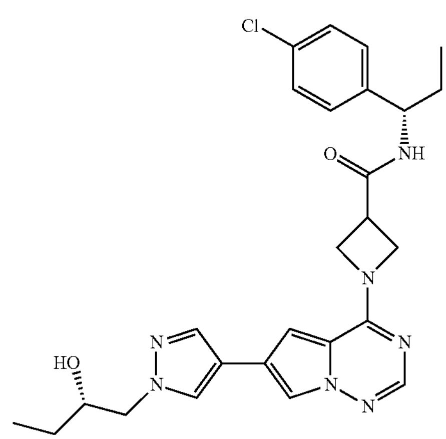 [SMILES: CC[C@H](O)Cn1cc(-c2cc3c(N4CC(C(=O)N[C@@H](CC)c5ccc(Cl)cc5)C4)ncnn3c2)cn1] |

365
-continued

| # | Structure |
|---|---|
| 283 | 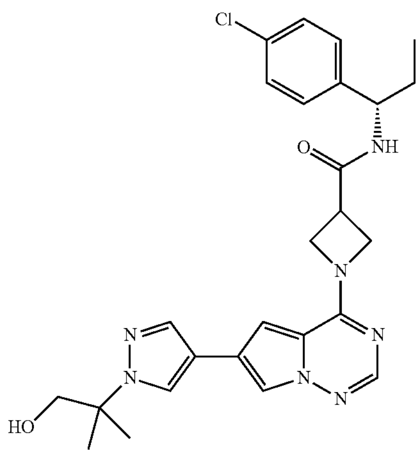 [SMILES: CC[C@H](NC(=O)C1CN(c2ncnn3cc(-c4cnn(C(C)(C)CO)c4)cc23)C1)c1ccc(Cl)cc1] |
| 284 | 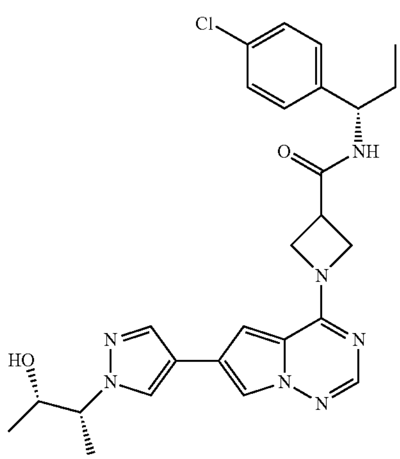 [SMILES: CC[C@H](NC(=O)C1CN(c2ncnn3cc(-c4cnn([C@H](C)[C@H](C)O)c4)cc23)C1)c1ccc(Cl)cc1] |
| 285 | 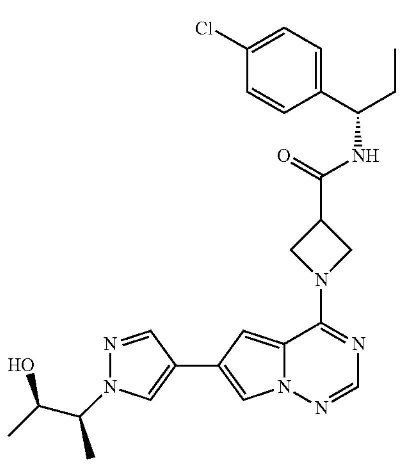 [SMILES: CC[C@H](NC(=O)C1CN(c2ncnn3cc(-c4cnn([C@@H](C)[C@@H](C)O)c4)cc23)C1)c1ccc(Cl)cc1] |

366
-continued

| # | Structure |
|---|---|
| 286 | 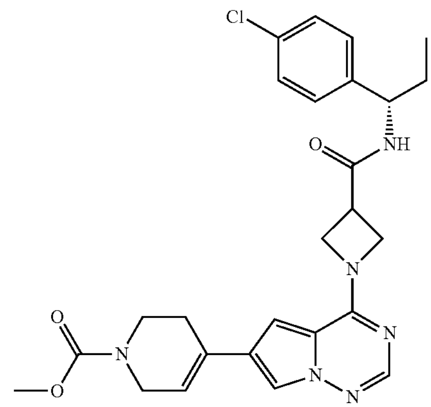 [SMILES: CC[C@H](NC(=O)C1CN(c2ncnn3cc(C4=CCN(C(=O)OC)CC4)cc23)C1)c1ccc(Cl)cc1] |
| 287 | 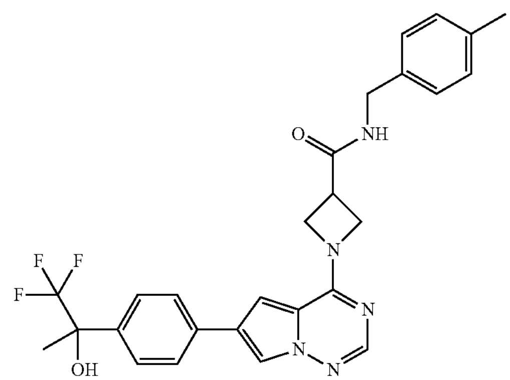 [SMILES: Cc1ccc(CNC(=O)C2CN(c3ncnn4cc(-c5ccc(C(C)(O)C(F)(F)F)cc5)cc34)C2)cc1] |
| 288 | 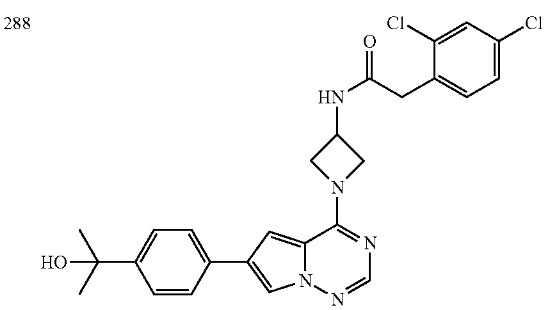 |
| 289 | 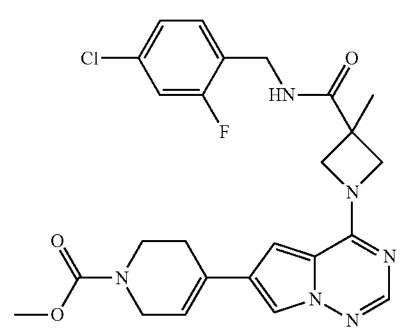 |

367
-continued
| # | Structure |
|---|---|
| 290 | 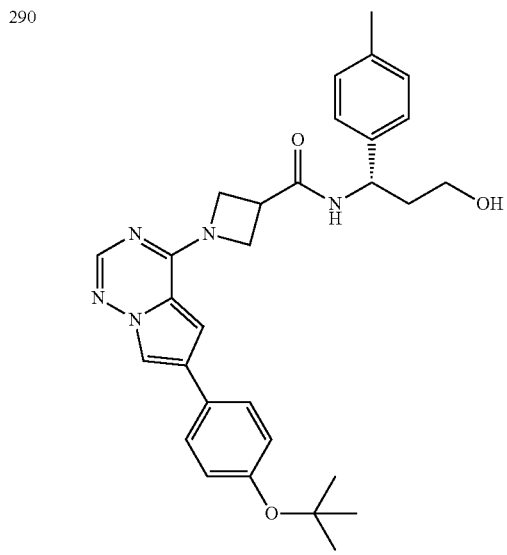 |
| 291 | 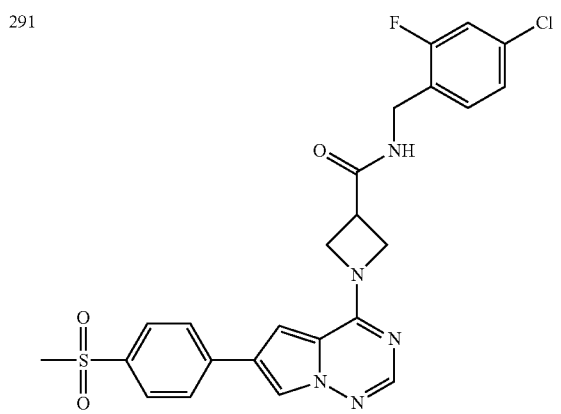 |
| 292 | 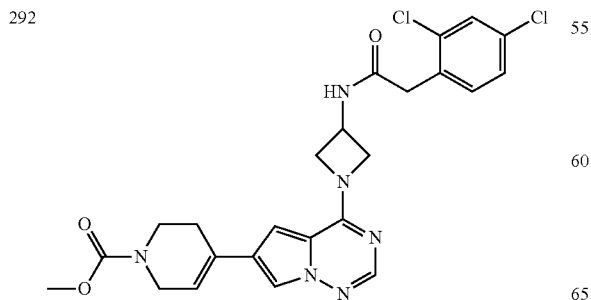 |
368
-continued
| # | Structure |
|---|---|
| 293 | 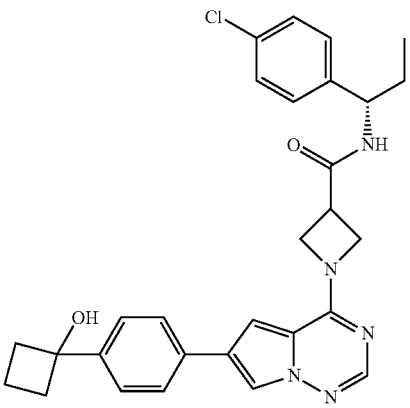 [SMILES: CC[C@H](NC(=O)C1CN(c2ncnn3cc(-c4ccc(C5(O)CCC5)cc4)cc23)C1)c1ccc(Cl)cc1] |
| 294 | 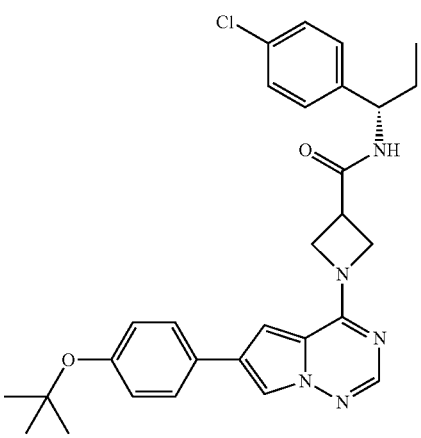 [SMILES: CC[C@H](NC(=O)C1CN(c2ncnn3cc(-c4ccc(OC(C)(C)C)cc4)cc23)C1)c1ccc(Cl)cc1] |
| 295 | 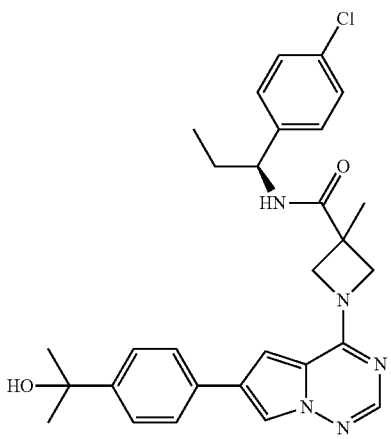 [SMILES: CC[C@H](NC(=O)C1(C)CN(c2ncnn3cc(-c4ccc(C(C)(C)O)cc4)cc23)C1)c1ccc(Cl)cc1] |

369
-continued
| # | Structure |
|---|---|
| 296 | 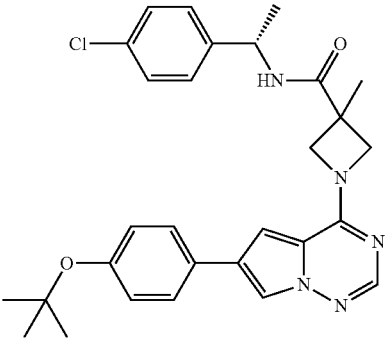 [SMILES: C[C@H](NC(=O)C1(C)CN(c2ncnn3cc(-c4ccc(OC(C)(C)C)cc4)cc23)C1)c1ccc(Cl)cc1] |
| 297 | 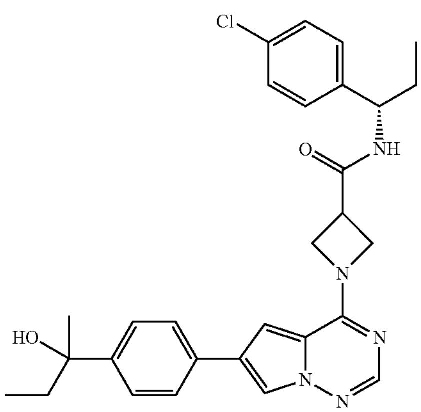 [SMILES: CC[C@H](NC(=O)C1CN(c2ncnn3cc(-c4ccc(C(C)(O)CC)cc4)cc23)C1)c1ccc(Cl)cc1] |
| 298 | 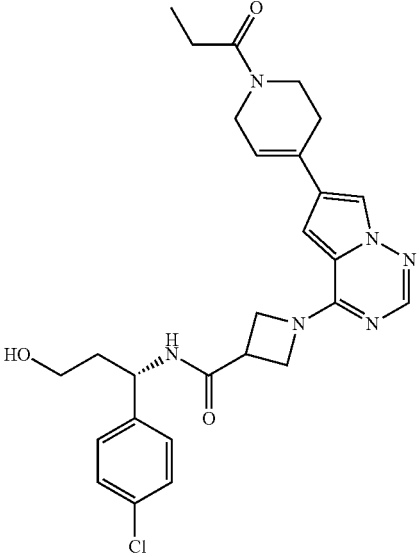 |
370
-continued
| # | Structure |
|---|---|
| 299 | 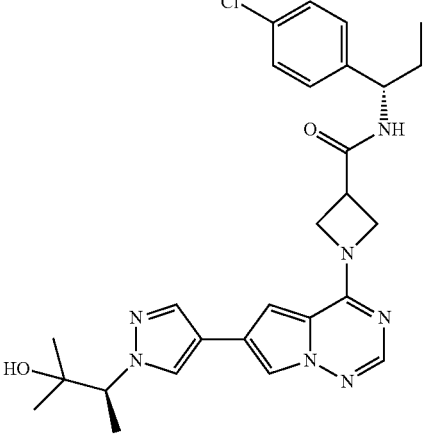 |
| 300 | 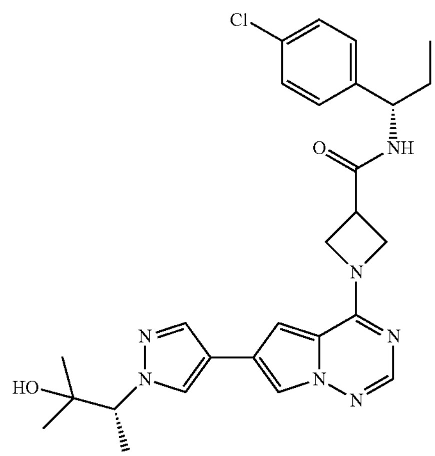 [SMILES: CC[C@H](NC(=O)C1CN(c2ncnn3cc(-c4cnn([C@H](C)C(C)(C)O)c4)cc23)C1)c1ccc(Cl)cc1] |
| 301 | 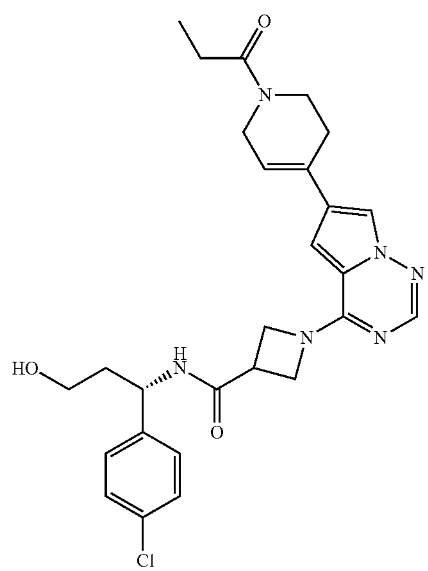 [SMILES: CCC(=O)N1CC=C(c2cc3c(N4CC(C(=O)N[C@@H](CCO)c5ccc(Cl)cc5)C4)ncnn3c2)CC1] |

-continued

| # | Structure |
|---|---|
| 302 | 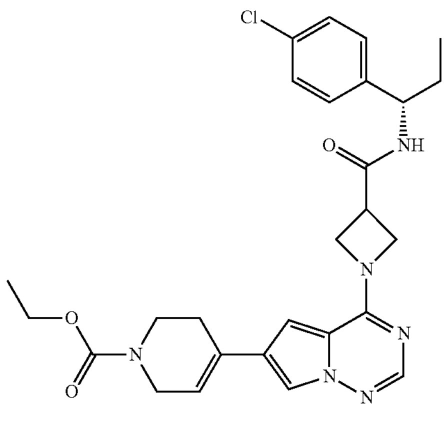 [SMILES: CCOC(=O)N1CC=C(c2cc3c(N4CC(C(=O)N[C@@H](CC)c5ccc(Cl)cc5)C4)ncnn3c2)CC1] |
| 303 | 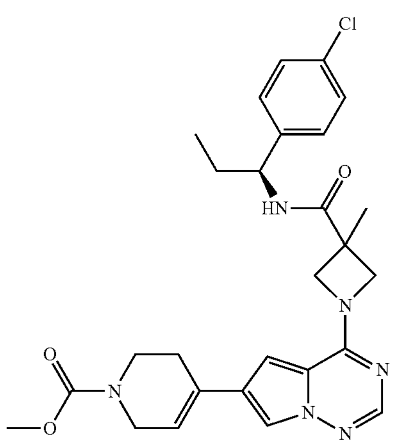 [SMILES: CC[C@H](NC(=O)C1(C)CN(c2ncnn3cc(C4=CCN(C(=O)OC)CC4)cc23)C1)c1ccc(Cl)cc1] |
| 304 | 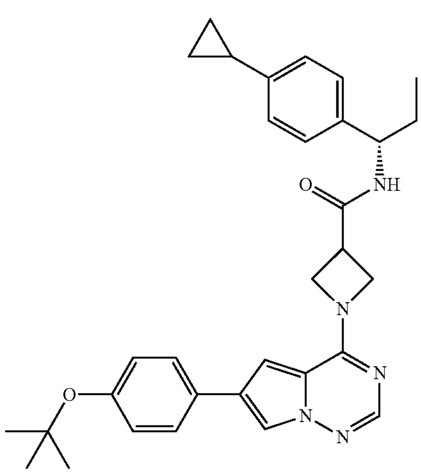 [SMILES: CC[C@H](NC(=O)C1CN(c2ncnn3cc(-c4ccc(OC(C)(C)C)cc4)cc23)C1)c1ccc(C2CC2)cc1] |

-continued

| # | Structure |
|---|---|
| 305 | 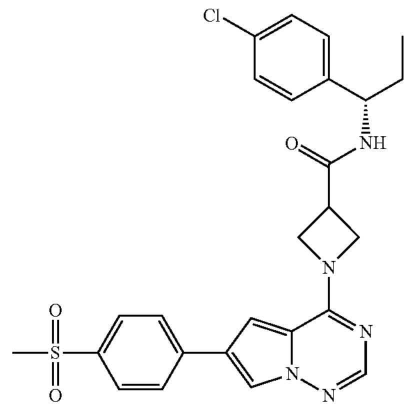 [SMILES: CC[C@H](NC(=O)C1CN(c2ncnn3cc(-c4ccc(S(C)(=O)=O)cc4)cc23)C1)c1ccc(Cl)cc1] |
| 306 | 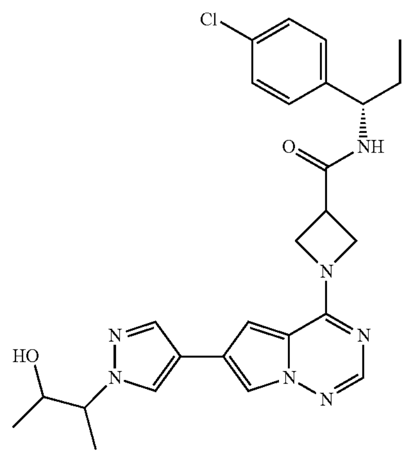 |
| 307 | 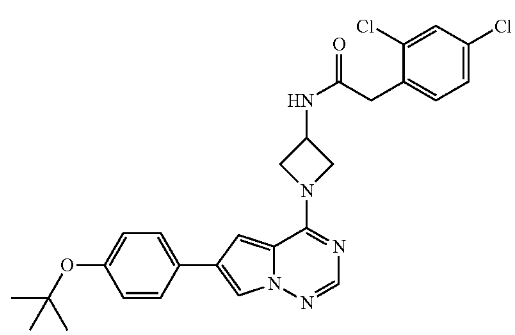 [SMILES: CC(C)(C)Oc1ccc(-c2cc3c(N4CC(NC(=O)Cc5ccc(Cl)cc5Cl)C4)ncnn3c2)cc1] |
| 308 | 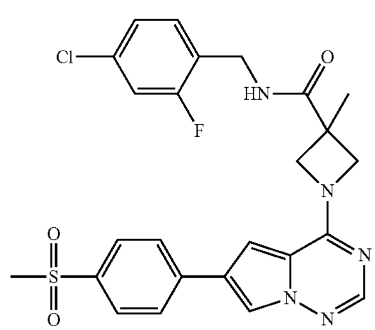 [SMILES: CC1(C(=O)NCc2ccc(Cl)cc2F)CN(c2ncnn3cc(-c4ccc(S(C)(=O)=O)cc4)cc23)C1] |

| # | Structure |
|---|---|
| 309 | 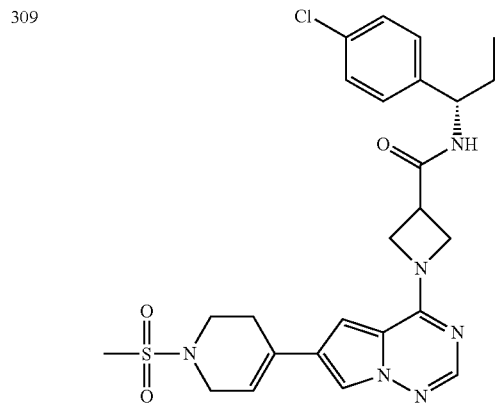 |
| 310 | 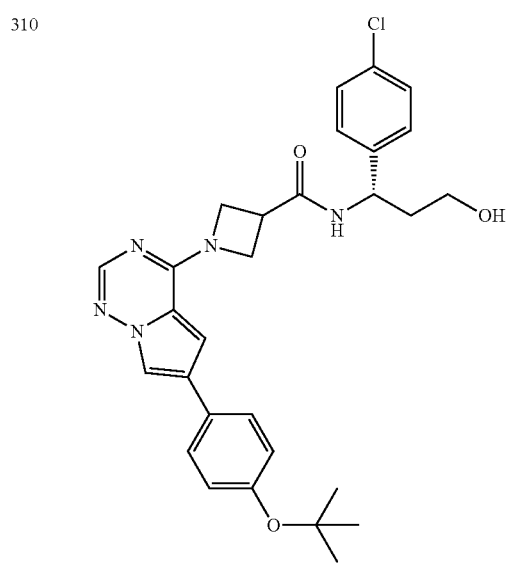 |
| 311 | 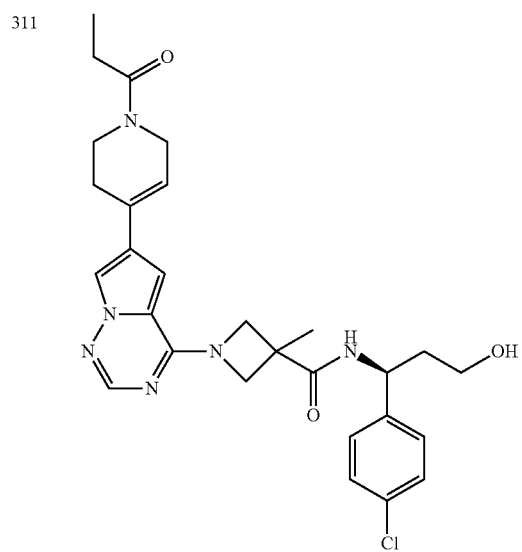 |
| # | Structure |
|---|---|
| 312 | 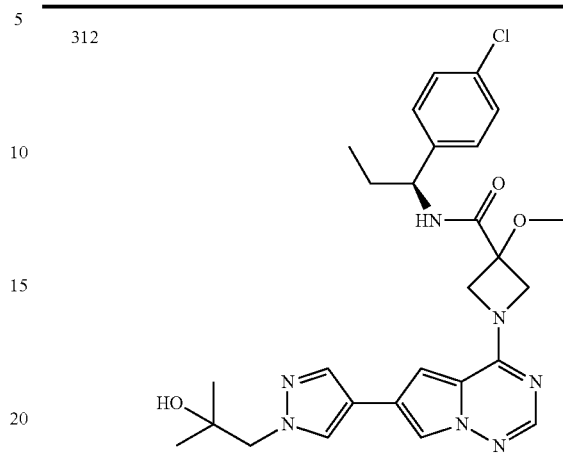 |
| 313 | 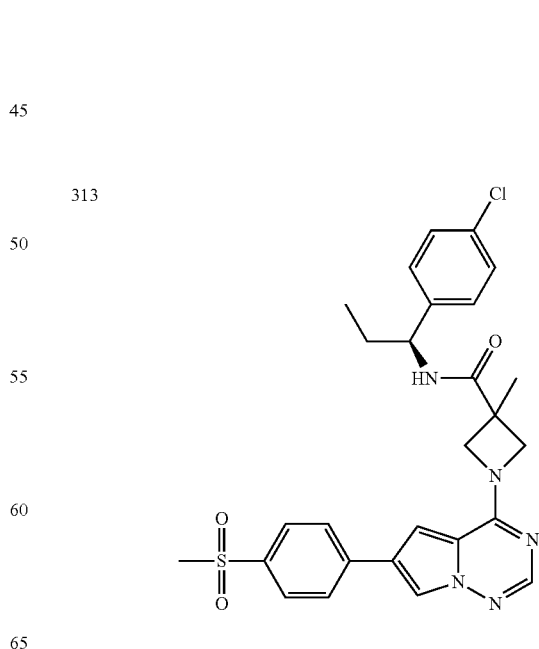 |

| # | Structure |
|---|---|
| 314 | 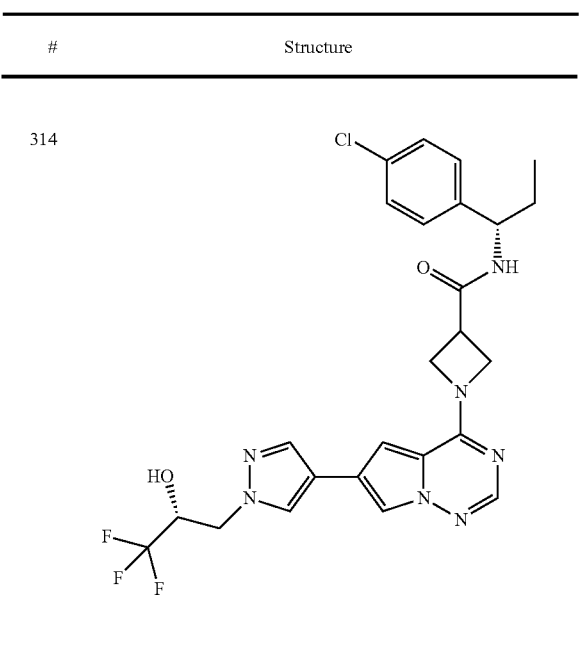 |
| 315 | 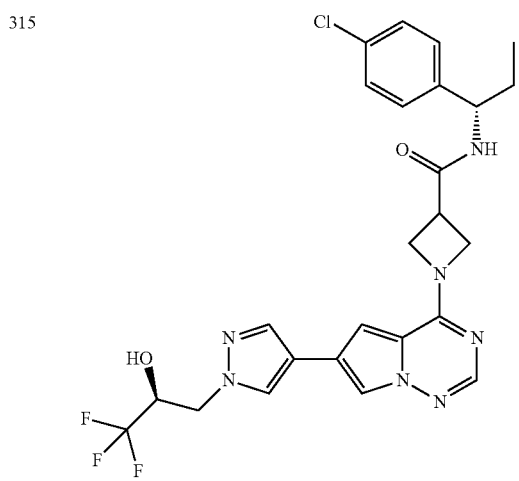 |
| # | Structure |
|---|---|
| 316 | 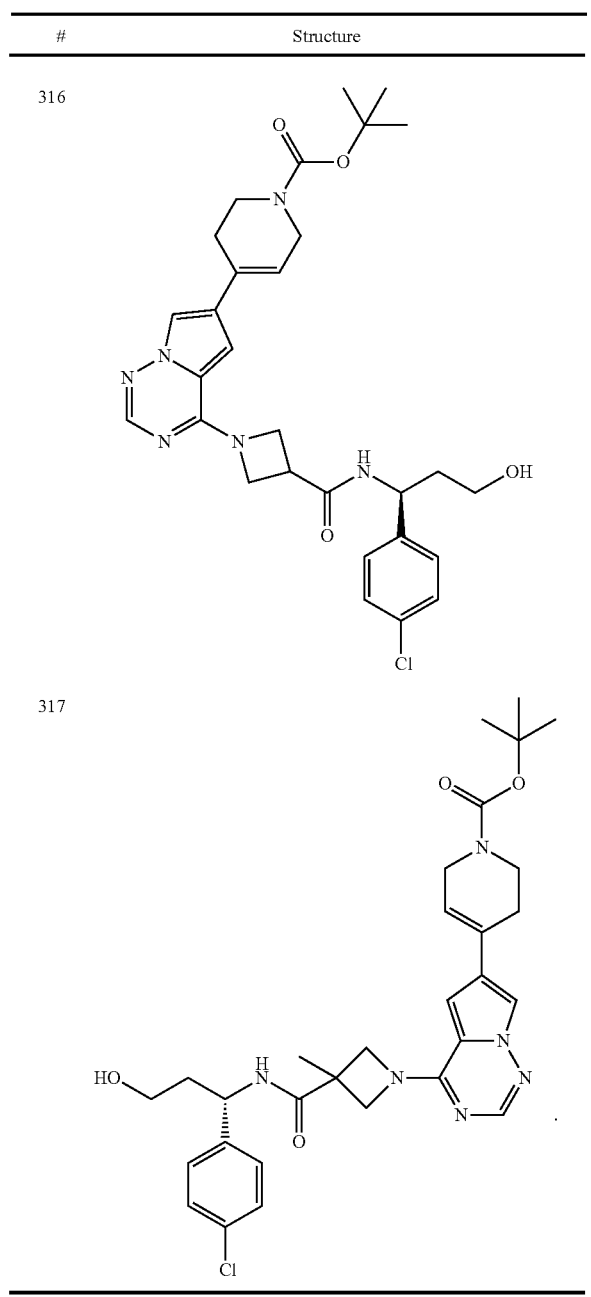 |
| 317 | |
* * * * *